United States Patent
Olsen et al.

(10) Patent No.: US 11,897,857 B2
(45) Date of Patent: Feb. 13, 2024

(54) ISOTOPICALLY-STABILIZED TETRONIMIDE COMPOUNDS

(71) Applicant: Midwestern University, Downers Grove, IL (US)

(72) Inventors: Mark Jon Olsen, Phoenix, AZ (US); Jean Paul Seerden, Groningen (NL)

(73) Assignee: Midwestern University, Downers Grove, IL (US)

( * ) Notice: Subject to any disclaimer, the term of this patent is extended or adjusted under 35 U.S.C. 154(b) by 0 days.

(21) Appl. No.: 17/119,602

(22) Filed: Dec. 11, 2020

(65) Prior Publication Data
US 2021/0094927 A1   Apr. 1, 2021

Related U.S. Application Data

(63) Continuation of application No. 16/791,252, filed on Feb. 14, 2020, now Pat. No. 10,961,211.

(60) Provisional application No. 62/806,327, filed on Feb. 15, 2019.

(51) Int. Cl.
*C07D 307/66* (2006.01)
*A61P 35/04* (2006.01)

(52) U.S. Cl.
CPC ............ *C07D 307/66* (2013.01); *A61P 35/04* (2018.01); *C07B 2200/05* (2013.01)

(58) Field of Classification Search
CPC .... C07D 307/66; A61P 35/04; C07B 2200/05
See application file for complete search history.

(56) References Cited

U.S. PATENT DOCUMENTS

| | | | |
|---|---|---|---|
| 9,771,356 B2 | 9/2017 | Wands et al. | |
| 2015/0210677 A1* | 7/2015 | Wands | C07D 405/12 514/314 |
| 2018/0009798 A1 | 1/2018 | Olsen et al. | |

FOREIGN PATENT DOCUMENTS

| | | |
|---|---|---|
| CN | 104902889 A | 9/2015 |
| WO | 2014047519 A2 | 3/2014 |
| WO | 2017117514 A1 | 7/2017 |

OTHER PUBLICATIONS

Aihara, A., C. K. Huang, M. J. Olsen, Q. Lin, W. Chung, Q. Tang, X. Dong and J. R. Wands (2014). "A cell-surface beta-hydroxylase is a biomarker and therapeutic target for hepatocellular carcinoma." Hepatology 60(4): 1302-1313.

Borgas, D. L., J. S. Gao, M. Tong and S. M. De La Monte (2015). "Potential Role of Phosphorylation as a Regulator of Aspartyl-(asparaginyl)-beta-hydroxylase: Relevance to Infiltrative Spread of Human Hepatocellular Carcinoma." Liver Cancer 4(3): 139-153.

Borgas, D. L., J. S. Gao, M. Tong, N. Roper and S. M. De La Monte (2015). "Regulation of Aspartyl-(Asparaginyl)-beta-Hydroxylase Protein Expression and Function by Phosphorylation in Hepatocellular Carcinoma Cells." J Nat Sci 1(4).

Cantarini, M. C., S. M. De La Monte, M. Pang, M. Tong, A. D'Errico, F. Trevisani and J. R. Wands (2006). "Aspartyl-asparagyl beta hydroxylase over-expression in human hepatoma is linked to activation of insulin-like growth factor and notch signaling mechanisms." Hepatology 44(2): 446-457.

Dinchuk, J. E., R. J. Focht, J. A. Kelley, N. L. Henderson, N. I. Zolotarjova, R. Wynn, N. T. Neff, J. Link, R. M. Huber, T. C. Burn, M. J. Rupar, M. R. Cunningham, B. H. Selling, J. Ma, A. A. Stern, G. F. Hollis, R. B. Stein and P. A. Friedman (2002). "Absence of post-translational aspartyl beta-hydroxylation of epidermal growth factor domains in mice leads to developmental defects and an increased incidence of intestinal neoplasia." J Biol Chem 277(15): 12970-12977.

Drakenberg, T., P. Fernlund, P. Roepstorff and J. Stenflo (1983). "beta-Hydroxyaspartic acid in vitamin K-dependent protein C." Proc Natl Acad Sci U S A 80(7): 1802-1806.

El Asmar, Z., J. Terrand, M. Jenty, L. Host, M. Mlih, A. Zerr, H. Justiniano, R. L. Matz, C. Boudier, E. Scholler, J. M. Garnier, D. Bertaccini, D. Thierse, C. Schaeffer, A. Van Dorsselaer, J. Herz, V. Bruban and P. Boucher (2016). "Convergent Signaling Pathways Controlled by LRP1 (Receptor-related Protein 1) Cytoplasmic and Extracellular Domains Limit Cellular Cholesterol Accumulation." J Biol Chem 291(10): 5116-5127.

Furler, R. L., D. F. Nixon, C. A. Brantner, A. Popratiloff and C. H. Uittenbogaart (2018). "TGF-beta Sustains Tumor Progression through Biochemical and Mechanical Signal Transduction." Cancers (Basel) 10(6).

Gundogan, F., G. Elwood, D. Greco, L. P. Rubin, H. Pinar, R. I. Carlson, J. R. Wands and S. M. De La Monte (2007). "Role of aspartyl-(asparaginyl) beta-hydroxylase in placental implantation: Relevance to early pregnancy loss." Hum Pathol 38(1): 50-59.

Iwagami, Y., S. Casulli, K. Nagaoka, M. Kim, R. I. Carlson, K. Ogawa, M. S. Lebowitz, S. Fuller, B. Biswas, S. Stewart, X. Dong, H. Ghanbari and J. R. Wands (2017). "Lambda phage-based vaccine induces antitumor immunity in hepatocellular carcinoma." Heliyon 3(9): e00407.

(Continued)

*Primary Examiner* — Timothy R Rozof
(74) *Attorney, Agent, or Firm* — The Intellectual Property Law Office of Verne A. Luckow LLC; Matthew S. Gibson

(57) ABSTRACT

Isotopically-stabilized tetronimide compounds comprising one or more deuterium atoms, derivatives, and intermediates, thereof, including methods for their synthesis, pharmaceutical compositions thereof, and methods of using these compounds to interact with target molecules in cell-free samples, cell- and tissue-based assays, animal models, and in a subject are disclosed. One aspect relates to molecules that modulate the expression or catalytic activity of aspartyl (asparaginyl) β-hydroxylase (ASPH) within or on the surface of a cell. Other aspects of the invention relate to use of the molecules disclosed herein to diagnose, ameliorate, or treat cell proliferation disorders and related diseases. Related aspects include uses of the compounds to modulate the activity of viruses, as anti-hyperlipidemia agents, and as agents to ameliorate or treat thrombosis and related cardiovascular and metabolic disorders.

8 Claims, 71 Drawing Sheets

Specification includes a Sequence Listing.

(56) References Cited

OTHER PUBLICATIONS

Lavaissiere, L., S. Jia, M. Nishiyama, S. De La Monte, A. M. Stern, J. R. Wands and P. A. Friedman (1996). "Overexpression of human aspartyl(asparaginyl)beta-hydroxylase in hepatocellular carcinoma and cholangiocarcinoma." J Clin Invest 98(6): 1313-1323.

Noda, T., M. Shimoda, V. Ortiz, A. E. Sirica and J. R. Wands (2012). "Immunization with aspartate-beta-hydroxylase-loaded dendritic cells produces antitumor effects in a rat model of intrahepatic cholangiocarcinoma." Hepatology 55(1): 86-97.

Revskaya, E., Z. Jiang, A. Morgenstern, F. Bruchertseifer, M. Sesay, S. Walker, S. Fuller, M. S. Lebowitz, C. Gravekamp, H. A. Ghanbari and E. Dadachova (2017). "A Radiolabeled Fully Human Antibody to Human Aspartyl (Asparaginyl) beta-Hydroxylase is a Promising Agent for Imaging and Therapy of Metastatic Breast Cancer." Cancer Biother Radiopharm 32(2): 57-65.

Tong, M., J. S. Gao, D. Borgas and S. M. De La Monte (2013). "Phosphorylation Modulates Aspartyl-(Asparaginyl)-beta Hydroxylase Protein Expression, Catalytic Activity and Migration in Human Immature Neuronal Cerebellar Cells." Cell Biol (Henderson, NV) 6(2).

Wu, G., Z. Ma, Y. Cheng, W. Hu, C. Deng, S. Jiang, T. Li, F. Chen and Y. Yang (2018). "Targeting Gas6/TAM in cancer cells and tumor microenvironment." Mol Cancer 17(1): 20.

Yang, H., K. Song, T. Xue, X. P. Xue, T. Huyan, W. Wang and H. Wang (2010). "The distribution and expression profiles of human Aspartyl/Asparaginyl beta-hydroxylase in tumor cell lines and human tissues." Oncol Rep 24(5): 1257-1264.

Yeung, Y. A., A. H. Finney, I. A. Koyrakh, M. S. Lebowitz, H. A. Ghanbari, J. R. Wands and K. D. Wittrup (2007). "Isolation and characterization of human antibodies targeting human aspartyl (asparaginyl) beta-hydroxylase." Hum Antibodies 16(3-4): 163-176.

Dahn, H., Lawendel, J.S., Hoegger, E.F. et al. (1954) "Über eine neue Herstellung aromatisch substituierter Reduktone." Experientia 10: 245. (In German with English Abstract).

PDB ID 5JZZ: McDonough, M.A., Pfeffer, I., Munzel, M. (2016) Aspartyl/Asparaginyl beta-hydroxylase (AspH) oxygenase and TPR domains in complex with manganese, N-oxalylglycine and cyclic peptide substrate mimic of factor X. DOI: 10.2210/pdb5JZZ/pdb. Deposited as PDB ID 5JZZ on May 16, 2016, Released on Jun. 6, 2017.

Timmins, G.S. (2014) "Deuterated drugs: where are we now?" Expert Opin. Ther. Patents 24(10):1067-1075.

European Search Report dated Feb. 28, 2022 in European Patent Application 20756730.6.

Foster AB: "Deuterium isotope effects in the metabolism of drugs and xenobiotics: implications for drug design", Advances in Drug Research, Academic Press, London, GB, vol. 14, Jan. 1, 1985 (Jan. 1, 1985), pp. 1-40, XP009086953, ISSN: 0065-2490/.

Leitch: "Organic Deuterium Compounds", Canadian Journal of Chemistry, vol. 35, 1957, pp. 345-347, XP055730967.

Search Report and Office Action of the Intellectual Property Office dated Oct. 4, 2022 issued in Taiwan Patent Application 109104899.

\* cited by examiner

Experimentally confirmed and computationally predicted substrates of ASPH
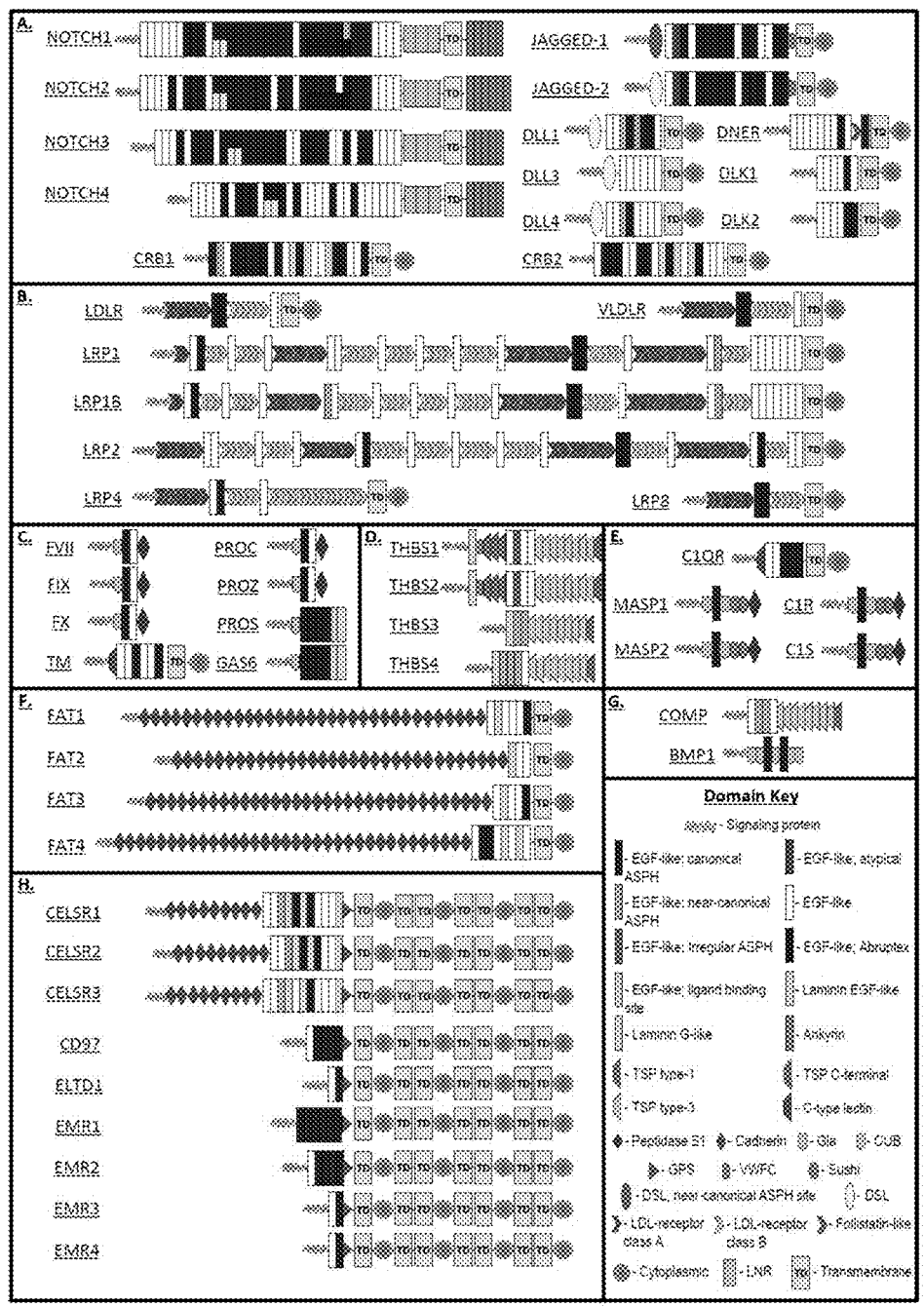
Figure 2 (Panels A-H, plus domain key)

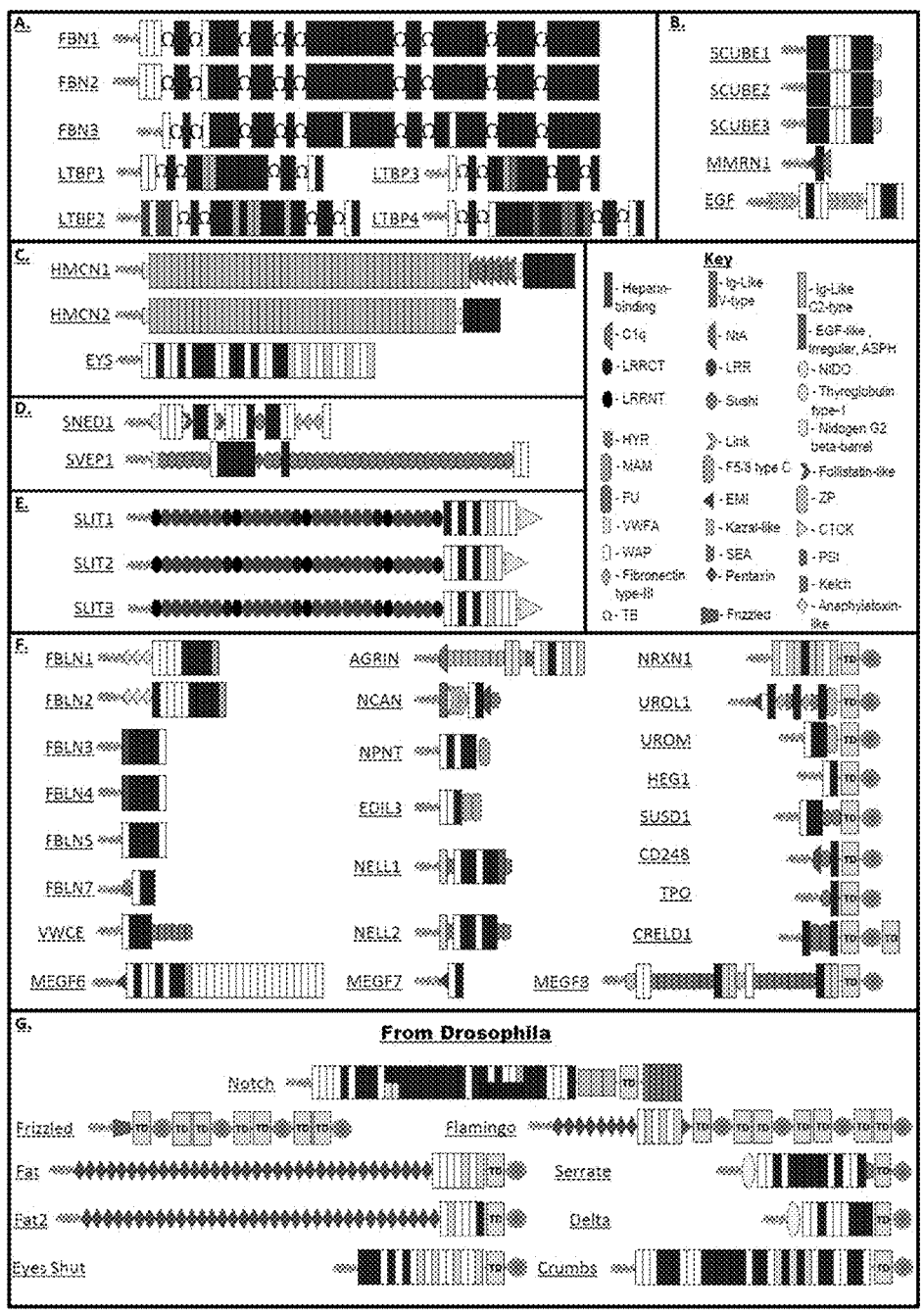
Figure 3 (panels A-G, plus domain key)

Synthesis of Deuterated Tetronimide Modulator Compounds
Scheme 1
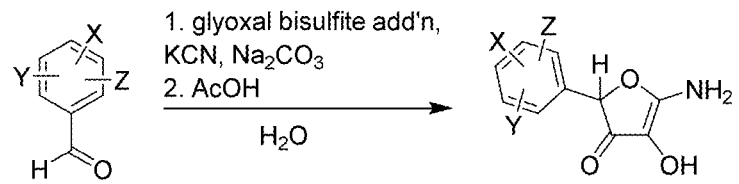
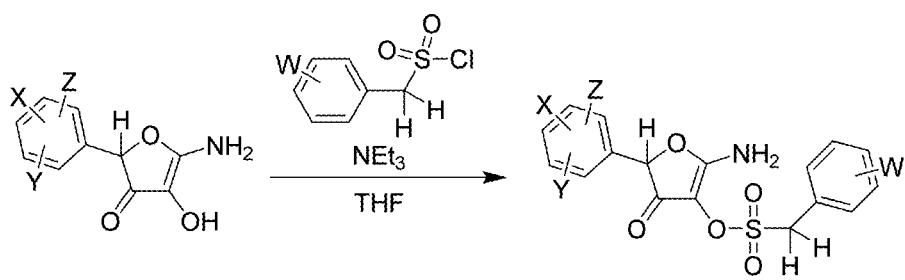
Scheme 2
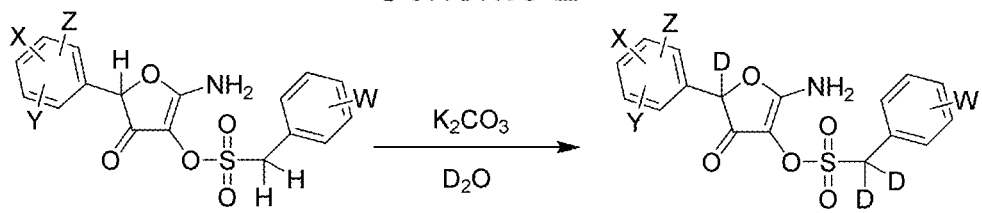
Scheme 3
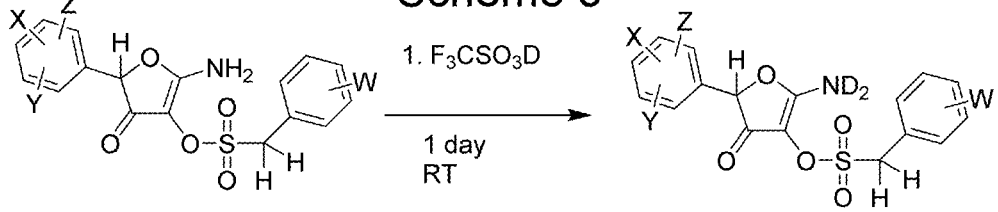
Scheme 4
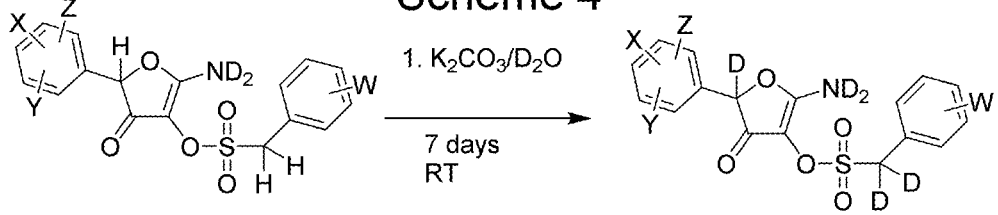
Fig. 5 (Schemes 1-4)

Synthesis of Deuterated Tetronimide Modulators (Continued)
Scheme 5
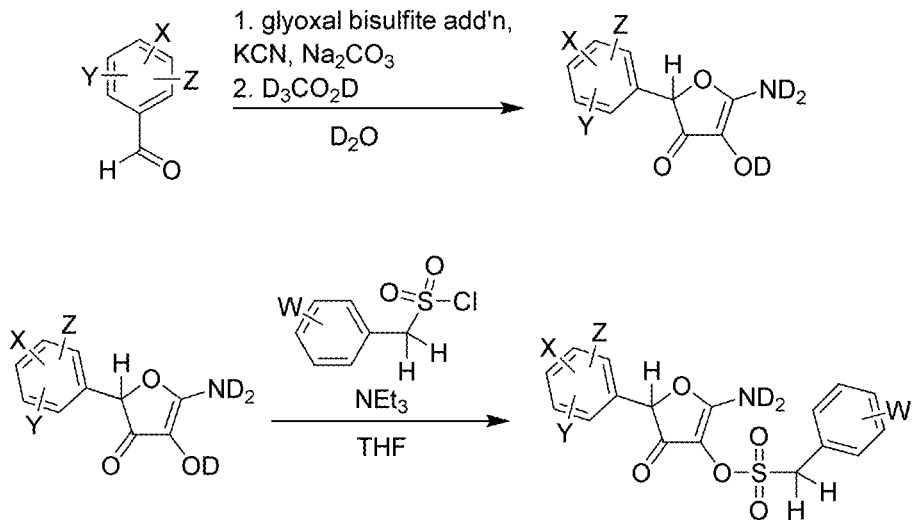
Scheme 6
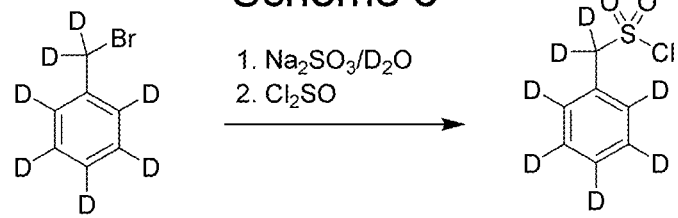
Scheme 7
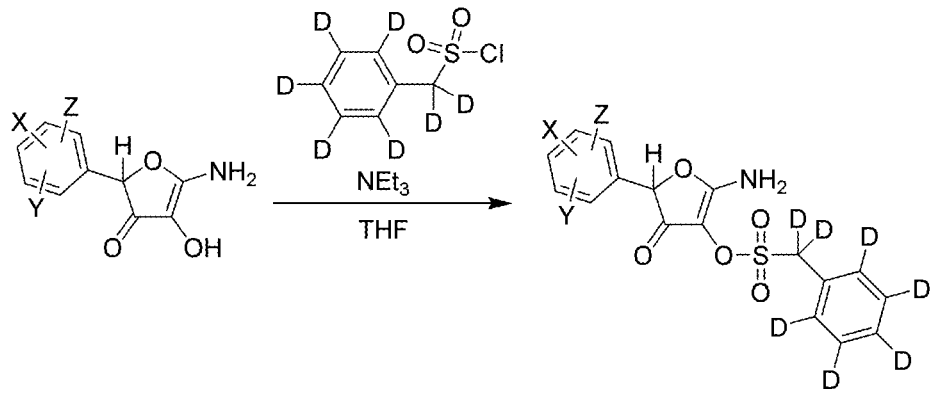
Figure 6 (Schemes 5-7)

Synthesis of Deuterated Tetronimide Modulators (Continued)
Scheme 8
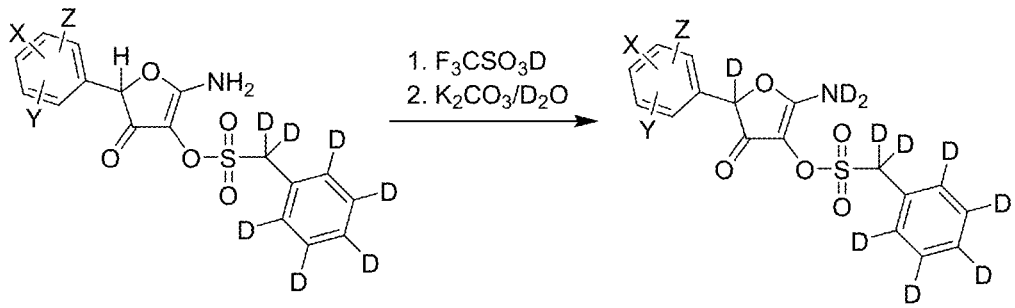
Scheme 9
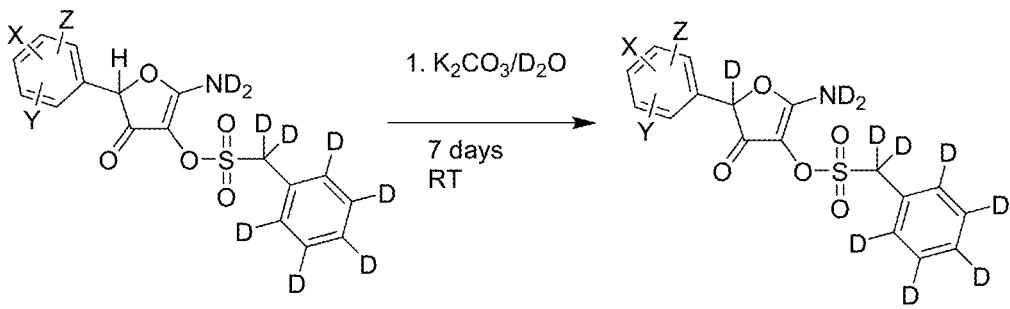
Scheme 10
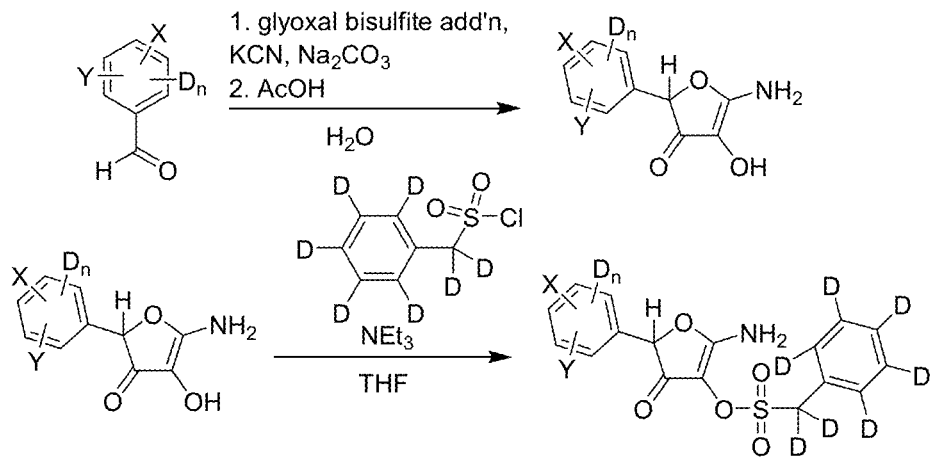
Figure 7 (Schemes 8-10)

Activities of Undeuterated, Racemic, and Deuterated Enantiomers of Tetronimide Modulator Compounds Against ASPH in Liver Microsome Assays

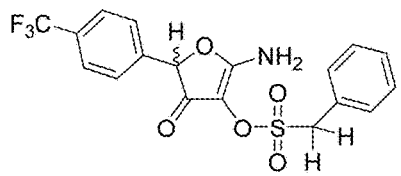

1066

Human
Clint = 183.9
$T_{1/2}$ = 37.9 min

Mouse
Clint = 264.8
$T_{1/2}$ = 26.2

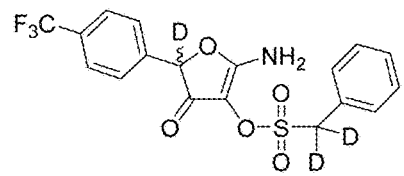

2066

Human
Clint = 144.1
$T_{1/2}$ = 48.7 min

Mouse
Clint = 268.7
$T_{1/2}$ = 25.8

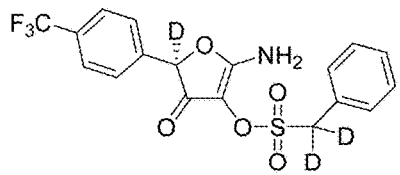

2066(R)

Human
Clint < 115.5
$T_{1/2}$ > 60 min

Mouse
Clint = 285
$T_{1/2}$ = 24.3

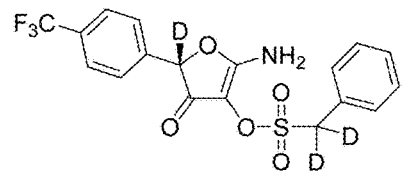

2066(S)

Human
Clint = 292.5
$T_{1/2}$ = 23.8 min

Mouse
Clint = 191.1
$T_{1/2}$ = 36.4

Compounds with indicated clearance (Clint) and $T_{1/2}$ in human and mouse liver microsome assays.

Figure 8

**Activities of Specific Compounds Against MCF-7 Cells *In Vitro***

Concentrations: 1 = 0 µM, 2 = 1.25 µM, 3 = 2.5 µM, 4 = 5 µM, 5 = 10 µM

MOI-I-1151 = Compound #1066, unlabeled

MOI-I-1151B02000 = Compound #2066(R), deuterated enantiomer

MOI-I-1151C02000 = Compound #2066(S), deuterated enantiomer

FIG. 10-35

ISOTOPICALLY-STABILIZED TETRONIMIDE COMPOUNDS

CROSS REFERENCE TO RELATED APPLICATIONS

This application is a continuation of claims the benefit of Non-Provisional U.S. application Ser. No. 16/791,252 filed Feb. 14, 2020, now allowed, and Provisional U.S. Application No. 62/806,327, filed Feb. 15, 2019, the entire contents of which are incorporated by reference in their entirety.

INCORPORATION-BY-REFERENCE OF A SEQUENCE LISTING

The sequence listing contained in the file "761_190_034_US_01_Sequence_Listing_ST25.txt", created on 2020-11-30, modified on 2020-11-20, file size 2,455 bytes, containing SEQ ID NO: 1, and any sequence files referenced in U.S. Ser. No. 16/791,252 and U.S. 62/806,327, noted above, are incorporated by reference in their entirety herein.

FIELD OF THE INVENTION

Isotopically-stabilized tetronimide compounds comprising one or more deuterium atoms, derivatives, and intermediates, thereof, including methods for their synthesis, pharmaceutical compositions thereof, and methods of using these compounds to interact with target molecules in cell-free samples, cell- and tissue-based assays, animal models, and in a subject are disclosed. One aspect relates to molecules that modulate the expression or catalytic activity of aspartyl (asparaginyl) p-hydroxylase (ASPH) within or on the surface of a cell. Other aspects of the invention relate to use of the molecules disclosed herein to diagnose, ameliorate, or treat cell proliferation disorders and related diseases. Related aspects include uses of the compounds to modulate the activity of viruses, as anti-hyperlipidemia agents, and as agents to ameliorate or treat thrombosis and related cardiovascular and metabolic disorders.

BACKGROUND OF THE INVENTION

Aspartyl(asparaginyl)-β-hydroxylase (ASPH) is an iron-dependent dioxygenase that catalyzes the hydroxylation of β carbons of aspartic acid and asparagine residues in calcium binding Epidermal Growth Factor (cbEGF)-like domains of a variety of proteins, including Notch and Notch ligand homologs (Dinchuk, Focht et al. 2002) extracellular matrix proteins, and low density lipoprotein (LDL) receptors. ASPH was first observed to be involved in the hydroxylation of a specific aspartic acid residue in the blood coagulation cascade proteins (Drakenberg, Fernlund et al. 1983), where the hydroxylated residue is underlined in the consensus sequence CX[D/N]X$_4$[Y/F]XC (SEQ ID NO: 1). The role of the hydroxylated residue is presently unknown, but the sole known crystal structure with a beta-hydroxylated asparagine (PDB ID 5JZZ: McDonough, M. A., Pfeffer, I., and Munzel (2016) Aspartyl/Asparaginyl beta-hydroxylase (AspH)oxygenase and TPR domains in complex with manganese, N-oxalylglycine and cyclic peptide substrate mimic of factor X. DOI: 10.2210/pdb5JZZ/pdb).

ASPH is generally classified as a peptide-aspartate beta-dioxygenase (EC 1.14.11.16), a member of the alpha-keto-glutarate-dependent hydroxylases superfamily, which catalyzes the following chemical reaction, facilitated by iron as a cofactor.

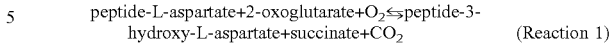
peptide-L-aspartate+2-oxoglutarate+$O_2$⇌peptide-3-hydroxy-L-aspartate+succinate+$CO_2$  (Reaction 1)

ASPH is not normally expressed in adult cells (Lavaissiere, Jia et al. 1996), but is expressed during invasion of the uterine wall by trophoblasts during development of the placenta (Gundogan, Elwood et al. 2007). ASPH is overexpressed in a variety of tumors, including hepatocellular, cholangiocarcinoma, gastric cancer, pancreatic cancer, non-small cell lung cancer, glioblastoma multiform, osteosarcoma, cervical cancer, ovarian cancer and breast cancer (Yang, Song et al. 2010), and enhances signaling in the Notch pathway (Cantarini, de la Monte et al. 2006).

FIG. 1 sets forth an illustration showing the Activation of Notch Signaling Pathway by ASPH. FIG. 2 (Panels A-H, plus domain key) and FIG. 3 (Panels A-G, plus domain key) both set forth illustrations showing the Locations of Epitopes of Interest on ASPH.

Known and computationally predicted ASPH substrates are illustrated in FIG. 4 and FIG. 5. Prediction of ASPH substrates is based upon the protein possessing A) a cbEGF domain and B) the consensus sequence CX[D/N]X$_4$[Y/F]XC (SEQ ID NO: 1). Of particular interest are nearly all of the Notch signaling proteins, not only including the receptors Notch1-4, but many of the known ligands such as Jagged1&2 and Dll1&4, but also known Notch pathway modulator human homologues of Crumbs from *Drosophila*. ASPH is known to hydroxylate lipid receptor proteins, including Lrp1. Lrp1 is known to have an interaction with Wnt5a of the canonical Wnt signaling pathway (El Asmar, Terrand et al. 2016). ASPH substrate Gas6 is the ligand of the Tyro3, Axel and Mer (TAM) kinases, which have been implicated in cancer (Wu, Ma et al. 2018). Known ASPH substrates including the fibrillins are involved in the release of TGF-beta, which is implicated in cancer (Furler, Nixon et al. 2018). In addition to cancer, ASPH hydroxylated substrates are found in nearly all of the blood coagulation proteins involved in thrombosis (see panel D in FIG. 2), and many of the proteins involved in lipid uptake including LDLR, VLDLR and Lrp1 (see panel B in FIG. 2) and cholesterol homeostasis. Thus, ASPH expression is expected to have a cascade of effects, but may have particular value in the treatment of cancer, as well as thrombosis and lipid/cholesterol associated cardiovascular diseases. ASPH expression may be correlated with viral infection, particularly with hepatitis B, D and human papillomavirus, and may enhance viral replication either directly, by enhancing cellular proliferation, or by activating proteins (such as URG11/VWCE) that are specifically upregulated by the virus.

ASPH is known to contain multiple phosphorylation sites (Tong, Gao et al. 2013), including T748. Phosphorylation of ASPH is known to alter the expression and function of ASPH (Borgas, Gao et al. 2015), and plays a potential role in migration and tissue invasion of hepatocellular carcinoma (Borgas, Gao et al. 2015). Antibodies selective for ASPH phosphorylation state should be useful in the diagnosis of cancer and distinguishing ASPH expressed in normal cells compared to ASPH expressed in tumor cells.

Other strategies for modulating the expression or activity of ASPH include synthesis and testing of small molecule compounds that inhibit the activity of the enzyme (Aihara, Huang et al. 2014), a cellular approach relying on use of dendritic cells (Noda, Shimoda et al. 2012), and an approach directed to the synthesis and testing of vaccines against ASPH and related polypeptides (Iwagami, Casulli et al. 2017).

U.S. Pat. No. 9,771,356 discloses ASPH modulating compounds that possess a stereocenter that is easily racemized, which cannot be isolated as pure enantiomers under experimental conditions. While deuterated versions of existing drug products are known (Timmins, G. S., 2014), the use of deuterium to limit racemization of the tetronimide ring core, permitting stable isolation of pure enantiomers as disclosed herein, is surprising and unexpected. The deuterated versions of many tetronimide compounds disclosed herein have superior chemical and drug product properties, compared to the properties of undeuterated tetronimide compounds, precursor compounds, intermediates, and related derivatives.

SUMMARY OF THE INVENTION

Isotopically-stabilized tetronimide compounds comprising one or more deuterium atoms, derivatives, and intermediates, thereof, including methods for their synthesis, pharmaceutical compositions thereof, and methods of using these compounds to interact with target molecules in cell-free samples, cell- and tissue-based assays, animal models, and in human and animal subjects are disclosed.

One aspect of the invention is directed to a deuterated compound of any one of formulas {I-A, I-B, I-C, I-D, I-E, I-F, I-G, or I-H}:

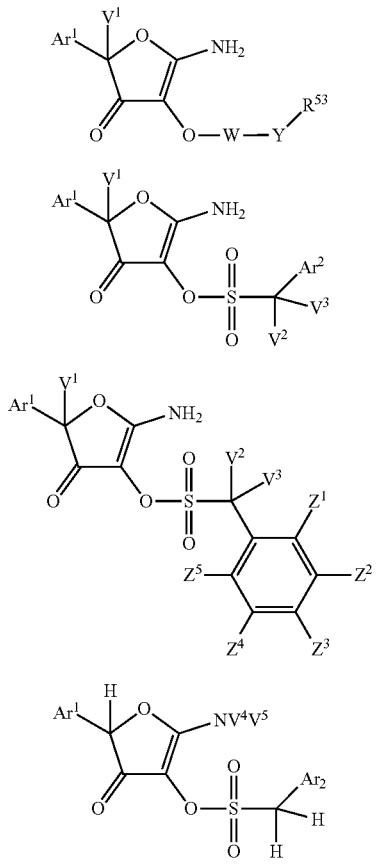

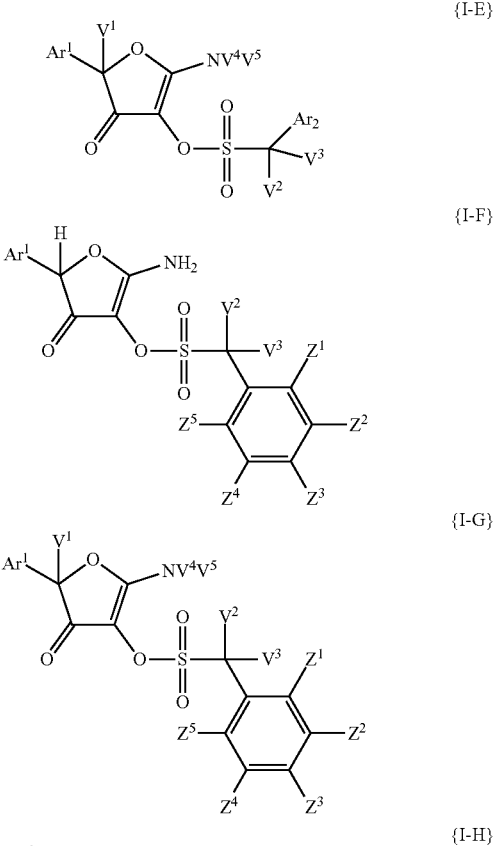

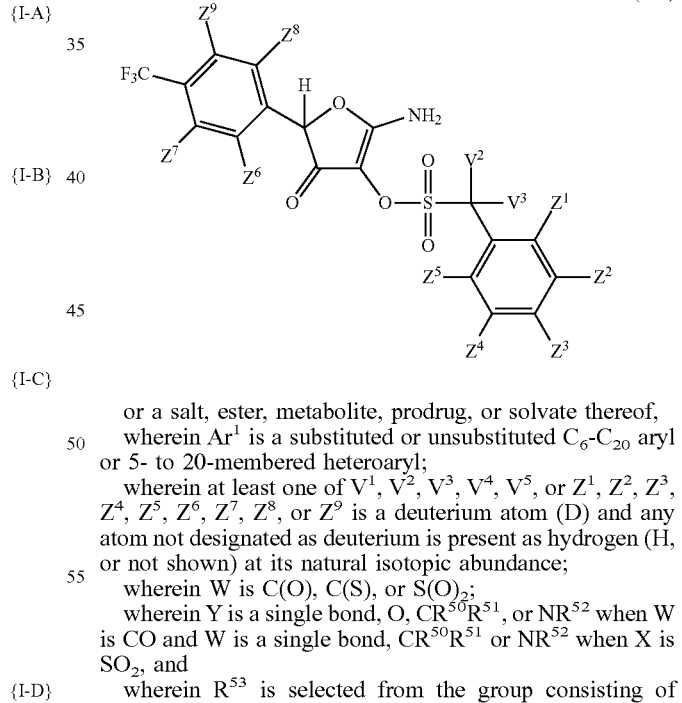

or a salt, ester, metabolite, prodrug, or solvate thereof, wherein $Ar^1$ is a substituted or unsubstituted $C_6$-$C_{20}$ aryl or 5- to 20-membered heteroaryl;

wherein at least one of $V^1$, $V^2$, $V^3$, $V^4$, $V^5$, or $Z^1$, $Z^2$, $Z^3$, $Z^4$, $Z^5$, $Z^6$, $Z^7$, $Z^8$, or $Z^9$ is a deuterium atom (D) and any atom not designated as deuterium is present as hydrogen (H, or not shown) at its natural isotopic abundance;

wherein W is C(O), C(S), or $S(O)_2$;

wherein Y is a single bond, O, $CR^{50}R^{51}$, or $NR^{52}$ when W is CO and W is a single bond, $CR^{50}R^{51}$ or $NR^{52}$ when X is $SO_2$, and wherein $R^{53}$ is selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 20-membered heteroaryl, and substituted or unsubstituted 6-26 membered heteroarylalkyl; and wherein $Ar^2$, designated as an unsubstituted or substituted $C_6$-$C_{20}$ heteroaryl is selected from the group consisting of:

phenyl; naphthyl; pyridyl; pyridone; pyrimidine; pyradazine; pyrazine; purine; furan; thiophene; oxazole; thiazole; isoxazole; isothiazole; oxadiazole; thiadiazole; pyrrole; imidazole; triazole; tetrazole; and diazepine.

Also described are methods of synthesizing a deuterated compound of any one of formulas {I-A, I-B, I-C, I-D, I-E, I-F, I-G, or I-H} from an unlabeled precursor compound and a donor molecule comprising one or more deuterium atoms.

Also described are methods of using a deuterated compound of any one of formulas {I-A, I-B, I-C, I-D, I-E, I-F, I-G, or I-H} to facilitated the manufacture of a medicament, including pharmaceutically-acceptable compositions comprising one or more excipients and the compound or a salt, ester, metabolite, prodrug, or solvate thereof.

Also described is use of a deuterated compound of any one of formulas {I-A, I-B, I-C, I-D, I-E, I-F, I-G, or I-H} to facilitate the diagnosis, treatment, or ameliorating of a condition associated with cell proliferation disorders and related diseases. Related aspects include uses of the deuterated compounds to modulate the activity of viruses, or as anti-hyperlipidemia agents, and as agents to ameliorate or treat thrombosis and related cardiovascular and metabolic disorders.

BRIEF DESCRIPTION OF THE DRAWINGS

Statement Concerning Drawings Executed in Color

The patent or application file contains at least one drawing executed in color. Copies of this patent or patent application with color drawing(s) will be provided by the Office upon request and payment of the necessary fee.

Figure 1:
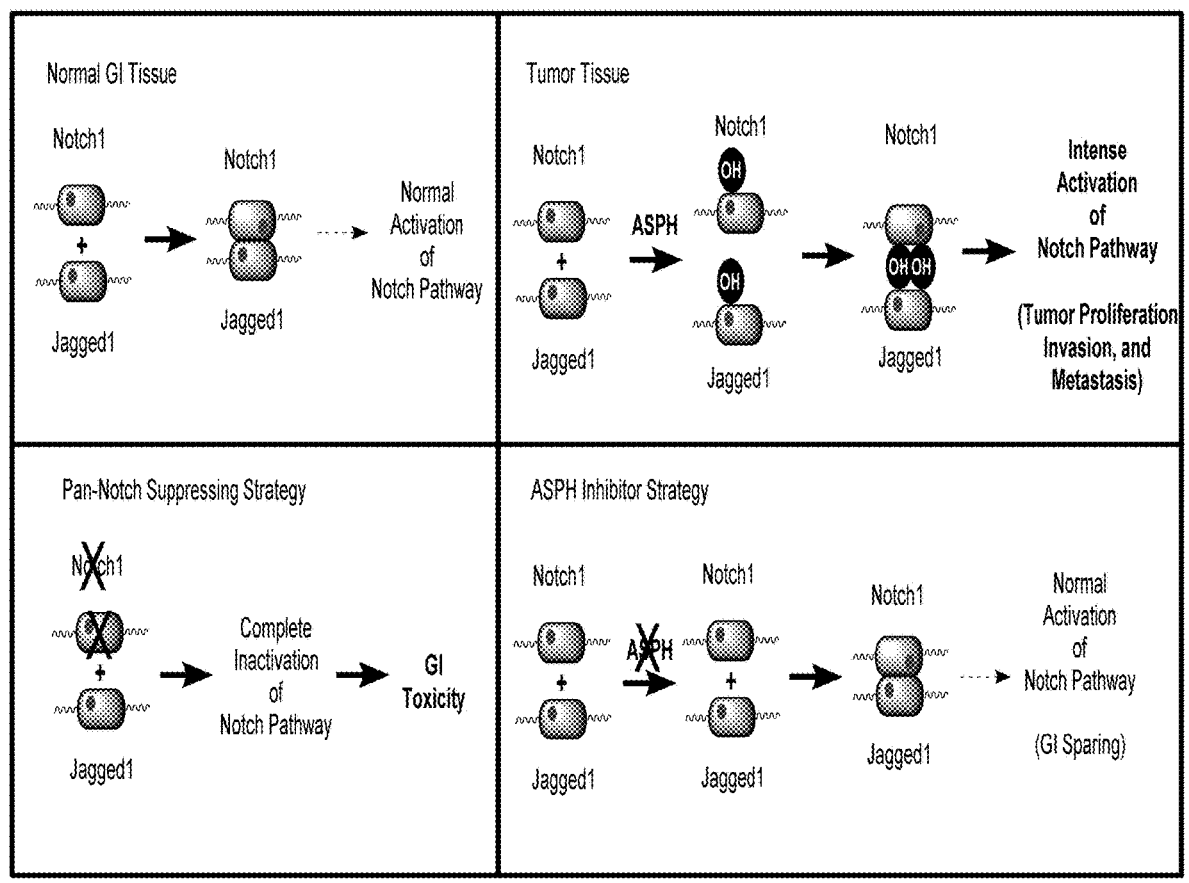

Statement Concerning Aspects of the Invention Understood by Reference to the Drawings The foregoing aspects and many of the attendant advantages of this invention will become more readily appreciated as the same become better understood by reference to the following detailed description, when taken in conjunction with the accompanying drawings, wherein:

FIG. 1 sets forth an illustration showing the Activation of Notch Signaling Pathway by ASPH.

Figures 1, 10:
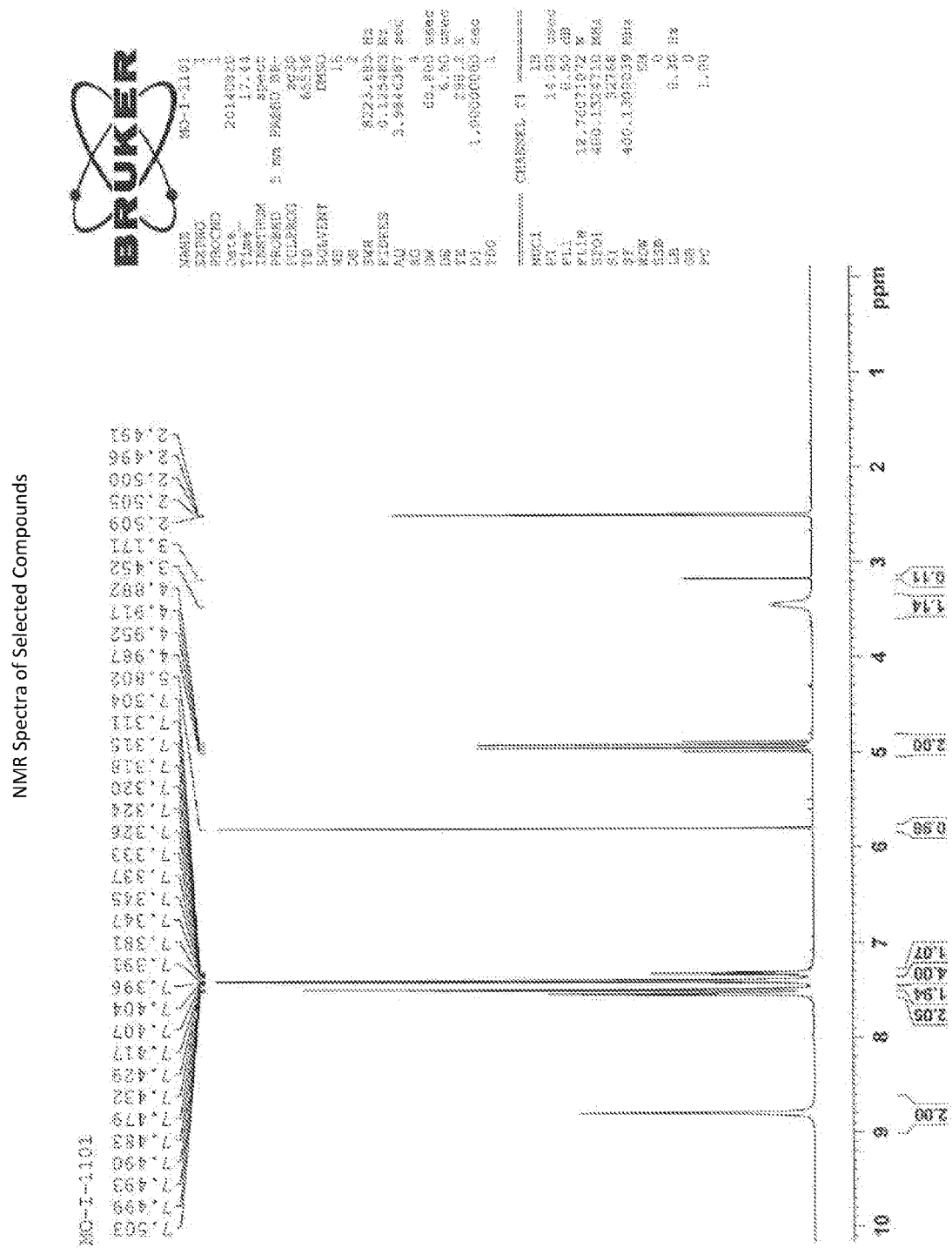
Figures 2, 10:
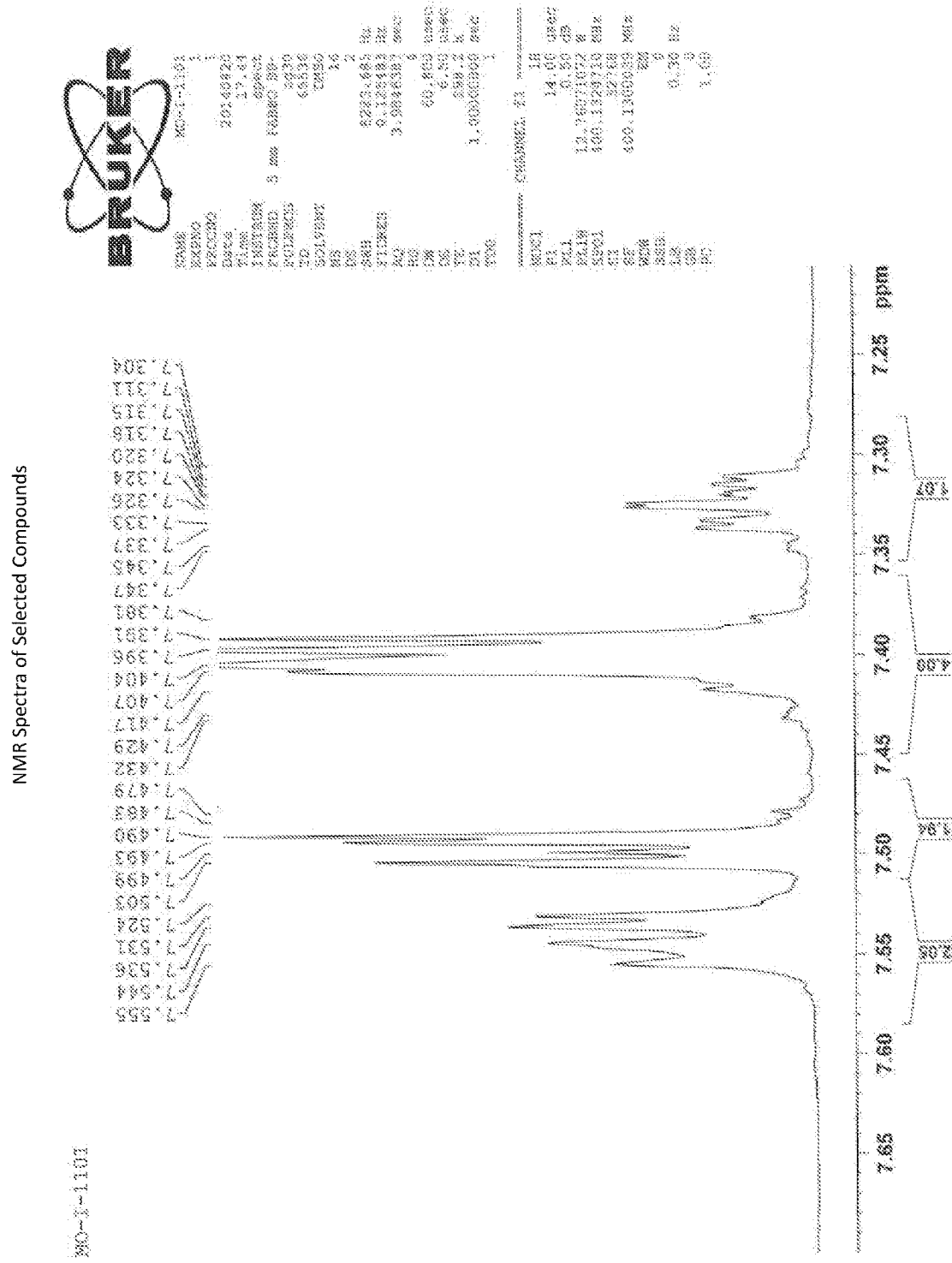

FIG. 2 (Panels A-H, plus a polypeptide domain key) sets forth an illustration showing experimentally confirmed and computationally predicted substrates of ASPH, including those found in the following types of proteins: A. Notch signaling pathway, B. Lipid receptors, C. Blood coagulation cascade proteins, D. Thrombospondins, E. Complement cascade proteins, F. FAT cadherin domain proteins, G. Bone associated proteins, and H. 7-transmembrane domain containing proteins.

Figures 3, 10:
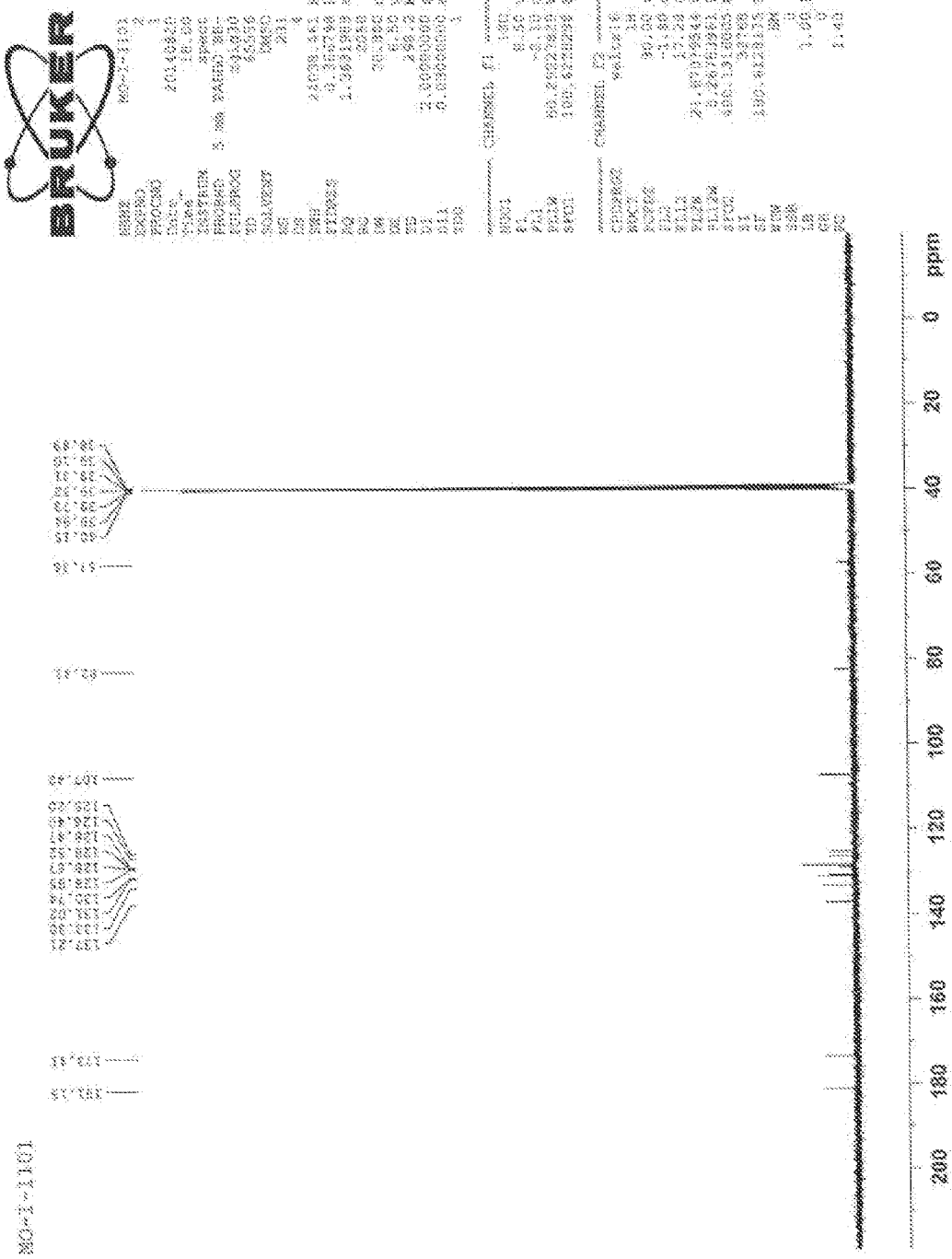
Figures 4, 10:
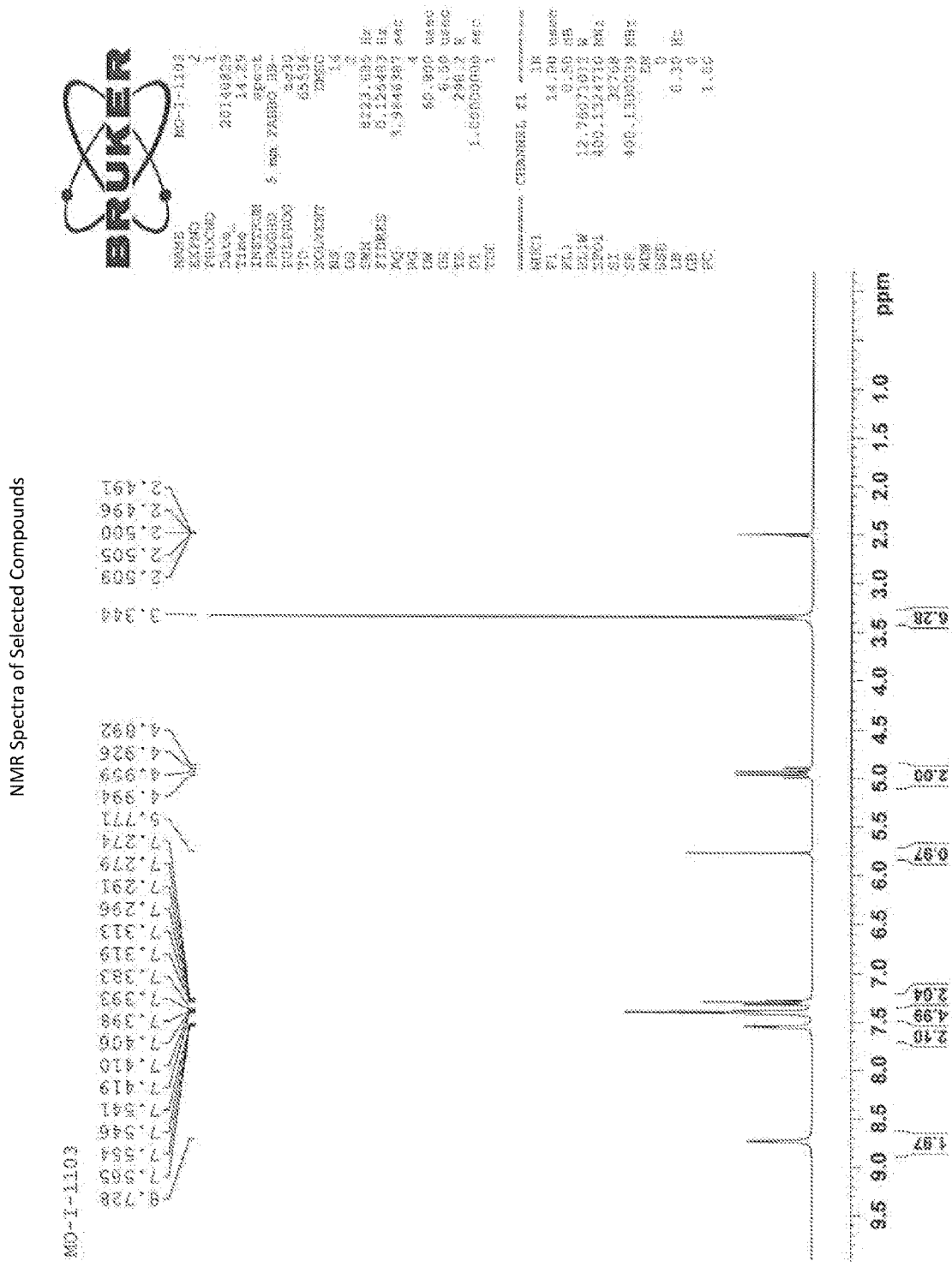

FIG. 3 (Panels A-G, plus a polypeptide domain key) sets forth an illustration showing experimentally confirmed and computationally predicted substrates of ASPH (continued), including those found in the following types of proteins: A. TGF-b containing proteins, B. Platelet associated proteins, C. Eye/retina associated proteins, D. Mammary cancer metastasis proteins, E. Slit proteins, F. Miscellaneous proteins, and G. *Drosophila* homologues.

Figure 4:
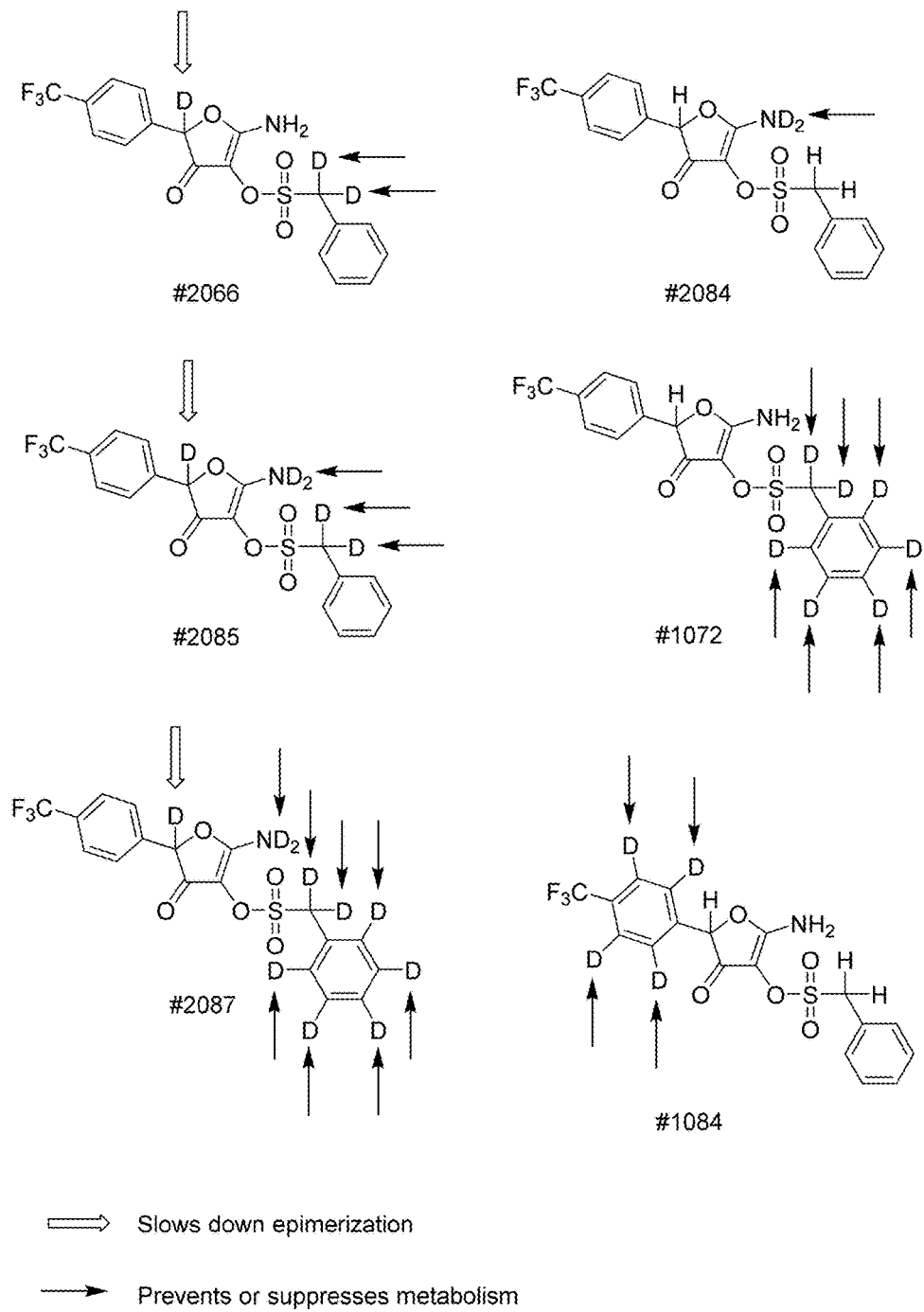

FIG. 4 sets forth an illustration demonstrating the mechanism of action of tetronimide modulating compounds. Deuterium can stabilize a stereo-center, or can be used to slow down or suppress metabolism. Compound #2066 has a deuterium at the stereocenter, as well as two deuteriums at the benzylic position adjacent to the "C" ring. Compound #2084 has two deuteriums on the amino of the tetronimide ring. Compound #2085 has a deuterium at the stereocenter, two deuteriums at the benzylic position adjacent to the "C" ring, and two deuteriums on the amino of the tetronimide ring. Compound #1072 has two deuteriums at the benzylic position adjacent to the "C" ring, and the "C" ring is perdeuterated. Compound #2087 is deuterated at the stereocenter, the benzylic position adjacent to the "C" ring, two deuteriums on the amine of the tetronimide ring, and the "C" ring is perdeuterated. Compound #1084 has the "A" ring perdeuterated.

Figures 5, 10:
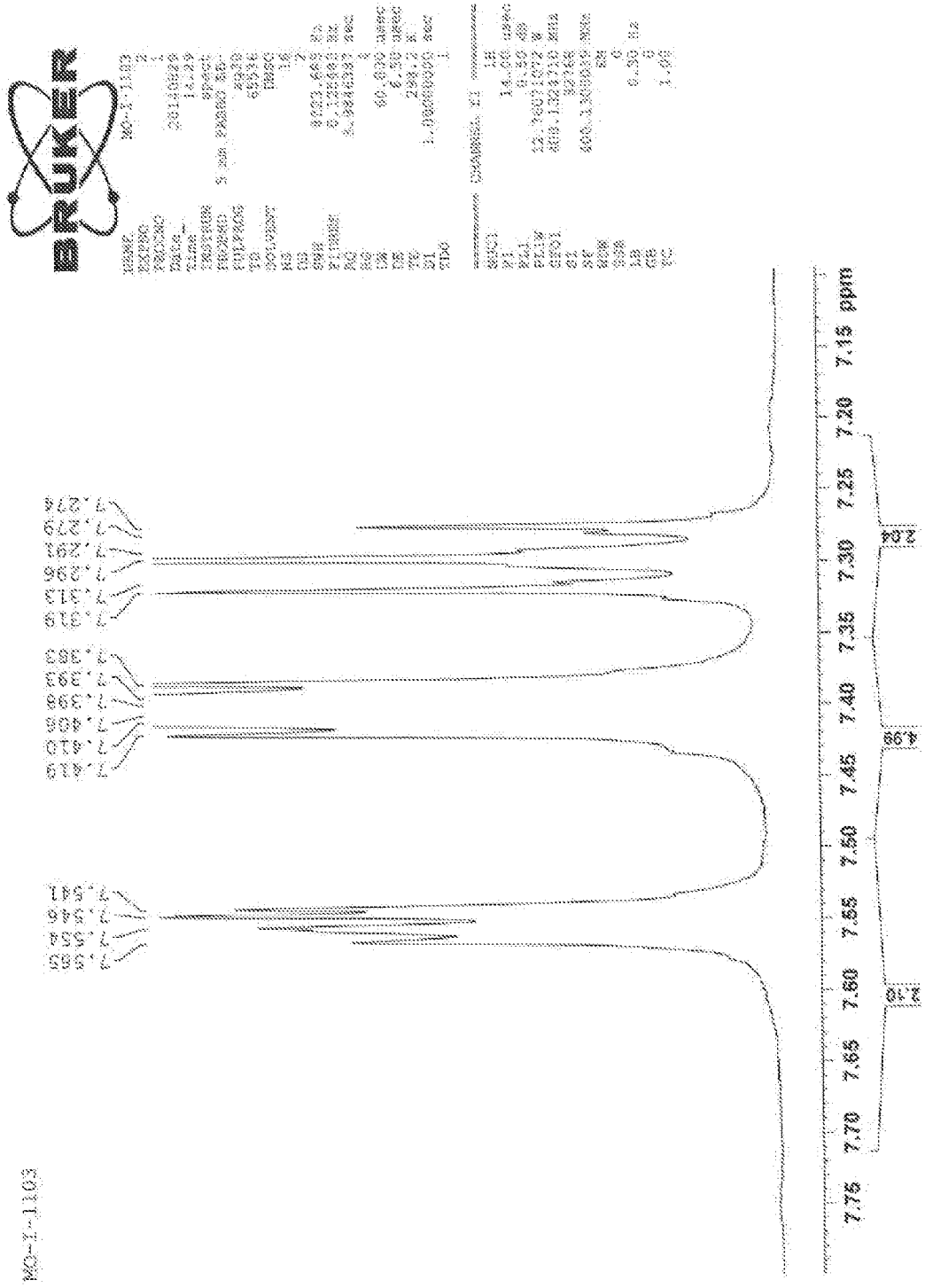

FIG. 5 illustrates the synthesis of non-deuterated ASPH tetronimide modulator compounds in Scheme 1. Scheme 2 illustrates the synthesis of compounds of the formulas {I-A} and {I-B}. Scheme 3 illustrates the synthesis of compounds of the formula {I-D}. Scheme 4 illustrates the synthesis of compounds of the formula {I-E}.

Figures 6, 10:
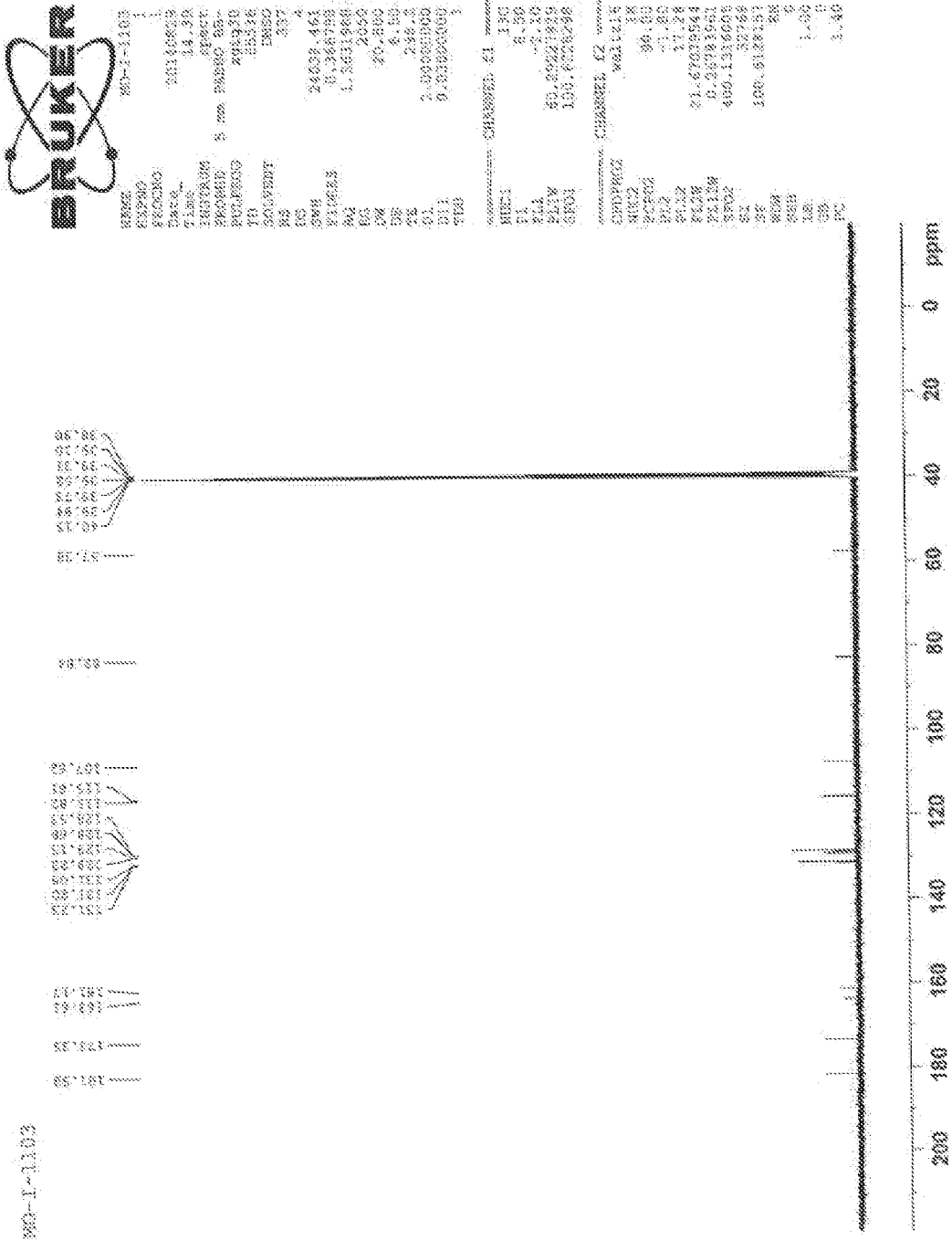

FIG. 6 illustrates an alternate synthesis of compounds of the formula {I-D}. Scheme 6 illustrates the synthesis of perdeuterated phenylmethanesulfonyl chloride. Scheme 7 illustrates the synthesis of compounds of the formula {I-F}.

Figures 7, 10:
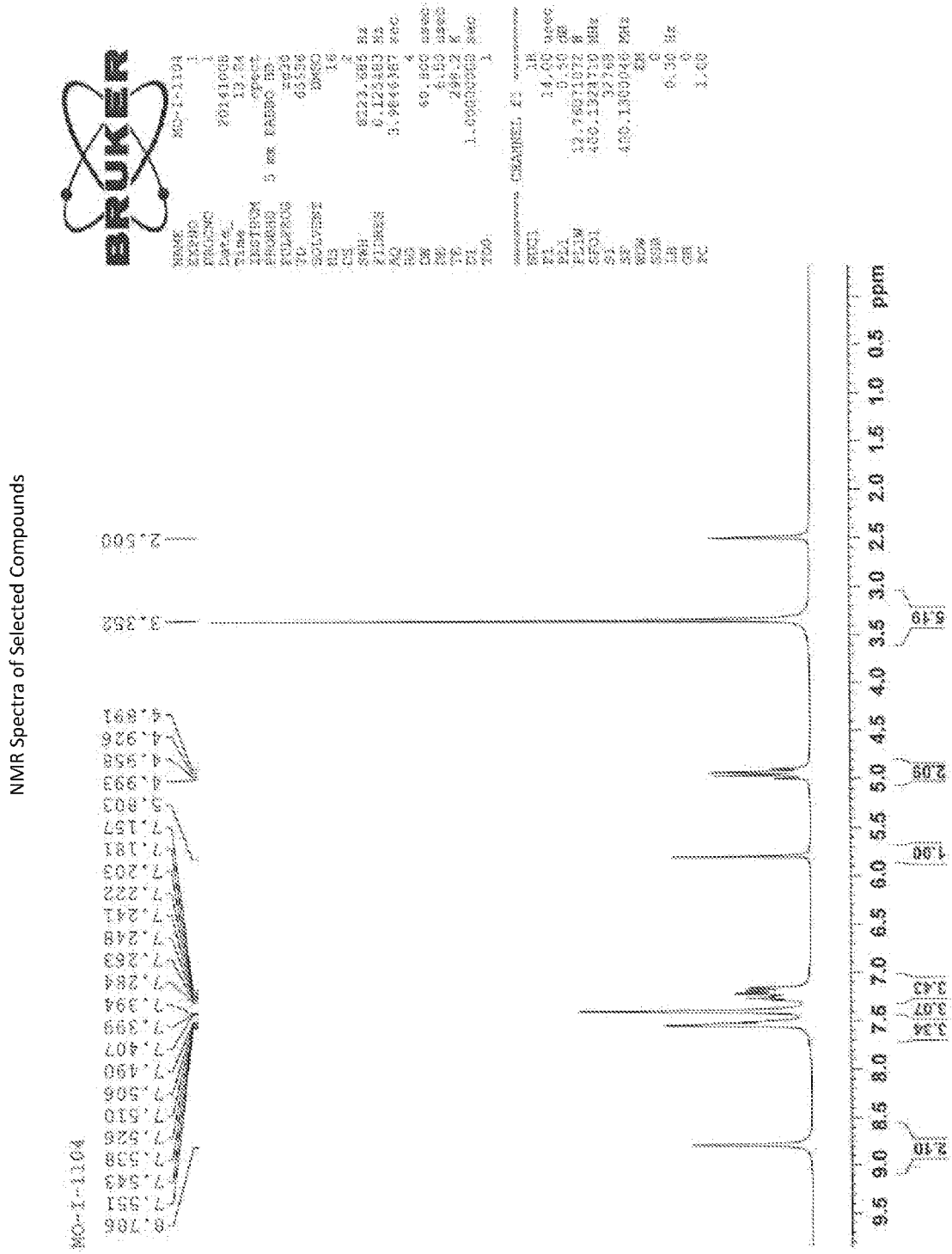

FIG. 7 illustrates the synthesis of compounds of the formula {I-G} according to Scheme 8. Scheme 9 illustrates the synthesis of compounds of the formula {I-G}. Scheme 10 illustrates the synthesis of compounds of the formula {I-H}.

Figures 8, 10:
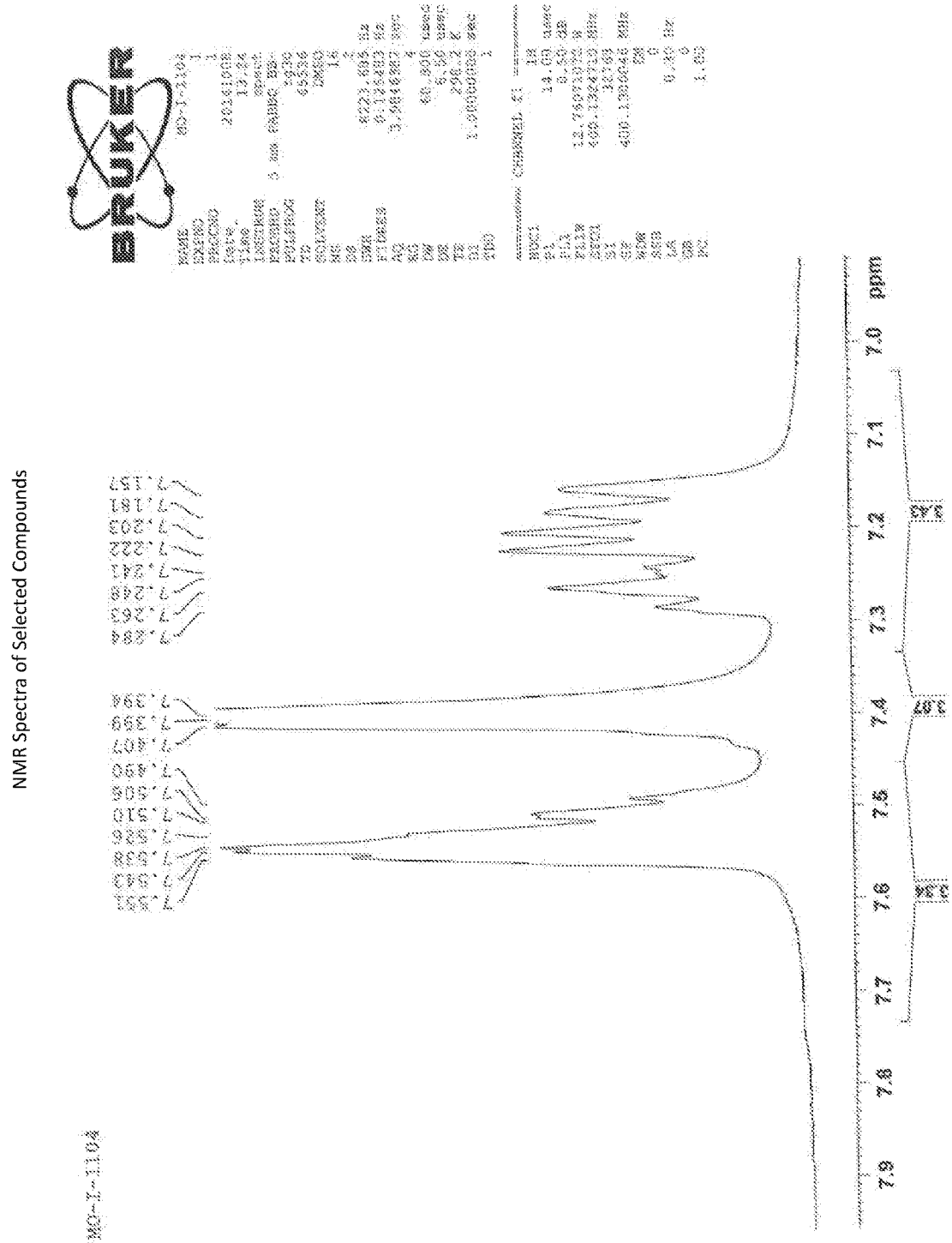
Figures 9, 10:
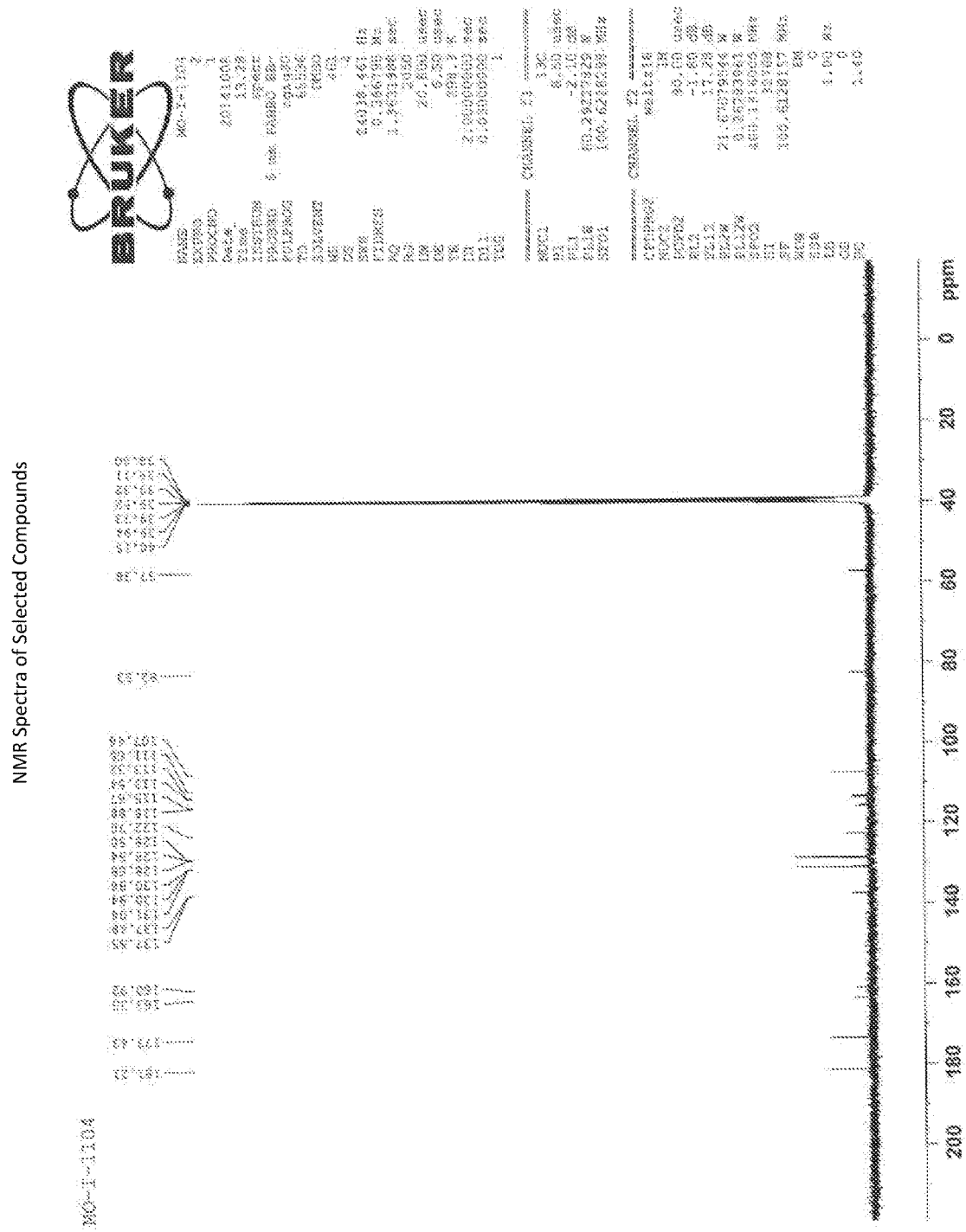
Figure 10:
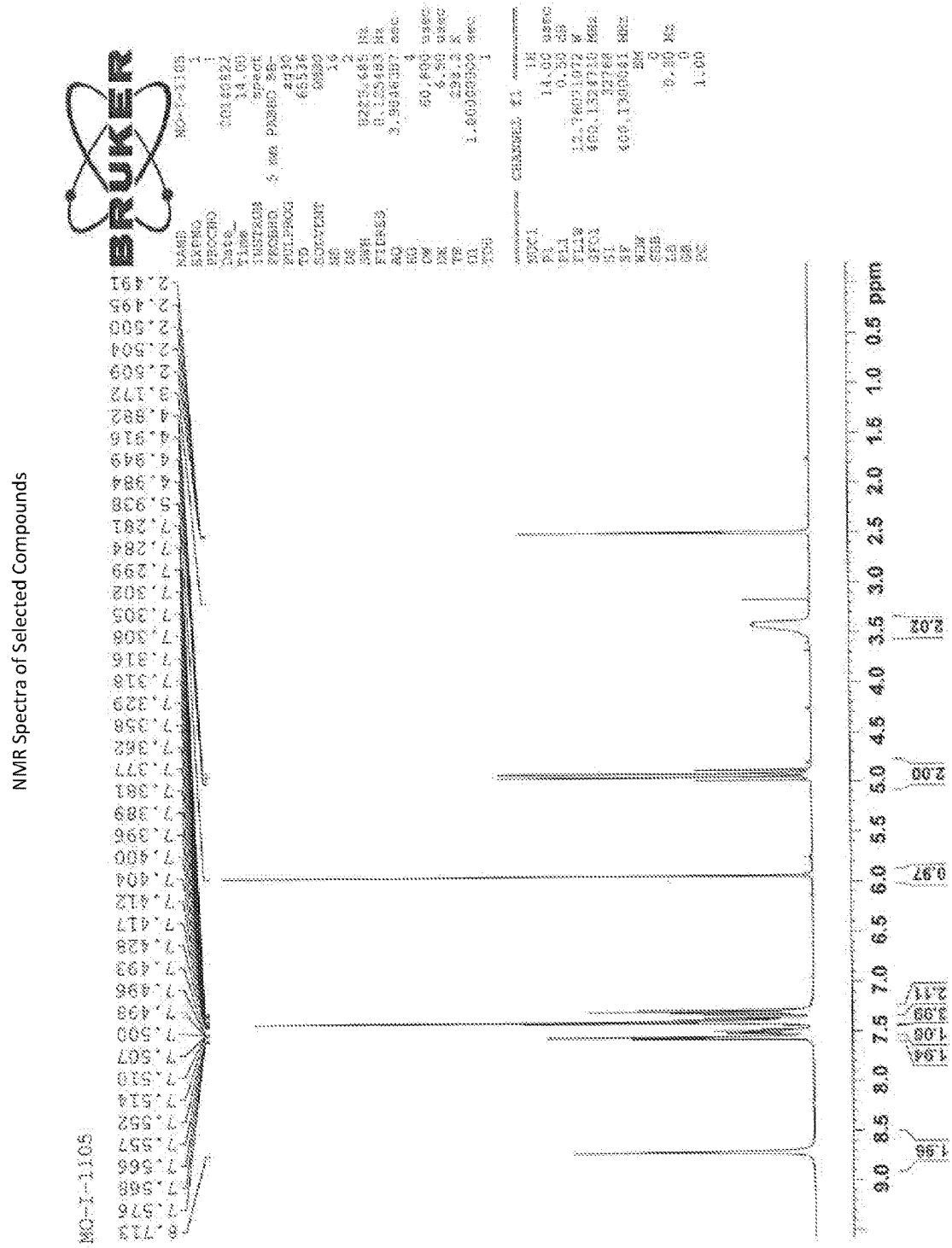
Figures 10, 11:
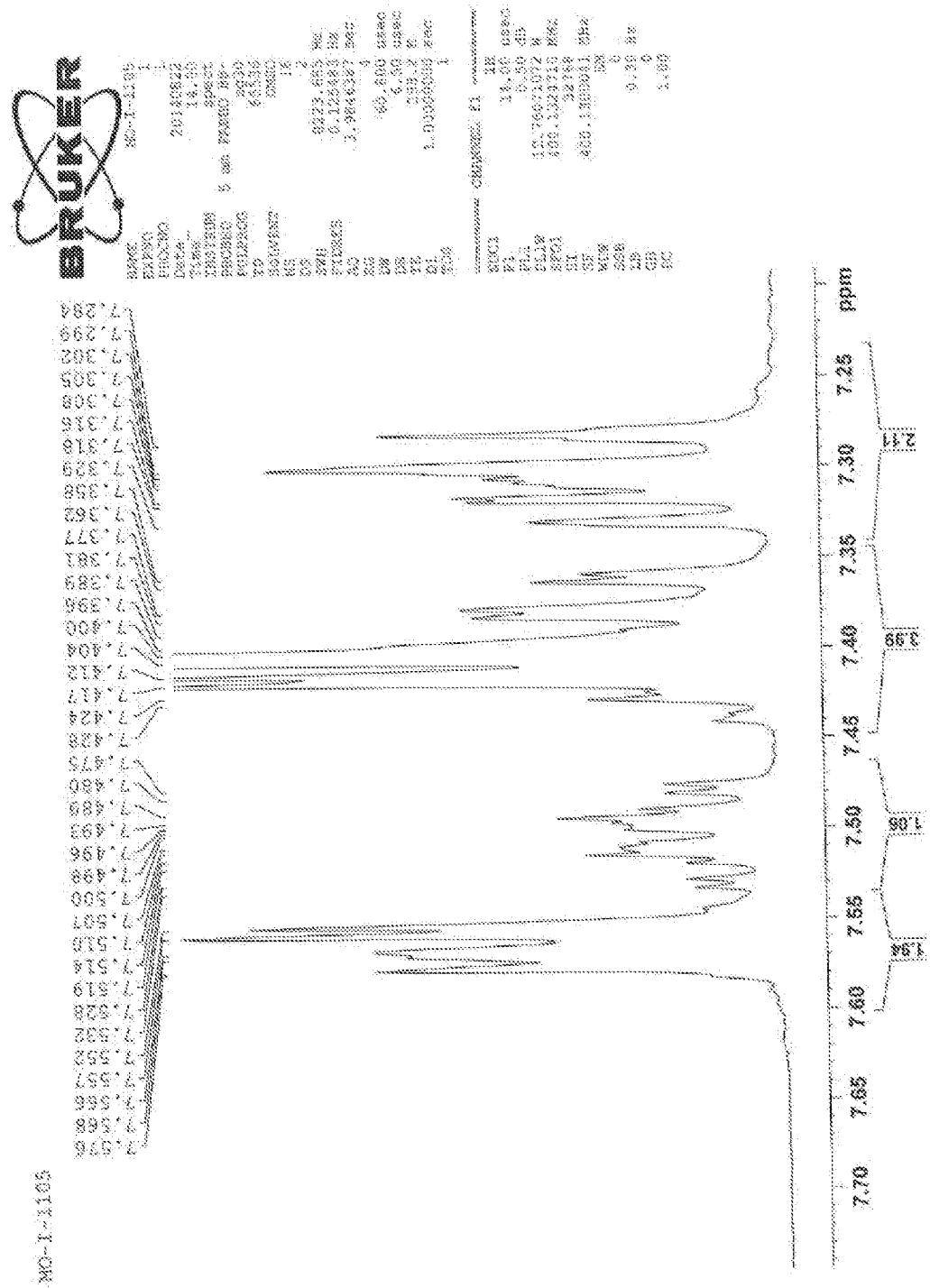
Figures 10, 11, 12:
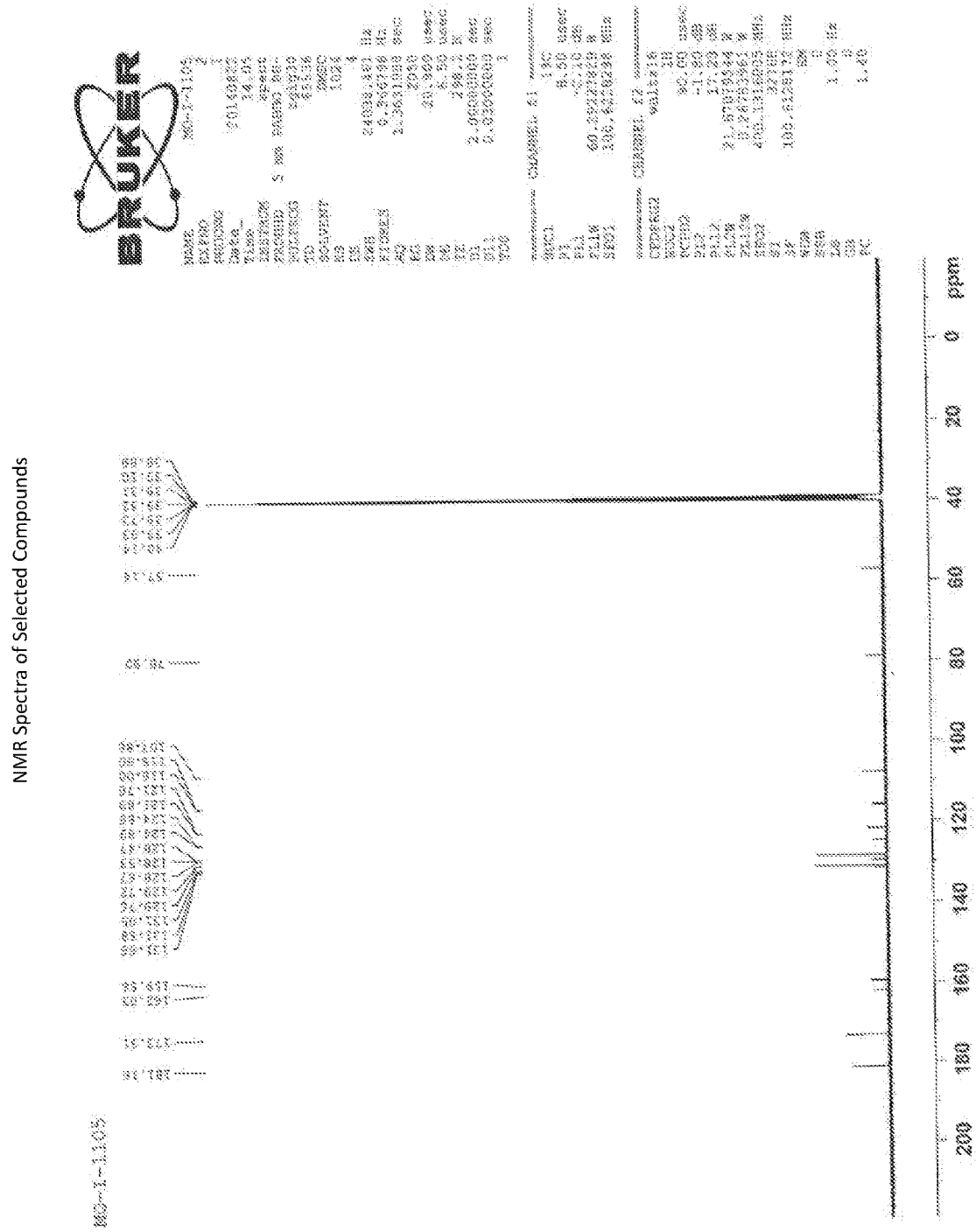
Figures 10, 11, 12, 13:
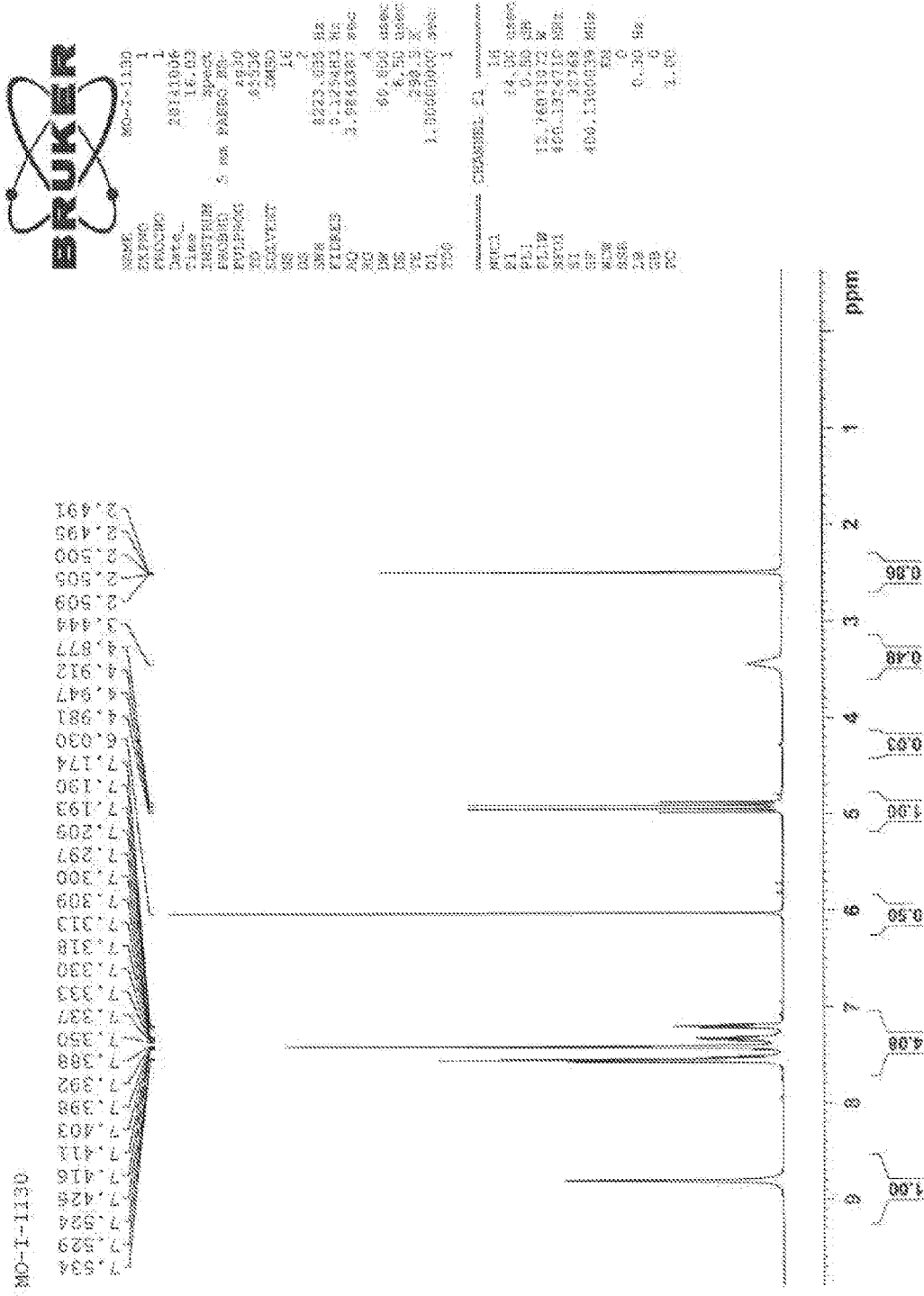
Figures 10, 11, 12, 13, 14:
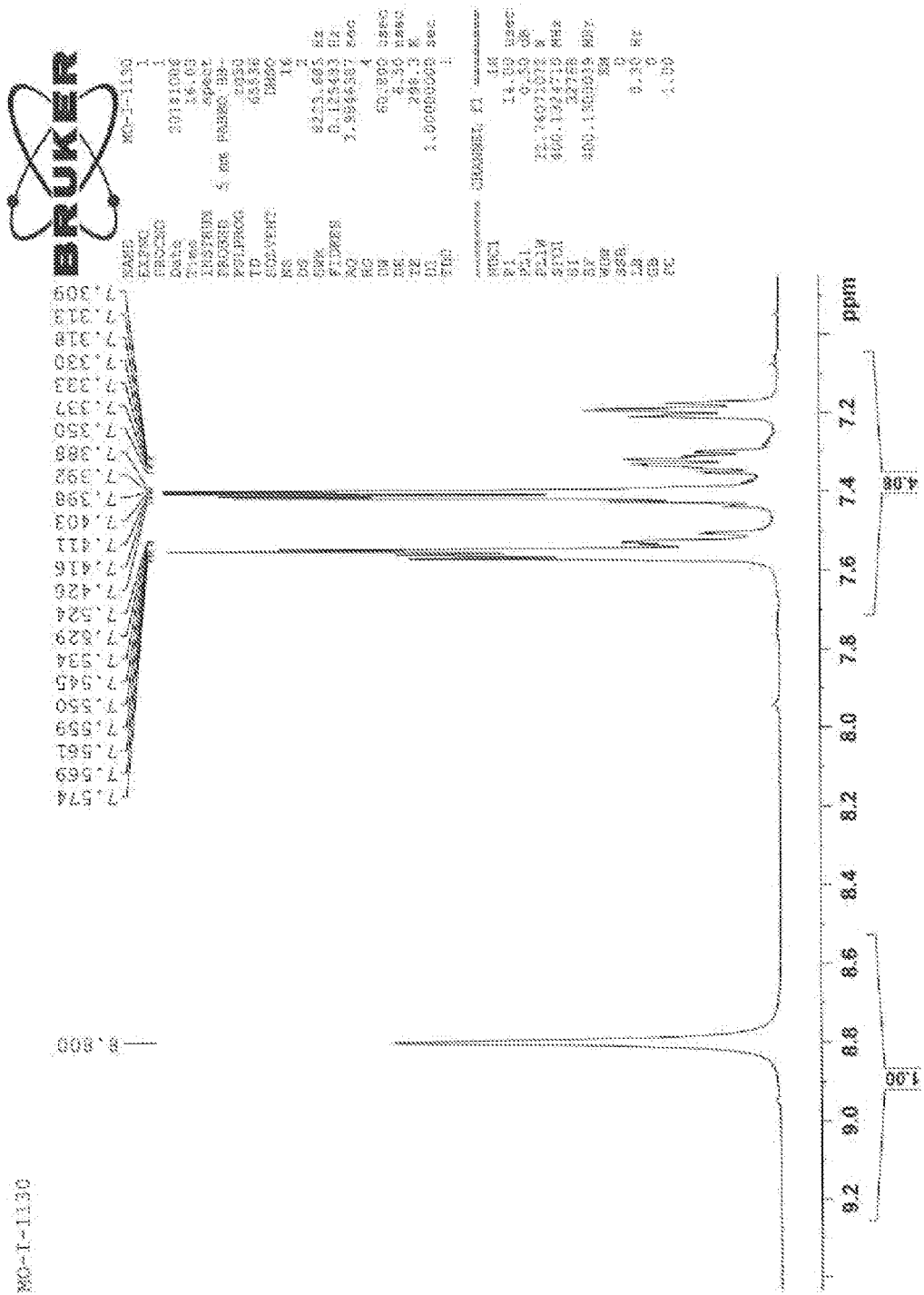
Figures 10, 11, 12, 13, 14, 15:
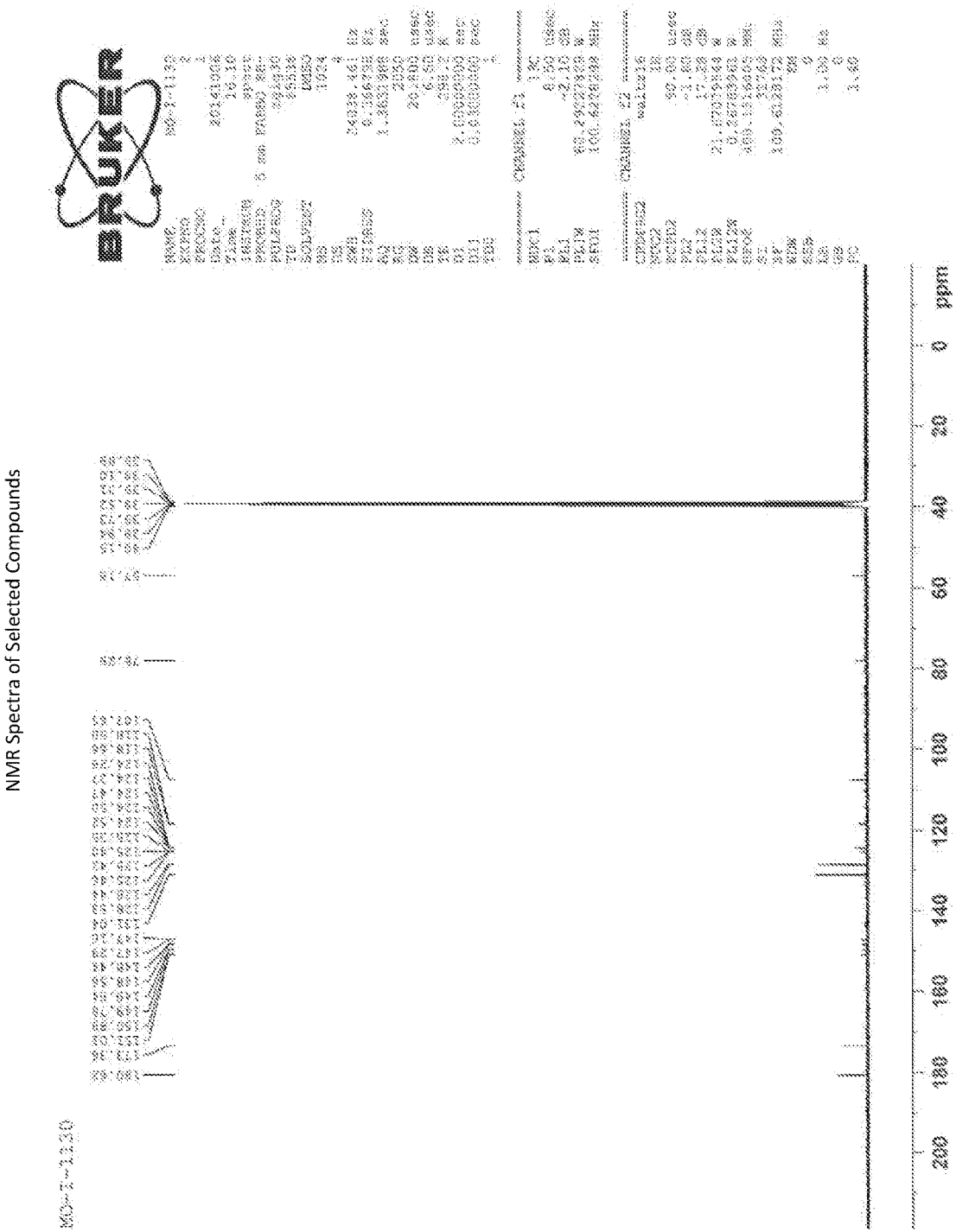
Figures 10, 11, 12, 13, 14, 15, 16:
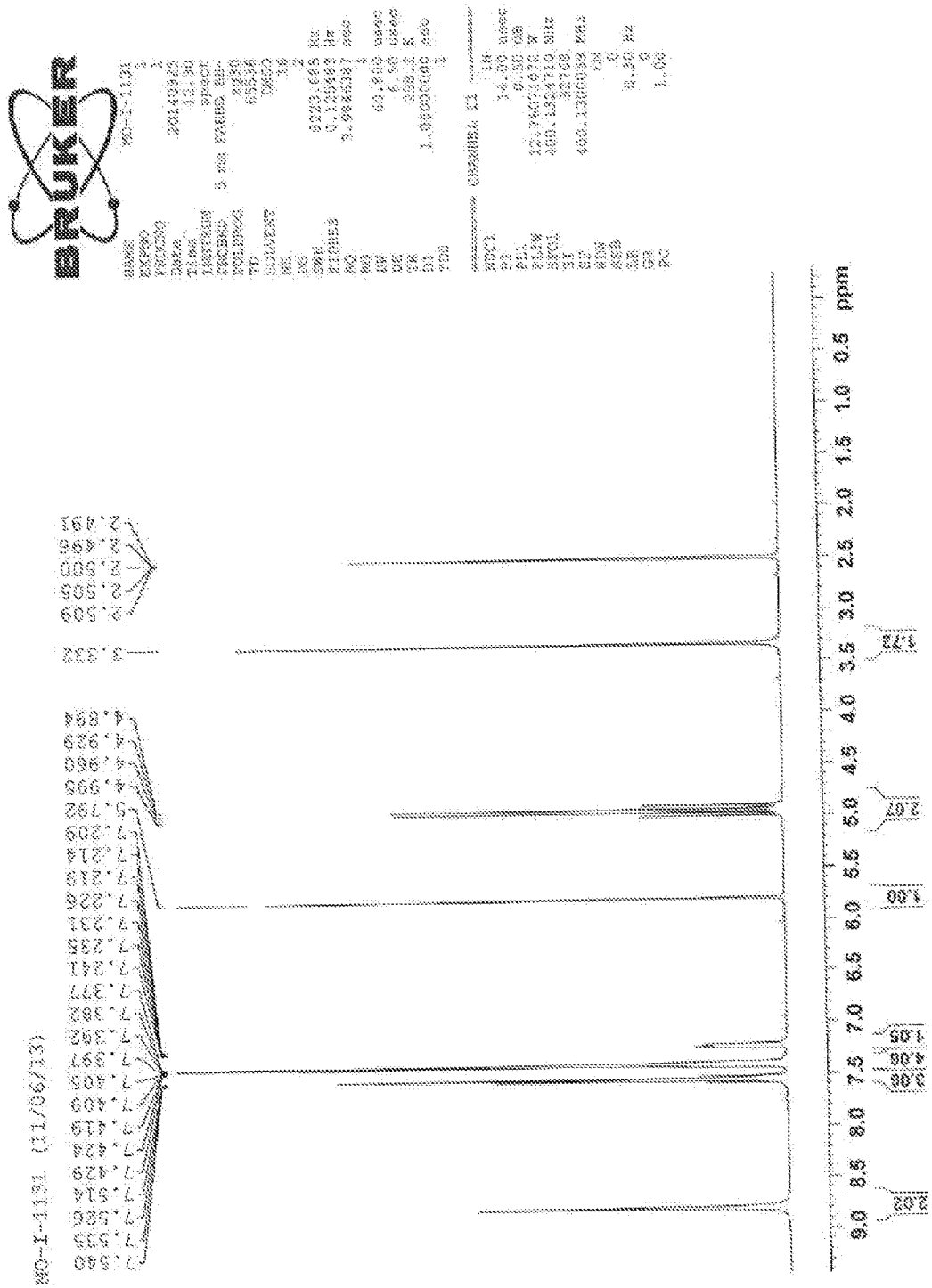
Figures 10, 11, 12, 13, 14, 15, 16, 17:
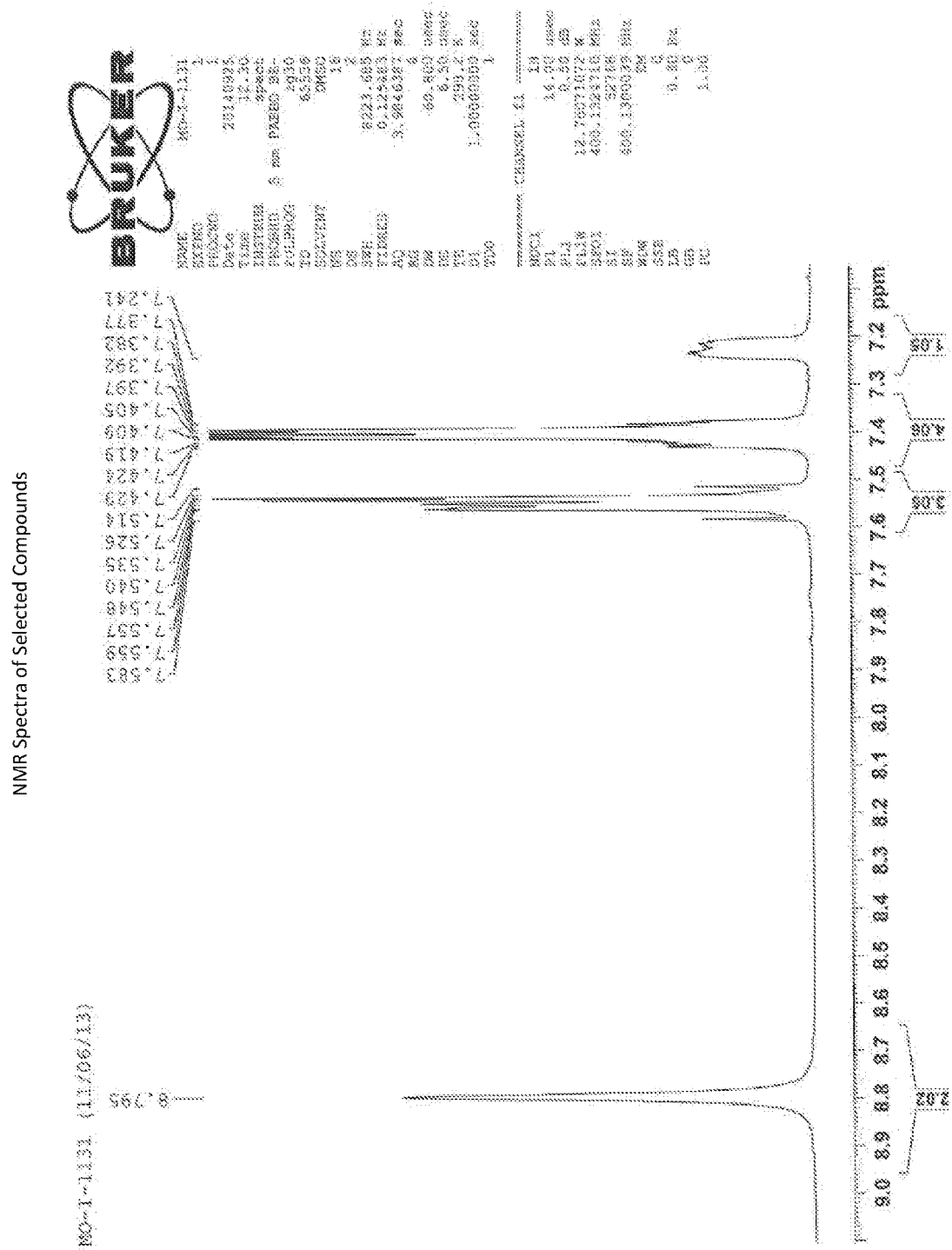
Figures 10, 11, 12, 13, 14, 15, 16, 17, 18:
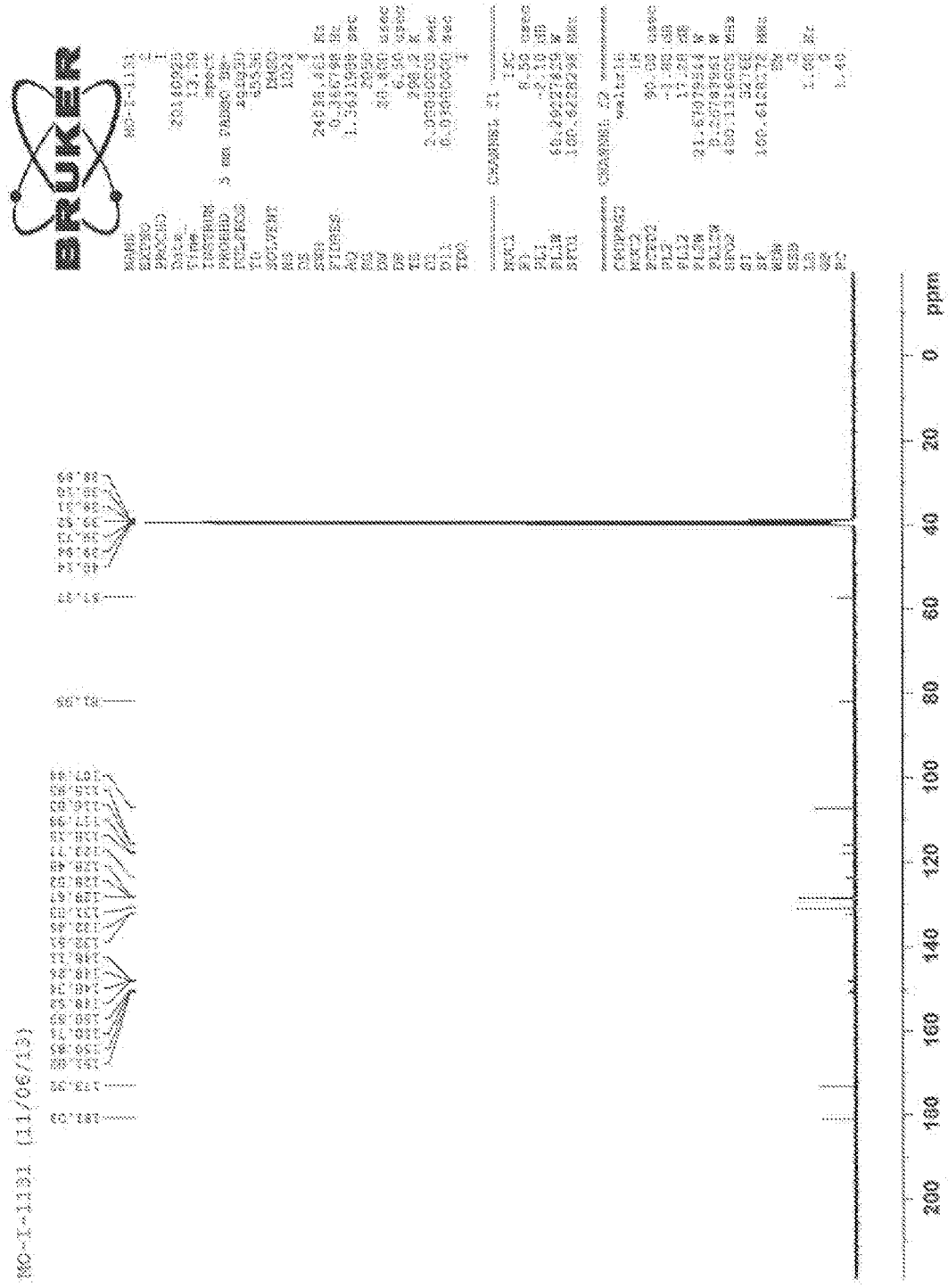
Figures 10, 11, 12, 13, 14, 15, 16, 17, 18, 19:
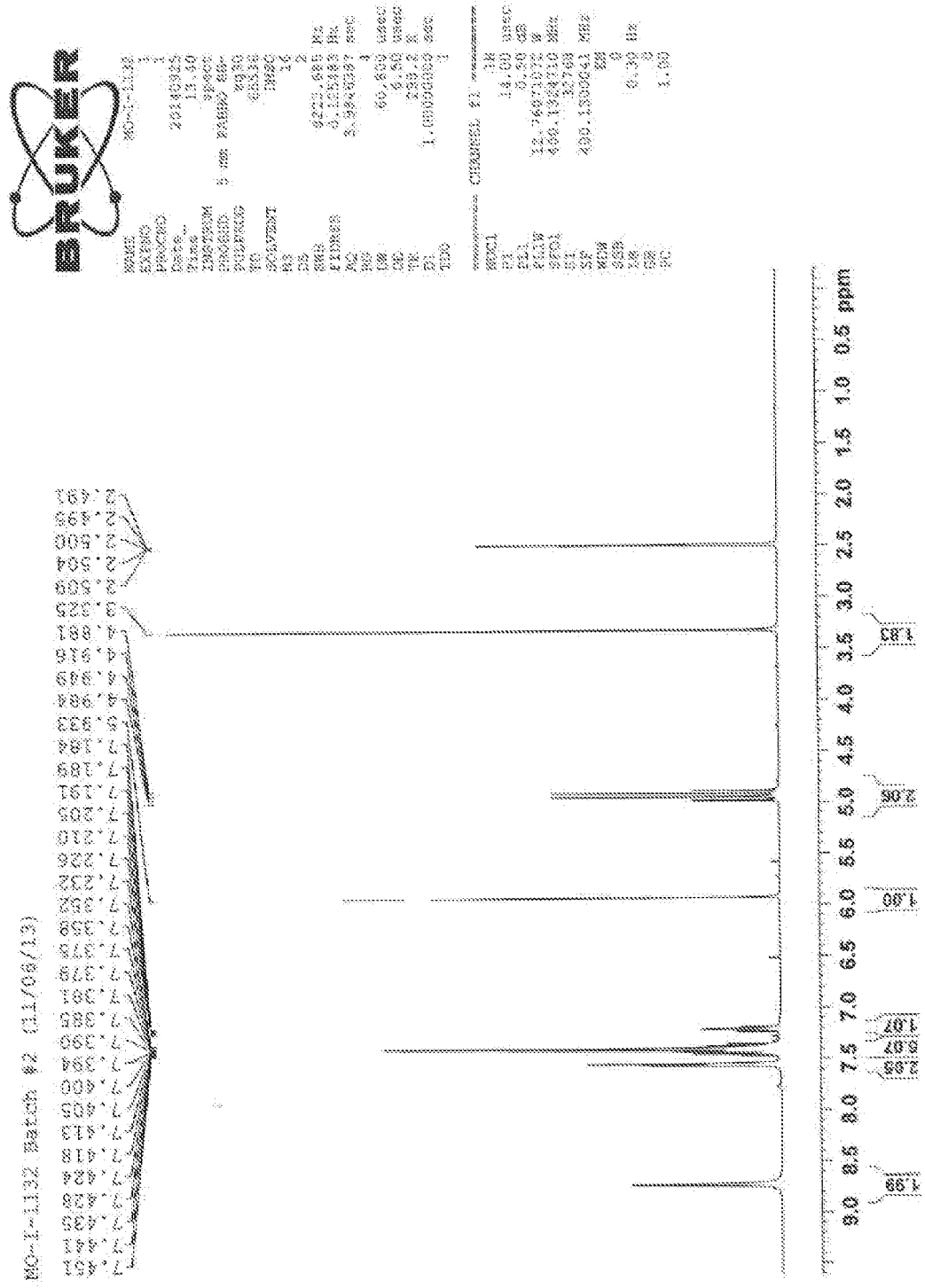
Figures 10, 11, 12, 13, 14, 15, 16, 17, 18, 19, 20:
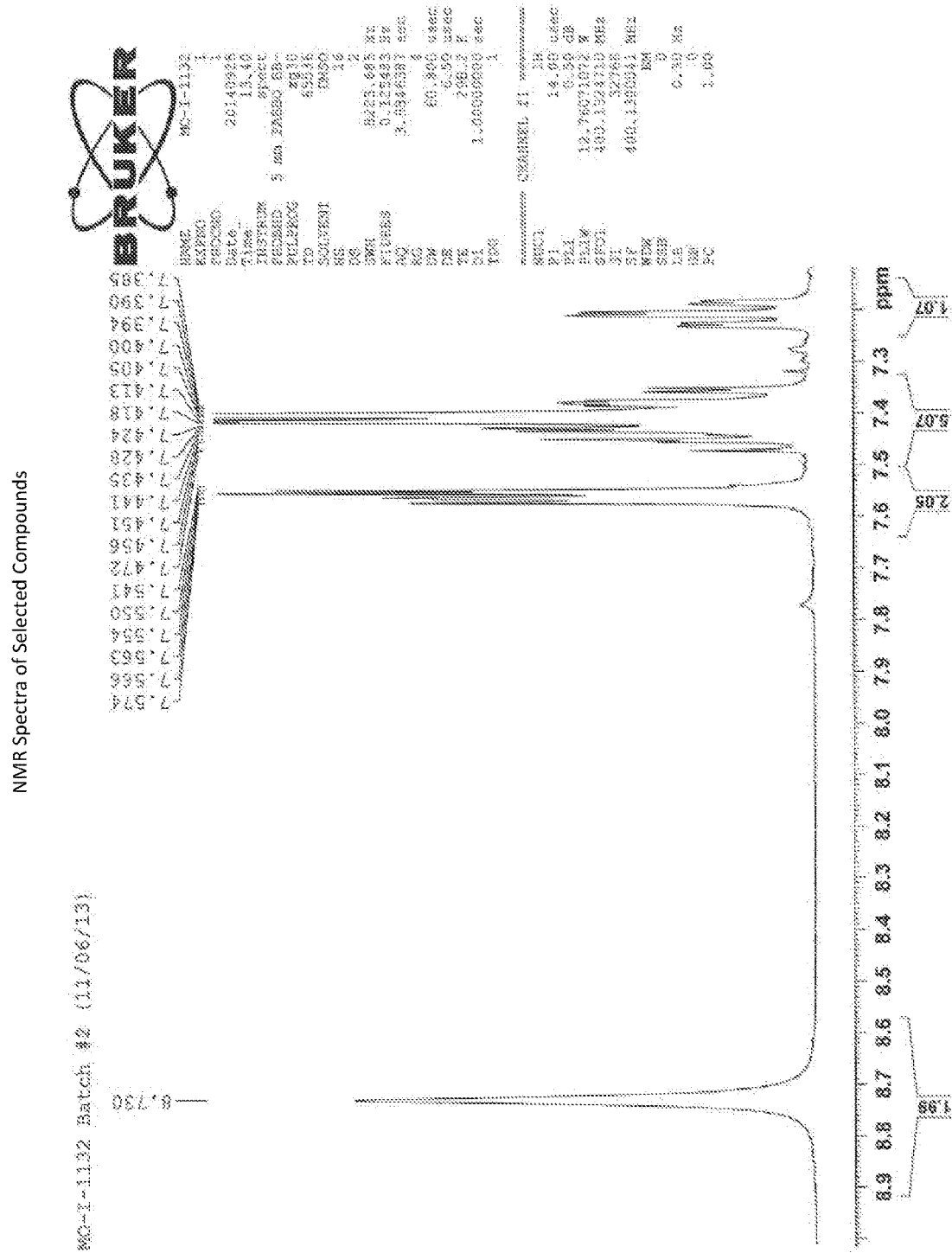
Figures 10, 11, 12, 13, 14, 15, 16, 17, 18, 19, 20, 21:
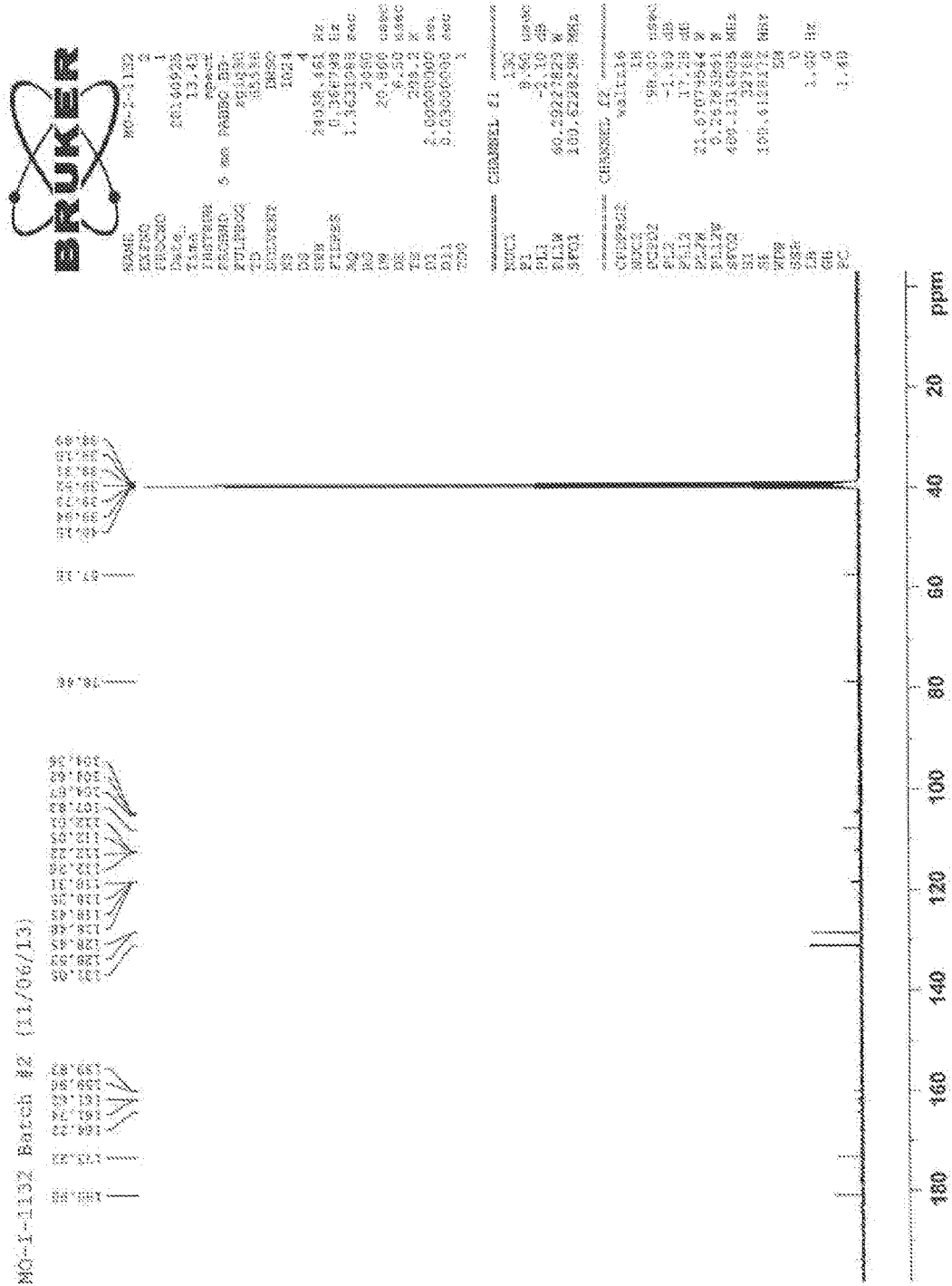
Figures 10, 11, 12, 13, 14, 15, 16, 17, 18, 19, 20, 21, 22:
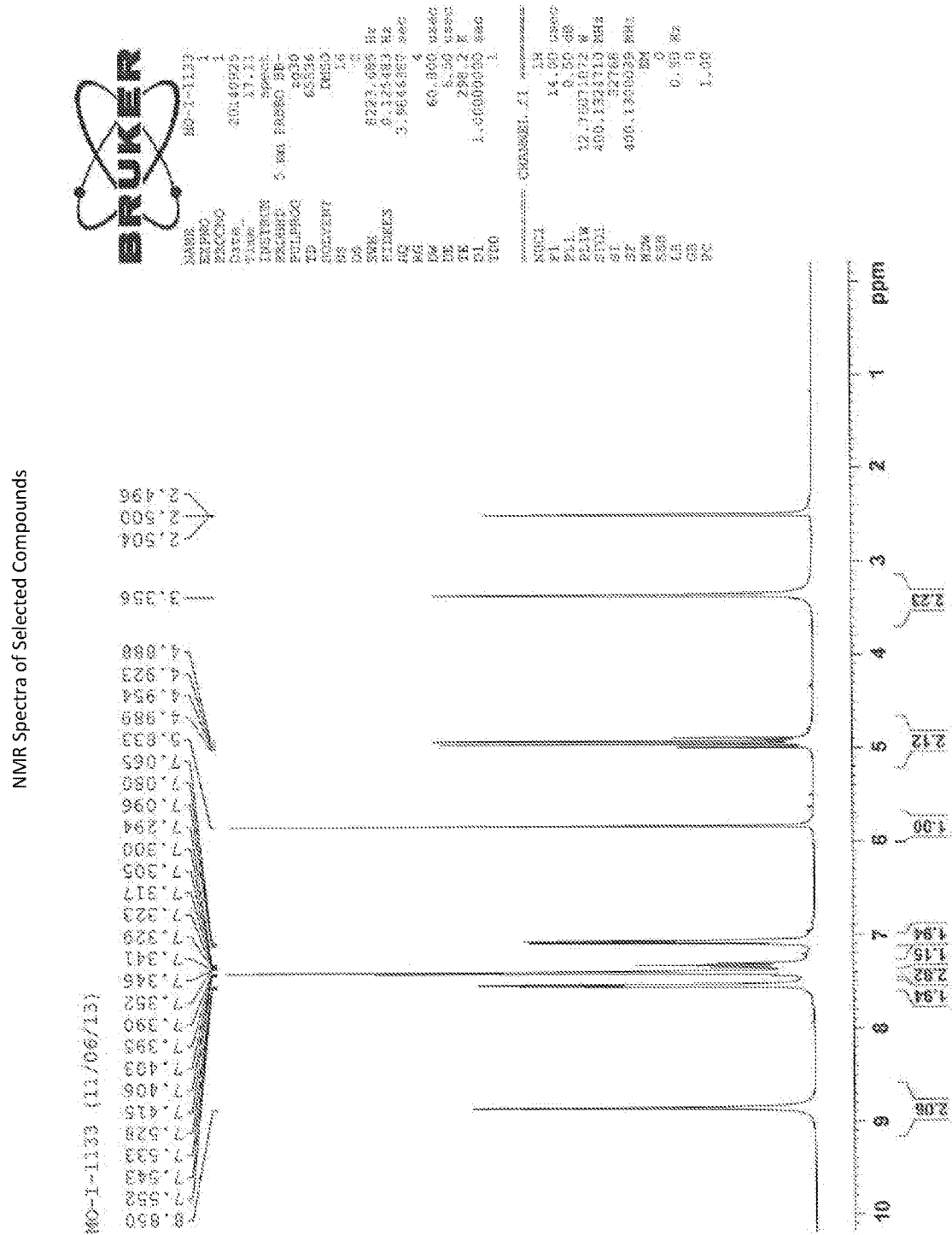
Figures 10, 11, 12, 13, 14, 15, 16, 17, 18, 19, 20, 21, 22, 23:
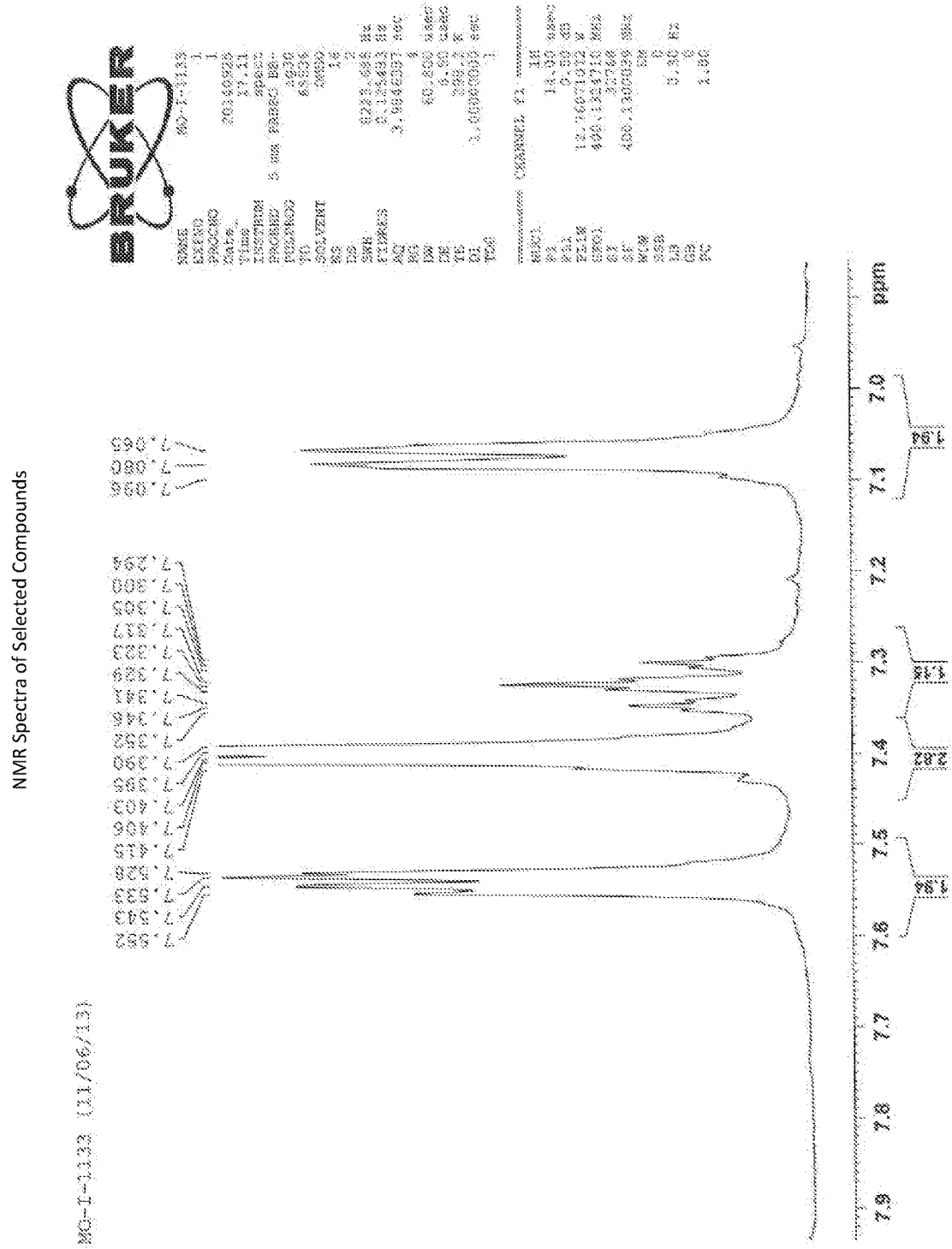
Figures 10, 11, 12, 13, 14, 15, 16, 17, 18, 19, 20, 21, 22, 23, 24:
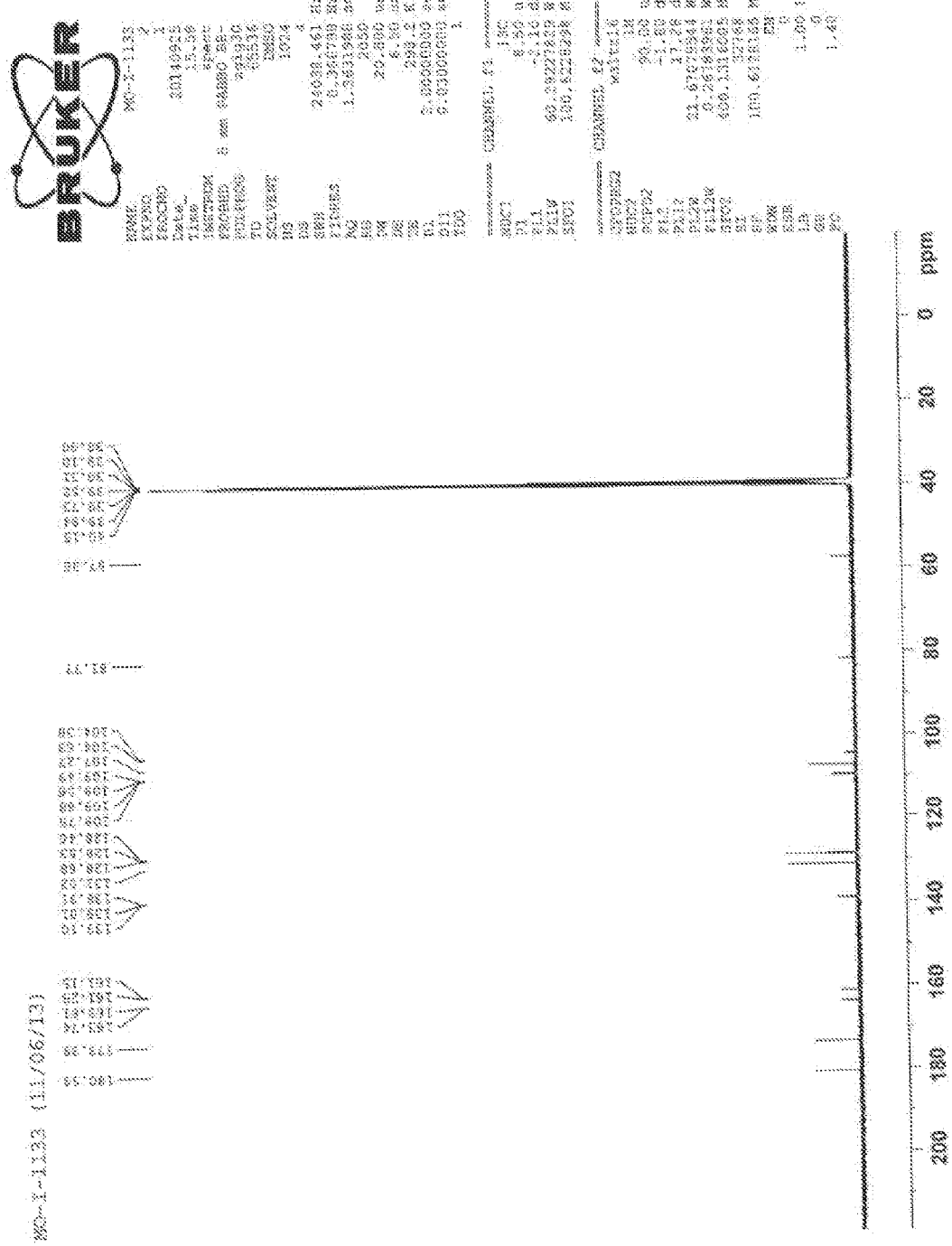
Figures 10, 11, 12, 13, 14, 15, 16, 17, 18, 19, 20, 21, 22, 23, 24, 25:
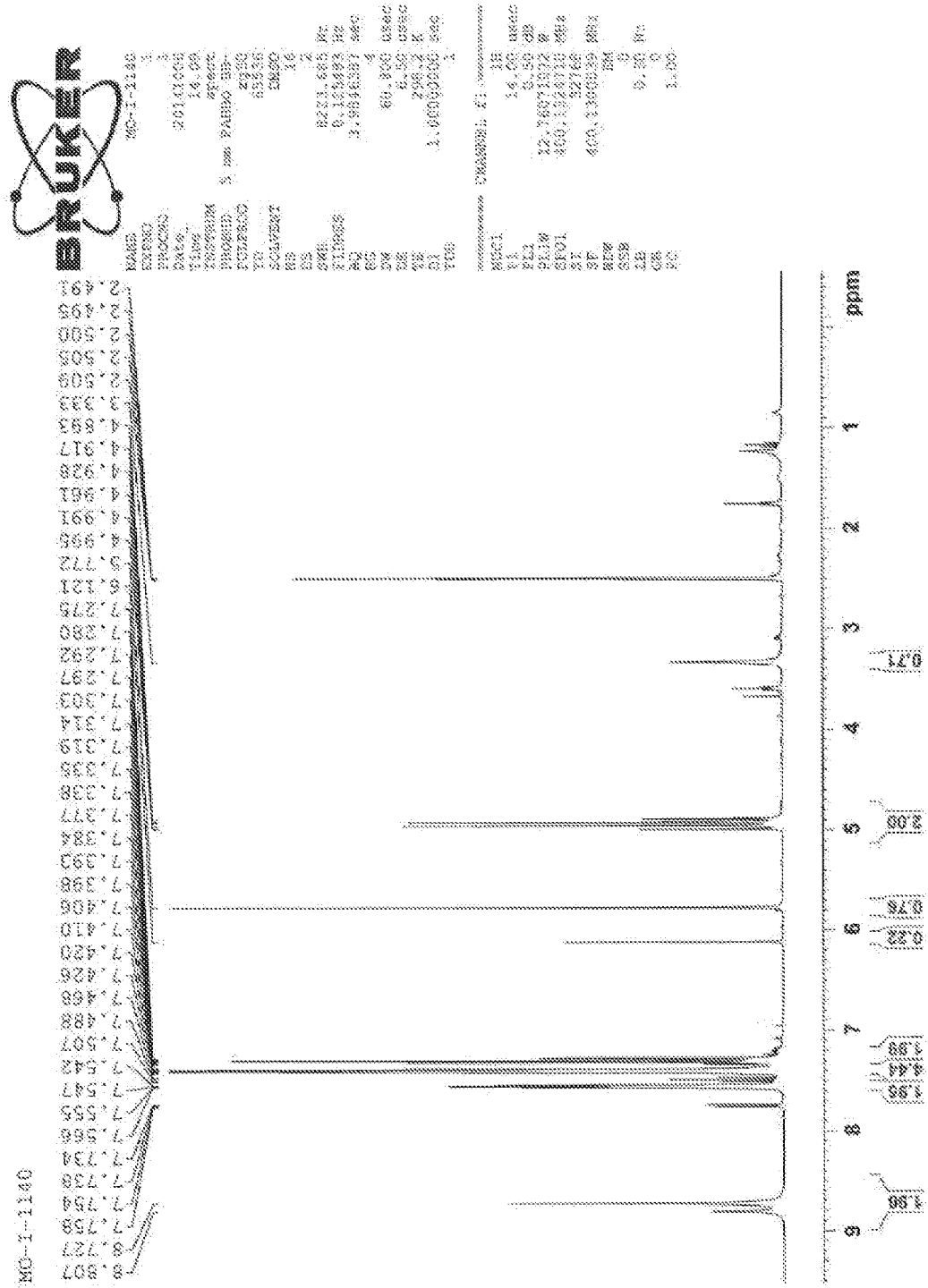
Figures 10, 11, 12, 13, 14, 15, 16, 17, 18, 19, 20, 21, 22, 23, 24, 25, 26:
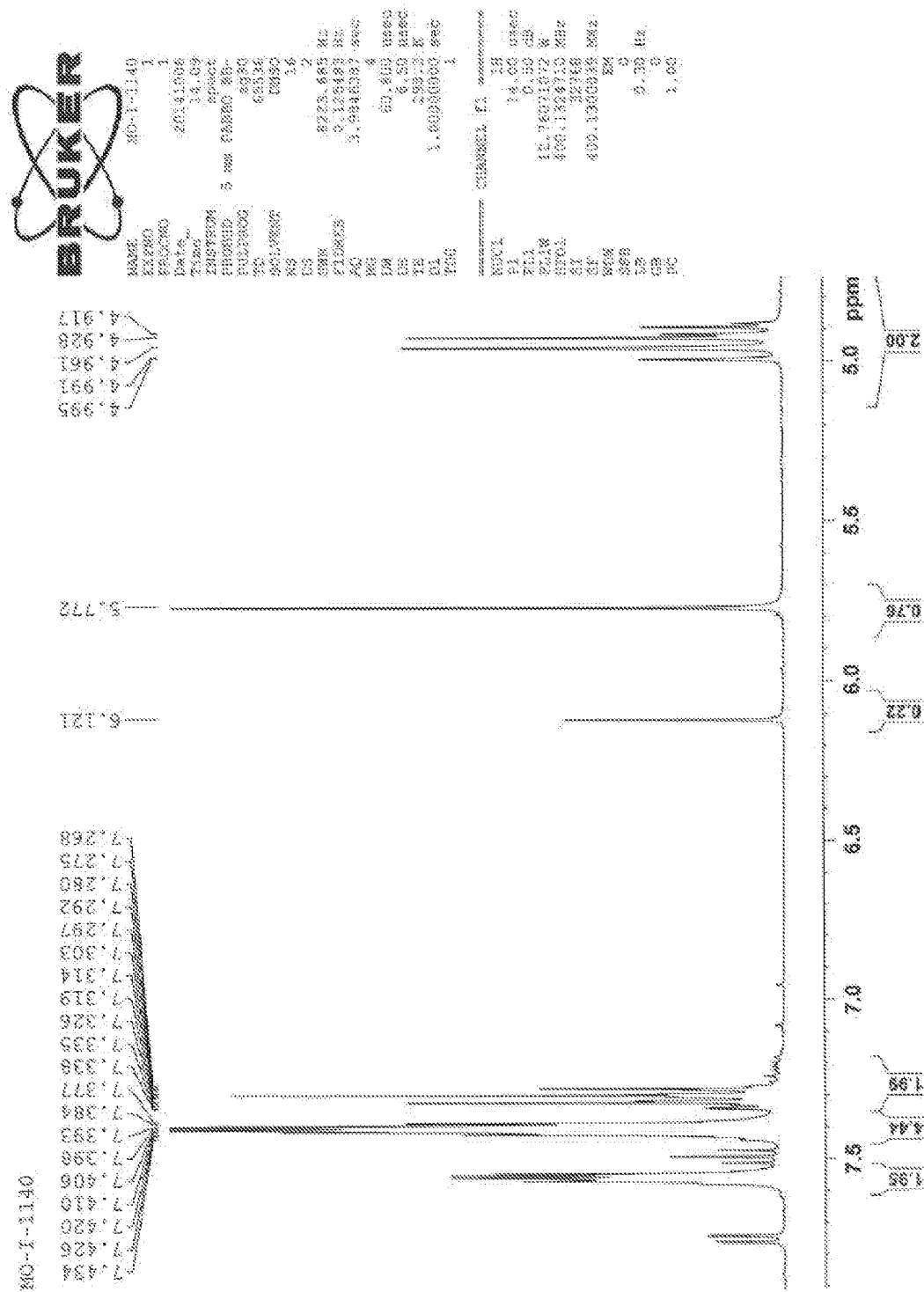
Figures 10, 11, 12, 13, 14, 15, 16, 17, 18, 19, 20, 21, 22, 23, 24, 25, 26, 27:
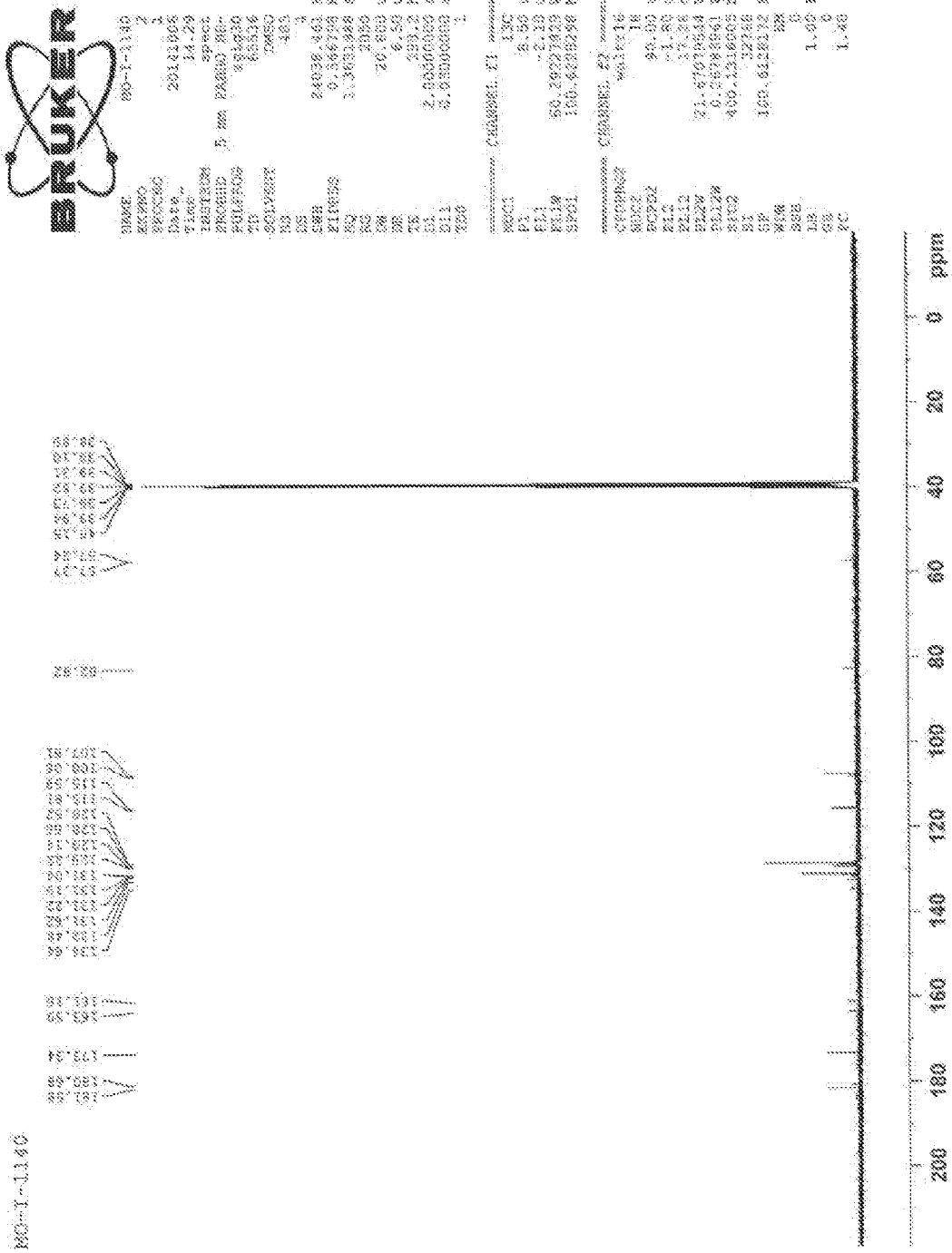
Figures 10, 11, 12, 13, 14, 15, 16, 17, 18, 19, 20, 21, 22, 23, 24, 25, 26, 27, 28:
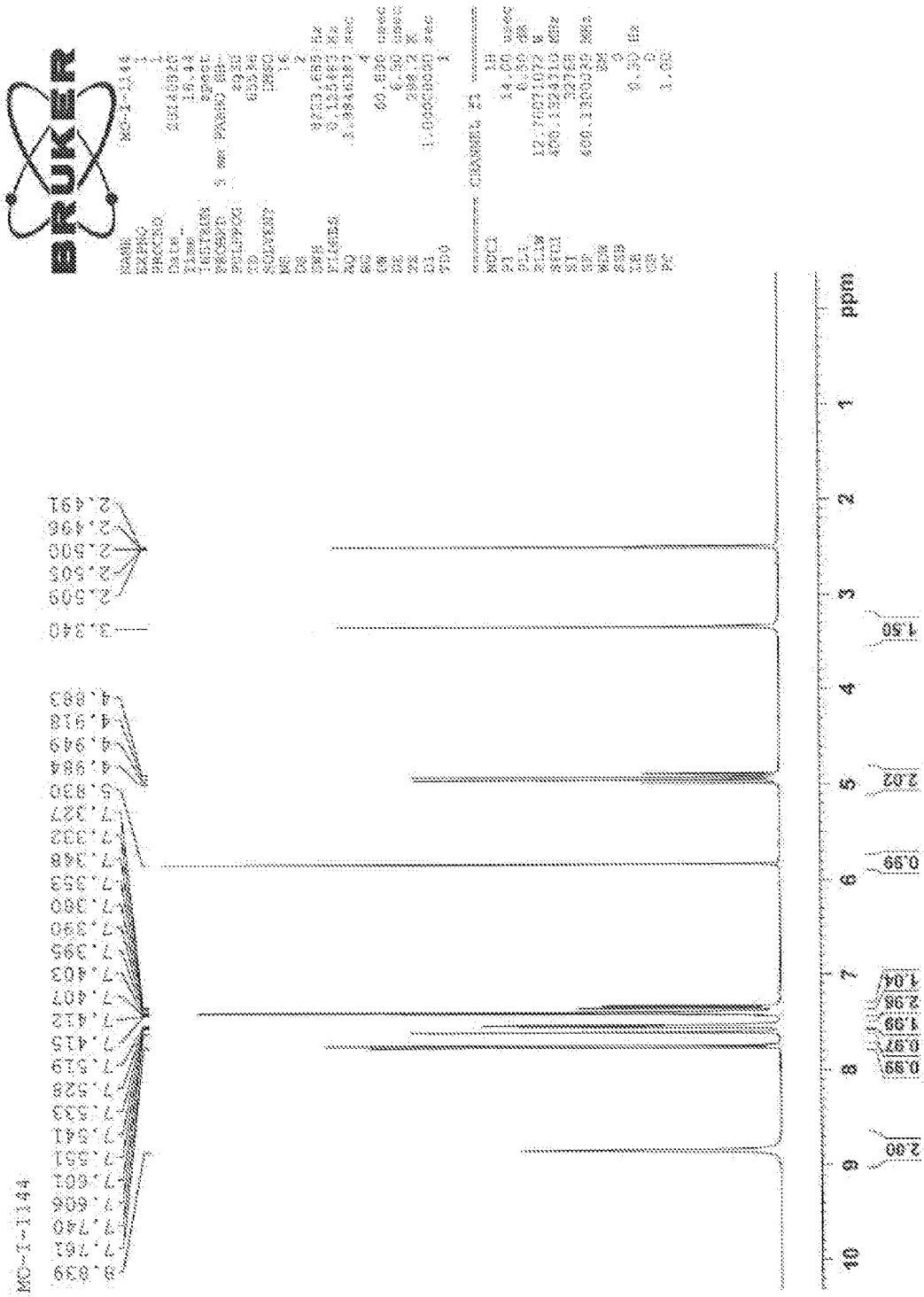
Figures 10, 11, 12, 13, 14, 15, 16, 17, 18, 19, 20, 21, 22, 23, 24, 25, 26, 27, 28, 29:
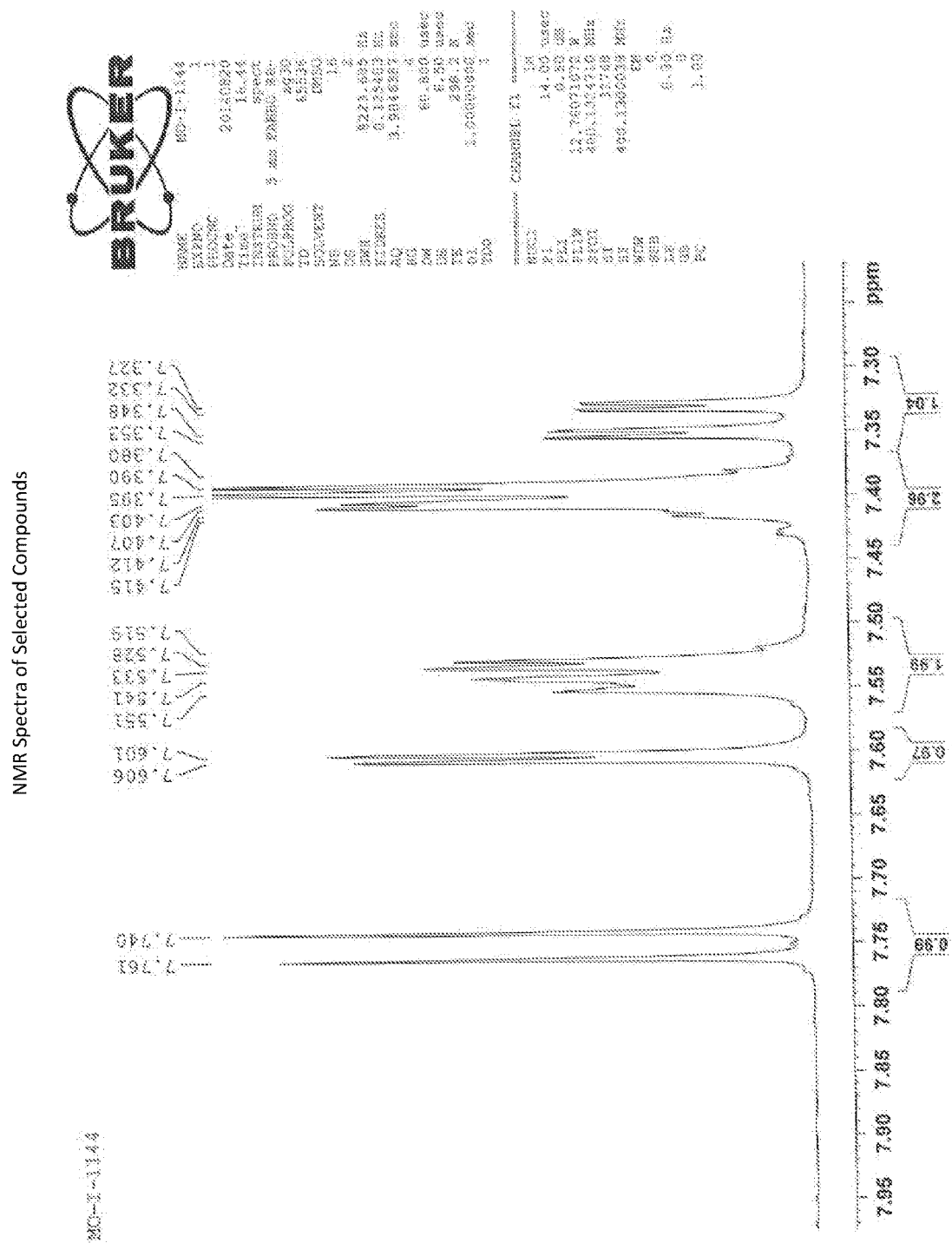
Figures 10, 11, 12, 13, 14, 15, 16, 17, 18, 19, 20, 21, 22, 23, 24, 25, 26, 27, 28, 29, 30:
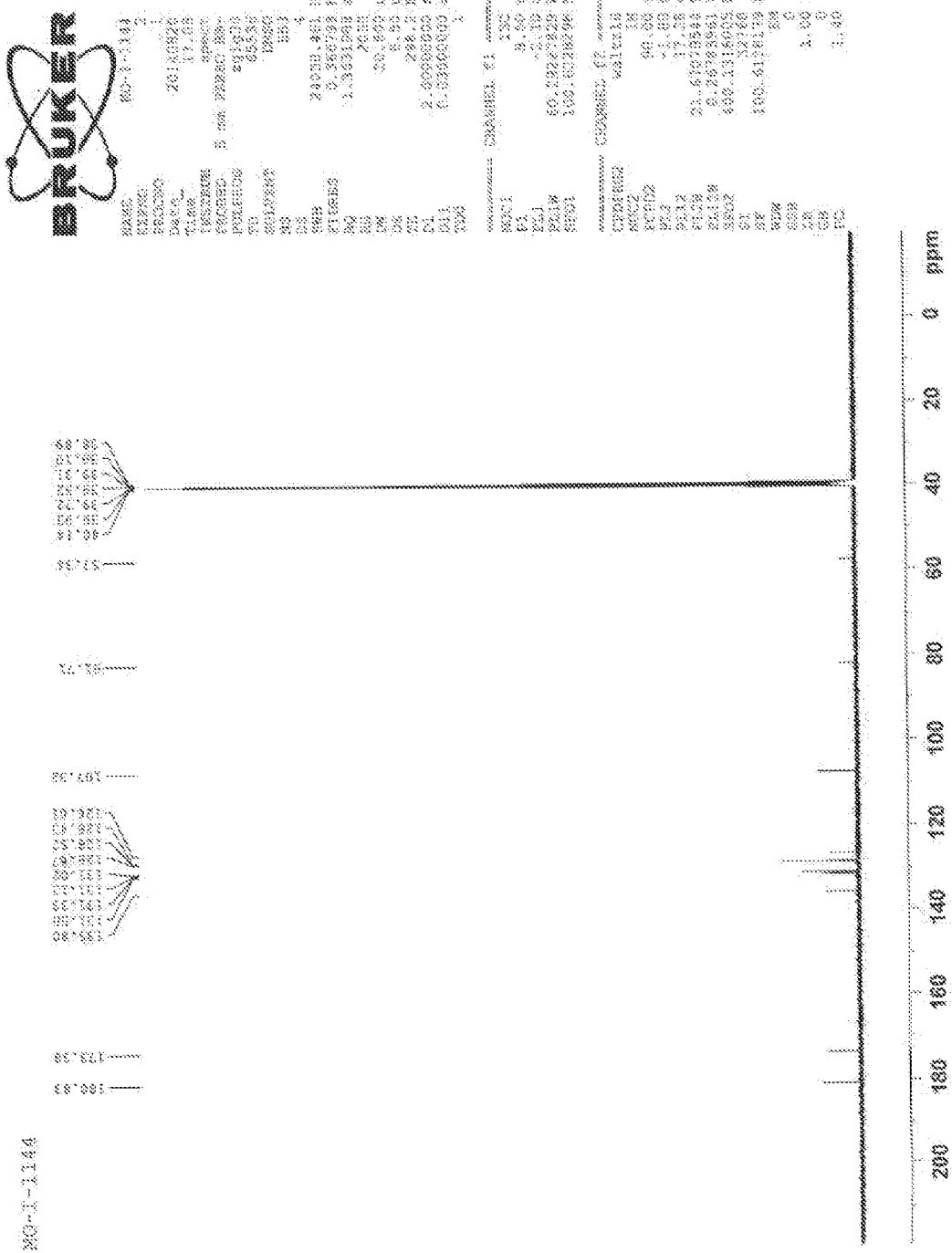
Figures 10, 11, 12, 13, 14, 15, 16, 17, 18, 19, 20, 21, 22, 23, 24, 25, 26, 27, 28, 29, 30, 31:
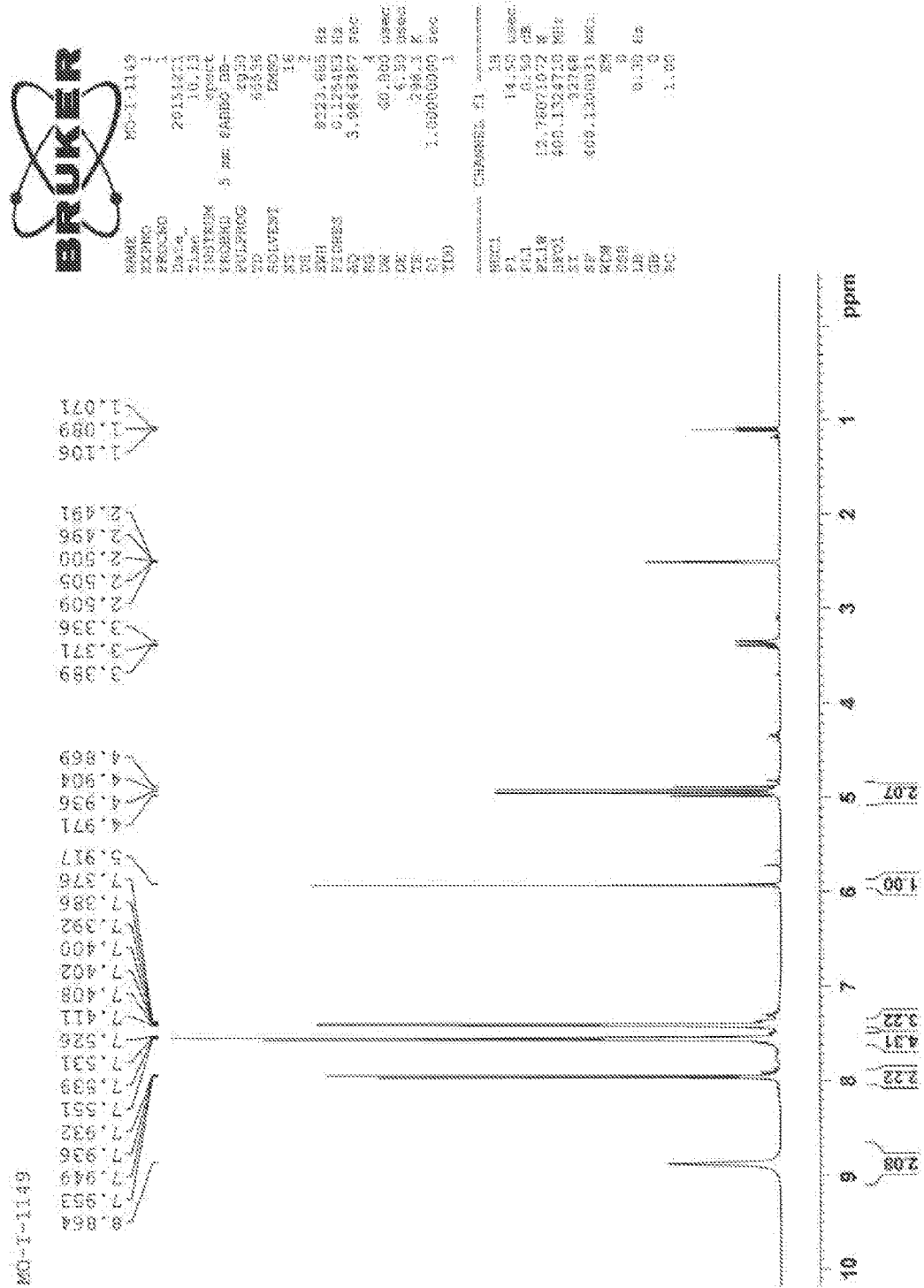
Figures 10, 11, 12, 13, 14, 15, 16, 17, 18, 19, 20, 21, 22, 23, 24, 25, 26, 27, 28, 29, 30, 31, 32:
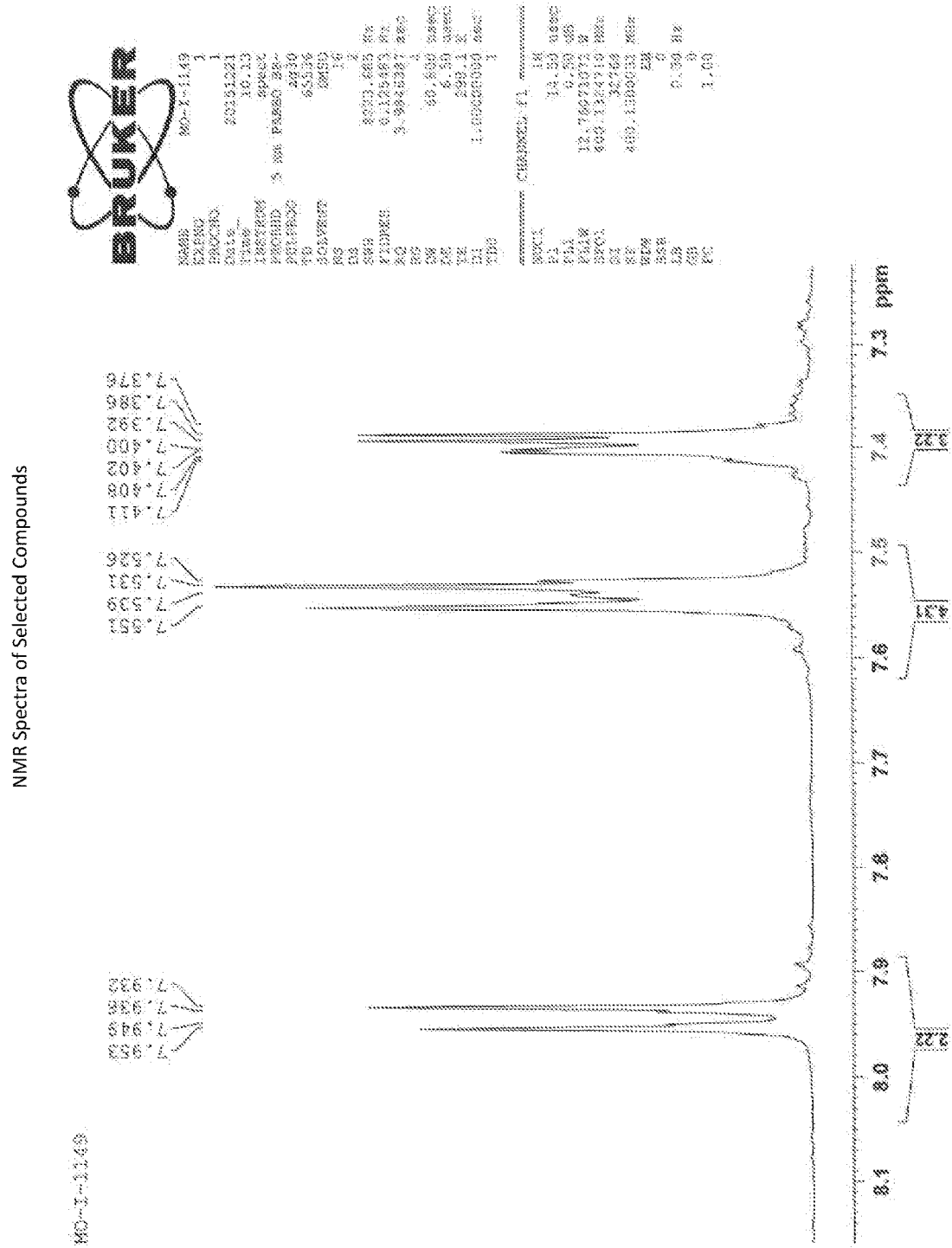
Figures 10, 11, 12, 13, 14, 15, 16, 17, 18, 19, 20, 21, 22, 23, 24, 25, 26, 27, 28, 29, 30, 31, 32, 33:
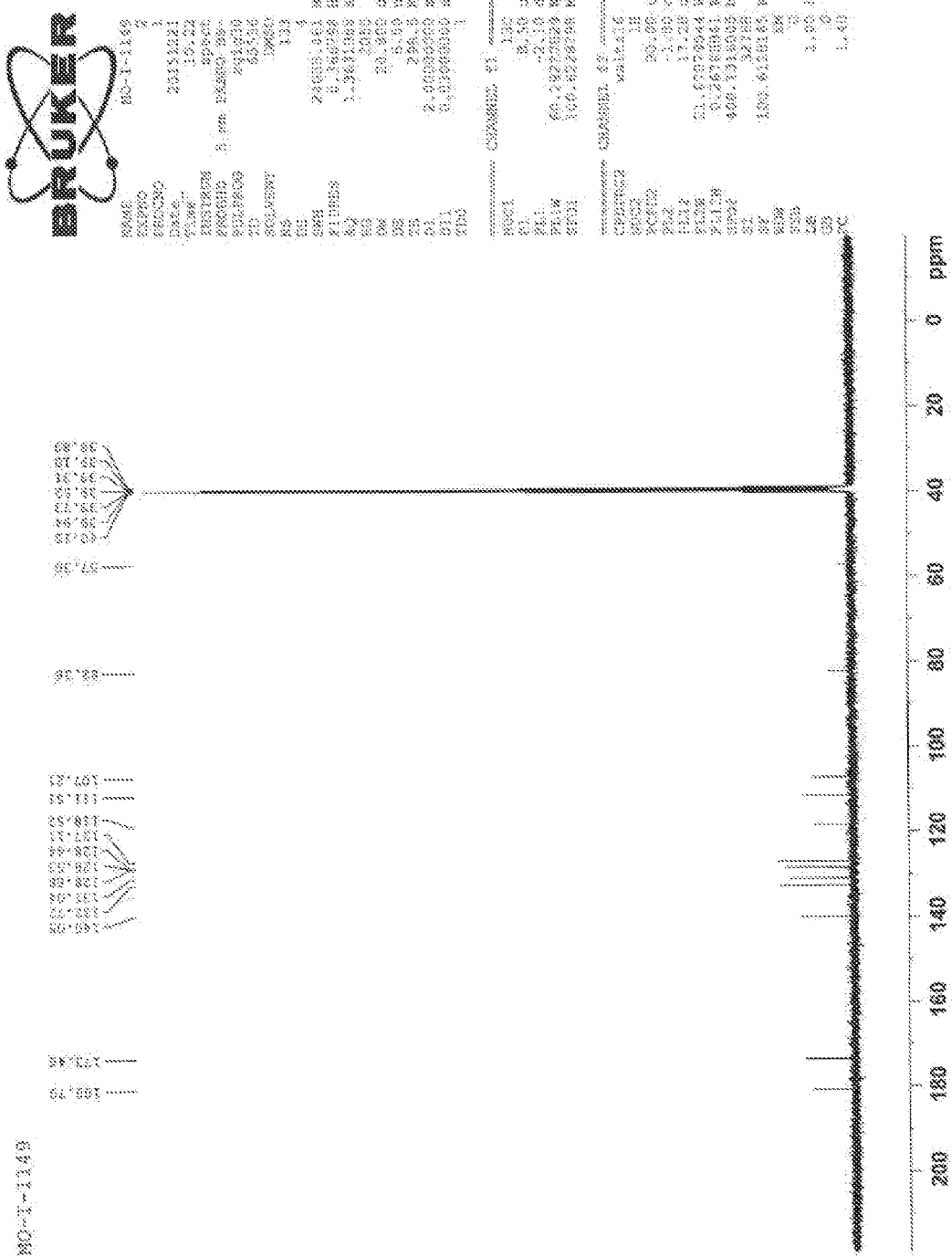
Figures 10, 11, 12, 13, 14, 15, 16, 17, 18, 19, 20, 21, 22, 23, 24, 25, 26, 27, 28, 29, 30, 31, 32, 33, 34:
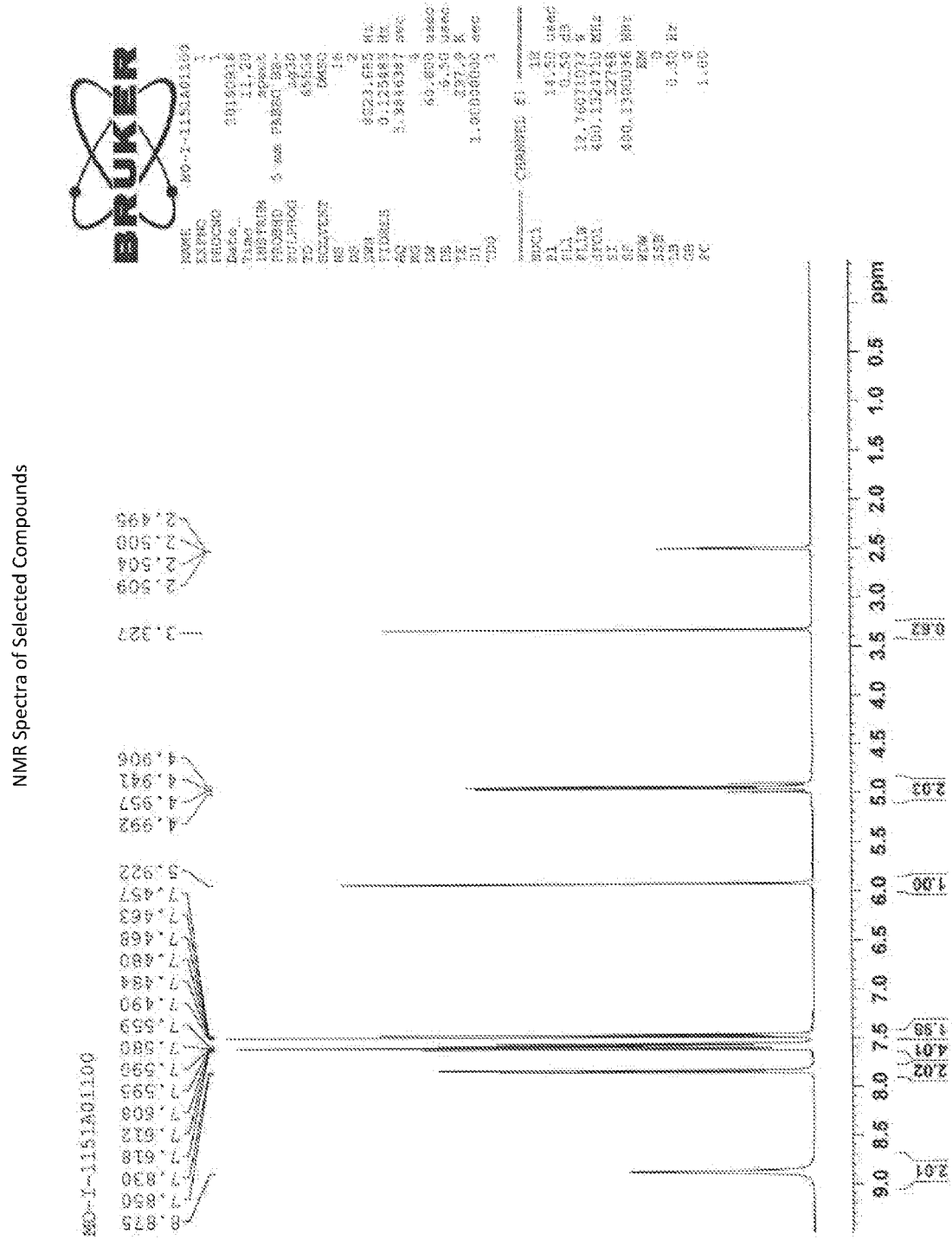
Figures 10, 11, 12, 13, 14, 15, 16, 17, 18, 19, 20, 21, 22, 23, 24, 25, 26, 27, 28, 29, 30, 31, 32, 33, 34, 35, 36:
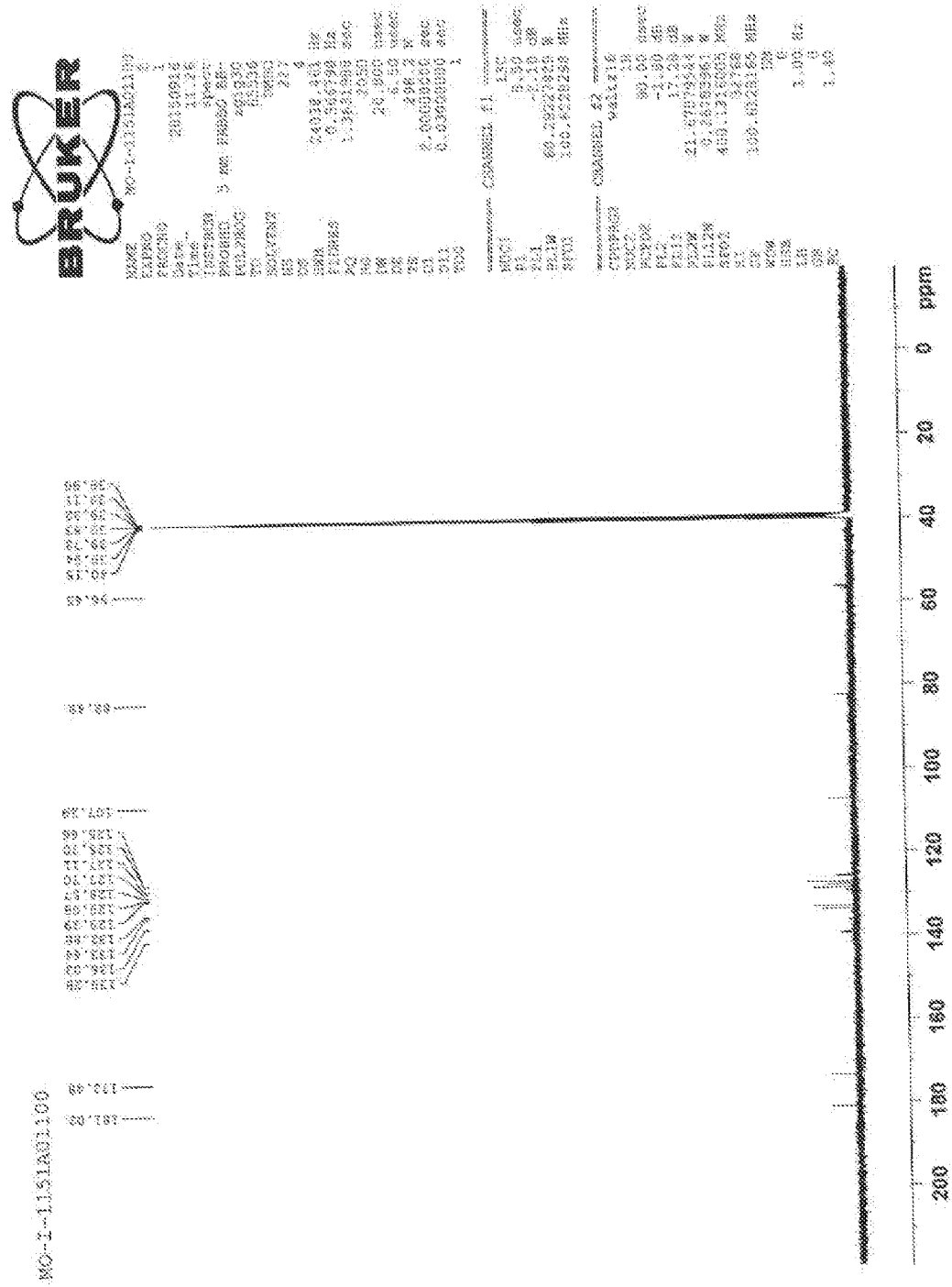
Figures 10, 11, 12, 13, 14, 15, 16, 17, 18, 19, 20, 21, 22, 23, 24, 25, 26, 27, 28, 29, 30, 31, 32, 33, 34, 35, 36, 37:
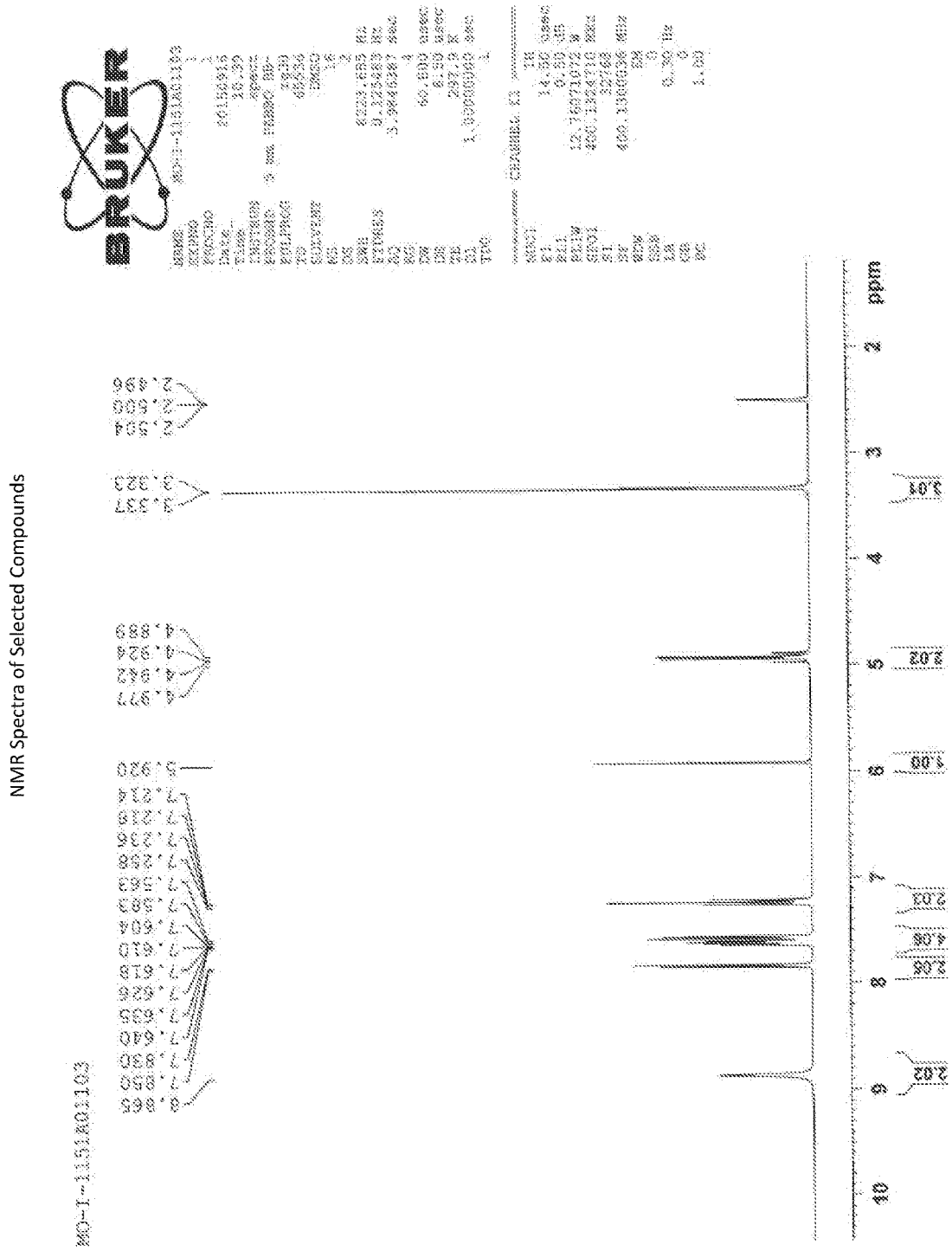
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38:
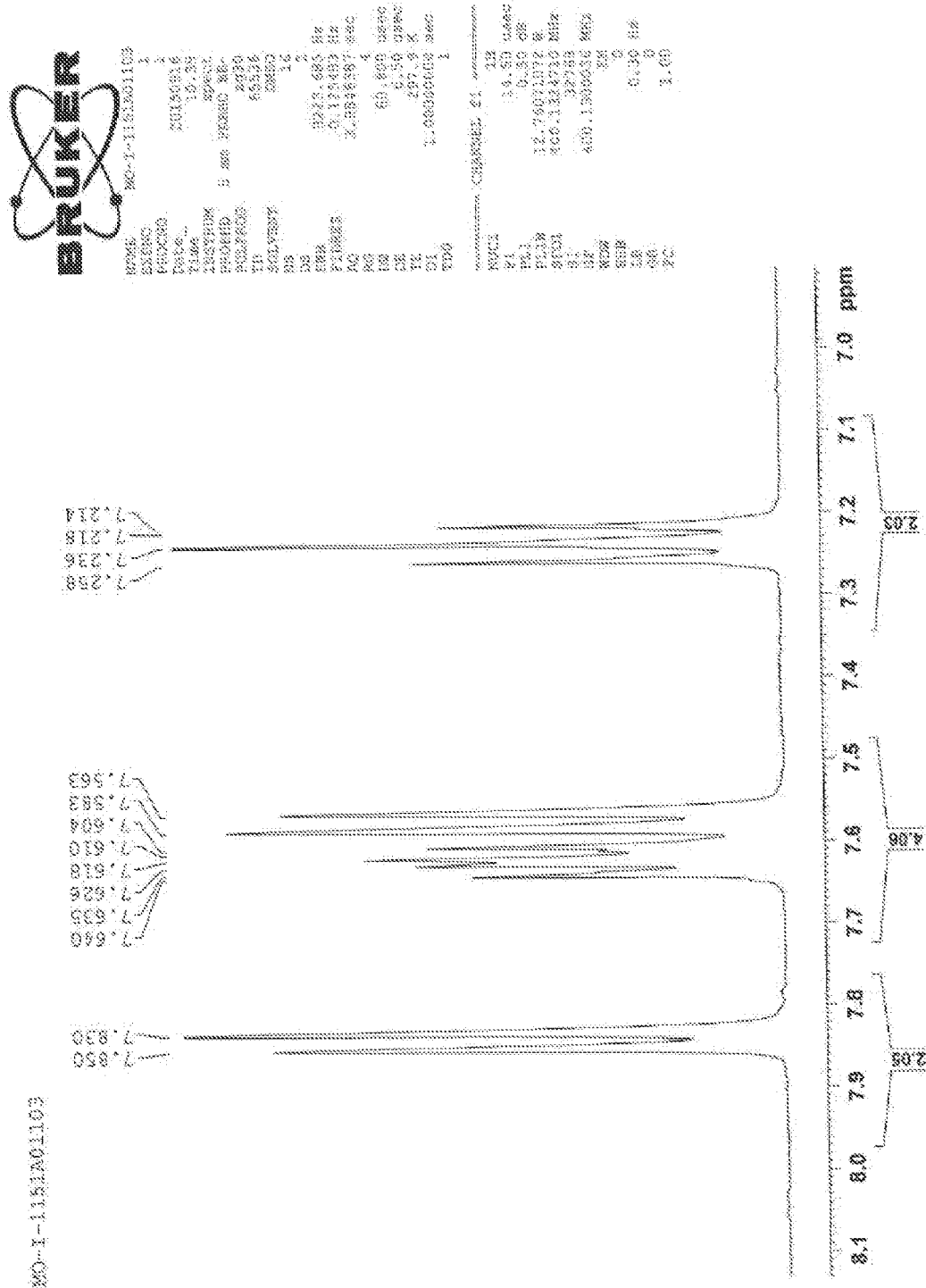
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
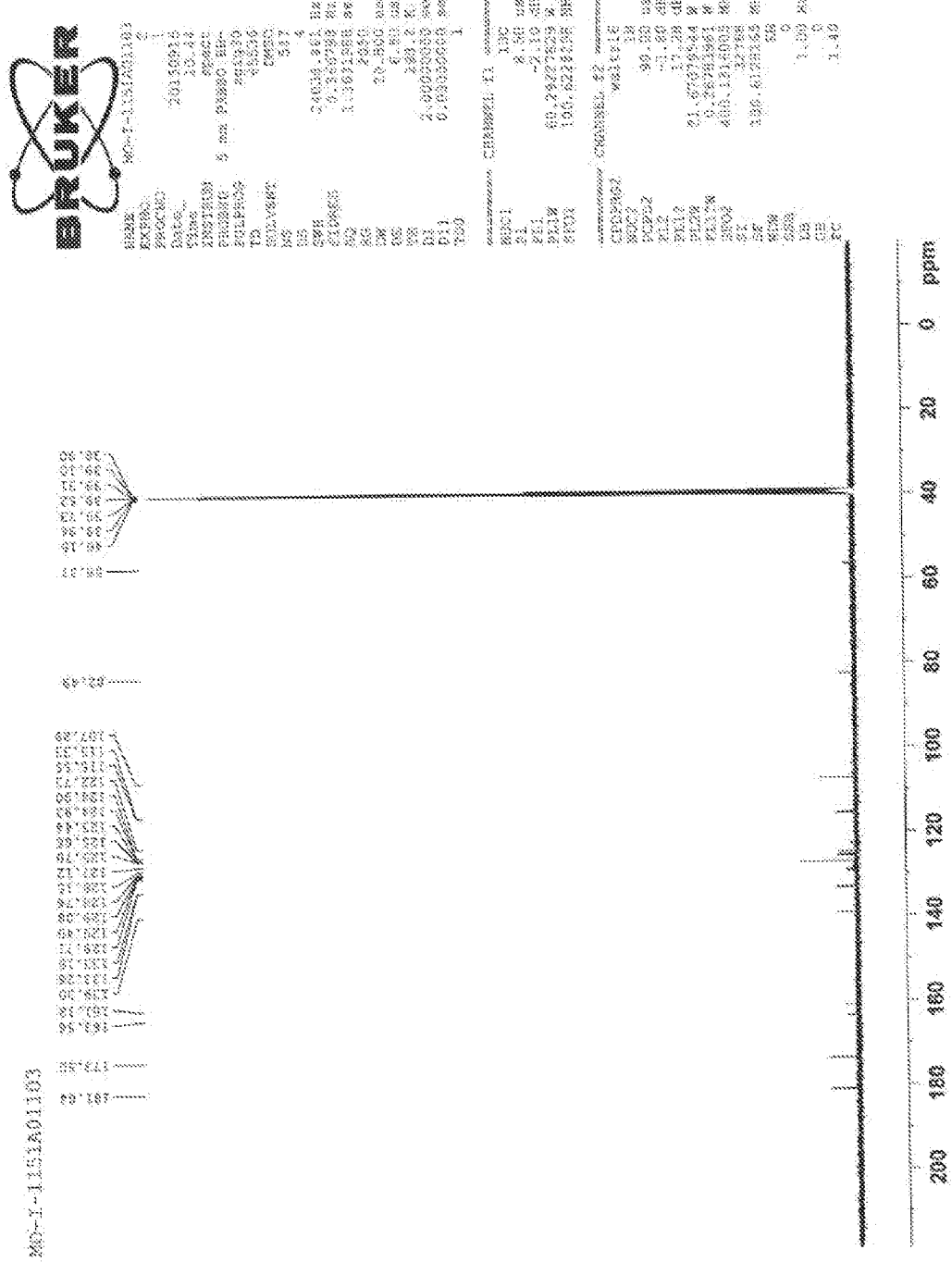
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
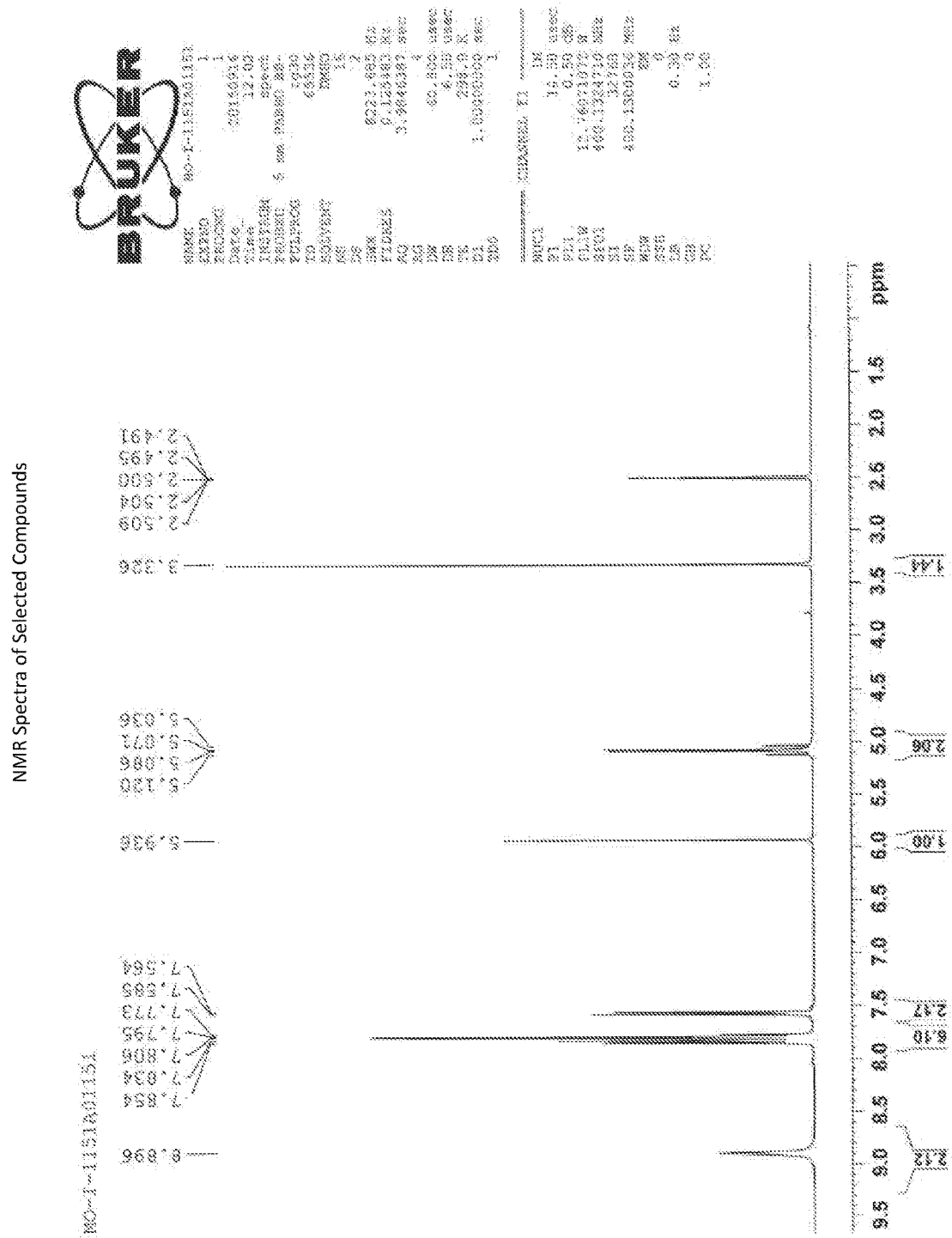
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
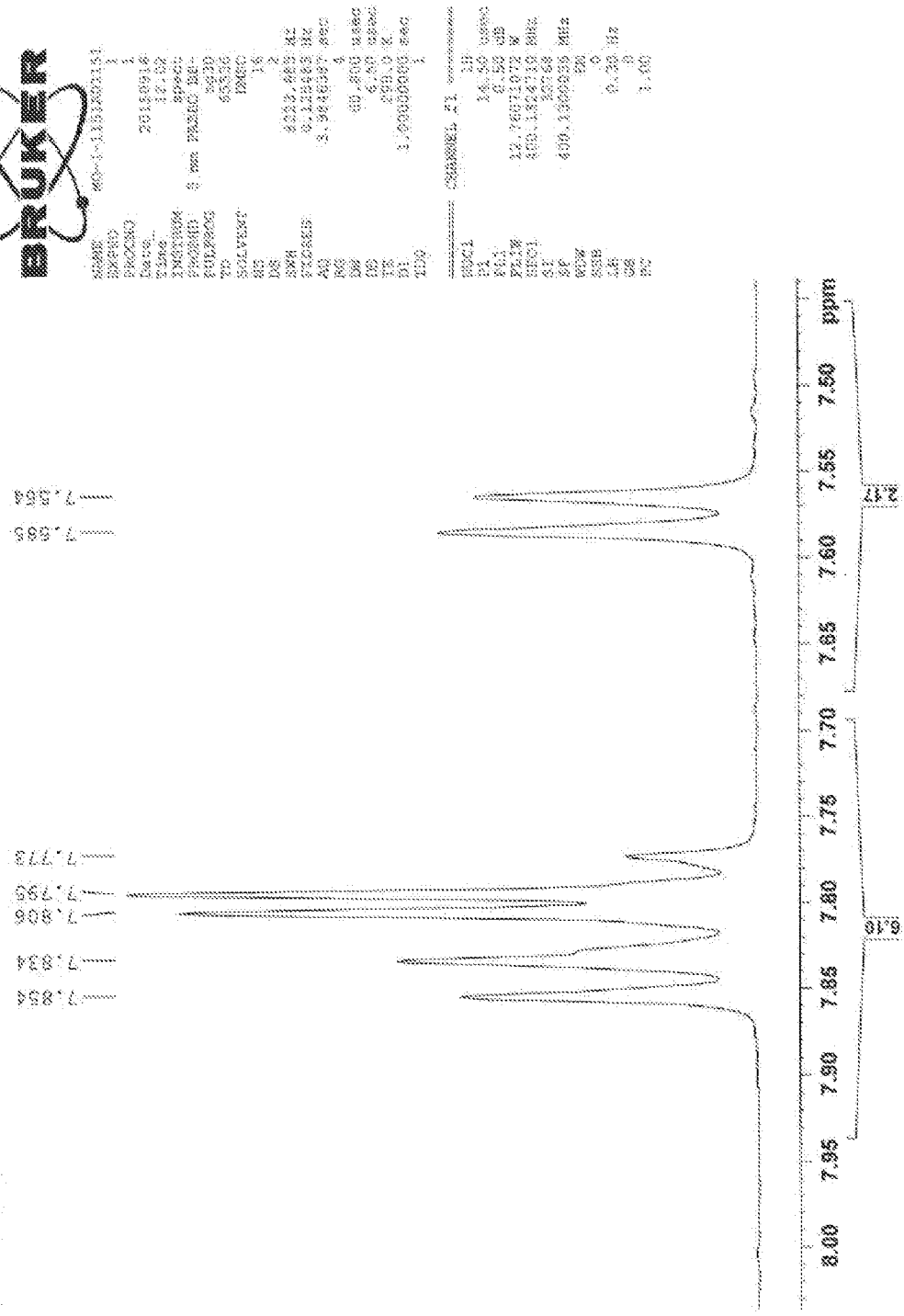
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
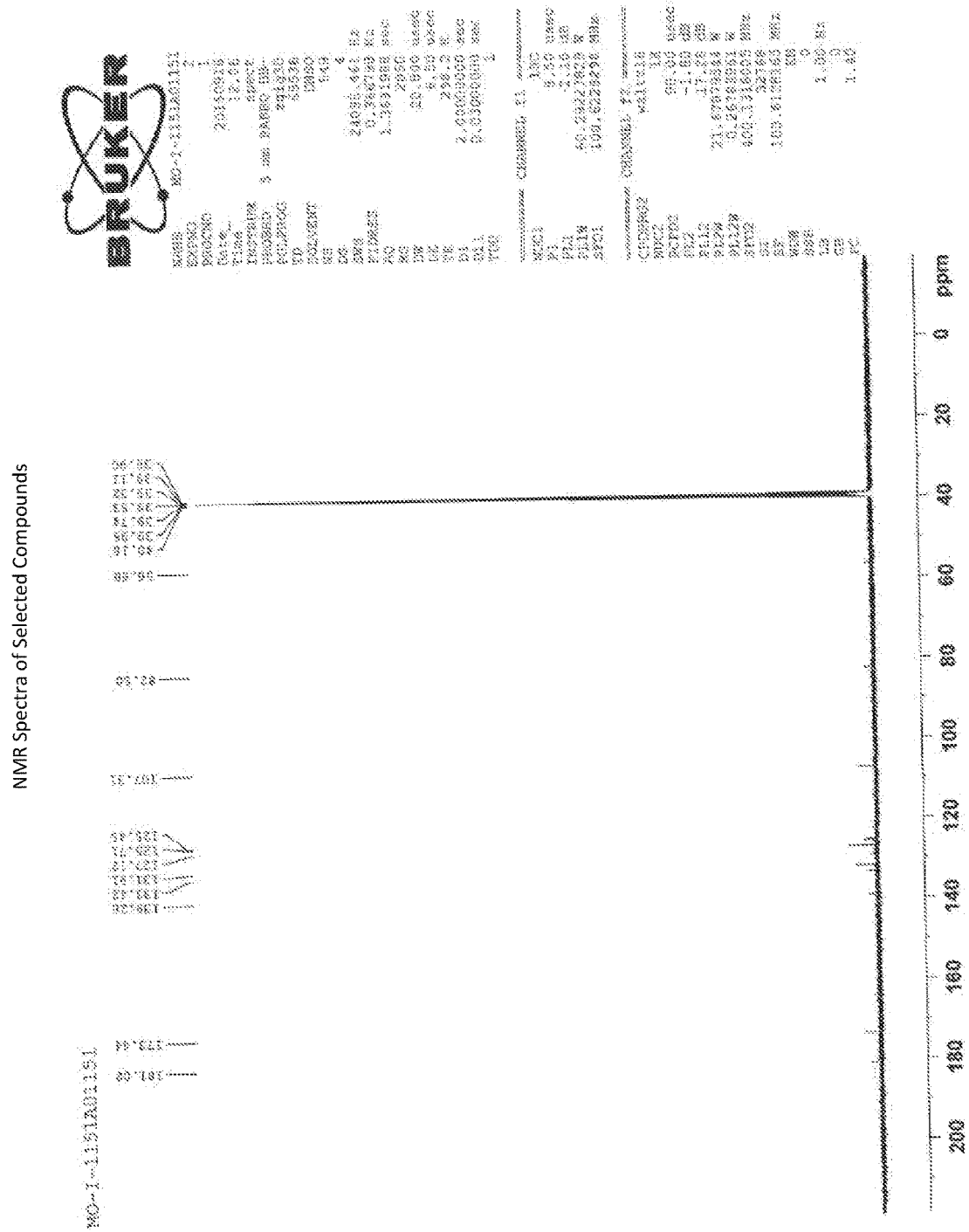
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
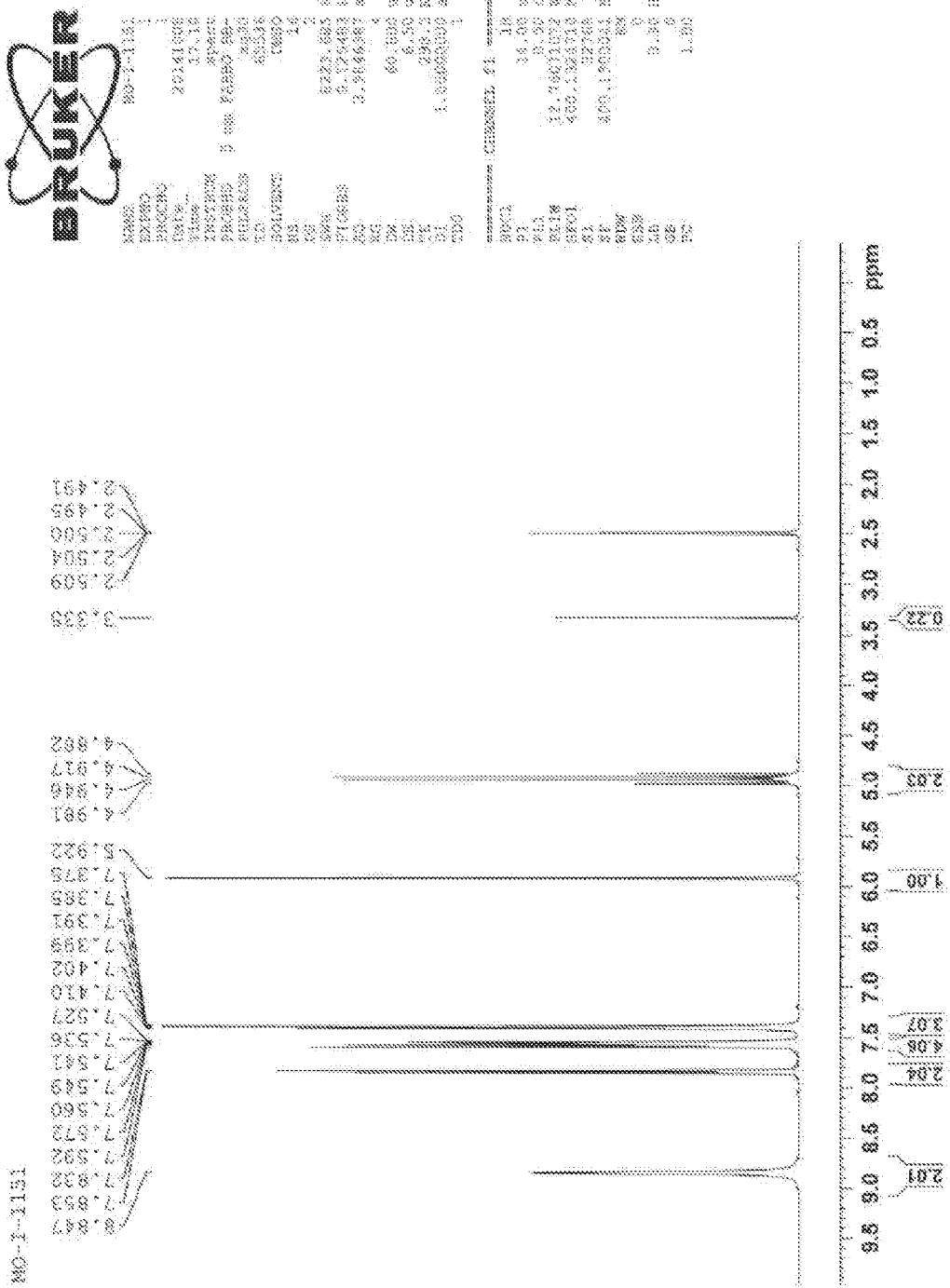
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
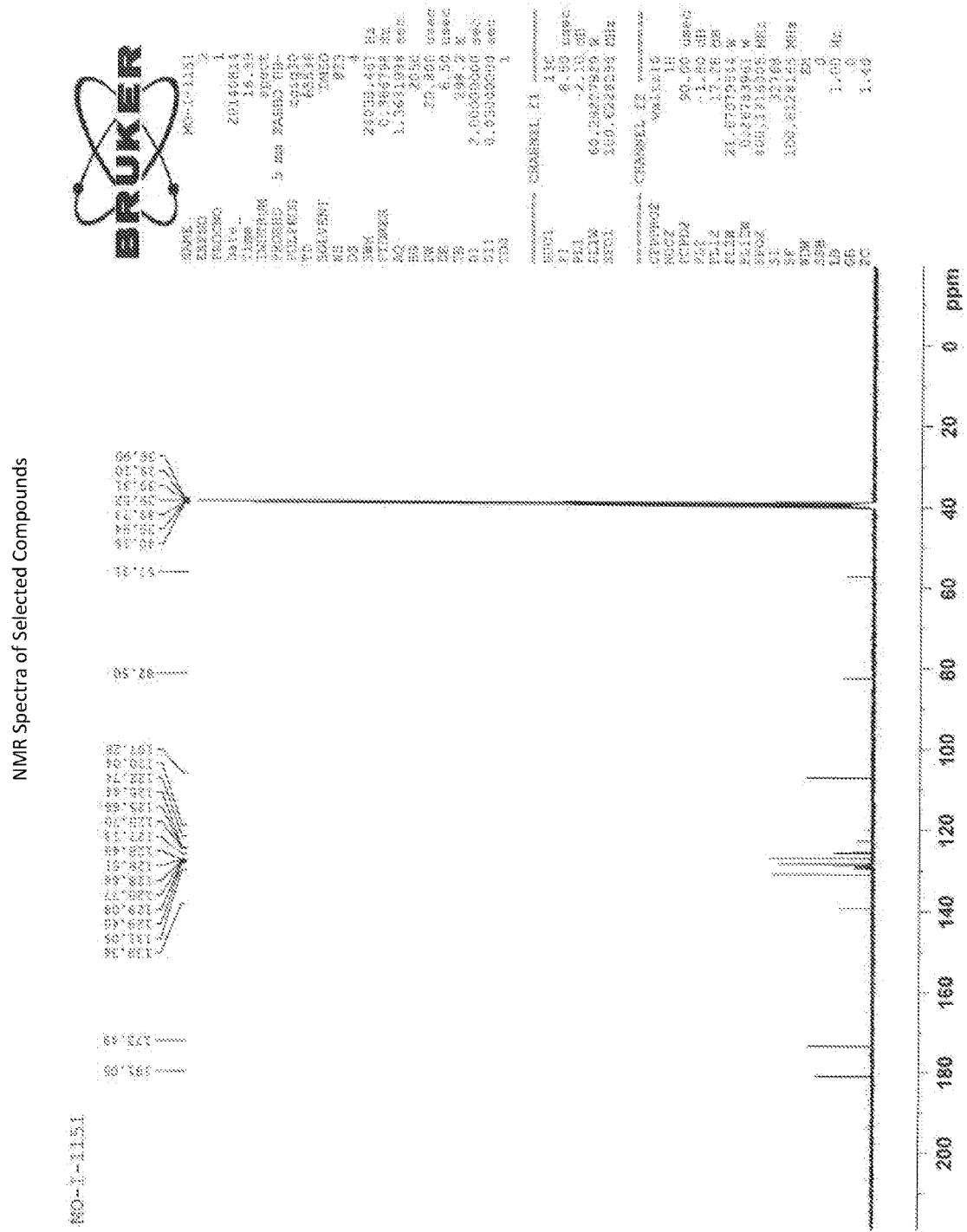
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
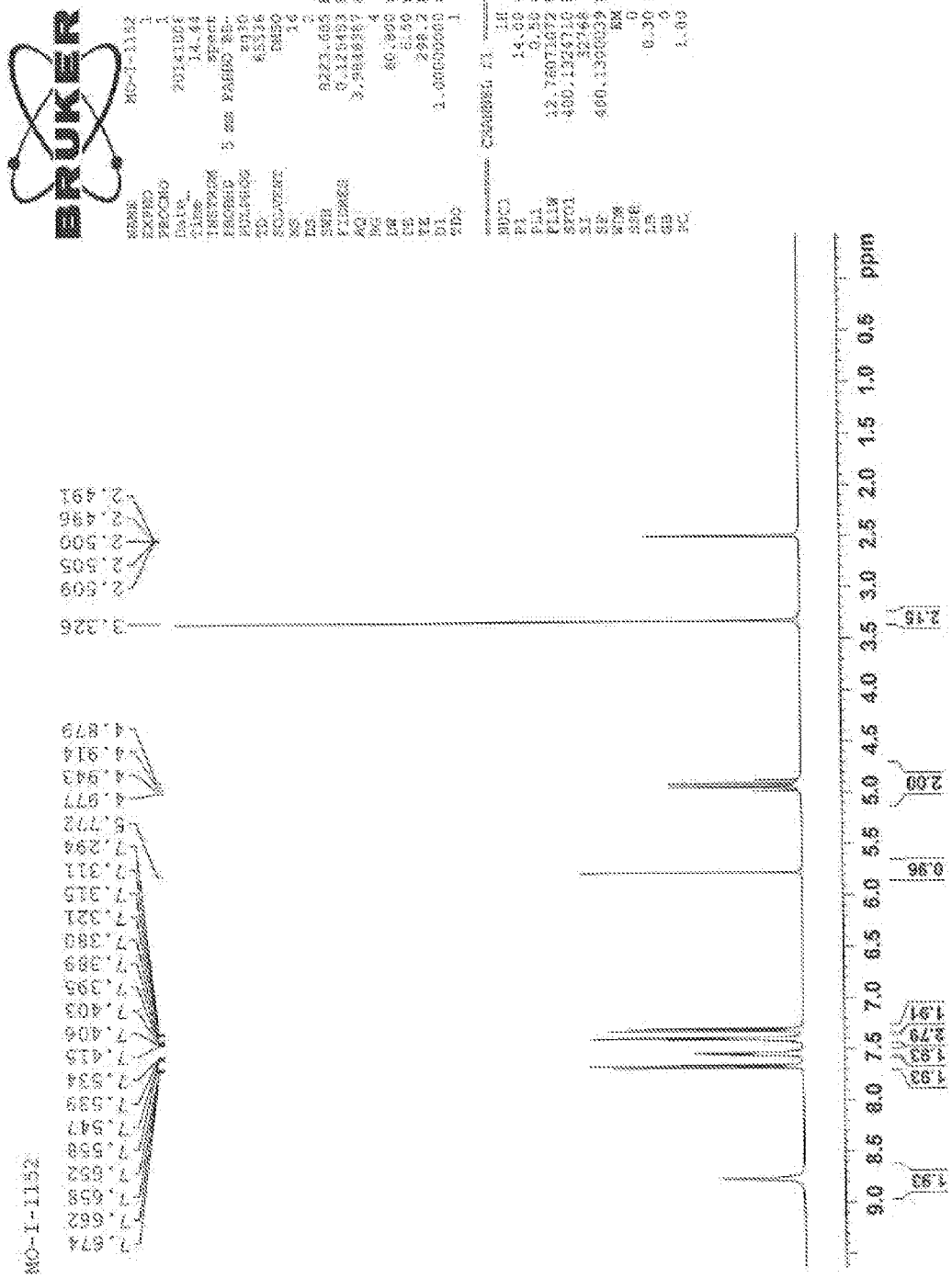
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
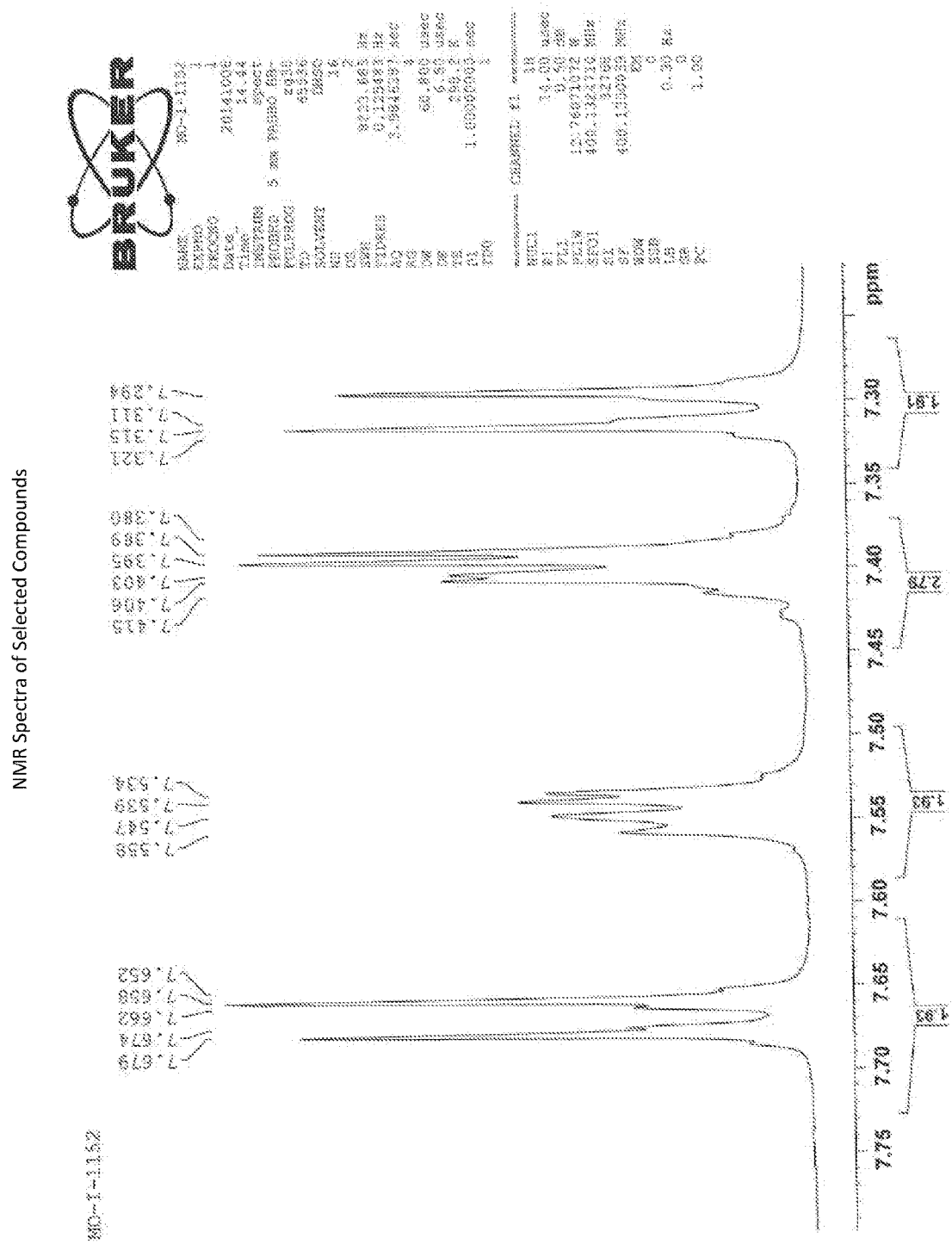
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
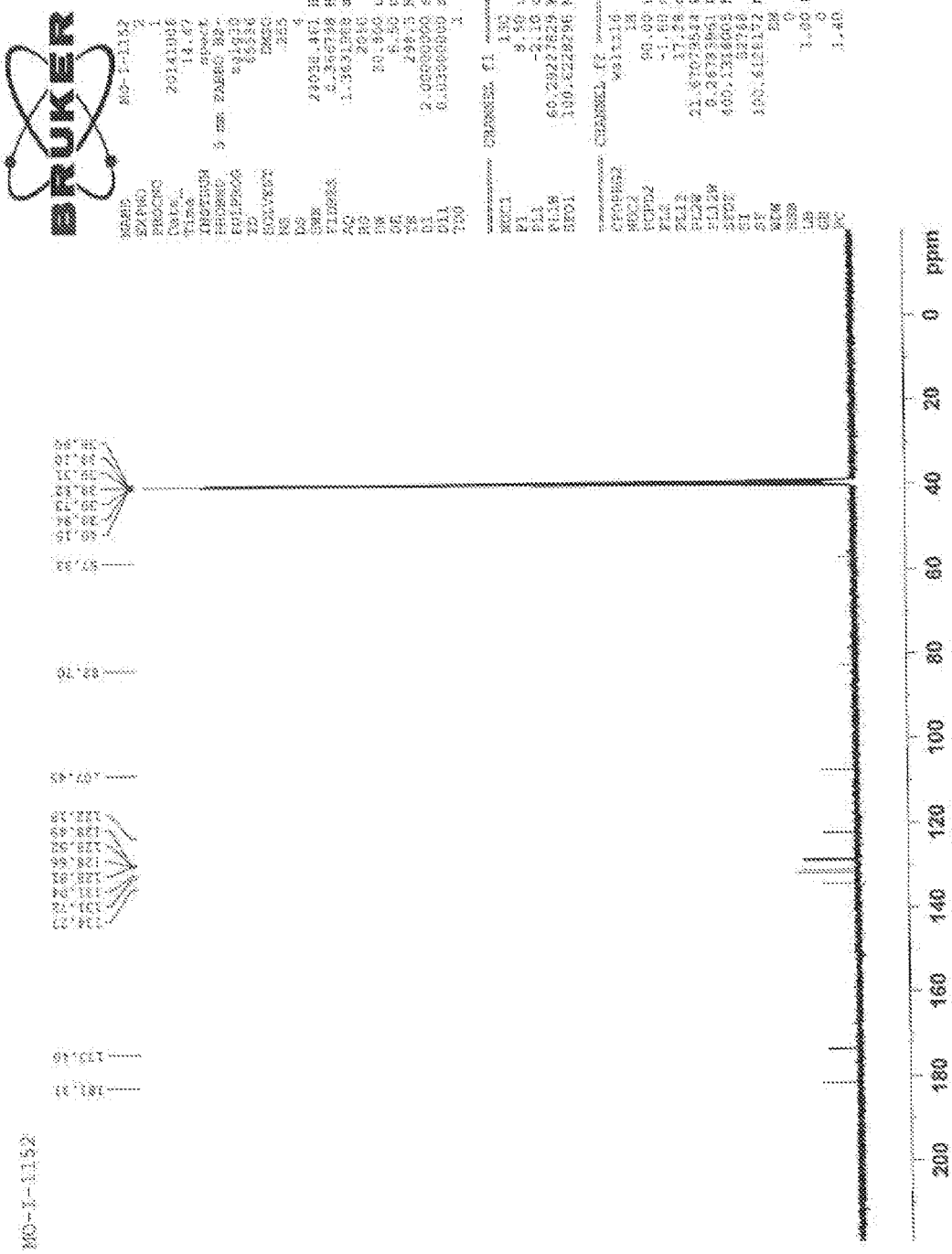
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
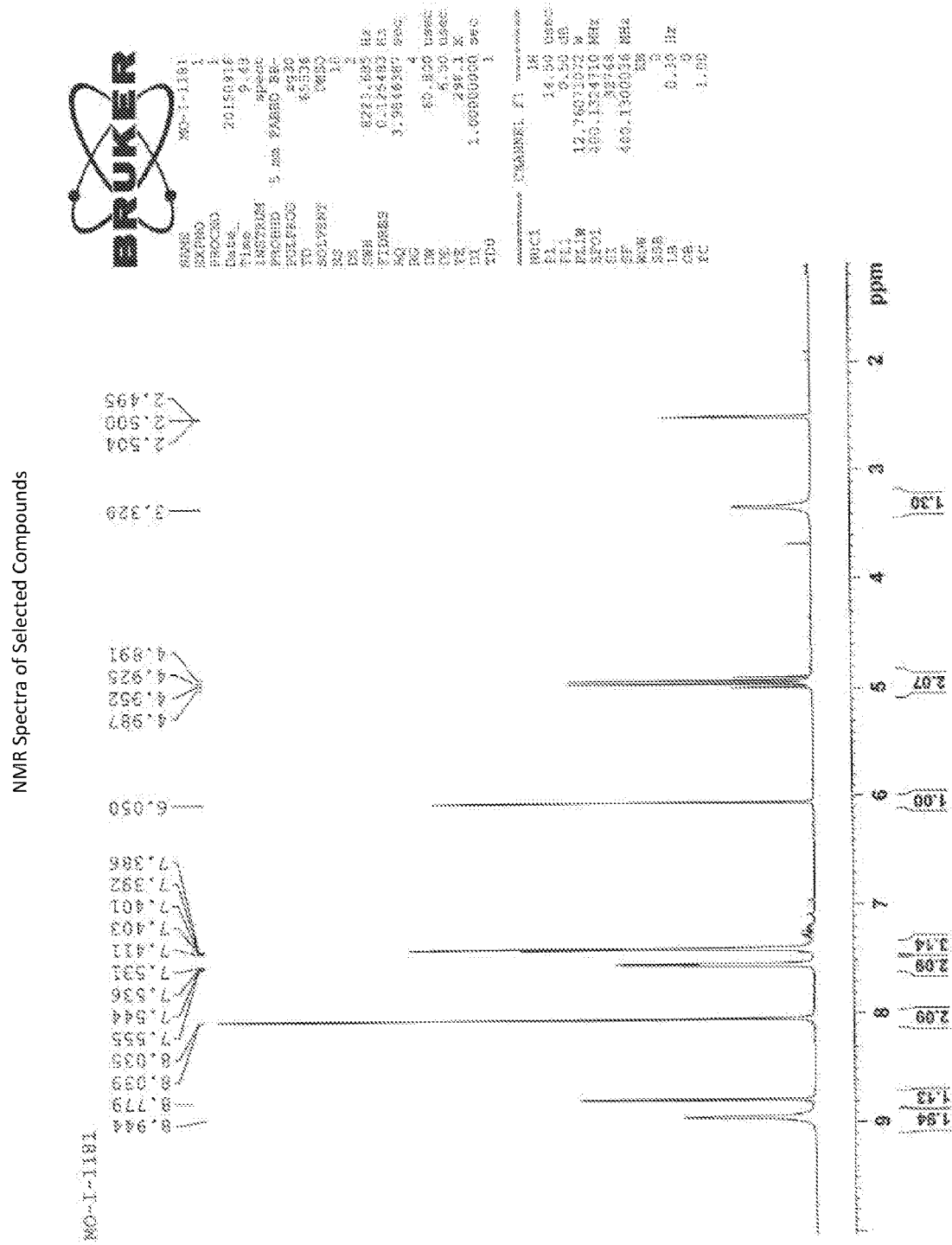
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
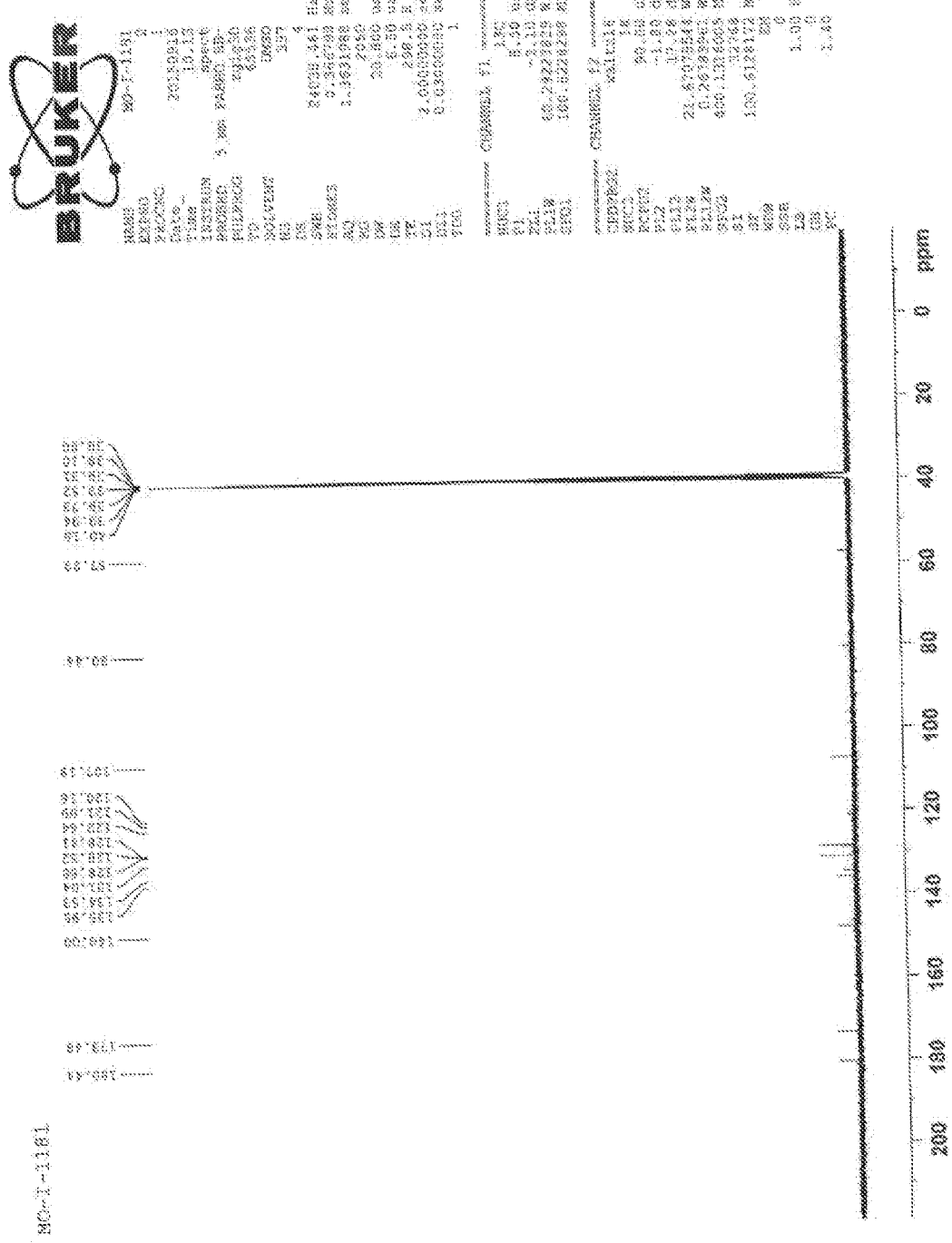
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
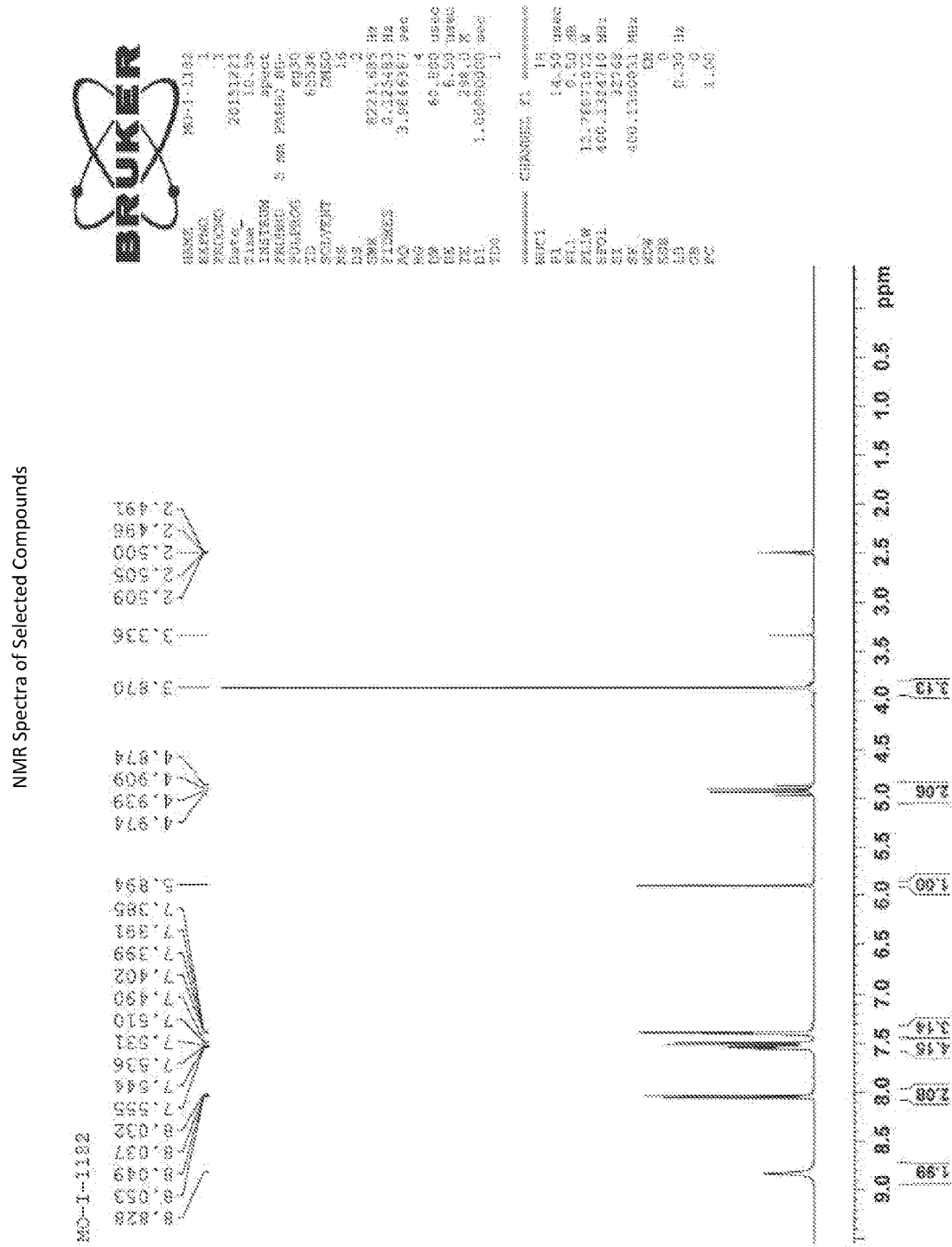
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
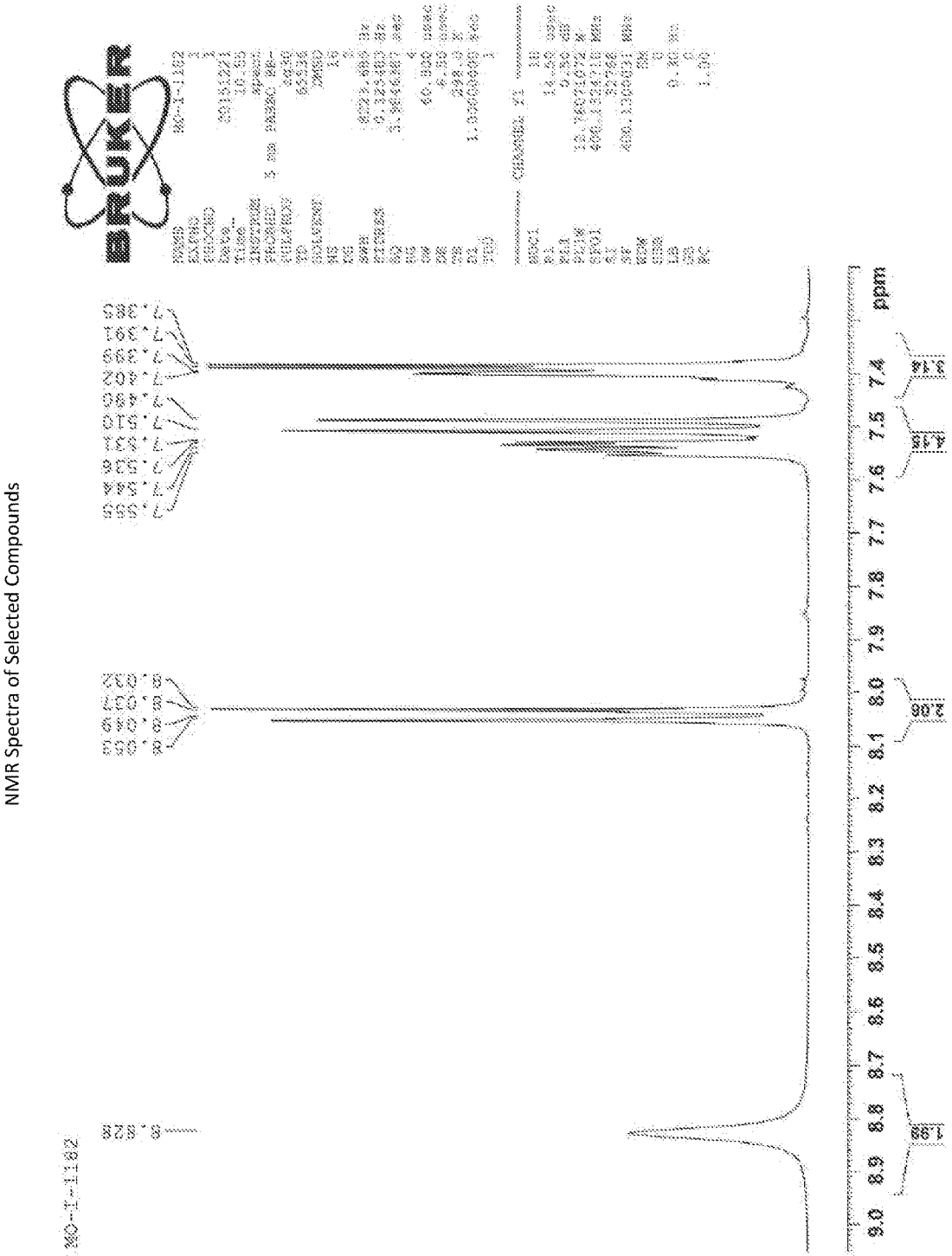
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
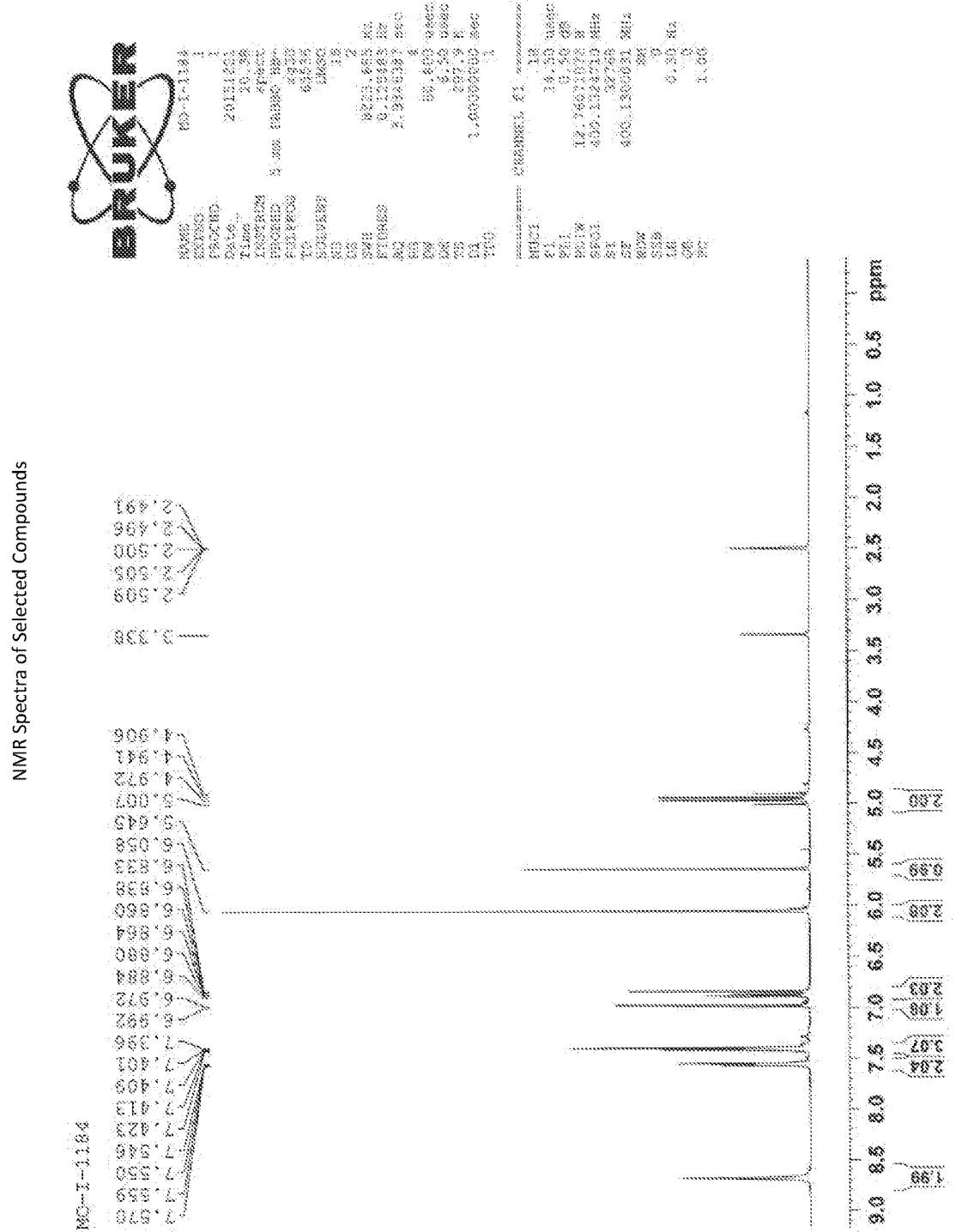
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
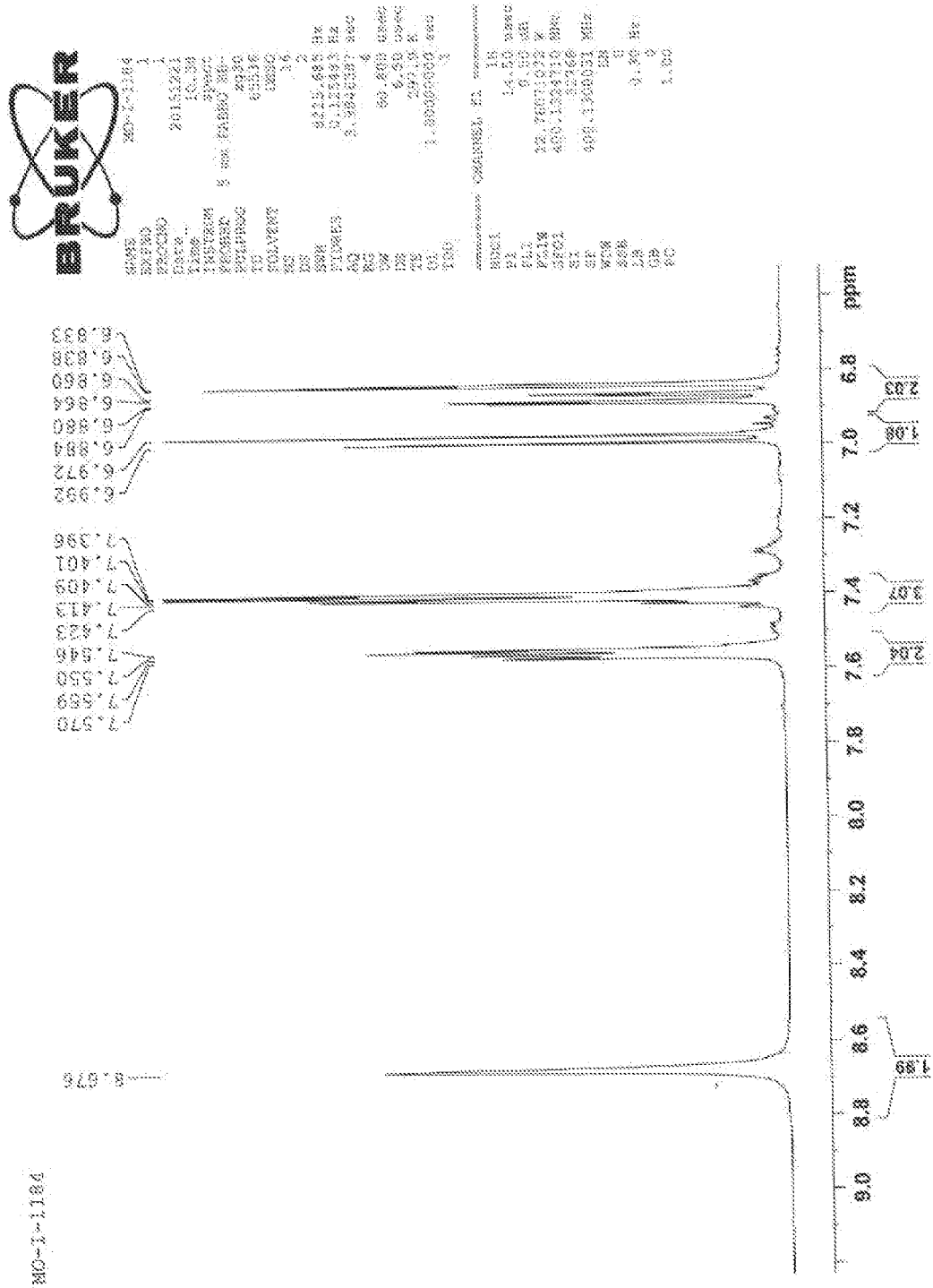
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55:
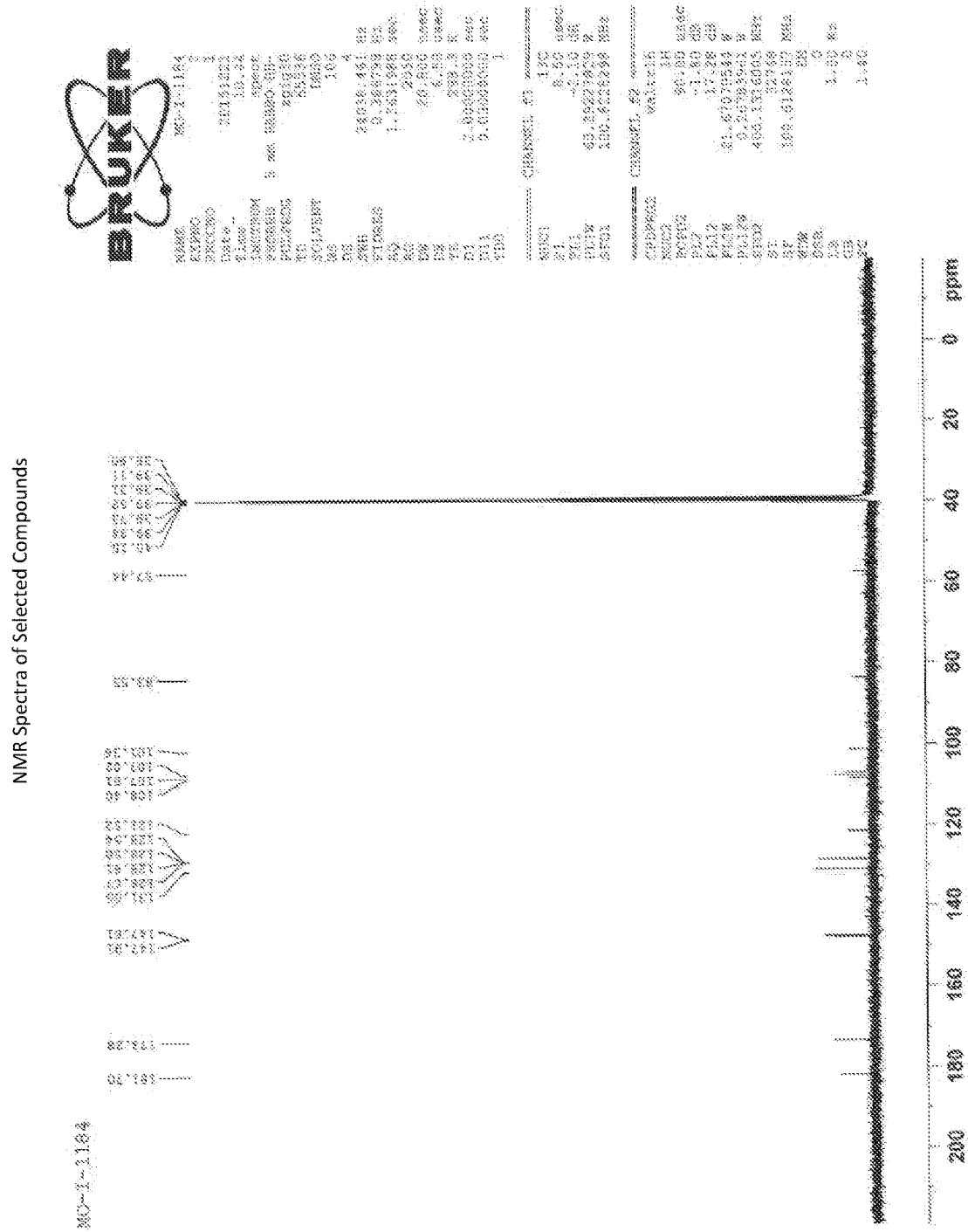
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56:
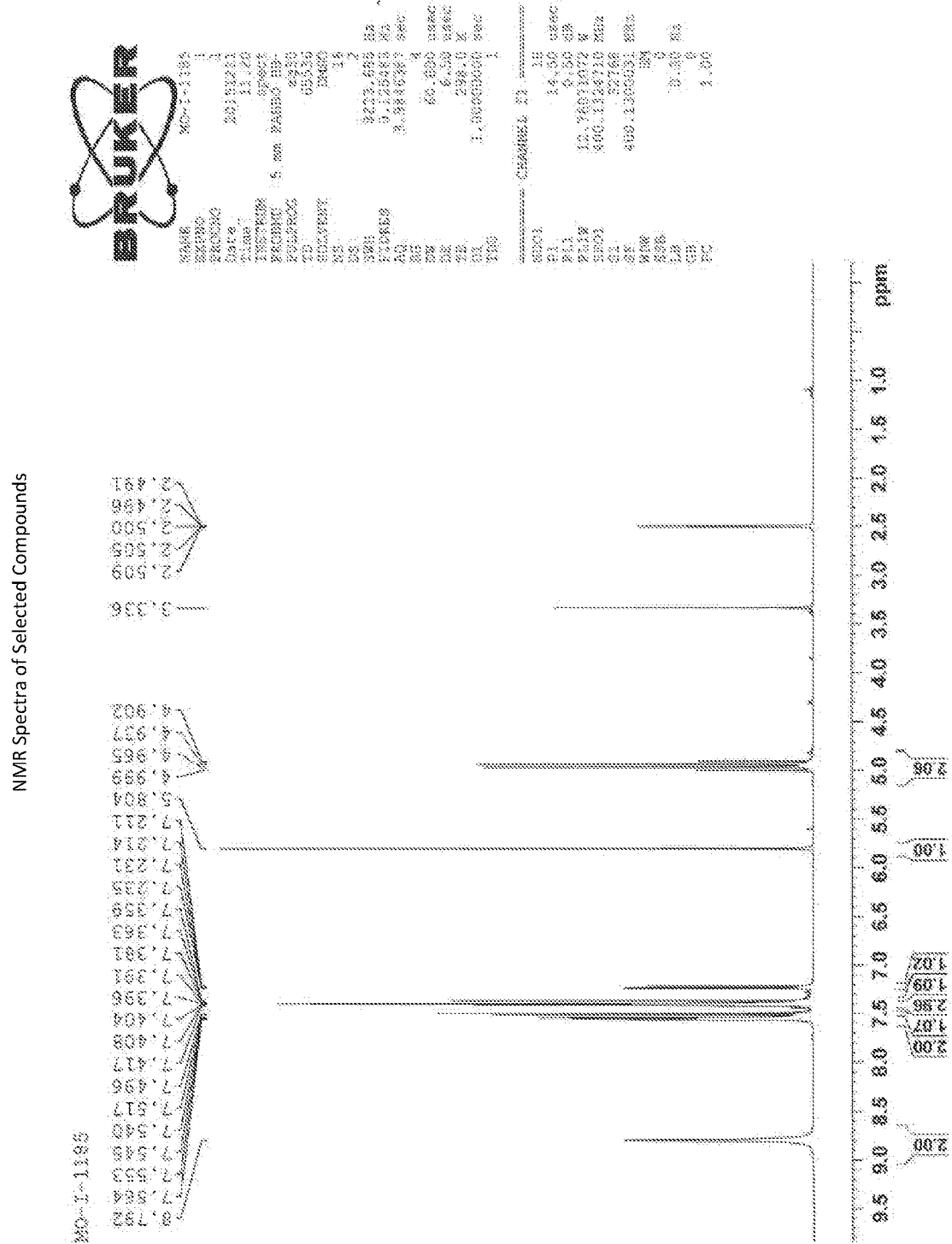
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57:
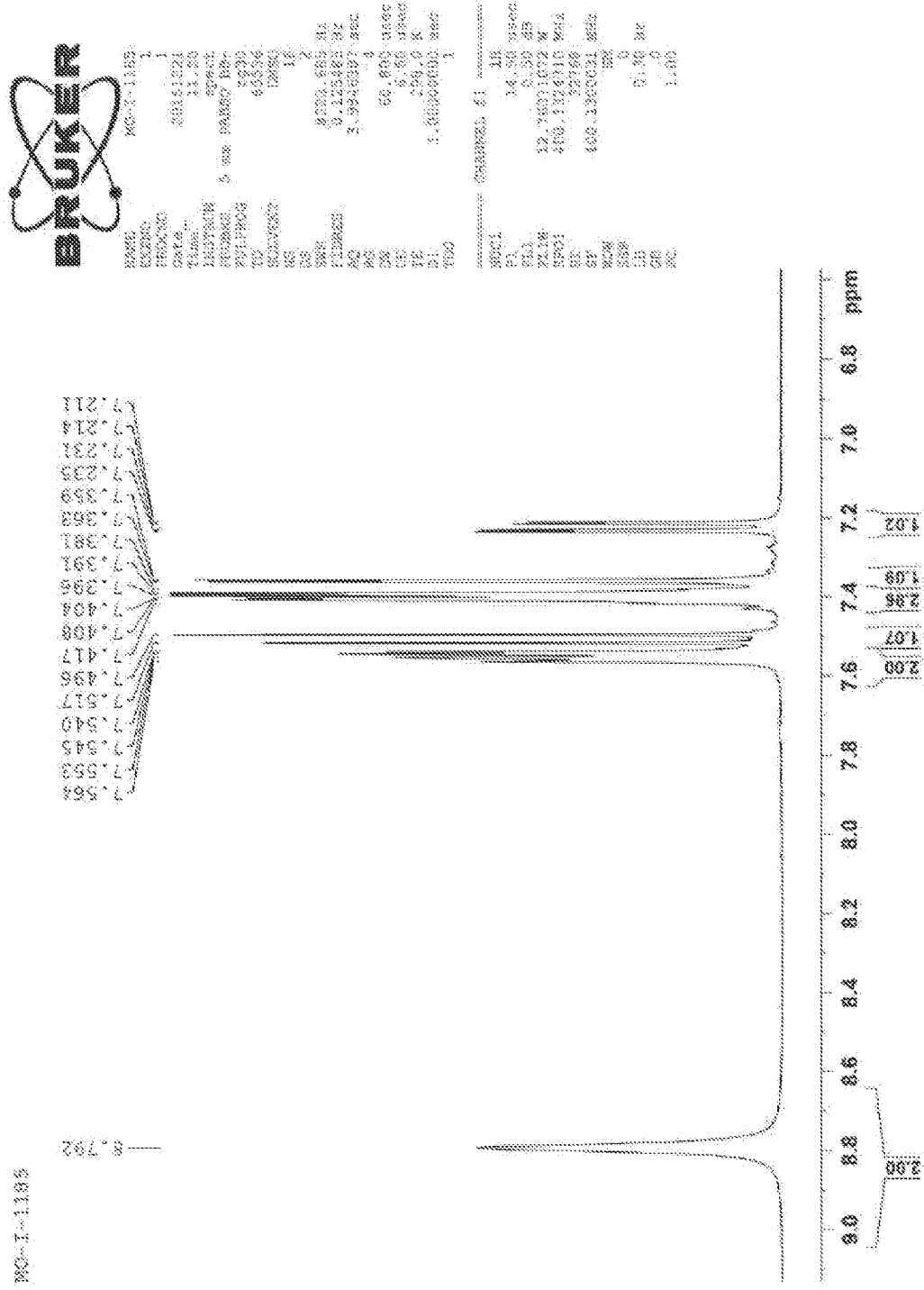
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58:
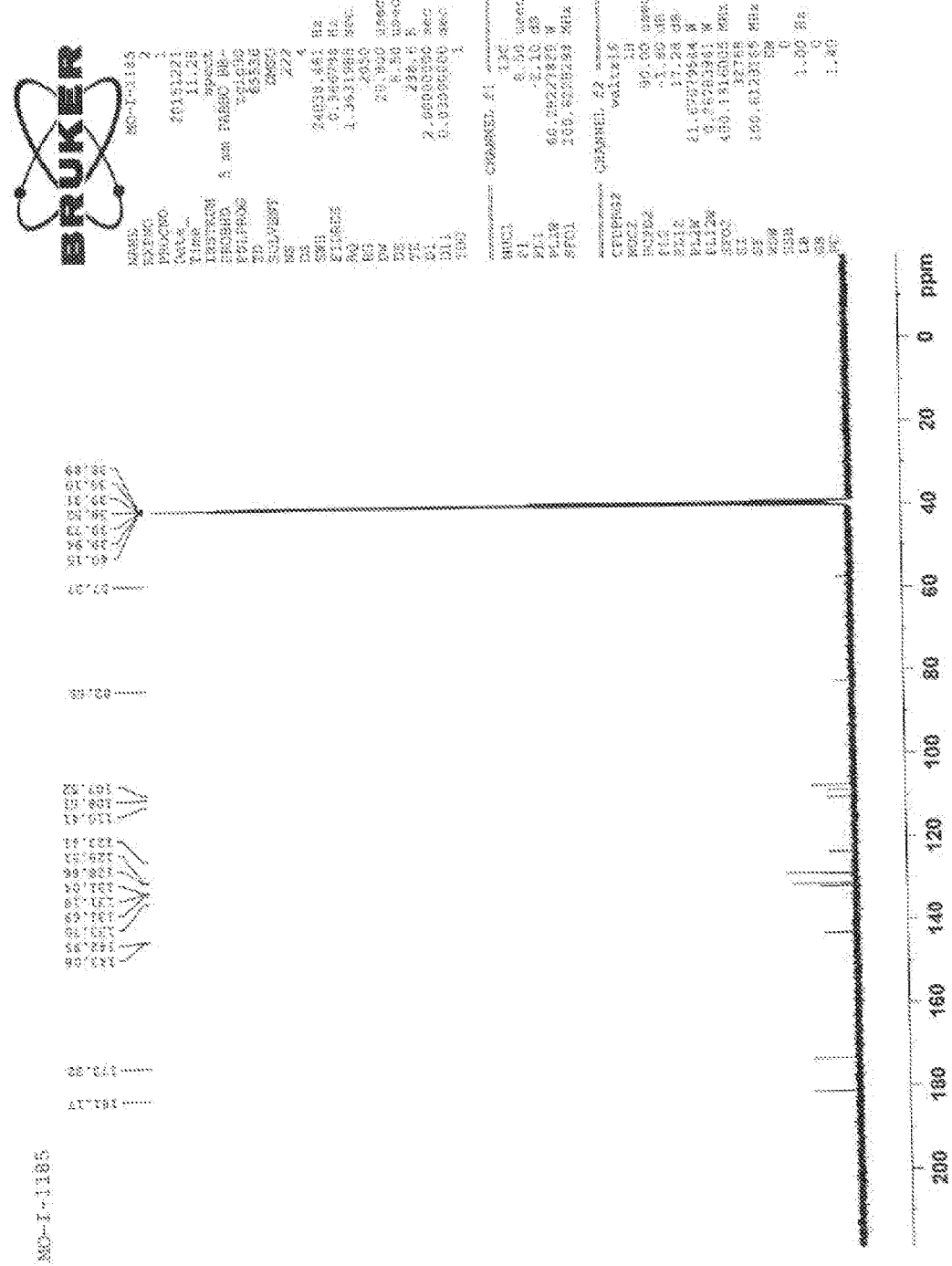
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59:
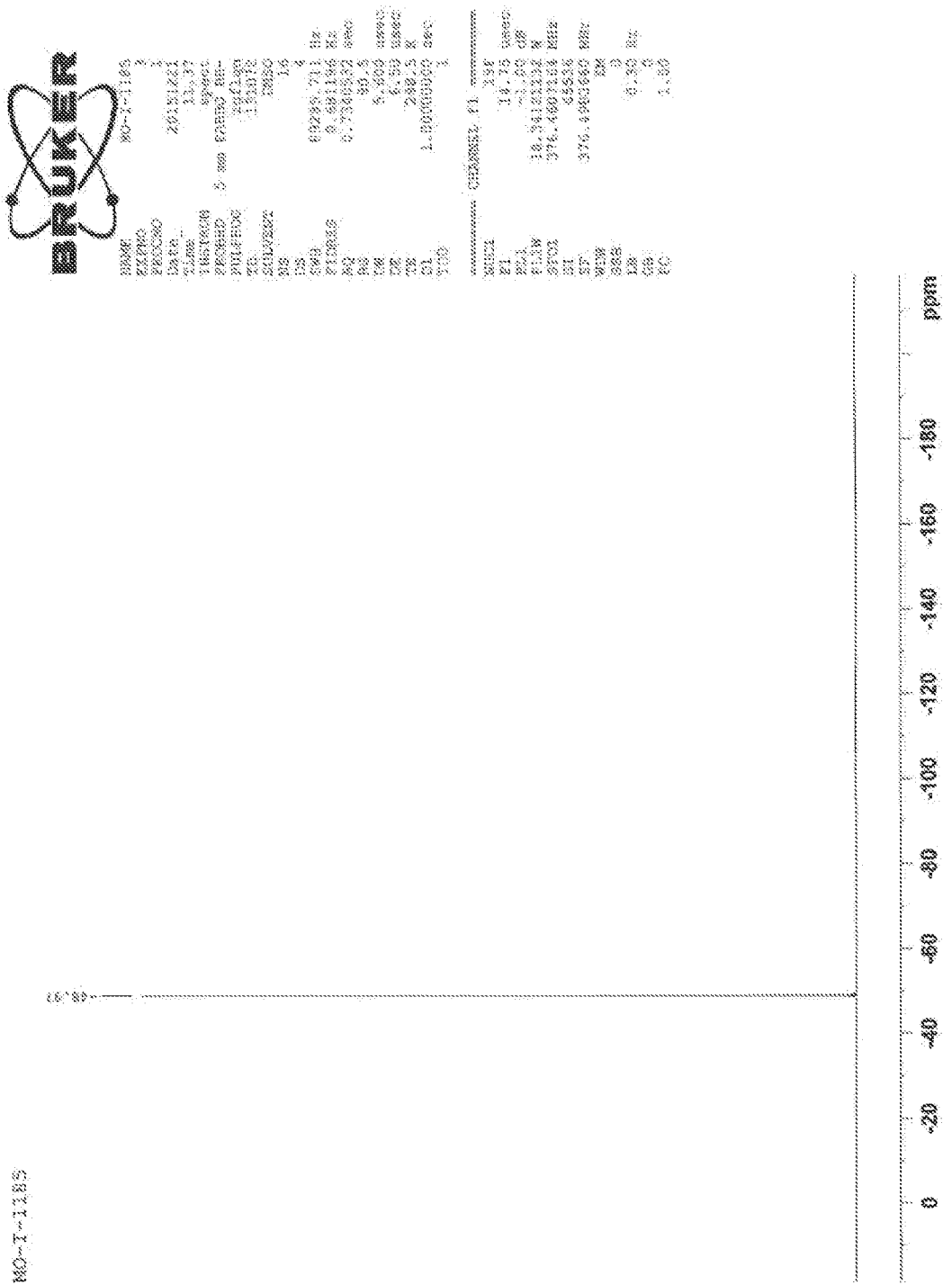
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60:
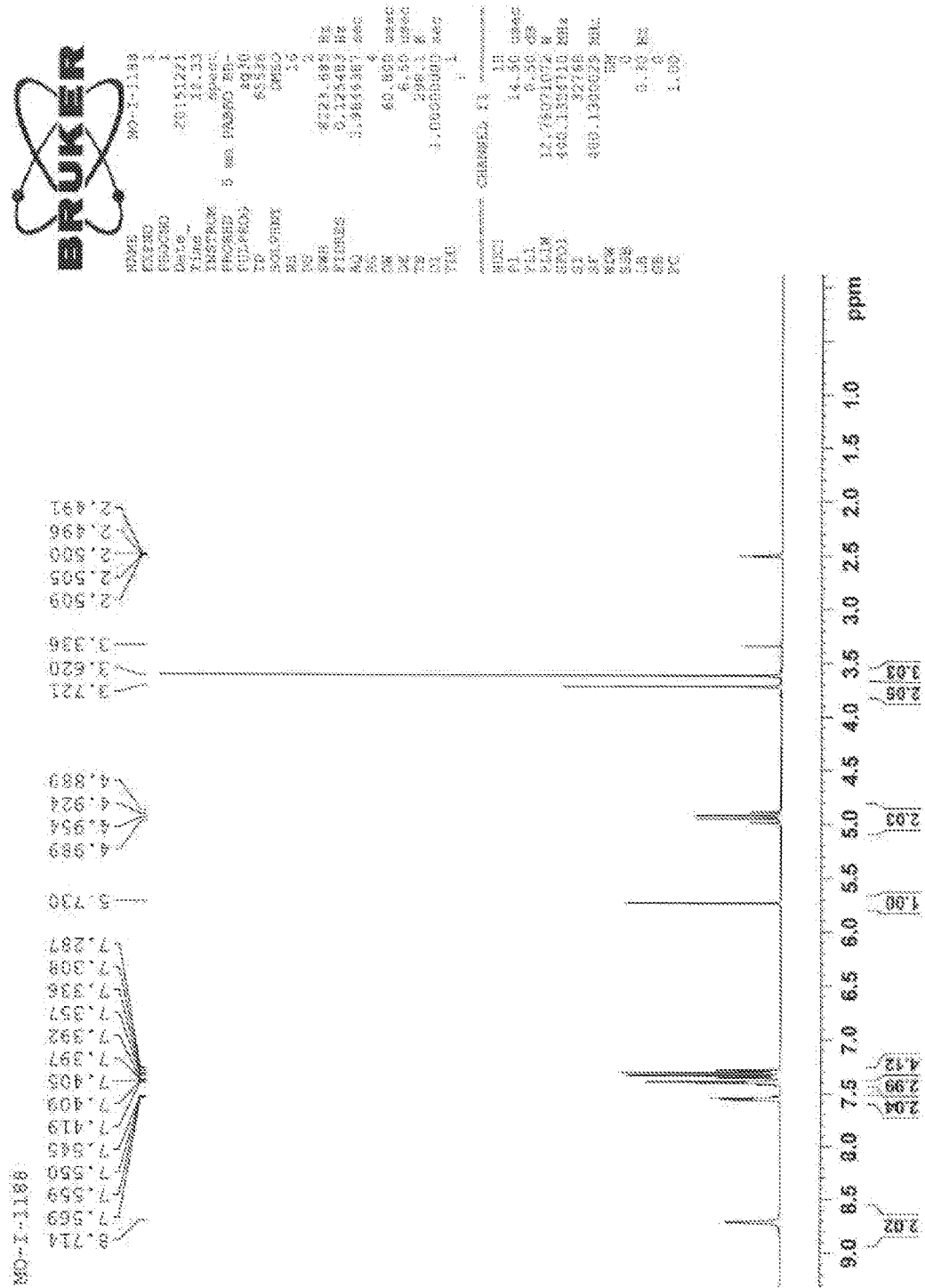
Figures 10, 61:
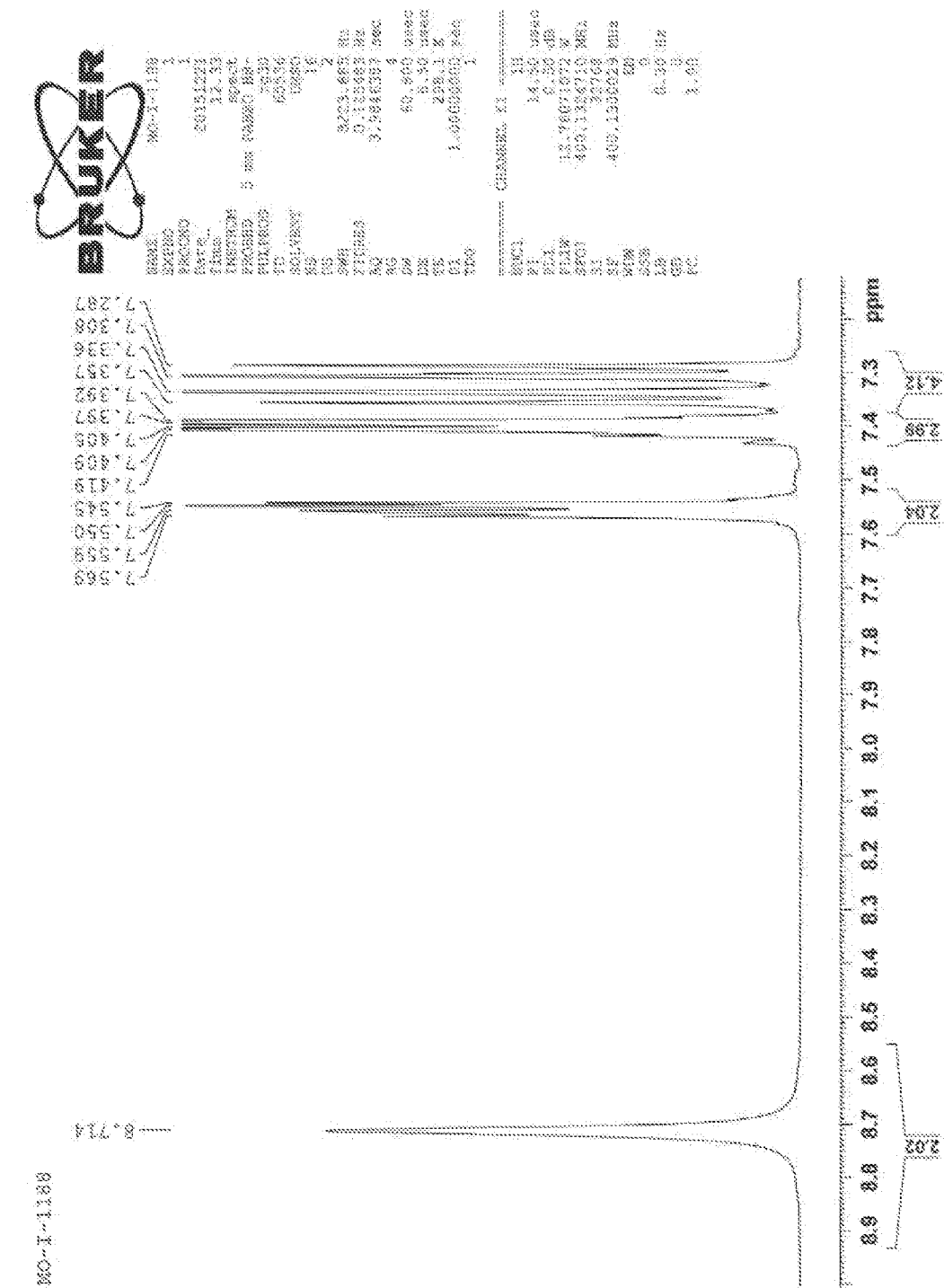

FIG. 8 illustrates the Activities of Undeuterated, Racemic, and Deuterated Enantiomers of Tetronimide Modulator Compounds Against ASPH in Liver Microsome Assays.

Figure 9:
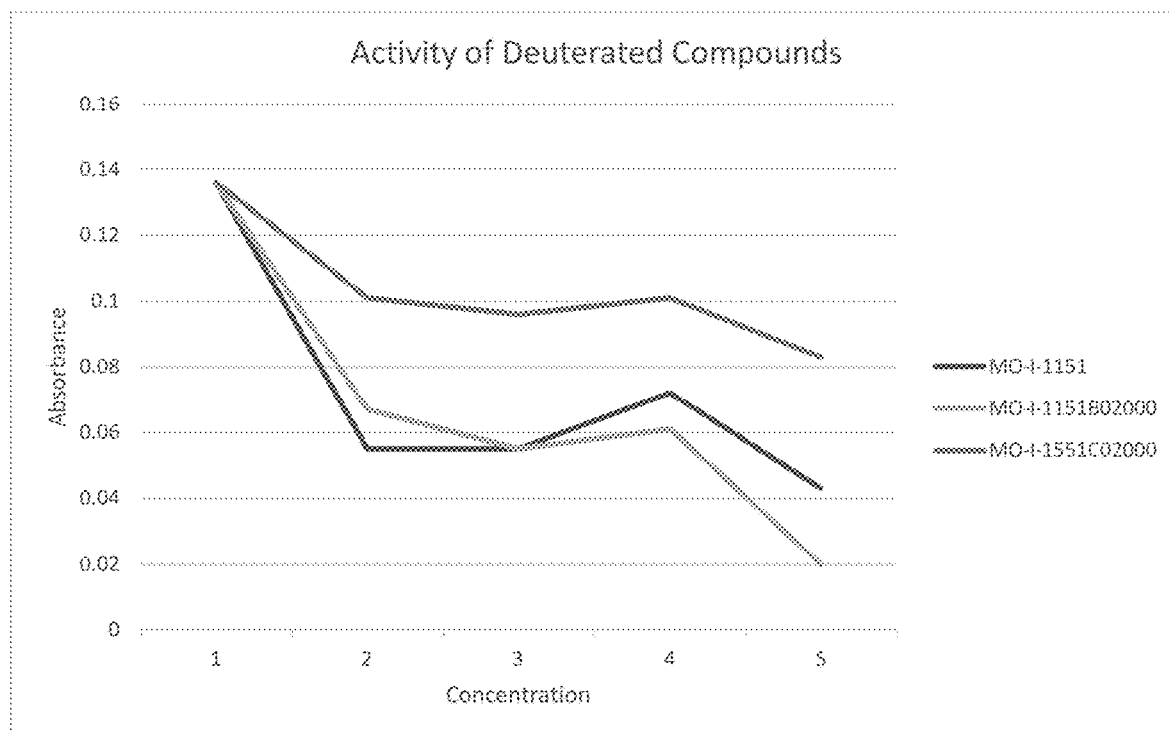

FIG. 9 illustrates the Activities of Specific Compounds Against MCF-7 Cells In Vitro.

Figures 10, 62:
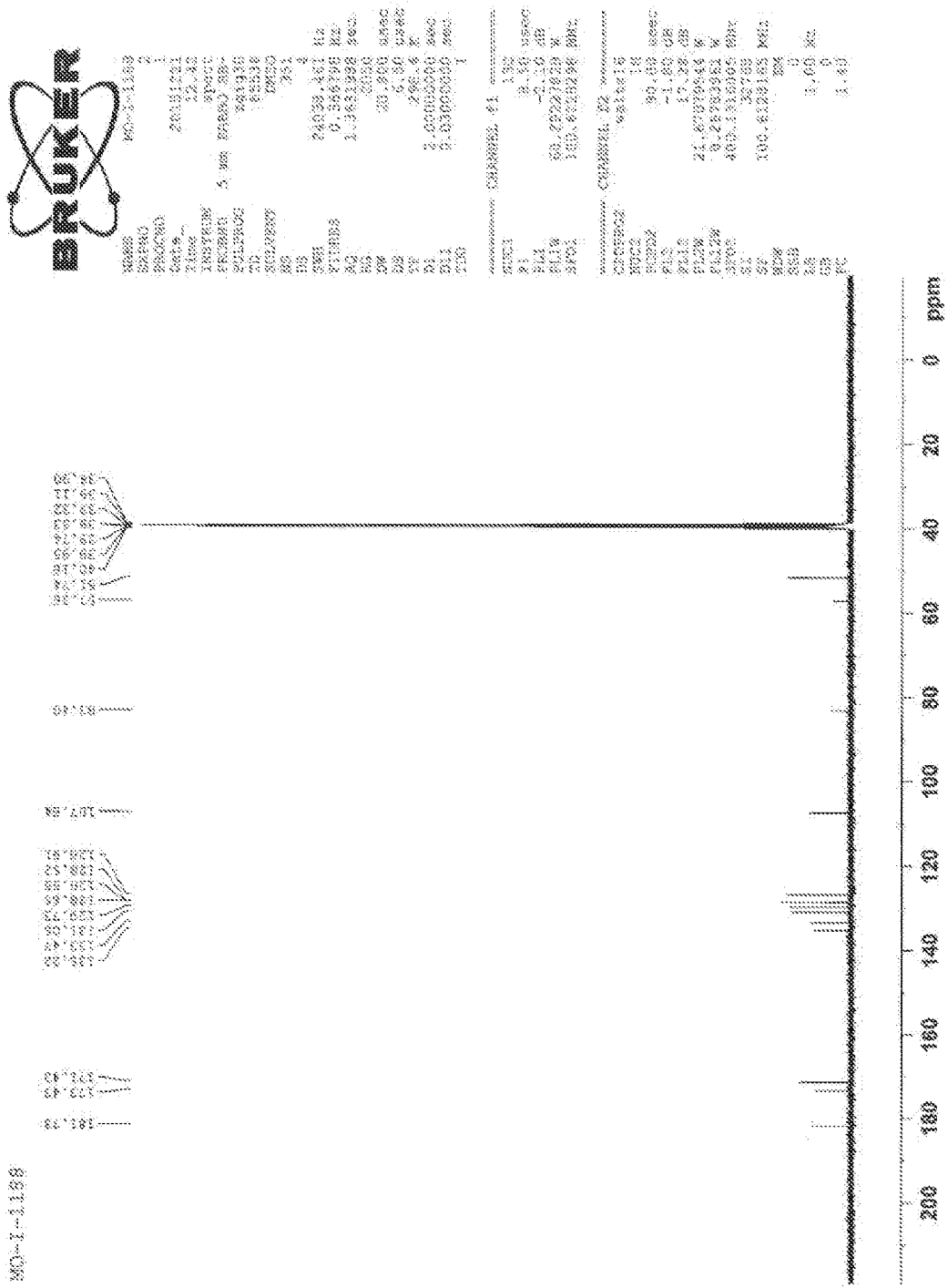

FIGS. 10-1 to 10-62 illustrate the raw and tabulated NMR spectra of 21 compounds over 62 pages for the compounds listed in Table 3, entitled "Table of Compounds by Informal Number and Chemical Name with NMR Spectra".

TERMS AND DEFINITIONS

The following is a list of abbreviations, plus terms and their definitions, used throughout the specification and the claims:

General abbreviations and their corresponding meanings include: aa or AA=amino acid; mg=milligram(s); ml or mL=milliliter(s); mm=millimeter(s); mM=millimolar; nmol=nanomole(s); pmol=picomole(s); ppm=parts per million; RT=room temperature; U=units; ug, µg=microgram(s); ul, µl=micro liter(s); uM, µM=micromolar, TEA=triethylamine, LDA=lithium diisopropyl amine, THF=tetrahydrofuran, DMAP=4-dimethylaminopyridine, DMF=N,N'-dimethylformamide.

Specific abbreviations and their corresponding meanings include:

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as a transgenic animal.

The term "modulator", which is meant to be inclusive, refers to one or more activities, such as stimulation of activity, inhibition of enzymatic activity, stimulation of protein expression, or suppression of protein expression. Common examples of stimulation of activity include allosteric activators. Common examples of inhibition of enzymatic activity include allosteric deactivators, competitive inhibitors, non-competitive inhibitors, and uncompetitive inhibitors. Common examples of stimulation of protein expression include kinase inhibitors or activators. Common examples of suppression of protein expression include kinase inhibitors or activators.

The term "amino acid" encompasses both naturally occurring and non-naturally occurring amino acids unless otherwise designated.

The phrase "isotopic enrichment factor" means the ratio between the isotopic abundance and the natural abundance of a specified isotope.

The term "isotopologue" means a species in which the chemical structure differs from a specific compound of the invention only in the isotopic composition thereof.

The symbols "D" and "d" mean deuterium.

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as an unmodified or a transgenic animal.

The term "an effective amount" means an amount of the substance in question which produces a statistically significant effect. For example, an "effective amount" for therapeutic uses is the amount of the composition comprising an active compound herein required to provide a clinically significant alteration in a measurable trait. Such effective amounts will be determined using routine optimization techniques and are dependent on the particular condition to be treated, the condition of the patient, the route of administration, dosage required for the compounds of the invention is manifested as that which induces a statistically significant difference between treatment and control groups.

A "therapeutically effective amount" refers to an amount effective, at dosages and for periods of time necessary, to achieve the desired therapeutic result. A therapeutically effective amount of modulator may vary according to factors such as the disease state, age, sex, and weight of the individual, and the ability of the modulator to elicit a desired response in the individual. Dosage regimens may be adjusted to provide the optimum therapeutic response. A therapeutically-effective amount is also one in which any toxic or detrimental effects of the modulator are outweighed by the therapeutically beneficial effects.

A "prophylactically effective amount" refers to an amount effective, at dosages and for periods of time necessary, to achieve the desired prophylactic result. A prophylactically effective amount can be determined as described above for the therapeutically-effective amount. Typically, since a prophylactic dose is used in subjects prior to or at an earlier stage of disease, the prophylactically effective amount will be less than the therapeutically-effective amount.

As used herein, the term "cell proliferative disorder" refers to conditions in which unregulated or abnormal growth, or both, of cells can lead to the development of an unwanted condition or disease, which may or may not be cancerous. Exemplary cell proliferative disorders that may be treated with the compounds of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. The methods and uses provided herein can be or may be used to treat or alleviate a symptom of cancer or to identify suitable candidates for such purposes. The term "cancer" includes solid tumors, as well as, hematologic tumors and/or malignancies. A "precancer cell" or "precancerous cell" is a cell manifesting a cell proliferative disorder that is a pre-cancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, prodrug, metabolite, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

As used herein, the term "alleviate" is meant to describe a process by which the severity of a sign or symptom of a disorder is decreased. Importantly, a sign or symptom can be alleviated without being eliminated. The administration of pharmaceutical compositions of the invention can or may lead to the elimination of a sign or symptom, however, elimination is not required. Effective dosages should be expected to decrease the severity of a sign or symptom. For instance, a sign or symptom of a disorder such as cancer, which can occur in multiple locations, is alleviated if the severity of the cancer is decreased within at least one of multiple locations.

As used herein, a "subject" is interchangeable with a "subject in need thereof", both of which refer to a subject having a cell proliferation disorder, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one aspect, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. The term "animal" includes human beings.

The term "optionally substituted" moiety refers to either unsubstituted chemical moiety (e.g., alkyl, aryl, heteroaryl, etc.) or a chemical moiety having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "substituted aryl or heteroaryl" refers to aromatic or heteroaromatic rings may contain one or more substituents such as —OH, SH, —CN, —F, —C, —Br, —R, —NO$_2$—NO, —NH$_2$, —NHR, —NRR, —C(O)R, —C(O)OH, —C(O)OR, —C(O)NH$_2$, —C(O)NHR, —C(O)NRR, and the like where each R is independently (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl or substituted 6-26 membered heteroarylalkyl.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

A "derivative" of a compound X (e.g., a peptide or amino acid) refers to a form of X in which one or more reactive groups on the compound have been derivatized with a substituent group. Peptide derivatives include pep tides in which an amino acid side chain, the peptide backbone, or the amino' or carboxy-terminus has been derivatized (e.g., peptidic compounds with 5 methylated amide linkages).

An "analogue" of a compound X refers to a compound which retains chemical structures of X necessary for functional activity of X yet which also contains certain chemical structures which differ from X. An analogue of a naturally-occurring peptide, is a peptide which includes one or more non-naturally-occurring amino acids.

The term "mimetic refers to a compound having similar functional and/or structural properties to another known compound or a particular fragment of that known compound. A "mimetic" of a compound X refers to a compound in which chemical structures of X necessary for functional activity of X have been replaced with other chemical structures which mimic the conformation of X. The term mimetic, and in particular, peptidomimetic, is intended to include isosteres.

The term "cyclic group", as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with halogens, alkyls, cycloalkyls, alkenyls, alkynyls, aryls, heterocycles, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, CF$_3$, CN, or the like.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine and pyridine. The heterocyclic ring can be substituted at one or more positions with such substituents as, for example, halogens, alkyls, cycloalkyls, alkenyls, alkynyls, aryls, other heterocycles, hydroxyl, amino, nitro thiol, amines, imines, amides, phosphonates, phosphines, carbonyls, carboxyls, silyls, ethers, thioethers, sulfonyls, selenoethers, ketones, aldehydes, esters, CF$_3$, CN, or the like. Heterocycles may also be bridged or fused to other cyclic groups as described below.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

The term "polycyclic group" as used herein is intended to refer to two or more saturated or unsaturated (i.e., aromatic) cyclic rings in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, $CF_3$, CN, or the like.

As used herein, the term "modulating group" and "modifying group" are used interchangeably to describe a chemical group directly or indirectly attached, generally, to a peptidic structure. For example, a modifying group(s) can be directly attached by covalent coupling to a peptide structure or a modifying group(s) can be attached indirectly by a stable non-covalent association.

The compounds described herein include the compounds themselves, as well as their salts, their solvates, and their prodrugs, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Examples of prodrugs include esters and other pharmaceutically acceptable derivatives, which, upon administration to a subject, are capable of providing active substituted benzene compounds.

The compounds of the present invention, for example, the salts of the compounds, can also exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The structural formula of the compound generally represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of ketone-enol tautomerism in the tetronimide ring system is illustrated below.

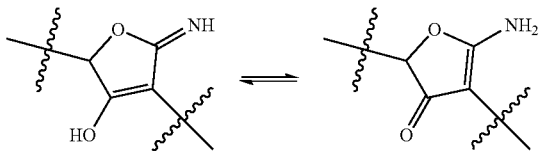 [SMILES: *C1=C(O)C(*)OC1=N ; *C1=C(N)OC(*)C1=O]

A small molecule is a compound that is less than 2000 Daltons in mass. The molecular mass of the small molecule is preferably less than 1000 Daltons, more preferably less than 600 Daltons, e.g., the compound is less than 500 Daltons, 400 Daltons, 300 Daltons, 200 Daltons, or 100 Daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Compounds such as small molecule inhibitors, polynucleotides, polypeptides, or other agents are purified and/or isolated. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. An "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified also defines a degree of sterility that is safe for administration to a human subject, e.g., lacking infectious or toxic agents.

DETAILED DESCRIPTION

One aspect of the invention is directed to a deuterated compound of any one of formulas {I-A, I-B, I-C, I-D, I-E, I-F, I-G, or I-H}:

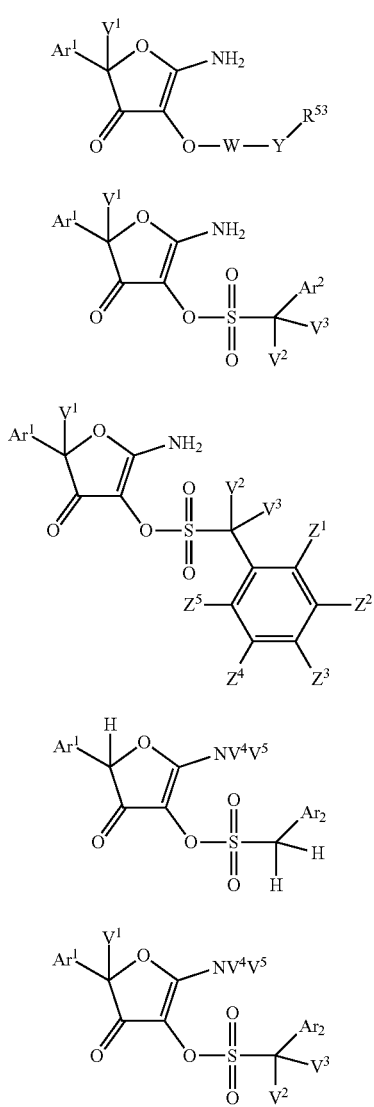

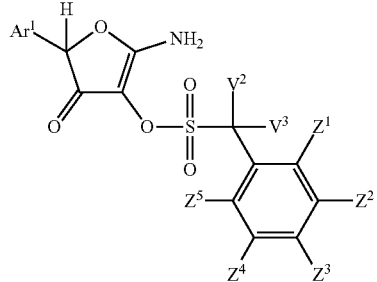

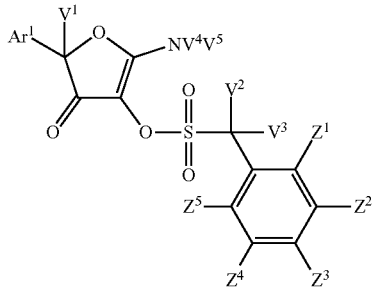

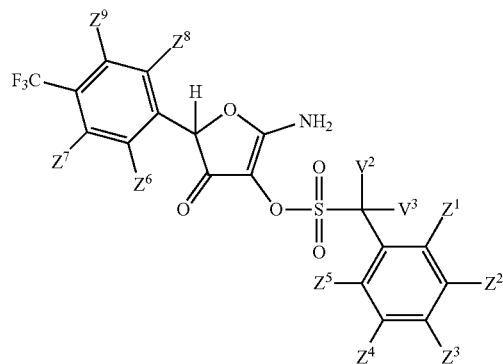

or a salt, ester, metabolite, prodrug, or solvate thereof, wherein $Ar^1$ is a substituted or unsubstituted $C_6$-$C_{20}$ aryl or 5- to 20-membered heteroaryl;

wherein at least one of $V^1$, $V^2$, $V^3$, $V^4$, $V^5$, or $Z^1$, $Z^2$, $Z^3$, $Z^4$, $Z^5$, $Z^6$, $Z^7$, $Z^8$, or $Z^9$ is a deuterium atom (D) and any atom not designated as deuterium is present as hydrogen (H, or not shown) at its natural isotopic abundance;

wherein W is C(O), C(S), or S(O)$_2$;

wherein Y is a single bond, O, $CR^{50}R^{51}$, or $NR^{52}$ when W is CO and W is a single bond, $CR^{50}R^{51}$ or $NR^{52}$ when X is SO$_2$, and wherein $R^{53}$ is selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 20-membered heteroaryl, and substituted or unsubstituted 6-26 membered heteroarylalkyl; and wherein $Ar^2$, designated as an unsubstituted or substituted $C_6$-$C_{20}$ heteroaryl is selected from the group consisting of: phenyl; naphthyl; pyridyl; pyridone; pyrimidine; pyradazine; pyrazine; purine; furan; thiophene; oxazole; thiazole; isoxazole; isothiazole; oxadiazole; thiadiazole; pyrrole; imidazole; triazole; tetrazole; and diazepine.

Another aspect is directed to a deuterated compound having formula {I-A},

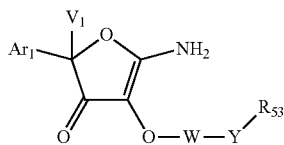

(I-A)

or a salt, ester, metabolite, prodrug, or solvate thereof, wherein $V^1$ is deuterium (D) and any atom not designated as deuterium is present as hydrogen (H, or not shown) at its natural isotopic abundance.

Another aspect is directed to a deuterated compound having formula {I-B},

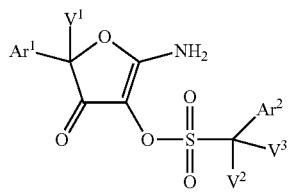

{I-B} or a salt, ester, metabolite, prodrug, or solvate thereof, wherein at least one of $V^1$, $V^2$, and $V^3$ is a deuterium atom (D) and any atom not designated as deuterium is present as hydrogen (H, or not shown) at its natural isotopic abundance;

Another aspect is directed to a deuterated compound having formula {I-C},

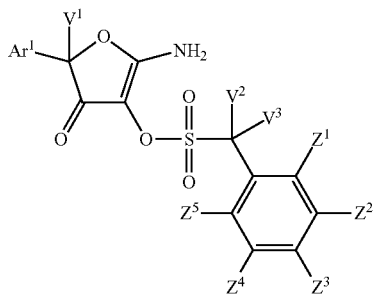

{I-C} or a salt, ester, metabolite, prodrug, or solvate thereof, wherein at least one of $V^1$, $V^2$, $V^3$, or $Z^1$, $Z^2$, $Z^3$, $Z^4$, and $Z^5$ is a deuterium atom (D) and any atom not designated as deuterium is present as hydrogen (H, or not shown) at its natural isotopic abundance.

Another aspect is directed to a deuterated compound having formula {I-D},

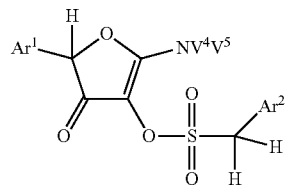

{I-D} or a salt, ester, metabolite, prodrug, or solvate thereof, wherein at least one of $V^4$ or $V^5$ is a deuterium atom (D) and any atom not designated as deuterium is present as hydrogen (H, or not shown) at its natural isotopic abundance.

Another aspect is directed to a deuterated compound having formula {I-E},

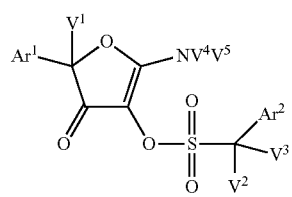

{I-E} or a salt, ester, metabolite, prodrug, or solvate thereof, wherein at least one of $V^1$, $V^2$, $V^3$, $V^4$, or $V^5$ is a deuterium atom (D) and any atom not designated as deuterium is present as hydrogen (H, or not shown) at its natural isotopic abundance.

Another aspect is directed to a deuterated compound having formula {I-F},

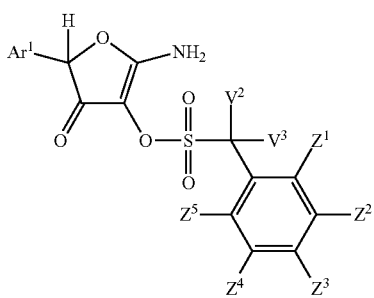

{I-F} or a salt, ester, metabolite, prodrug, or solvate thereof, wherein at least one of $V^2$, $V^3$, or $Z^1$, $Z^2$, $Z^3$, $Z^4$, or $Z^5$ is a deuterium atom (D) and any atom not designated as deuterium is present as hydrogen (H, or not shown) at its natural isotopic abundance.

Another aspect is directed to a deuterated compound having formula {I-G},

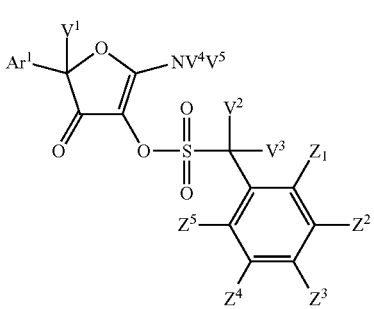

{I-G} or a salt, ester, metabolite, prodrug, or solvate thereof, wherein at least one of $V^1$, $V^2$, $V^3$, $V^4$, $V^5$, or $Z^1$, $Z^2$, $Z^3$, $Z^4$, $Z^5$ is a deuterium atom (D) and any atom not designated as deuterium is present as hydrogen (H, or not shown) at its natural isotopic abundance.

Another aspect is directed to a deuterated compound having formula {I-H},

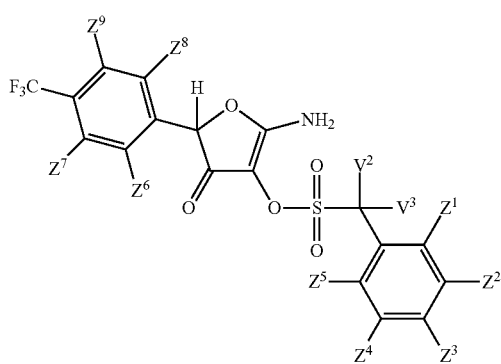

{I-H} or a salt, ester, metabolite, prodrug, or solvate thereof, wherein at least one of $V^2$, $V^3$, $Z^1$, $Z^2$, $Z^3$, $Z^4$, $Z^5$, $Z^6$, $Z^7$, $Z^8$, or $Z^9$ is a deuterium atom (D) and any atom not designated as deuterium is present as hydrogen (H, or not shown) at its natural isotopic abundance.

Another aspect relates to a deuterated compound having any one of formulas {I-A, I-B, I-C, I-D, I-E, I-F, or I-G} wherein $Ar^1$ is a substituted $C_6$-$C_{20}$ aryl group selected from the group consisting of one or more substituents selected from the group consisting of mono F, Cl, or Br at any position; difluoro or dichloro at different positions; mono and di methyl any position; mono di and trifluoromethyl; mono and di OMe at any position; mono and di chlorophenyl at any position; $CO_2Me$; F and $CO_2Me$; $CO_2Et$; $C(O)CH_3$; $C(O)NH_2$; $C(O):ND_2$; $COO^-Na^+$; $COO^-K^+$; $[COO^-]_2Mg^{+2}$; $[COO^-]_2Ca^{+2}$; mono and di CN at different positions; phenyl; $CF_3$; $CO_3Me$; $CO_2Et$; $CO_2D$; $CO_2Me$ and F; $CF_3$; $CO_2Me$; $CO_2Et$; $CO_2D$; $CO_2Me$; benzo[d][1,3]dixol-5-yl; and difluorobenzo[d][1,3]dixol-5-yl.

Another aspect relates to a deuterated compound having formula {I-A}, wherein $R^{53}$ is $Ar^2$, designated as an unsubstituted or substituted $C_6$-$C_{20}$ heteroaryl selected from the group consisting of: phenyl; naphthyl; pyridyl; pyridone; pyrimidine; pyradazine; pyrazine; purine; furan; thiophene; oxazole; thiazole; isoxazole; isothiazole; oxadiazole; thiadiazole; pyrrole; imidazole; triazole; tetrazole; and diazepine.

Another aspect relates to a deuterated compound having formula {I-A}, wherein $R^{53}$ is an unsubstituted or substituted phenyl, selected from the group consisting of one or more substituents selected from the group consisting of: mono F, C, or Br at any position; difluoro or dichloro at different positions; mono and di methyl any position; mono di and trifluoromethyl; mono and di OMe at any position; mono and di chlorophenyl at any position; $CO_2Me$; F and $CO_2Me$; $CO_2Et$; $C(O)CH_3$; $C(O)NH_2$; $C(O):ND_2$; $COO^-Na^+$; $COO^-K^+$; $[COO^-]_2Mg^{+2}$; $[COO^-]_2Ca^{+2}$; mono and di CN at different positions; phenyl; $CF_3$; $CO_3Me$; $CO_2D$; $CF_3$; $CO_2Me$; benzo[d][1,3]dixol-5-yl; and difluorobenzo[d][1,3]dixol-5-yl.

Another aspect relates to a deuterated compound wherein any atom not designated as deuterium is present at its natural isotopic abundance, and where the percentage of isotopic enrichment for each designated deuterium is at least 50%. Related aspects also include compounds where the enrichment for each designated deuterium is at least 75%, 90%, 95%, and 99%.

Another aspect of the invention relates to a method of preparing a deuterated compound having any of formulas {I-A, I-B, I-C, I-F} by contacting an undeuterated precursor compound with a suitable base and a deuterated solvent. In one aspect, said suitable base is selected from the group consisting of LiOD, NaOD, KOD, CsOD, Ba(OD)$_2$, Ca(OD)$_2$, Mg(OD)$_2$, Mn(OD)$_2$, Li$_2$CO$_3$, Na$_2$CO$_3$, K$_2$CO$_3$, Cs$_2$CO$_3$, MgCO$_3$, and CaCO$_3$. In another aspect, said deuterated solvent is D$_2$O.

Another aspect relates to a method of preparing a deuterated compound having formula {I-D}, by contacting an undeuterated precursor compound with deuterium in an acidic medium. In one aspect, said deuterium in an acidic medium is selected from the group consisting of one or more of D$_2$O, DF, DCl, DBr, DI, D$_2$NO$_3$, D$_2$SO$_4$, CF$_3$SO$_3$D, CD$_3$CO$_2$D, CF$_3$CO$_2$D, CCl$_3$CO$_2$D.

Another aspect relates to a method of preparing a deuterated compound having any one of formulas {I-E, I-G}, by contacting an undeuterated precursor compound with an acidic medium followed by a deuterated basic medium. In one aspect, said acidic medium is selected from the group consisting of one or more of D$_2$O, DF, DCl, DBr, DI, D$_2$NO$_3$, D$_2$SO$_4$, CF$_3$SO$_3$D, CD$_3$CO$_2$D, CF$_3$CO$_2$D, CCl$_3$CO$_2$D. In another aspect said deuterated basic medium is selected from the group consisting of LiOD, NaOD, KOD, Ba(OD)$_2$, Ca(OD)$_2$, Mg(OD)$_2$, Mn(OD)$_2$, Li$_2$CO$_3$, Na$_2$CO$_3$, K$_2$CO$_3$, Cs$_2$CO$_3$, MgCO$_3$, and CaCO$_3$.

Another aspect relates to a method of preparing a deuterated compound of Claim 1 having any one of formulas {I-F, I-H}, by contacting an undeuterated precursor tetronimide compound with a deuterated sulfonyl chloride. In one aspect, said deuterated sulfonyl chloride is selected from the group consisting of d5-sulfonyl chloride and d7-sulfonyl chloride.

Specific aspects of the invention include a deuterated compound selected from the group consisting of racemic and (R) and (S) forms of a compound selected from the group consisting of:

2001 2-amino-5-(4-chlorophenyl)-4-oxo-4,5-dihydrofuran-3-yl-5-d methanesulfonate-d3;
2001(R) (R)-2-amino-5-(4-chlorophenyl)-4-oxo-4,5-dihydrofuran-3-yl-5-d methanesulfonate-d3;
2001(S) (S)-2-amino-5-(4-chlorophenyl)-4-oxo-4,5-dihydrofuran-3-yl-5-d methanesulfonate-d3;
2002 2-amino-5-(4-chlorophenyl)-4-oxo-4,5-dihydrofuran-3-yl-5-d ethane-1-sulfonate-1,1-d2;
2002(R) (R)-2-amino-5-(4-chlorophenyl)-4-oxo-4,5-dihydrofuran-3-yl-5-d ethane-1-sulfonate-1,1-d2;
2002(S) (S)-2-amino-5-(4-chlorophenyl)-4-oxo-4,5-dihydrofuran-3-yl-5-d ethane-1-sulfonate-1,1-d2;
2003 2-amino-5-(4-chlorophenyl)-4-oxo-4,5-dihydrofuran-3-yl-5-d propane-1-sulfonate-1,1-d2;
2003(R) (R)-2-amino-5-(4-chlorophenyl)-4-oxo-4,5-dihydrofuran-3-yl-5-d propane-1-sulfonate-1,1-d2;
2003(S) (S)-2-amino-5-(4-chlorophenyl)-4-oxo-4,5-dihydrofuran-3-yl-5-d propane-1-sulfonate-1,1-d2;
2004 2-amino-5-(4-chlorophenyl)-4-oxo-4,5-dihydrofuran-3-yl-5-d propane-2-sulfonate-2-d;
2004(R) (R)-2-amino-5-(4-chlorophenyl)-4-oxo-4,5-dihydrofuran-3-yl-5-d propane-2-sulfonate-2-d;
2004(S) (S)-2-amino-5-(4-chlorophenyl)-4-oxo-4,5-dihydrofuran-3-yl-5-d propane-2-sulfonate-2-d;
2005 2-amino-5-(4-chlorophenyl)-4-oxo-4,5-dihydrofuran-3-yl-5-d butane-1-sulfonate-1,1-d2;
2005(R) (R)-2-amino-5-(4-chlorophenyl)-4-oxo-4,5-dihydrofuran-3-yl-5-d butane-1-sulfonate-1,1-d2;

2005(S) (S)-2-amino-5-(4-chlorophenyl)-4-oxo-4,5-dihydrofuran-3-yl-5-d butane-1-sulfonate-1,1-d2;
2006 2-amino-5-(4-chlorophenyl)-4-oxo-4,5-dihydrofuran-3-yl-5-d 2-methylpropane-1-sulfonate-1,1-d2;
2006(R) (R)-2-amino-5-(4-chlorophenyl)-4-oxo-4,5-dihydrofuran-3-yl-5-d 2-methylpropane-1-sulfonate-1,1-d2;
2006(S) (S)-2-amino-5-(4-chlorophenyl)-4-oxo-4,5-dihydrofuran-3-yl-5-d 2-methylpropane-1-sulfonate-1,1-d2;
2007 2-amino-5-(4-chlorophenyl)-4-oxo-4,5-dihydrofuran-3-yl-5-d benzenesulfonate;
2007(R) (R)-2-amino-5-(4-chlorophenyl)-4-oxo-4,5-dihydrofuran-3-yl-5-d benzenesulfonate;
2007(S) (S)-2-amino-5-(4-chlorophenyl)-4-oxo-4,5-dihydrofuran-3-yl-5-d benzenesulfonate;
2008 2-amino-5-(4-chlorophenyl)-4-oxo-4,5-dihydrofuran-3-yl-5-d phenylmethanesulfonate-d2;
2008(R) (R)-2-amino-5-(4-chlorophenyl)-4-oxo-4,5-dihydrofuran-3-yl-5-d phenylmethanesulfonate-d2;
2008(S) (S)-2-amino-5-(4-chlorophenyl)-4-oxo-4,5-dihydrofuran-3-yl-5-d phenylmethanesulfonate-d2;
2009 2-amino-5-(2-chlorophenyl)-4-oxo-4,5-dihydrofuran-3-yl-5-d phenylmethanesulfonate-d2;
2009(R) (R)-2-amino-5-(2-chlorophenyl)-4-oxo-4,5-dihydrofuran-3-yl-5-d phenylmethanesulfonate-d2;
2009(S) (S)-2-amino-5-(2-chlorophenyl)-4-oxo-4,5-dihydrofuran-3-yl-5-d phenylmethanesulfonate-d2;
2010 2-amino-5-(3-chlorophenyl)-4-oxo-4,5-dihydrofuran-3-yl-5-d phenylmethanesulfonate-d2;
2010(R) (R)-2-amino-5-(3-chlorophenyl)-4-oxo-4,5-dihydrofuran-3-yl-5-d phenylmethanesulfonate-d2;
2010(S) (S)-2-amino-5-(3-chlorophenyl)-4-oxo-4,5-dihydrofuran-3-yl-5-d phenylmethanesulfonate-d2;
2011 2-amino-5-(2,3-dichlorophenyl)-4-oxo-4,5-dihydrofuran-3-yl-5-d phenylmethanesulfonate-d2;
2011(R) (R)-2-amino-5-(2,3-dichlorophenyl)-4-oxo-4,5-dihydrofuran-3-yl-5-d phenylmethanesulfonate-d2;
2011(S) (S)-2-amino-5-(2,3-dichlorophenyl)-4-oxo-4,5-dihydrofuran-3-yl-5-d phenylmethanesulfonate-d2;
2012 2-amino-5-(2,4-dichlorophenyl)-4-oxo-4,5-dihydrofuran-3-yl-5-d phenylmethanesulfonate-d2;
2012(R) (R)-2-amino-5-(2,4-dichlorophenyl)-4-oxo-4,5-dihydrofuran-3-yl-5-d phenylmethanesulfonate-d2;
2012(S) (S)-2-amino-5-(2,4-dichlorophenyl)-4-oxo-4,5-dihydrofuran-3-yl-5-d phenylmethanesulfonate-d2;
2013 2-amino-5-(2,5-dichlorophenyl)-4-oxo-4,5-dihydrofuran-3-yl-5-d phenylmethanesulfonate-d2;
2013(R) (R)-2-amino-5-(2,5-dichlorophenyl)-4-oxo-4,5-dihydrofuran-3-yl-5-d phenylmethanesulfonate-d2;
2013(S) (S)-2-amino-5-(2,5-dichlorophenyl)-4-oxo-4,5-dihydrofuran-3-yl-5-d phenylmethanesulfonate-d2;
2014 2-amino-5-(3,4-dichlorophenyl)-4-oxo-4,5-dihydrofuran-3-yl-5-d phenylmethanesulfonate-d2;
2014(R) (R)-2-amino-5-(3,4-dichlorophenyl)-4-oxo-4,5-dihydrofuran-3-yl-5-d phenylmethanesulfonate-d2;
2014(S) (S)-2-amino-5-(3,4-dichlorophenyl)-4-oxo-4,5-dihydrofuran-3-yl-5-d phenylmethanesulfonate-d2;
2015 2-amino-5-(3,5-dichlorophenyl)-4-oxo-4,5-dihydrofuran-3-yl-5-d phenylmethanesulfonate-d2;
2015(R) (R)-2-amino-5-(3,5-dichlorophenyl)-4-oxo-4,5-dihydrofuran-3-yl-5-d phenylmethanesulfonate-d2;
2015(S) (S)-2-amino-5-(3,5-dichlorophenyl)-4-oxo-4,5-dihydrofuran-3-yl-5-d phenylmethanesulfonate-d2;
2016 methyl 3-(5-amino-3-oxo-4-(((phenylmethyl-d2)sulfonyl)oxy)-2,3-dihydrofuran-2-yl-2-d)benzoate;
2016(R) methyl (R)-3-(5-amino-3-oxo-4-(((phenylmethyl-d2)sulfonyl)oxy)-2,3-dihydrofuran-2-yl-2-d)benzoate;
2016(S) methyl (S)-3-(5-amino-3-oxo-4-(((phenylmethyl-d2)sulfonyl)oxy)-2,3-dihydrofuran-2-yl-2-d)benzoate;
2017 methyl 4-(5-amino-3-oxo-4-(((phenylmethyl-d2)sulfonyl)oxy)-2,3-dihydrofuran-2-yl-2-d)benzoate;
2017(R) methyl (R)-4-(5-amino-3-oxo-4-(((phenylmethyl-d2)sulfonyl)oxy)-2,3-dihydrofuran-2-yl-2-d)benzoate;
2017(S) methyl (S)-4-(5-amino-3-oxo-4-(((phenylmethyl-d2)sulfonyl)oxy)-2,3-dihydrofuran-2-yl-2-d)benzoate;
2018 methyl 4-(5-amino-3-oxo-4-(((phenylmethyl-d2)sulfonyl)oxy)-2,3-dihydrofuran-2-yl-2-d)-2-fluorobenzoate;
2018(R) methyl (R)-4-(5-amino-3-oxo-4-(((phenylmethyl-d2)sulfonyl)oxy)-2,3-dihydrofuran-2-yl-2-d)-2-fluorobenzoate;
2018(S) methyl (S)-4-(5-amino-3-oxo-4-(((phenylmethyl-d2)sulfonyl)oxy)-2,3-dihydrofuran-2-yl-2-d)-2-fluorobenzoate;
2019 ethyl 4-(5-amino-3-oxo-4-(((phenylmethyl-d2)sulfonyl)oxy)-2,3-dihydrofuran-2-yl-2-d)benzoate;
2019(R) ethyl (R)-4-(5-amino-3-oxo-4-(((phenylmethyl-d2)sulfonyl)oxy)-2,3-dihydrofuran-2-yl-2-d)benzoate;
2019(S) ethyl (S)-4-(5-amino-3-oxo-4-(((phenylmethyl-d2)sulfonyl)oxy)-2,3-dihydrofuran-2-yl-2-d)benzoate;
2020 5-(4-acetylphenyl)-2-amino-4-oxo-4,5-dihydrofuran-3-yl-5-d phenylmethanesulfonate-d2;
2020(R) (R)-5-(4-acetylphenyl)-2-amino-4-oxo-4,5-dihydrofuran-3-yl-5-d phenylmethanesulfonate-d2;
2020(S) (S)-5-(4-acetylphenyl)-2-amino-4-oxo-4,5-dihydrofuran-3-yl-5-d phenylmethanesulfonate-d2;
2021 2-amino-5-(4-carbamoylphenyl)-4-oxo-4,5-dihydrofuran-3-yl-5-d phenylmethanesulfonate-d2;
2021(R) (R)-2-amino-5-(4-carbamoylphenyl)-4-oxo-4,5-dihydrofuran-3-yl-5-d phenylmethanesulfonate-d2;
2021(S) (S)-2-amino-5-(4-carbamoylphenyl)-4-oxo-4,5-dihydrofuran-3-yl-5-d phenylmethanesulfonate-d2;
2022 4-(5-amino-3-oxo-4-(((phenylmethyl-d2)sulfonyl)oxy)-2,3-dihydrofuran-2-yl-2-d)benzoic acid-d;
2022(R) (R)-4-(5-amino-3-oxo-4-(((phenylmethyl-d2)sulfonyl)oxy)-2,3-dihydrofuran-2-yl-2-d)benzoic acid-d;
2022(S) (S)-4-(5-amino-3-oxo-4-(((phenylmethyl-d2)sulfonyl)oxy)-2,3-dihydrofuran-2-yl-2-d)benzoic acid-d;
2023 sodium 4-(5-amino-3-oxo-4-(((phenylmethyl-d2)sulfonyl)oxy)-2,3-dihydrofuran-2-yl-2-d)benzoate;
2023(R) sodium (R)-4-(5-amino-3-oxo-4-(((phenylmethyl-d2)sulfonyl)oxy)-2,3-dihydrofuran-2-yl-2-d)benzoate;
2023(S) sodium (S)-4-(5-amino-3-oxo-4-(((phenylmethyl-d2)sulfonyl)oxy)-2,3-dihydrofuran-2-yl-2-d)benzoate;
2024 potassium 4-(5-amino-3-oxo-4-(((phenylmethyl-d2)sulfonyl)oxy)-2,3-dihydrofuran-2-yl-2-d)benzoate;
2024(R) potassium (R)-4-(5-amino-3-oxo-4-(((phenylmethyl-d2)sulfonyl)oxy)-2,3-dihydrofuran-2-yl-2-d)benzoate;
2024(S) potassium (S)-4-(5-amino-3-oxo-4-(((phenylmethyl-d2)sulfonyl)oxy)-2,3-dihydrofuran-2-yl-2-d)benzoate;
2027 2-amino-5-(2-fluorophenyl)-4-oxo-4,5-dihydrofuran-3-yl-5-d phenylmethanesulfonate-d2;
2027(R) (R)-2-amino-5-(2-fluorophenyl)-4-oxo-4,5-dihydrofuran-3-yl-5-d phenylmethanesulfonate-d2;
2027(S) (S)-2-amino-5-(2-fluorophenyl)-4-oxo-4,5-dihydrofuran-3-yl-5-d phenylmethanesulfonate-d2;
2028 2-amino-5-(3-fluorophenyl)-4-oxo-4,5-dihydrofuran-3-yl-5-d phenylmethanesulfonate-d2;
2028(R) (R)-2-amino-5-(3-fluorophenyl)-4-oxo-4,5-dihydrofuran-3-yl-5-d phenylmethanesulfonate-d2;
2028(S) (S)-2-amino-5-(3-fluorophenyl)-4-oxo-4,5-dihydrofuran-3-yl-5-d phenylmethanesulfonate-d2;

2029 2-amino-5-(4-fluorophenyl)-4-oxo-4,5-dihydrofuran-3-yl-5-d phenylmethanesulfonate-d2;
2029(R) (R)-2-amino-5-(4-fluorophenyl)-4-oxo-4,5-dihydrofuran-3-yl-5-d phenylmethanesulfonate-d2;
2029(S) (S)-2-amino-5-(4-fluorophenyl)-4-oxo-4,5-dihydrofuran-3-yl-5-d phenylmethanesulfonate-d2;
2030 2-amino-5-(2,3-difluorophenyl)-4-oxo-4,5-dihydrofuran-3-yl-5-d phenylmethanesulfonate-d2;
2030(R) (R)-2-amino-5-(2,3-difluorophenyl)-4-oxo-4,5-dihydrofuran-3-yl-5-d phenylmethanesulfonate-d2;
2030(S) (S)-2-amino-5-(2,3-difluorophenyl)-4-oxo-4,5-dihydrofuran-3-yl-5-d phenylmethanesulfonate-d2;
2031 2-amino-5-(2,4-difluorophenyl)-4-oxo-4,5-dihydrofuran-3-yl-5-d phenylmethanesulfonate-d2;
2031(R) (R)-2-amino-5-(2,4-difluorophenyl)-4-oxo-4,5-dihydrofuran-3-yl-5-d phenylmethanesulfonate-d2;
2031(S) (S)-2-amino-5-(2,4-difluorophenyl)-4-oxo-4,5-dihydrofuran-3-yl-5-d phenylmethanesulfonate-d2;
2032 2-amino-5-(2,5-difluorophenyl)-4-oxo-4,5-dihydrofuran-3-yl-5-d phenylmethanesulfonate-d2;
2032(R) (R)-2-amino-5-(2,5-difluorophenyl)-4-oxo-4,5-dihydrofuran-3-yl-5-d phenylmethanesulfonate-d2;
2032(S) (S)-2-amino-5-(2,5-difluorophenyl)-4-oxo-4,5-dihydrofuran-3-yl-5-d phenylmethanesulfonate-d2;
2033 2-amino-5-(2,6-difluorophenyl)-4-oxo-4,5-dihydrofuran-3-yl-5-d phenylmethanesulfonate-d2;
2033(R) (R)-2-amino-5-(2,6-difluorophenyl)-4-oxo-4,5-dihydrofuran-3-yl-5-d phenylmethanesulfonate-d2;
2033(S) (S)-2-amino-5-(2,6-difluorophenyl)-4-oxo-4,5-dihydrofuran-3-yl-5-d phenylmethanesulfonate-d2;
2034 2-amino-5-(3,4-difluorophenyl)-4-oxo-4,5-dihydrofuran-3-yl-5-d phenylmethanesulfonate-d2;
2034(R) (R)-2-amino-5-(3,4-difluorophenyl)-4-oxo-4,5-dihydrofuran-3-yl-5-d phenylmethanesulfonate-d2;
2034(S) (S)-2-amino-5-(3,4-difluorophenyl)-4-oxo-4,5-dihydrofuran-3-yl-5-d phenylmethanesulfonate-d2;
2035 2-amino-5-(3,5-difluorophenyl)-4-oxo-4,5-dihydrofuran-3-yl-5-d phenylmethanesulfonate-d2;
2035(R) (R)-2-amino-5-(3,5-difluorophenyl)-4-oxo-4,5-dihydrofuran-3-yl-5-d phenylmethanesulfonate-d2;
2035(S) (S)-2-amino-5-(3,5-difluorophenyl)-4-oxo-4,5-dihydrofuran-3-yl-5-d phenylmethanesulfonate-d2;
2036 2-amino-5-(2-methoxyphenyl)-4-oxo-4,5-dihydrofuran-3-yl-5-d phenylmethanesulfonate-d2;
2036(R) (R)-2-amino-5-(2-methoxyphenyl)-4-oxo-4,5-dihydrofuran-3-yl-5-d phenylmethanesulfonate-d2;
2036(S) (S)-2-amino-5-(2-methoxyphenyl)-4-oxo-4,5-dihydrofuran-3-yl-5-d phenylmethanesulfonate-d2;
2037 2-amino-5-(3-methoxyphenyl)-4-oxo-4,5-dihydrofuran-3-yl-5-d phenylmethanesulfonate-d2;
2037(R) (R)-2-amino-5-(3-methoxyphenyl)-4-oxo-4,5-dihydrofuran-3-yl-5-d phenylmethanesulfonate-d2;
2037(S) (S)-2-amino-5-(3-methoxyphenyl)-4-oxo-4,5-dihydrofuran-3-yl-5-d phenylmethanesulfonate-d2;
2038 2-amino-5-(4-methoxyphenyl)-4-oxo-4,5-dihydrofuran-3-yl-5-d phenylmethanesulfonate-d2;
2038(R) (R)-2-amino-5-(4-methoxyphenyl)-4-oxo-4,5-dihydrofuran-3-yl-5-d phenylmethanesulfonate-d2;
2038(S) (S)-2-amino-5-(4-methoxyphenyl)-4-oxo-4,5-dihydrofuran-3-yl-5-d phenylmethanesulfonate-d2;
2039 2-amino-5-(2,3-dimethoxyphenyl)-4-oxo-4,5-dihydrofuran-3-yl-5-d phenylmethanesulfonate-d2;
2039(R) (R)-2-amino-5-(2,3-dimethoxyphenyl)-4-oxo-4,5-dihydrofuran-3-yl-5-d phenylmethanesulfonate-d2;
2039(S) (S)-2-amino-5-(2,3-dimethoxyphenyl)-4-oxo-4,5-dihydrofuran-3-yl-5-d phenylmethanesulfonate-d2;
2040 2-amino-5-(2,4-dimethoxyphenyl)-4-oxo-4,5-dihydrofuran-3-yl-5-d phenylmethanesulfonate-d2;
2040(R) (R)-2-amino-5-(2,4-dimethoxyphenyl)-4-oxo-4,5-dihydrofuran-3-yl-5-d phenylmethanesulfonate-d2;
2040(S) (S)-2-amino-5-(2,4-dimethoxyphenyl)-4-oxo-4,5-dihydrofuran-3-yl-5-d phenylmethanesulfonate-d2;
2041 2-amino-5-(2,5-dimethoxyphenyl)-4-oxo-4,5-dihydrofuran-3-yl-5-d phenylmethanesulfonate-d2;
2041(R) (R)-2-amino-5-(2,5-dimethoxyphenyl)-4-oxo-4,5-dihydrofuran-3-yl-5-d phenylmethanesulfonate-d2;
2041(S) (S)-2-amino-5-(2,5-dimethoxyphenyl)-4-oxo-4,5-dihydrofuran-3-yl-5-d phenylmethanesulfonate-d2;
2042 2-amino-5-(2,6-dimethoxyphenyl)-4-oxo-4,5-dihydrofuran-3-yl-5-d phenylmethanesulfonate-d2;
2042(R) (R)-2-amino-5-(2,6-dimethoxyphenyl)-4-oxo-4,5-dihydrofuran-3-yl-5-d phenylmethanesulfonate-d2;
2042(S) (S)-2-amino-5-(2,6-dimethoxyphenyl)-4-oxo-4,5-dihydrofuran-3-yl-5-d phenylmethanesulfonate-d2;
2043 2-amino-5-(3,4-dimethoxyphenyl)-4-oxo-4,5-dihydrofuran-3-yl-5-d phenylmethanesulfonate-d2;
2043(R) (R)-2-amino-5-(3,4-dimethoxyphenyl)-4-oxo-4,5-dihydrofuran-3-yl-5-d phenylmethanesulfonate-d2;
2043(S) (S)-2-amino-5-(3,4-dimethoxyphenyl)-4-oxo-4,5-dihydrofuran-3-yl-5-d phenylmethanesulfonate-d2;
2044 2-amino-5-(3,5-dimethoxyphenyl)-4-oxo-4,5-dihydrofuran-3-yl-5-d phenylmethanesulfonate-d2;
2044(R) (R)-2-amino-5-(3,5-dimethoxyphenyl)-4-oxo-4,5-dihydrofuran-3-yl-5-d phenylmethanesulfonate-d2;
2044(S) (S)-2-amino-5-(3,5-dimethoxyphenyl)-4-oxo-4,5-dihydrofuran-3-yl-5-d phenylmethanesulfonate-d2;
2045 2-amino-5-(2-bromophenyl)-4-oxo-4,5-dihydrofuran-3-yl-5-d phenylmethanesulfonate-d2;
2045(R) (R)-2-amino-5-(2-bromophenyl)-4-oxo-4,5-dihydrofuran-3-yl-5-d phenylmethanesulfonate-d2;
2045(S) (S)-2-amino-5-(2-bromophenyl)-4-oxo-4,5-dihydrofuran-3-yl-5-d phenylmethanesulfonate-d2;
2046 2-amino-5-(3-bromophenyl)-4-oxo-4,5-dihydrofuran-3-yl-5-d phenylmethanesulfonate-d2;
2046(R) (R)-2-amino-5-(3-bromophenyl)-4-oxo-4,5-dihydrofuran-3-yl-5-d phenylmethanesulfonate-d2;
2046(S) (S)-2-amino-5-(3-bromophenyl)-4-oxo-4,5-dihydrofuran-3-yl-5-d phenylmethanesulfonate-d2;
2047 2-amino-5-(4-bromophenyl)-4-oxo-4,5-dihydrofuran-3-yl-5-d phenylmethanesulfonate-d2;
2047(R) (R)-2-amino-5-(4-bromophenyl)-4-oxo-4,5-dihydrofuran-3-yl-5-d phenylmethanesulfonate-d2;
2047(S) (S)-2-amino-5-(4-bromophenyl)-4-oxo-4,5-dihydrofuran-3-yl-5-d phenylmethanesulfonate-d2;
2048 2-amino-5-(2-chloro-3-fluorophenyl)-4-oxo-4,5-dihydrofuran-3-yl-5-d phenylmethanesulfonate-d2;
2048(R) (R)-2-amino-5-(2-chloro-3-fluorophenyl)-4-oxo-4,5-dihydrofuran-3-yl-5-d phenylmethanesulfonate-d2;
2048(S) (S)-2-amino-5-(2-chloro-3-fluorophenyl)-4-oxo-4,5-dihydrofuran-3-yl-5-d phenylmethanesulfonate-d2;
2049 2-amino-5-(2-chloro-4-fluorophenyl)-4-oxo-4,5-dihydrofuran-3-yl-5-d phenylmethanesulfonate-d2;
2049(R) (R)-2-amino-5-(2-chloro-4-fluorophenyl)-4-oxo-4,5-dihydrofuran-3-yl-5-d phenylmethanesulfonate-d2;
2049(S) (S)-2-amino-5-(2-chloro-4-fluorophenyl)-4-oxo-4,5-dihydrofuran-3-yl-5-d phenylmethanesulfonate-d2;
2050 2-amino-5-(2-chloro-5-fluorophenyl)-4-oxo-4,5-dihydrofuran-3-yl-5-d phenylmethanesulfonate-d2;
2050(R) (R)-2-amino-5-(2-chloro-5-fluorophenyl)-4-oxo-4,5-dihydrofuran-3-yl-5-d phenylmethanesulfonate-d2;
2050(S) (S)-2-amino-5-(2-chloro-5-fluorophenyl)-4-oxo-4,5-dihydrofuran-3-yl-5-d phenylmethanesulfonate-d2;

2051 2-amino-5-(2-chloro-6-fluorophenyl)-4-oxo-4,5-dihydrofuran-3-yl-5-d phenylmethanesulfonate-d2;
2051(R) (R)-2-amino-5-(2-chloro-6-fluorophenyl)-4-oxo-4,5-dihydrofuran-3-yl-5-d phenylmethanesulfonate-d2;
2051(S) (S)-2-amino-5-(2-chloro-6-fluorophenyl)-4-oxo-4,5-dihydrofuran-3-yl-5-d phenylmethanesulfonate-d2;
2052 2-amino-5-(3-chloro-2-fluorophenyl)-4-oxo-4,5-dihydrofuran-3-yl-5-d phenylmethanesulfonate-d2;
2052(R) (R)-2-amino-5-(3-chloro-2-fluorophenyl)-4-oxo-4,5-dihydrofuran-3-yl-5-d phenylmethanesulfonate-d2;
2052(S) (S)-2-amino-5-(3-chloro-2-fluorophenyl)-4-oxo-4,5-dihydrofuran-3-yl-5-d phenylmethanesulfonate-d2;
2053 2-amino-5-(3-chloro-4-fluorophenyl)-4-oxo-4,5-dihydrofuran-3-yl-5-d phenylmethanesulfonate-d2;
2053(R) (R)-2-amino-5-(3-chloro-4-fluorophenyl)-4-oxo-4,5-dihydrofuran-3-yl-5-d phenylmethanesulfonate-d2;
2053(S) (S)-2-amino-5-(3-chloro-4-fluorophenyl)-4-oxo-4,5-dihydrofuran-3-yl-5-d phenylmethanesulfonate-d2;
2054 2-amino-5-(3-chloro-5-fluorophenyl)-4-oxo-4,5-dihydrofuran-3-yl-5-d phenylmethanesulfonate-d2;
2054(R) (R)-2-amino-5-(3-chloro-5-fluorophenyl)-4-oxo-4,5-dihydrofuran-3-yl-5-d phenylmethanesulfonate-d2;
2054(S) (S)-2-amino-5-(3-chloro-5-fluorophenyl)-4-oxo-4,5-dihydrofuran-3-yl-5-d phenylmethanesulfonate-d2;
2055 2-amino-5-(5-chloro-2-fluorophenyl)-4-oxo-4,5-dihydrofuran-3-yl-5-d phenylmethanesulfonate-d2;
2055(R) (R)-2-amino-5-(5-chloro-2-fluorophenyl)-4-oxo-4,5-dihydrofuran-3-yl-5-d phenylmethanesulfonate-d2;
2055(S) (S)-2-amino-5-(5-chloro-2-fluorophenyl)-4-oxo-4,5-dihydrofuran-3-yl-5-d phenylmethanesulfonate-d2;
2056 2-amino-5-(4-chloro-2-fluorophenyl)-4-oxo-4,5-dihydrofuran-3-yl-5-d phenylmethanesulfonate-d2;
2056(R) (R)-2-amino-5-(4-chloro-2-fluorophenyl)-4-oxo-4,5-dihydrofuran-3-yl-5-d phenylmethanesulfonate-d2;
2056(S) (S)-2-amino-5-(4-chloro-2-fluorophenyl)-4-oxo-4,5-dihydrofuran-3-yl-5-d phenylmethanesulfonate-d2;
2057 2-amino-5-(4-chloro-3-fluorophenyl)-4-oxo-4,5-dihydrofuran-3-yl-5-d phenylmethanesulfonate-d2;
2057(R) (R)-2-amino-5-(4-chloro-3-fluorophenyl)-4-oxo-4,5-dihydrofuran-3-yl-5-d phenylmethanesulfonate-d2;
2057(S) (S)-2-amino-5-(4-chloro-3-fluorophenyl)-4-oxo-4,5-dihydrofuran-3-yl-5-d phenylmethanesulfonate-d2;
2058 2-amino-4-oxo-5-(o-tolyl)-4,5-dihydrofuran-3-yl-5-d phenylmethanesulfonate-d2;
2058(R) (R)-2-amino-4-oxo-5-(o-tolyl)-4,5-dihydrofuran-3-yl-5-d phenylmethanesulfonate-d2;
2058(S) (S)-2-amino-4-oxo-5-(o-tolyl)-4,5-dihydrofuran-3-yl-5-d phenylmethanesulfonate-d2;
2059 2-amino-4-oxo-5-(m-tolyl)-4,5-dihydrofuran-3-yl-5-d phenylmethanesulfonate-d2;
2059(R) (R)-2-amino-4-oxo-5-(m-tolyl)-4,5-dihydrofuran-3-yl-5-d phenylmethanesulfonate-d2;
2059(S) (S)-2-amino-4-oxo-5-(m-tolyl)-4,5-dihydrofuran-3-yl-5-d phenylmethanesulfonate-d2;
2060 2-amino-4-oxo-5-(p-tolyl)-4,5-dihydrofuran-3-yl-5-d phenylmethanesulfonate-d2;
2060(R) (R)-2-amino-4-oxo-5-(p-tolyl)-4,5-dihydrofuran-3-yl-5-d phenylmethanesulfonate-d2;
2060(S) (S)-2-amino-4-oxo-5-(p-tolyl)-4,5-dihydrofuran-3-yl-5-d phenylmethanesulfonate-d2;
2061 2-amino-5-(3-cyanophenyl)-4-oxo-4,5-dihydrofuran-3-yl-5-d phenylmethanesulfonate-d2;
2061(R) (R)-2-amino-5-(3-cyanophenyl)-4-oxo-4,5-dihydrofuran-3-yl-5-d phenylmethanesulfonate-d2;
2061(S) (S)-2-amino-5-(3-cyanophenyl)-4-oxo-4,5-dihydrofuran-3-yl-5-d phenylmethanesulfonate-d2;
2062 2-amino-5-(4-cyanophenyl)-4-oxo-4,5-dihydrofuran-3-yl-5-d phenylmethanesulfonate-d2;
2062(R) (R)-2-amino-5-(4-cyanophenyl)-4-oxo-4,5-dihydrofuran-3-yl-5-d phenylmethanesulfonate-d2;
2062(S) (S)-2-amino-5-(4-cyanophenyl)-4-oxo-4,5-dihydrofuran-3-yl-5-d phenylmethanesulfonate-d2;
2063 2-amino-4-oxo-5-phenyl-4,5-dihydrofuran-3-yl-5-d phenylmethanesulfonate-d2;
2063(R) (R)-2-amino-4-oxo-5-phenyl-4,5-dihydrofuran-3-yl-5-d phenylmethanesulfonate-d2;
2063(S) (S)-2-amino-4-oxo-5-phenyl-4,5-dihydrofuran-3-yl-5-d phenylmethanesulfonate-d2;
2064 2-amino-4-oxo-5-(2-(trifluoromethyl)phenyl)-4,5-dihydrofuran-3-yl-5-d phenylmethanesulfonate-d2;
2064(R) (R)-2-amino-4-oxo-5-(2-(trifluoromethyl)phenyl)-4,5-dihydrofuran-3-yl-5-d phenylmethanesulfonate-d2;
2064(S) (S)-2-amino-4-oxo-5-(2-(trifluoromethyl)phenyl)-4,5-dihydrofuran-3-yl-5-d phenylmethanesulfonate-d2;
2065 2-amino-4-oxo-5-(3-(trifluoromethyl)phenyl)-4,5-dihydrofuran-3-yl-5-d phenylmethanesulfonate-d2;
2065(R) (R)-2-amino-4-oxo-5-(3-(trifluoromethyl)phenyl)-4,5-dihydrofuran-3-yl-5-d phenylmethanesulfonate-d2;
2065(S) (S)-2-amino-4-oxo-5-(3-(trifluoromethyl)phenyl)-4,5-dihydrofuran-3-yl-5-d phenylmethanesulfonate-d2;
2066 2-amino-4-oxo-5-(4-(trifluoromethyl)phenyl)-4,5-dihydrofuran-3-yl-5-d phenylmethanesulfonate-d2;
2066(R) (R)-2-amino-4-oxo-5-(4-(trifluoromethyl)phenyl)-4,5-dihydrofuran-3-yl-5-d phenylmethanesulfonate-d2;
2066(S) (S)-2-amino-4-oxo-5-(4-(trifluoromethyl)phenyl)-4,5-dihydrofuran-3-yl-5-d phenylmethanesulfonate-d2;
2067 2-amino-4-oxo-5-(4-(trifluoromethyl)phenyl)-4,5-dihydrofuran-3-yl-5-d (4-fluorophenyl)methanesulfonate-d2;
2067(R) (R)-2-amino-4-oxo-5-(4-(trifluoromethyl)phenyl)-4,5-dihydrofuran-3-yl-5-d (4-fluorophenyl)methanesulfonate-d2;
2067(S) (S)-2-amino-4-oxo-5-(4-(trifluoromethyl)phenyl)-4,5-dihydrofuran-3-yl-5-d (4-fluorophenyl)methanesulfonate-d2;
2068 methyl 4-(5-amino-4-((((4-fluorophenyl)methyl-d2)sulfonyl)oxy)-3-oxo-2,3-dihydrofuran-2-yl-2-d)benzoate;
2068(R) methyl (R)-4-(5-amino-4-((((4-fluorophenyl)methyl-d2)sulfonyl)oxy)-3-oxo-2,3-dihydrofuran-2-yl-2-d)benzoate;
2068(S) methyl (S)-4-(5-amino-4-((((4-fluorophenyl)methyl-d2)sulfonyl)oxy)-3-oxo-2,3-dihydrofuran-2-yl-2-d)benzoate;
2069 ethyl 4-(5-amino-4-((((4-fluorophenyl)methyl-d2)sulfonyl)oxy)-3-oxo-2,3-dihydrofuran-2-yl-2-d)benzoate;
2069(R) ethyl (R)-4-(5-amino-4-((((4-fluorophenyl)methyl-d2)sulfonyl)oxy)-3-oxo-2,3-dihydrofuran-2-yl-2-d)benzoate;
2069(S) ethyl (S)-4-(5-amino-4-((((4-fluorophenyl)methyl-d2)sulfonyl)oxy)-3-oxo-2,3-dihydrofuran-2-yl-2-d)benzoate;
2070 4-(5-amino-4-((((4-fluorophenyl)methyl-d2)sulfonyl)oxy)-3-oxo-2,3-dihydrofuran-2-yl-2-d)benzoic acid-d;
2070(R) (R)-4-(5-amino-4-((((4-fluorophenyl)methyl-d2)sulfonyl)oxy)-3-oxo-2,3-dihydrofuran-2-yl-2-d)benzoic acid-d;
2070(S) (S)-4-(5-amino-4-((((4-fluorophenyl)methyl-d2)sulfonyl)oxy)-3-oxo-2,3-dihydrofuran-2-yl-2-d)benzoic acid-d;

2071 methyl 4-(5-amino-4-((((4-fluorophenyl)methyl-d2)sulfonyl)oxy)-3-oxo-2,3-dihydrofuran-2-yl-2-d)-2-fluorobenzoate;

2071(R) methyl (R)-4-(5-amino-4-((((4-fluorophenyl)methyl-d2)sulfonyl)oxy)-3-oxo-2,3-dihydrofuran-2-yl-2-d)-2-fluorobenzoate;

2071(S) methyl (S)-4-(5-amino-4-((((4-fluorophenyl)methyl-d2)sulfonyl)oxy)-3-oxo-2,3-dihydrofuran-2-yl-2-d)-2-fluorobenzoate;

2072 2-amino-4-oxo-5-(4-(trifluoromethyl)phenyl)-4,5-dihydrofuran-3-yl-5-d (phenyl-d5)methanesulfonate-d2;

2072(R) (R)-2-amino-4-oxo-5-(4-(trifluoromethyl)phenyl)-4,5-dihydrofuran-3-yl-5-d (phenyl-d5)methanesulfonate-d2;

2072(S) (S)-2-amino-4-oxo-5-(4-(trifluoromethyl)phenyl)-4,5-dihydrofuran-3-yl-5-d (phenyl-d5)methanesulfonate-d2;

2073 methyl 4-(5-amino-3-oxo-4-((((phenyl-d5)methyl-d2)sulfonyl)oxy)-2,3-dihydrofuran-2-yl-2-d)benzoate;

2073(R) methyl (R)-4-(5-amino-3-oxo-4-((((phenyl-d5)methyl-d2)sulfonyl)oxy)-2,3-dihydrofuran-2-yl-2-d)benzoate;

2073(S) methyl (S)-4-(5-amino-3-oxo-4-((((phenyl-d5)methyl-d2)sulfonyl)oxy)-2,3-dihydrofuran-2-yl-2-d)benzoate;

2074 ethyl 4-(5-amino-3-oxo-4-((((phenyl-d5)methyl-d2)sulfonyl)oxy)-2,3-dihydrofuran-2-yl-2-d)benzoate;

2074(R) ethyl (R)-4-(5-amino-3-oxo-4-((((phenyl-d5)methyl-d2)sulfonyl)oxy)-2,3-dihydrofuran-2-yl-2-d)benzoate;

2074(S) ethyl (S)-4-(5-amino-3-oxo-4-((((phenyl-d5)methyl-d2)sulfonyl)oxy)-2,3-dihydrofuran-2-yl-2-d)benzoate;

2075 4-(5-amino-3-oxo-4-((((phenyl-d5)methyl-d2)sulfonyl)oxy)-2,3-dihydrofuran-2-yl-2-d)benzoic acid-d;

2075(R) (R)-4-(5-amino-3-oxo-4-((((phenyl-d5)methyl-d2)sulfonyl)oxy)-2,3-dihydrofuran-2-yl-2-d)benzoic acid-d;

2075(S) (S)-4-(5-amino-3-oxo-4-((((phenyl-d5)methyl-d2)sulfonyl)oxy)-2,3-dihydrofuran-2-yl-2-d)benzoic acid-d;

2076 methyl 4-(5-amino-3-oxo-4-((((phenyl-d5)methyl-d2)sulfonyl)oxy)-2,3-dihydrofuran-2-yl-2-d)-2-fluorobenzoate;

2076(R) methyl (R)-4-(5-amino-3-oxo-4-((((phenyl-d5)methyl-d2)sulfonyl)oxy)-2,3-dihydrofuran-2-yl-2-d)-2-fluorobenzoate;

2076(S) methyl (S)-4-(5-amino-3-oxo-4-((((phenyl-d5)methyl-d2)sulfonyl)oxy)-2,3-dihydrofuran-2-yl-2-d)-2-fluorobenzoate;

2077 2-amino-5-(benzo[d][1,3]dioxol-5-yl)-4-oxo-4,5-dihydrofuran-3-yl-5-d phenylmethanesulfonate-d2;

2077(R) (R)-2-amino-5-(benzo[d][1,3]dioxol-5-yl)-4-oxo-4,5-dihydrofuran-3-yl-5-d phenylmethanesulfonate-d2;

2077(S) (S)-2-amino-5-(benzo[d][1,3]dioxol-5-yl)-4-oxo-4,5-dihydrofuran-3-yl-5-d phenylmethanesulfonate-d2;

2078 2-amino-5-(2,2-difluorobenzo[d][1,3]dioxol-5-yl)-4-oxo-4,5-dihydrofuran-3-yl-5-d phenylmethanesulfonate-d2;

2078(R) (R)-2-amino-5-(2,2-difluorobenzo[d][1,3]dioxol-5-yl)-4-oxo-4,5-dihydrofuran-3-yl-5-d phenylmethanesulfonate-d2;

2078(S) (S)-2-amino-5-(2,2-difluorobenzo[d][1,3]dioxol-5-yl)-4-oxo-4,5-dihydrofuran-3-yl-5-d phenylmethanesulfonate-d2;

2079 methyl 2-(4-(5-amino-3-oxo-4-(((phenylmethyl-d2)sulfonyl)oxy)-2,3-dihydrofuran-2-yl-2-d)phenyl)acetate-d2;

2079(R) methyl (R)-2-(4-(5-amino-3-oxo-4-(((phenylmethyl-d2)sulfonyl)oxy)-2,3-dihydrofuran-2-yl-2-d)phenyl)acetate-d2;

2079(S) methyl (S)-2-(4-(5-amino-3-oxo-4-(((phenylmethyl-d2)sulfonyl)oxy)-2,3-dihydrofuran-2-yl-2-d)phenyl)acetate-d2;

2080 2-amino-5-(4-(carbamoyl-d2)phenyl)-4-oxo-4,5-dihydrofuran-3-yl-5-d phenylmethanesulfonate-d2;

2080(R) (R)-2-amino-5-(4-(carbamoyl-d2)phenyl)-4-oxo-4,5-dihydrofuran-3-yl-5-d phenylmethanesulfonate-d2;

2080(S) (S)-2-amino-5-(4-(carbamoyl-d2)phenyl)-4-oxo-4,5-dihydrofuran-3-yl-5-d phenylmethanesulfonate-d2;

2081 2-amino-4-oxo-5-(6-(trifluoromethyl)pyridin-3-yl)-4,5-dihydrofuran-3-yl-5-d phenylmethanesulfonate-d2;

2081(R) (R)-2-amino-4-oxo-5-(6-(trifluoromethyl)pyridin-3-yl)-4,5-dihydrofuran-3-yl-5-d phenylmethanesulfonate-d2;

2081(S) (S)-2-amino-4-oxo-5-(6-(trifluoromethyl)pyridin-3-yl)-4,5-dihydrofuran-3-yl-5-d phenylmethanesulfonate-d2;

2082 2-amino-4-oxo-5-(4-(trifluoromethyl)phenyl)-4,5-dihydrofuran-3-yl-5-d (4-chlorophenyl)methanesulfonate-d2;

2082(R) (R)-2-amino-4-oxo-5-(4-(trifluoromethyl)phenyl)-4,5-dihydrofuran-3-yl-5-d (4-chlorophenyl)methanesulfonate-d2;

2082(S) (S)-2-amino-4-oxo-5-(4-(trifluoromethyl)phenyl)-4,5-dihydrofuran-3-yl-5-d (4-chlorophenyl)methanesulfonate-d2;

2083 2-amino-4-oxo-5-(4-(trifluoromethyl)phenyl)-4,5-dihydrofuran-3-yl-5-d (4-(trifluoromethyl)phenyl)methanesulfonate-d2;

2083(R) (R)-2-amino-4-oxo-5-(4-(trifluoromethyl)phenyl)-4,5-dihydrofuran-3-yl-5-d (4-(trifluoromethyl)phenyl)methanesulfonate-d2;

2084 2-(amino-d2)-4-oxo-5-(4-(trifluoromethyl)phenyl)-4,5-dihydrofuran-3-yl phenylmethanesulfonate;

2085 2-(amino-d2)-4-oxo-5-(4-(trifluoromethyl)phenyl)-4,5-dihydrofuran-3-yl-5-d phenylmethanesulfonate-d2;

2085(R) (R)-2-(amino-d2)-4-oxo-5-(4-(trifluoromethyl)phenyl)-4,5-dihydrofuran-3-yl-5-d phenylmethanesulfonate-d2;

2085(S) (S)-2-(amino-d2)-4-oxo-5-(4-(trifluoromethyl)phenyl)-4,5-dihydrofuran-3-yl-5-d phenylmethanesulfonate-d2;

2086 2-(amino-d2)-4-oxo-5-(4-(trifluoromethyl)phenyl)-4,5-dihydrofuran-3-yl (phenyl-d5)methanesulfonate;

2087 2-(amino-d2)-4-oxo-5-(4-(trifluoromethyl)phenyl)-4,5-dihydrofuran-3-yl-5-d (phenyl-d5)methanesulfonate-d2;

2087(R) (R)-2-(amino-d2)-4-oxo-5-(4-(trifluoromethyl)phenyl)-4,5-dihydrofuran-3-yl-5-d (phenyl-d5)methanesulfonate-d2;

2087(S) (S)-2-(amino-d2)-4-oxo-5-(4-(trifluoromethyl)phenyl)-4,5-dihydrofuran-3-yl-5-d (phenyl-d5)methanesulfonate-d2;

2088 2-(amino-d2)-4-oxo-5-(4-(trifluoromethyl)phenyl-2,3,5,6-d4)-4,5-dihydrofuran-3-yl phenylmethanesulfonate;

2089 2-amino-4-oxo-5-(4-(trifluoromethyl)phenyl-2,3,5,6-d4)-4,5-dihydrofuran-3-yl-5-d phenylmethanesulfonate-d2;

2089(R) (R)-2-amino-4-oxo-5-(4-(trifluoromethyl)phenyl-2,3,5,6-d4)-4,5-dihydrofuran-3-yl-5-d phenylmethanesulfonate-d2;

2089(S) (S)-2-amino-4-oxo-5-(4-(trifluoromethyl)phenyl-2,3,5,6-d4)-4,5-dihydrofuran-3-yl-5-d phenylmethanesulfonate-d2;

2090 2-(amino-d2)-4-oxo-5-(4-(trifluoromethyl)phenyl-2,3,5,6-d4)-4,5-dihydrofuran-3-yl-5-d phenylmethanesulfonate-d2;

2090(R) (R)-2-(amino-d2)-4-oxo-5-(4-(trifluoromethyl)phenyl-2,3,5,6-d4)-4,5-dihydrofuran-3-yl-5-d phenylmethanesulfonate-d2;

2090(S) (S)-2-(amino-d2)-4-oxo-5-(4-(trifluoromethyl)phenyl-2,3,5,6-d4)-4,5-dihydrofuran-3-yl-5-d phenylmethanesulfonate-d2;

2091 2-(amino-d2)-4-oxo-5-(4-(trifluoromethyl)phenyl-2,3,5,6-d4)-4,5-dihydrofuran-3-yl (phenyl-d5)methanesulfonate;

2092 2-amino-4-oxo-5-(4-(trifluoromethyl)phenyl-2,3,5,6-d4)-4,5-dihydrofuran-3-yl-5-d (phenyl-d5)methanesulfonate-d2;

2092(R) (R)-2-amino-4-oxo-5-(4-(trifluoromethyl)phenyl-2,3,5,6-d4)-4,5-dihydrofuran-3-yl-5-d (phenyl-d5)methanesulfonate-d2;

2092(S) (S)-2-amino-4-oxo-5-(4-(trifluoromethyl)phenyl-2,3,5,6-d4)-4,5-dihydrofuran-3-yl-5-d (phenyl-d5)methanesulfonate-d2;

2093 2-(amino-d2)-4-oxo-5-(4-(trifluoromethyl)phenyl-2,3,5,6-d4)-4,5-dihydrofuran-3-yl-5-d (phenyl-d5)methanesulfonate-d2;

2093(R) (R)-2-(amino-d2)-4-oxo-5-(4-(trifluoromethyl)phenyl-2,3,5,6-d4)-4,5-dihydrofuran-3-yl-5-d (phenyl-d5)methanesulfonate-d2; and 2093(S) (S)-2-(amino-d2)-4-oxo-5-(4-(trifluoromethyl)phenyl-2,3,5,6-d4)-4,5-dihydrofuran-3-yl-5-d (phenyl-d5)methanesulfonate-d2.

Another specific aspect is a deuterated compound of having formula I-B.

Another specific aspect is a deuterated compound of having formula I-B, wherein $Ar^2$ is phenyl, and $Ar^1$ is a substituted $C_6$-$C_{20}$ aryl group selected from the group consisting of one or more substituents selected from the group consisting of mono F, C, or Br at any position; difluoro or dichloro at different positions; mono and di methyl any position; mono di and trifluoromethyl; mono and di OMe at any position; mono and di chlorophenyl at any position; $CO_2Me$; F and $CO_2Me$; $CO_2Et$; $C(O)CH_3$; $C(O)NH_2$; $C(O)ND_2$; $COO^-Na^+$; $COO^-K^+$; $[COO^-]_2Mg^{+2}$; $[COO^-]_2Ca^{+2}$; mono and di CN at different positions; phenyl; $CF_3$; $CO_3Me$; $CO_2D$; $CF_3$; $CO_2Me$; benzo[d][1,3]dixol-5-yl; and difluorobenzo[d][1,3]dixol-5-yl.

Specific aspects of the invention include a deuterated compound selected from the group consisting of:

2008 2-amino-5-(4-chlorophenyl)-4-oxo-4,5-dihydrofuran-3-yl-5-d phenylmethanesulfonate-d2;

2008(R) (R)-2-amino-5-(4-chlorophenyl)-4-oxo-4,5-dihydrofuran-3-yl-5-d phenylmethanesulfonate-d2;

2008(S) (S)-2-amino-5-(4-chlorophenyl)-4-oxo-4,5-dihydrofuran-3-yl-5-d phenylmethanesulfonate-d2;

2014 2-amino-5-(3,4-dichlorophenyl)-4-oxo-4,5-dihydrofuran-3-yl-5-d phenylmethanesulfonate-d2;

2014(R) (R)-2-amino-5-(3,4-dichlorophenyl)-4-oxo-4,5-dihydrofuran-3-yl-5-d phenylmethanesulfonate-d2;

2014(S) (S)-2-amino-5-(3,4-dichlorophenyl)-4-oxo-4,5-dihydrofuran-3-yl-5-d phenylmethanesulfonate-d2;

2017 methyl 4-(5-amino-3-oxo-4-(((phenylmethyl-d2)sulfonyl)oxy)-2,3-dihydrofuran-2-yl-2-d)benzoate;

2017(R) methyl (R)-4-(5-amino-3-oxo-4-(((phenylmethyl-d2)sulfonyl)oxy)-2,3-dihydrofuran-2-yl-2-d)benzoate;

2017(S) methyl (S)-4-(5-amino-3-oxo-4-(((phenylmethyl-d2)sulfonyl)oxy)-2,3-dihydrofuran-2-yl-2-d)benzoate;

2018 methyl 4-(5-amino-3-oxo-4-(((phenylmethyl-d2)sulfonyl)oxy)-2,3-dihydrofuran-2-yl-2-d)-2-fluorobenzoate;

2018(R) methyl (R)-4-(5-amino-3-oxo-4-(((phenylmethyl-d2)sulfonyl)oxy)-2,3-dihydrofuran-2-yl-2-d)-2-fluorobenzoate;

2018(S) methyl (S)-4-(5-amino-3-oxo-4-(((phenylmethyl-d2)sulfonyl)oxy)-2,3-dihydrofuran-2-yl-2-d)-2-fluorobenzoate;

2052 2-amino-5-(3-chloro-2-fluorophenyl)-4-oxo-4,5-dihydrofuran-3-yl-5-d phenylmethanesulfonate-d2;

2052(R) (R)-2-amino-5-(3-chloro-2-fluorophenyl)-4-oxo-4,5-dihydrofuran-3-yl-5-d phenylmethanesulfonate-d2;

2052(S) (S)-2-amino-5-(3-chloro-2-fluorophenyl)-4-oxo-4,5-dihydrofuran-3-yl-5-d phenylmethanesulfonate-d2;

2066 2-amino-4-oxo-5-(4-(trifluoromethyl)phenyl)-4,5-dihydrofuran-3-yl-5-d phenylmethanesulfonate-d2;

2066(R) (R)-2-amino-4-oxo-5-(4-(trifluoromethyl)phenyl)-4,5-dihydrofuran-3-yl-5-d phenylmethanesulfonate-d2;

2066(S) (S)-2-amino-4-oxo-5-(4-(trifluoromethyl)phenyl)-4,5-dihydrofuran-3-yl-5-d phenylmethanesulfonate-d2;

Related aspects of the invention include a pharmaceutical composition comprising a deuterated compound of Formulas {I-A} through {I-H}, noted above, or a pharmaceutical acceptable salt thereof and a pharmaceutically-acceptable carrier.

Related aspects of the invention include a pharmaceutical composition comprising a deuterated compound of Formulas {I-A} through {I-H}, noted above or a pharmaceutical acceptable ester, metabolite, prodrug, or solvate thereof and a pharmaceutically-acceptable carrier.

Related aspects of the invention include a pharmaceutical composition comprising a deuterated compound selected from the group consisting of a racemic, (R), and (S) named form of a compound, noted above or a pharmaceutical acceptable salt thereof and a pharmaceutically-acceptable carrier.

Related aspects of the invention include a pharmaceutical composition comprising a deuterated compound selected from the group consisting of a racemic, (R), and (S) named form of a compound, noted above or a pharmaceutical acceptable ester, metabolite, prodrug, or solvate thereof and a pharmaceutically-acceptable carrier.

Other aspects of the invention relate to a method of treating or ameliorating one or more conditions associated with a proliferative cellular disorder by administering one or more doses of a pharmaceutical composition comprising one or more deuterated compounds in one or more amounts effective to treat or ameliorate one or more conditions associated with the proliferative cellular disorder.

Related aspects of the invention include methods wherein said proliferative cellular disorder is selected from the group consisting of cancer, pancreatic cancer, lung cancer, breast cancer, glioblastomal cancer, neruobalstoma, osteosarcoma, ovarian cancer, cervical cancer, head and neck cancer, cholangiocarcinoma, and hepatocellular carcinoma.

Other related aspects of the invention relate to a method of treating or ameliorating one or more conditions associated with hyperlipidemia, blood coagulation, complement activation and viral infections by administering one or more doses of a pharmaceutical composition comprising one or more deuterated compounds in one or more amounts effective to treat or ameliorate one or more conditions associated with the proliferative cellular disorder.

One aspect of the invention relates to a method of treating hypercholesterolemia, comprising administering to a subject in need thereof, a therapeutically effective amount of a compound selected from the group consisting of one or more deuterated compounds in one or more amounts effective to treat or ameliorate one or more conditions associated with hyperlipidemia.

One aspect of the invention relates to a method of treating a viral disease, comprising administering to a subject in need thereof, a therapeutically effective amount of a compound selected from the group consisting of one or more deuterated compounds in one or more amounts effective to treat or ameliorate one or more conditions associated with viral disease.

One aspect also relates to a method wherein said viral disease is selected from the group consisting of hepatitis B, hepatitis C, hepatitis D, and human papillomavirus.

One aspect of the invention relates to a method of treating blood coagulation disorders, comprising administering to a subject in need thereof, a therapeutically effective amount of a compound selected from the group consisting of one or more deuterated compounds in one or more amounts effective to treat or ameliorate one or more conditions associated with blood coagulation.

One aspect also relates to a method wherein said blood coagulation disorder is selected from the group consisting of thrombosis, venous thrombosis, myocardial thrombosis, cerebral thrombosis, pulmonary thrombosis, and hepatic thrombosis.

Pharmaceutical Compositions

Related aspects of the invention are directed to compositions, including pharmaceutical compositions, comprising the compounds of the invention, noted above. One aspect of the invention is directed to a pharmaceutical composition comprising at least one pharmaceutically acceptable excipient and a therapeutically effective amount of the compound or salt disclosed above. Still another aspect of the invention relates to a method for pharmaceutical formulation of previously described compounds for use in oral and intravenous applications, and in implantable materials.

Another aspect of the present invention relates to a pharmaceutical composition including a pharmaceutically acceptable carrier and a compound according to the aspects of the present invention. The pharmaceutical composition can contain one or more of the above-identified compounds of the present invention.

Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, emulsions, or implantable disc.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

Dosage Forms

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Optional Coatings

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

Excipients

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

Modes of Administration

The active compounds of the present invention may be orally administered, for example, with an inert diluent, or with an assailable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The pharmaceutical forms suitable for implantable use include sterile wafers of polycarboxyphenoxypropane-sebacic-acid (pCPP:SA) polymers, poly(D,L-lactic acid), polyhydroxybutyrate, lysine diisocyanate (LDI)-glycerol polyurethane, and poly(D-L lactide-co-glycolide). In all cases, the form should be sterile and should be a wafer or disc of suitable dimensions for surgical implantation in the brain. The polymers should be stable under the conditions of manufacture and storage and should be preserved against the contaminating action of microorganisms, such as bacteria and fungi. The wafers should be biodegradable in the central nervous system, and should permit the slow release of the above mentioned compounds, ranging from 24 hours up to 6 months. Such wafers may be of particular value in enhancing the success of temporal lobe epilepsy surgery by suppressing persistent epileptogenic structures.

In one aspect, the invention provides compounds and compositions, including any aspect described herein, for use in any of the methods of this invention. In one aspect, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

Pharmaceutical Compositions Comprising Modulator Compounds of the Invention

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the modulators can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The mode of administration may be oral, for intestinal delivery; intranasal, for nasal delivery; and intravenous for delivery through the blood-brain barrier. Other modes of administration as are known in the art may also be used, including, but not limited to intrathecal, intramuscular, intrabronchial, intrarectal, intraocular, and intravaginal delivery, The modulator compounds can be administered as oral dosage compositions for small intestinal delivery. Such oral dosage compositions for small intestinal delivery are well-known in the art, and generally comprise gastroresistant tablets or capsules (Remington's Pharmaceutical Sciences, 16th Ed., Eds. Osol, Mack Publishing Co., Chapter 89 (1980); Digenis et al, J. Pharm. Sci., 83:915-921 (1994); Vantini et al, Clinica Terapeutica, 145:445-451 (1993); Yoshitomi et al, Chem. Pharm. Bull., 40:1902'1905 (1992); Thoma et al, Pharmazie, 46:331-336 (1991); Morishita et al, Drug Design and Delivery, 7:309-319 (1991); and Lin et al, Pharmaceutical Res., 8:919-924 (1991)); each of which is incorporated by reference herein in its entirety).

Tablets are made gastroresistent by the addition of compounds such as cellulose acetate phthalate or cellulose acetate terephthalate.

Capsules are solid dosage forms in which the modulator compound is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a modulator compound or a combination thereof at the exact dosage level considered best for the individual subject. The hard gelatin capsule consists of two sections, one slipping over the other, thus completely surrounding the modulator compound. These capsules are filled by introducing the modulator compound, or gastroresistent beads containing the modulator compound, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

In the context of the present invention, oral dosage compositions for small intestinal delivery also include liquid compositions which contain aqueous buffering agents that prevent the modulator compound from being significantly inactivated by gastric fluids in the stomach, thereby allowing the modulator compound to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized modulator compound in the aqueous buffering agent. Oral dosage compositions for small intestinal delivery also include liquid compositions which may optionally contain aqueous buffering agents that prevent the therapeutic agent and modulator compound from being significantly inactivated by gastric fluids in the stomach, thereby allowing the biologically active ingredient and modulator compound to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems.

In this case, the liquid composition can be prepared by dissolving lyophilized therapeutic agent and modulator compound in the aqueous buffering agent.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. For sterile powders used in the preparation of sterile injectable solutions, the preferred methods of preparation are vacuum drying and freeze-drying which yields a powder of the active ingredient plus any additional desired ingredient from a previously sterile-filtered solution thereof.

A "nasal" delivery composition differs from an "intestinal" delivery composition in that the latter must have gastroresistent properties in order to prevent the acidic degradation of the active agents in the stomach, whereas the former generally comprises water-soluble polymers with a diameter of about 50 μm order to reduce the mucociliary clearance, and to achieve a reproducible bioavailability of the nasally administered agents.

An "intravenous" delivery composition differs from both the "nasal" and "intestinal" delivery compositions in that there is no need for gastroresistance or water-soluble polymers in the "intravenous" delivery composition.

Nasal dosage compositions for nasal delivery are well-known in the art. Such nasal dosage compositions generally comprise water-soluble polymers that have been used extensively to prepare pharmaceutical dosage forms (Martin et al, In: Physical Chemical Principles of 20 Pharmaceutical Sciences, 3rd Ed., pages 592-638 (1983)) that can serve as carriers for peptides for nasal administration (Davis, In: Delivery Systems for Peptide Drugs, 125:1-21 (1986)). The nasal absorption of pap tides embedded in polymer matrices has been shown to be enhanced through retardation of nasal mucociliary clearance (Illum et al, Int. J. Pharm., 46:261-265 (1988). Other possible enhancement mechanisms include an increased concentration gradient or decreased diffusion path for peptides absorption (Ting et al, Pharm. Res., 9:1330-1335 (1992). However, reduction in mucociliary clearance rate has been predicted to be a good approach toward achievement or reproducible bioavailability of nasally administered systemic drugs (Gonda et al, Pharm. Res., 7:69-75 (1990)). Microparticles with a diameter of about 50 pm are expected to deposit in the nasal cavity (Bjork et al, Int. J. Pharm., 62:187-192 (1990); and Illum et al, Int. J. Pharm., 39:189-199 (1987), while microparticles with a diameter under 10 pm can escape the filtering system of the nose and deposit in the lower airways. Microparticles larger than 200 pm in diameter will not be retained in the nose after nasal administration (Lewis et al, Proc. Int. Symp. Control Rel. Bioact. Mater., 17:280-290 (1990)).

The particular water-soluble polymer employed is not critical to the present invention, and can be selected from any of the well-known water-soluble polymers employed for nasal dosage forms. A typical example of a water-soluble polymer useful for nasal delivery is polyvinyl alcohol (pvA). This material is a swellable hydrophilic polymer whose physical properties depend on the molecular weight, degree of hydrolysis, cross-linking density, and crystallinity (Peppas et al, In: Hydrogels in Medicine and Pharmacy, 3:109'131(1987). PYA can be used in the coating of dispersed materials through phase separation, spray-drying, spray-embedding, and spray-densation (Ting et al, supra).

A "skin" delivery composition comprising a modulator compound of the invention may include in addition a therapeutic or immunogenic agent, fragrance, creams, ointments, colorings, and other compounds so long as the added component does not deleteriously affect transdermal delivery of the therapeutic or immunogenic agent. Conventional pharmaceutically acceptable emulsifiers, surfactants, suspending agents, antioxidants, osmotic enhancers, extenders, diluents and preservatives may also be added. Water soluble polymers can also be used as carriers.

The particular therapeutic or immunogenic agent employed is not critical to the present invention, and can be, e.g., any drug compound, biologically active peptide, vaccine, or any other moiety otherwise not absorbed through the transcellular pathway, regardless of size or charge.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically-acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. A carrier may be suitable for administration into the central nervous system (e.g., intraspinally or intracerebrally). Alternatively, the carrier can be suitable for intravenous, intraperitoneal, or intramuscular administration. In another embodiment, the carrier is suitable for oral administration. Pharmaceutically-acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Various Modifications and Alternatives, Generally

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only, and not limiting as to the scope of the invention, which is to be given the full breadth of the appended claims, and any equivalent, thereof.

EXAMPLES

The foregoing discussion may be better understood in connection with the following representative examples which are presented for purposes of illustrating the principle methods and compositions of the invention, and not by way of limitation. Various other examples will be apparent to the person skilled in the art after reading the present disclosure without departing from the spirit and scope of the invention. It is intended that all such other examples be included within the scope of the appended claims.

General Materials and Methods

All parts are by weight (e.g., % w/w), and temperatures are in degrees centigrade (° C.), unless otherwise indicated. All reagents were from Sigma-Aldrich.

General Chemical Procedures

Melting points were determined with a Hoover melting point apparatus and are uncorrected.

Infrared (IR) spectra for the compounds were recorded in KBr discs on a Mattson Satellite FTIR in cm$^{-1}$. $^1$H and $^{13}$C spectra were recorded in DMSO-d, on a Bruker Avance III DPX 300 MHz instrument. $^{19}$F spectra were recorded in DMSO d$_6$ on a Bruker Avance III 600 (564.6 mHz). Chemical shifts were expressed in parts per million with tetramethylsilane as internal standard. Mass spectrometry was performed on a Thermo Scientific LTQ-FT at the University of Cincinnati Mass. Spectrometry facility.

The purity of the compounds was monitored by HPLC using a Waters 2695 separation module and a 2487 dual A absorbance detector with a NovaPak C18 4 µm 3.9 xl 50 mm column. The mobile phases consisted of acetonitrile/H20 using a 30 minute gradient. All compounds were 2:95%.

Microanalysis was performed by Atlantic Microlab Inc., and all compounds were found to be ±0.4%.

Log S, Log P, Log BBB, human intestinal absorption, p-glycoprotein category, CYP 2C9 pKi, hERG pIC50, CYP 2D$_6$ affinity category, oral CNS score, IV CNS score, MW, flexibility, and total polar surface area were calculated using StarDrop 5.1.1 release Build 178.

FIGS. 3, 4, 5, 6, and 7 illustrate the mechanism of action and synthetic reactions used to prepare unlabeled or isotopically stabilized tetronimide modulator compounds comprising one or more deuterium atoms.

FIG. 4 illustrates the mechanism of action of tetronimide modulating compounds. Deuterium can stabilize a stereocenter, or can be used to slow down or suppress metabolism. Compound #2066 has a deuterium at the stereocenter, as well as two deuteriums at the benzylic position adjacent to the "C" ring. Compound #2084 has two deuteriums on the amino of the tetronimide ring. Compound #2085 has a deuterium at the stereocenter, two deuteriums at the benzylic position adjacent to the "C" ring, and two deuteriums on the amino of the tetronimide ring. Compound #1072 has two deuteriums at the benzylic position adjacent to the "C" ring, and the "C" ring is perdeuterated. Compound #2087 is deuterated at the stereocenter, the benzylic position adjacent to the "C" ring, two deuteriums on the amine of the tetronimide, and the "C" ring is perdeuterated. Compound #1084 has the "A" ring perdeuterated.

FIG. 5 illustrates the synthesis of non-deuterated ASPH modulators in Scheme 1. Scheme 2 illustrates the synthesis of compounds of the formula {I-A} and {I-B}. Scheme 3 illustrates the synthesis of compounds of the formula {I-D} Scheme 4 illustrates the synthesis of compounds of the formula {I-E}.

FIG. 6 illustrates an alternate synthesis of compounds of the formula {I-D} in Scheme 5. Scheme 6 illustrates the synthesis of perdeuterated phenylmethanesulfonyl chloride. Scheme 7 illustrates the synthesis of compounds of the formula {I-F}.

FIG. 7 illustrates the synthesis of compounds of the formula {I-G} in Scheme 8. Scheme 9 illustrates the synthesis of compounds of the formula {I-G}. Scheme 10 illustrates the synthesis of compounds of the formula {I-H}.

FIGS. 10-1 to 10-62 illustrate NMR spectra of unlabeled precursor compounds, particularly multiple peaks for specific compounds, each compound given an MO-I number, which can be cross-correlated with current numbers, names, and structures of the #1000 series of compounds listed in Table 3.

Table 1 is a non-limiting list of unsubstituted and substituted aryl functional groups that can be incorporated into compounds of the invention represented by Formulas noted within the text and embedded or supplemental tables of the specification, the figures, and the claims.

TABLE 1

A Non-Limiting List of Aryl Functional Groups That Can Be Incorporated Formulas of the Invention

| Functional Group No | Structure | Aryl Name |
|---|---|---|
| a | 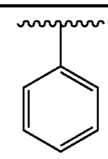 | phenyl |
| b | 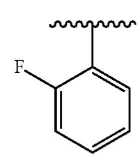 | 2-fluorophenyl |
| c | 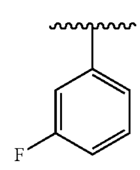 | 3-fluorophenyl |

TABLE 1-continued
A Non-Limiting List of Aryl Functional Groups That Can Be Incorporated Formulas of the Invention
| Functional Group No | Structure | Aryl Name |
|---|---|---|
| d | 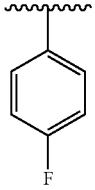 | 4-fluorophenyl |
| e | 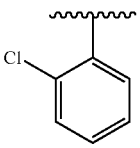 [SMILES: *c1ccccc1Cl] | 2-chlorophenyl |
| f | 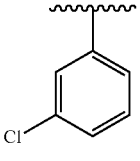 [SMILES: *c1cccc(Cl)c1] | 3-chlorophenyl |
| g | 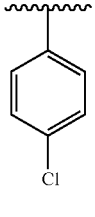 [SMILES: *c1ccc(Cl)cc1] | 4-chlorophenyl |
| h | 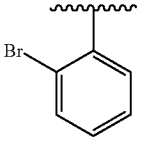 [SMILES: *c1ccccc1Br] | 2-bromophenyl |
| i | 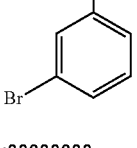 | 3-bromophenyl |
| j | 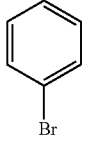 | 4-bromophenyl |
| k | 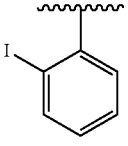 [SMILES: *c1ccccc1I] | 2-iodophenyl |

TABLE 1-continued
A Non-Limiting List of Aryl Functional Groups That Can Be Incorporated Formulas of the Invention
| Functional Group No | Structure | Aryl Name |
|---|---|---|
| l | 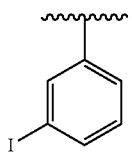 | 3-iodophenyl |
| m | 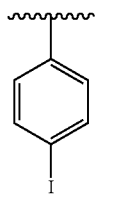 [SMILES: *c1ccc(I)cc1] | 4-iodophenyl |
| n | 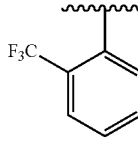 | 2-trifluoromethylphenyl |
| o | 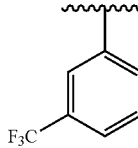 | 3-trifluoromethylphenyl |
| p | 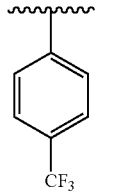 | 4-trifluoromethylphenyl |
| q | 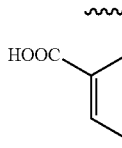 | 2-benzoic acid |
| r | 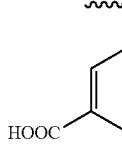 | 3-benzoic acid |
| s | 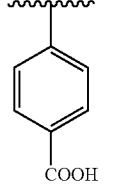 | 4-benzoic acid |

TABLE 1-continued
A Non-Limiting List of Aryl Functional Groups That Can Be Incorporated Formulas of the Invention
| Functional Group No | Structure | Aryl Name |
|---|---|---|
| t | 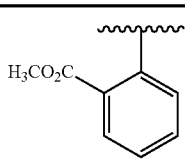 | 2-carboxymethylphenyl |
| u | 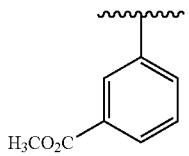 [SMILES: *c1cccc(C(=O)OC)c1] | 3-carboxymethylphenyl |
| v | 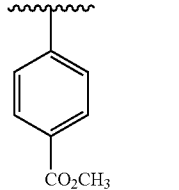 | 4-carboxymethylphenyl |
| w | 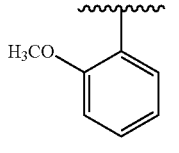 [SMILES: *c1ccccc1OC] | 2-methoxyphenyl |
| x | 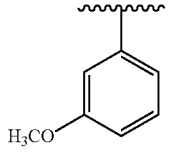 [SMILES: *c1cccc(OC)c1] | 3-methoxyphenyl |
| y | 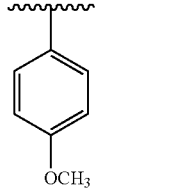 | 4-methoxyphenyl |
| z | 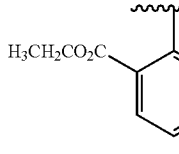 | 2-carboxyethylphenyl |
| aa | 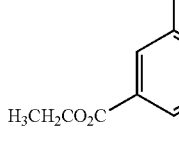 | 3-carboxyethylphenyl |

TABLE 1-continued

A Non-Limiting List of Aryl Functional Groups That Can Be Incorporated Formulas of the Invention

| Functional Group No | Structure | Aryl Name |
|---|---|---|
| ab | 4-CO$_2$CH$_2$CH$_3$-phenyl | 4-carboxyethylphenyl |
| ac | 2-NC-phenyl | 2-nitrilephenyl |
| ad | 3-NC-phenyl | 3-nitrilephenyl |
| ae | 4-CN-phenyl | 4-nitrilephenyl |
| af | 2-H$_2$NO$_2$S-phenyl | 2-sulfonamidophenyl |
| ag | 3-H$_2$NO$_2$S-phenyl | 3-sulfonamidophenyl |
| ah | 4-SO$_2$NH$_2$-phenyl | 4-sulfonamidophenyl |
| ai | 2,3-F,F-phenyl | 2,3-difluorophenyl |

TABLE 1-continued
A Non-Limiting List of Aryl Functional Groups That Can Be Incorporated Formulas of the Invention
| Functional Group No | Structure | Aryl Name |
|---|---|---|
| aj | 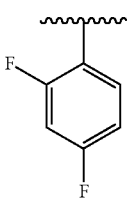 [SMILES: *c1ccc(F)cc1F] | 2,4-difluorophenyl |
| ak | 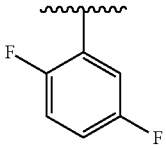 [SMILES: *c1cc(F)ccc1F] | 2,5-difluorophenyl |
| al | 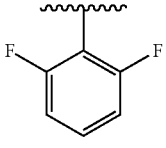 [SMILES: *c1c(F)cccc1F] | 2,6-difluorophenyl |
| am | 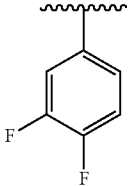 [SMILES: *c1ccc(F)c(F)c1] | 3,4-difluorophenyl |
| an | 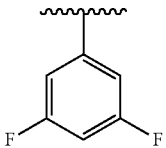 [SMILES: *c1cc(F)cc(F)c1] | 3,5-difluorophenyl |
| ap | 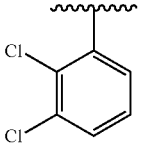 [SMILES: *c1cccc(Cl)c1Cl] | 2,3-dichlorophenyl |
| aq | 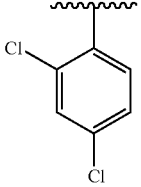 [SMILES: *c1ccc(Cl)cc1Cl] | 2,4-dichlorophenyl |
| ar | 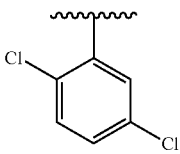 [SMILES: *c1cc(Cl)ccc1Cl] | 2,5-dichlorophenyl |

TABLE 1-continued
A Non-Limiting List of Aryl Functional Groups That Can Be Incorporated Formulas of the Invention
| Functional Group No | Structure | Aryl Name |
|---|---|---|
| as | 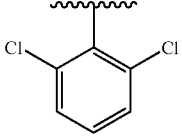 [SMILES: *c1c(Cl)cccc1Cl] | 2,6-dichlorophenyl |
| at | 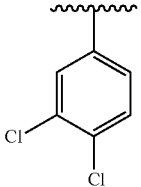 [SMILES: *c1ccc(Cl)c(Cl)c1] | 3,4-dichlorophenyl |
| au | 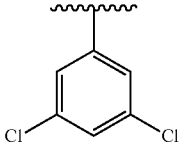 [SMILES: *c1cc(Cl)cc(Cl)c1] | 3,5-dichlorophenyl |
| av | 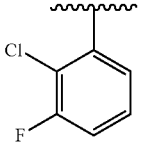 | 2-chloro-3-fluorophenyl |
| aw | 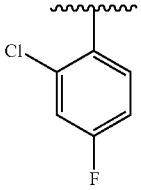 [SMILES: *c1ccc(F)cc1Cl] | 2-chloro-4-fluorophenyl |
| ax | 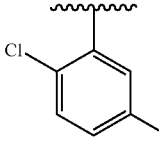 | 2-chloro-5-fluorophenyl |
| ay | 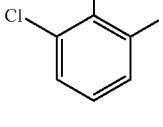 | 2-chloro-6-fluorophenyl |
| az | 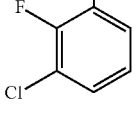 | 3-chloro-2-fluorophenyl |

TABLE 1-continued

A Non-Limiting List of Aryl Functional Groups That Can Be Incorporated Formulas of the Invention

| Functional Group No | Structure | Aryl Name |
|---|---|---|
| ba | 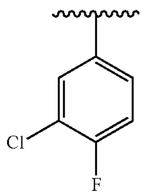 [SMILES: *c1ccc(F)c(Cl)c1] | 3-chloro-4-fluorophenyl |
| bb | 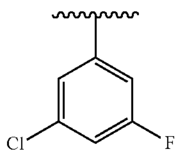 [SMILES: *c1cc(F)cc(Cl)c1] | 3-chloro-5-fluorophenyl |
| bc | 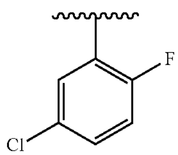 [SMILES: *c1cc(Cl)ccc1F] | 3-chloro-6-fluorophenyl |
| bd | 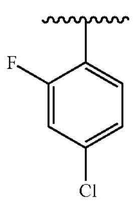 [SMILES: *c1ccc(Cl)cc1F] | 4-chloro-2-fluorophenyl |
| be | 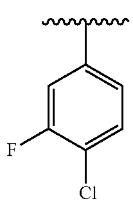 [SMILES: *c1ccc(Cl)c(F)c1] | 4-chloro-3-fluorophenyl |
| bf | 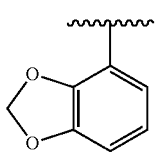 [SMILES: *c1cccc2c1OCO2] | 2,3-methylenedioxyphenyl |
| bg | 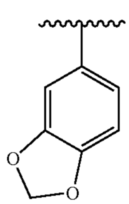 [SMILES: *c1ccc2c(c1)OCO2] | 3,4-methylenedioxyphenyl |
| bh | 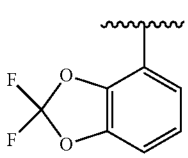 [SMILES: *c1cccc2c1OC(F)(F)O2] | 2,3-difluoromethylenedioxyphenyl |

TABLE 1-continued

A Non-Limiting List of Aryl Functional Groups That Can Be Incorporated Formulas of the Invention

| Functional Group No | Structure | Aryl Name |
|---|---|---|
| bi | 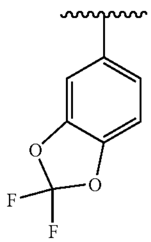 [SMILES: *c1ccc2c(c1)OC(F)(F)O2] | 3,4-difluoromethylenedioxyphenyl |
| bj | 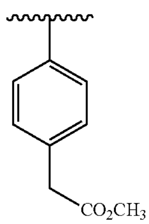 [SMILES: *c1ccc(CC(=O)OC)cc1] | Methyl-phenyl acetate |
| bk | 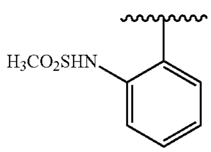 | N-2-phenyl-methanesulfonamide |
| bl | 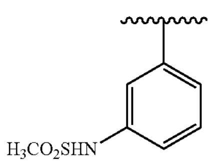 | N-3-phenyl-methanesulfonamide |
| bm | 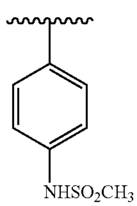 | N-4-phenyl-methanesulfonamide |
| bn | 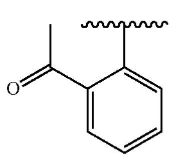 [SMILES: *c1ccccc1C(C)=O] | 2-acetylphenyl |
| bo | 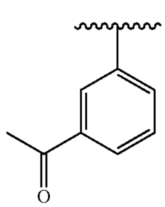 [SMILES: *c1cccc(C(C)=O)c1] | 3-acetylphenyl |

TABLE 1-continued

A Non-Limiting List of Aryl Functional Groups That Can Be Incorporated Formulas of the Invention

| Functional Group No | Structure | Aryl Name |
|---|---|---|
| bp | 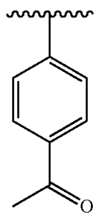 [SMILES: *c1ccc(C(C)=O)cc1] | 4-acetylphenyl |
| bq | 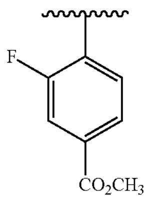 [SMILES: *c1ccc(C(=O)OC)cc1F] | 4-carboxymethyl-2-fluorophenyl |
| br | 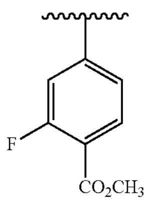 [SMILES: *c1ccc(C(=O)OC)c(F)c1] | 4-carboxymethyl-3-fluorophenyl |
| bs | 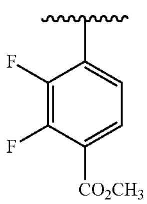 [SMILES: *c1ccc(C(=O)OC)c(F)c1F] | 4-carboxymethyl-2,3-difluorophenyl |
| bt | 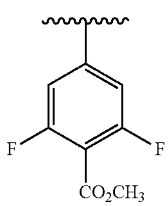 | 4-carboxymethyl-3,5-difluorophenyl |
| bu | 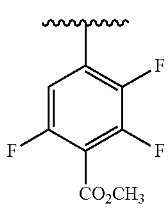 [SMILES: *c1cc(F)c(C(=O)OC)c(F)c1F] | 4-carboxymethyl-2,3,5-trifluorophenyl |
| bv | 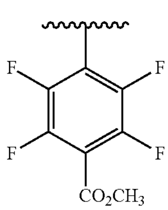 | 4-carboxymethyl-2,3,5,6-tetrafluorophenyl |

TABLE 1-continued

A Non-Limiting List of Aryl Functional Groups That Can Be Incorporated Formulas of the Invention

| Functional Group No | Structure | Aryl Name |
|---|---|---|
| bw | 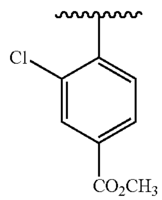 [SMILES: *c1ccc(C(=O)OC)cc1Cl] | 4-carboxymethyl-2-chlorophenyl |
| bx | 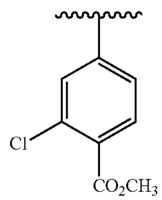 [SMILES: *c1ccc(C(=O)OC)c(Cl)c1] | 4-carboxymethyl-3-chlorophenyl |
| by | 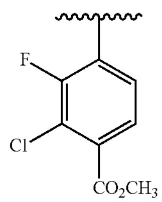 [SMILES: *c1ccc(C(=O)OC)c(Cl)c1F] | 4-carboxymethyl-3-chloro-2-fluorophenyl |
| bz | 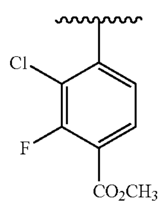 [SMILES: *c1ccc(C(=O)OC)c(F)c1Cl] | 4-carboxymethyl-2-chloro-3-fluorophenyl |
| ca | 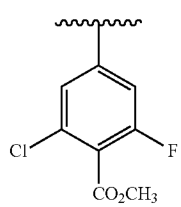 | 4-carboxymethyl-3-chloro-5-fluorophenyl |
| cb | 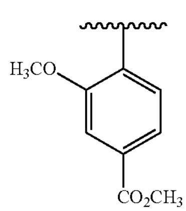 [SMILES: *c1ccc(C(=O)OC)cc1OC] | 4-carboxymethyl-2-methoxyphenyl |
| cc | 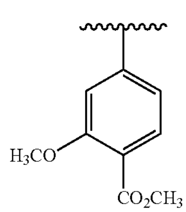 [SMILES: *c1ccc(C(=O)OC)c(OC)c1] | 4-carboxymethyl-3-methoxyphenyl |

TABLE 1-continued

A Non-Limiting List of Aryl Functional Groups That Can Be Incorporated Formulas of the Invention

| Functional Group No | Structure | Aryl Name |
|---|---|---|
| cd | (2-Br, 4-CO$_2$CH$_3$ phenyl) | 4-carboxymethyl-2-bromophenyl |
| ce | (3-Br, 4-CO$_2$CH$_3$ phenyl) | 4-carboxymethyl-3-bromophenyl |
| cf | (2-F, 4-CO$_2$H phenyl) | 2-fluoro-4-benzoic acid |
| cg | (3-F, 4-CO$_2$H phenyl) | 3-fluoro-4-benzoic acid |
| ch | (2,3-diF, 4-CO$_2$H phenyl) | 2,3-difluoro-4-benzoic acid |
| ci | (3,5-diF, 4-CO$_2$H phenyl) | 3,5-difluoro-4-benzoic acid |
| cj | (2,3,5-triF, 4-CO$_2$H phenyl) | 2,3,5-trifluoro-4-benzoic acid |

TABLE 1-continued

A Non-Limiting List of Aryl Functional Groups That Can Be Incorporated Formulas of the Invention

| Functional Group No | Structure | Aryl Name |
|---|---|---|
| ck | 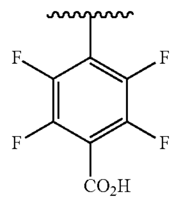 [SMILES: *c1c(F)c(F)c(C(=O)O)c(F)c1F] | 2,3,5,6-tetrafluoro-4-benzoic acid |
| cl | 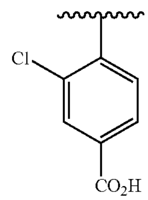 [SMILES: *c1ccc(C(=O)O)cc1Cl] | 2-chloro-4-benzoic acid |
| cm | 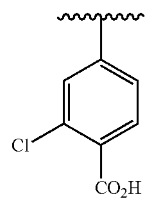 [SMILES: *c1ccc(C(=O)O)c(Cl)c1] | 3-chloro-4-benzoic acid |
| cn | 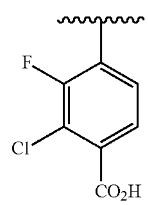 [SMILES: *c1ccc(C(=O)O)c(Cl)c1F] | 3-chloro-2-fluoro-4-benzoic acid |
| co | 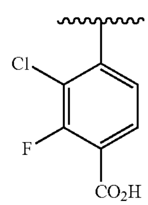 [SMILES: *c1ccc(C(=O)O)c(F)c1Cl] | 2-chloro-3-fluoro-4-benzoic acid |
| cp | 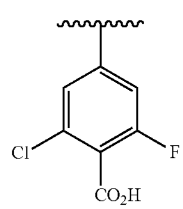 [SMILES: *c1cc(F)c(C(=O)O)c(Cl)c1] | 3-chloro-5-fluoro-4-benzoic acid |
| cq | 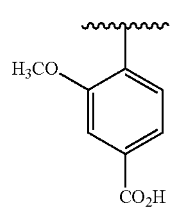 [SMILES: *c1ccc(C(=O)O)cc1OC] | 2-methoxy-4-benzoic acid |

TABLE 1-continued

A Non-Limiting List of Aryl Functional Groups That Can Be Incorporated Formulas of the Invention

| Functional Group No | Structure | Aryl Name |
|---|---|---|
| cr | 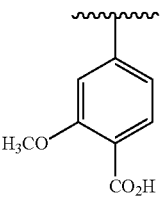 | 3-methoxy-4-benzoic acid |
| cs | 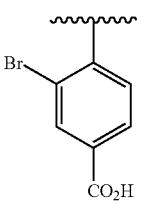 [SMILES: *c1ccc(C(=O)O)cc1Br] | 2-bromo-4-benzoic acid |
| ct | 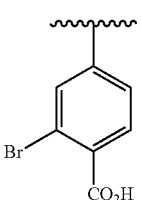 | 3-bromo-4-benzoic acid |

Example 1—Unlabeled Tetronimide Compounds (#1001-1079)

Synthesis of Exemplary Unlabeled Tetronimide Compounds

Table 2 provides a list illustrating the structures, names, and numbers of a variety of key compounds disclosed in this example.
Synthesis of exemplary compounds are described in one or more sections following the tables noted below. 2-(aryl)-4-hydroxy-5-amino-3(2H)furanones are prepared according to the method of Dahn (Experientia (1954), 10, 245-6.). Sulfonylated compounds are prepared according to U.S. Pat. No. 9,771,356.

TABLE 2

(#1001-1083)
Structures, Names, and Numbers of Key Unlabeled Compounds Listed in Example 1

| CP # | Structure | Name | Formula | MW |
|---|---|---|---|---|
| 1001 | 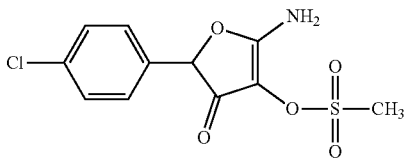 [SMILES: CS(=O)(=O)OC1=C(N)OC(c2ccc(Cl)cc2)C1=O] | 2-amino-5-(4-chlorophenyl)-4-oxo-4,5-dihydrofuran-3-yl methanesulfonate | $C_{11}H_{10}ClNO_5S$ | 303.71 |
| 1002 | 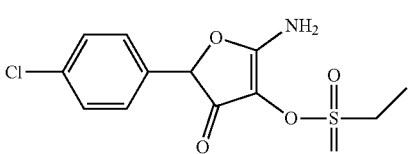 | 2-amino-5-(4-chlorophenyl)-4-oxo-4,5-dihydrofuran-3-yl ethanesulfonate | $C_{12}H_{12}ClNO_5S$ | 317.74 |

TABLE 2-continued (#1001-1083)
Structures, Names, and Numbers of Key Unlabeled Compounds Listed in Example 1

| CP # | Structure | Name | Formula | MW |
|------|-----------|------|---------|-----|
| 1003 | 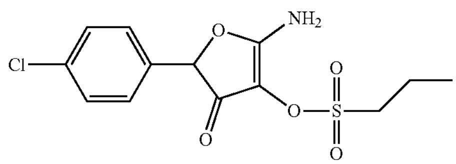 [SMILES: CCCS(=O)(=O)OC1=C(N)OC(c2ccc(Cl)cc2)C1=O] | 2-amino-5-(4-chlorophenyl)-4-oxo-4,5-dihydrofuran-3-yl propane-1-sulfonate | $C_{13}H_{14}ClNO_5S$ | 331.77 |
| 1004 | 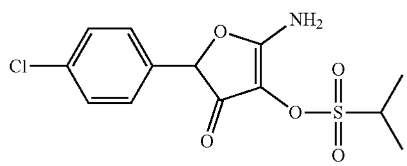 [SMILES: CC(C)S(=O)(=O)OC1=C(N)OC(c2ccc(Cl)cc2)C1=O] | 2-amino-5-(4-chlorophenyl)-4-oxo-4,5-dihydrofuran-3-yl propane-2-sulfonate | $C_{13}H_{14}ClNO_5S$ | 331.77 |
| 1005 | 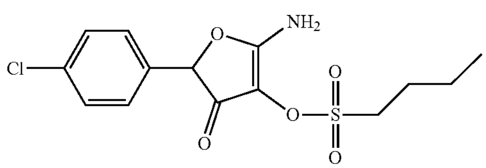 [SMILES: CCCCS(=O)(=O)OC1=C(N)OC(c2ccc(Cl)cc2)C1=O] | 2-amino-5-(4-chlorophenyl)-4-oxo-4,5-dihydrofuran-3-yl butane-1-sulfonate | $C_{14}H_{16}ClNO_5S$ | 345.79 |
| 1006 | 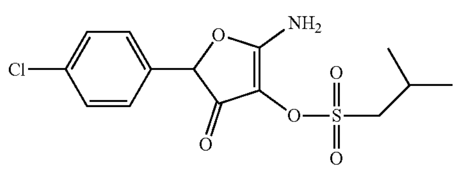 [SMILES: CC(C)CS(=O)(=O)OC1=C(N)OC(c2ccc(Cl)cc2)C1=O] | 2-amino-5-(4-chlorophenyl)-4-oxo-4,5-dihydrofuran-3-yl 2-methylpropane-1-sulfonate | $C_{14}H_{16}ClNO_5S$ | 345.79 |
| 1008 | 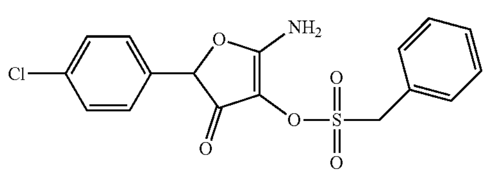 [SMILES: NC1=C(OS(=O)(=O)Cc2ccccc2)C(=O)C(c2ccc(Cl)cc2)O1] | 2-amino-5-(4-chlorophenyl)-4-oxo-4,5-dihydrofuran-3-yl phenylmethanesulfonate | $C_{17}H_{14}ClNO_5S$ | 379.81 |
| 1009 | 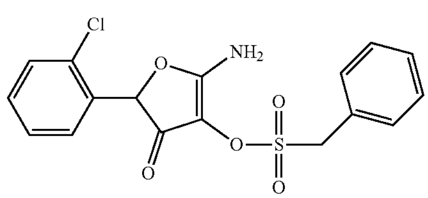 [SMILES: NC1=C(OS(=O)(=O)Cc2ccccc2)C(=O)C(c2ccccc2Cl)O1] | 2-amino-5-(2-chlorophenyl)-4-oxo-4,5-dihydrofuran-3-yl phenylmethanesulfonate | $C_{17}H_{14}ClNO_5S$ | 379.81 |
| 1010 | 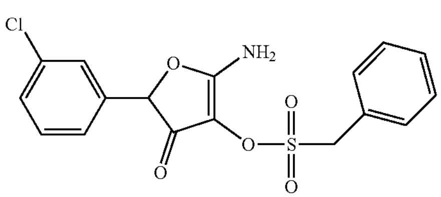 [SMILES: NC1=C(OS(=O)(=O)Cc2ccccc2)C(=O)C(c2cccc(Cl)c2)O1] | 2-amino-5-(3-chlorophenyl)-4-oxo-4,5-dihydrofuran-3-yl phenylmethanesulfonate | $C_{17}H_{14}ClNO_5S$ | 379.81 |
| 1011 | 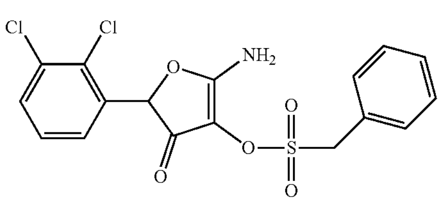 [SMILES: NC1=C(OS(=O)(=O)Cc2ccccc2)C(=O)C(c2cccc(Cl)c2Cl)O1] | 2-amino-5-(2,3-dichlorophenyl)-4-oxo-4,5-dihydrofuran-3-yl phenylmethanesulfonate | $C_{17}H_{13}Cl_2NO_5S$ | 414.25 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1012 | 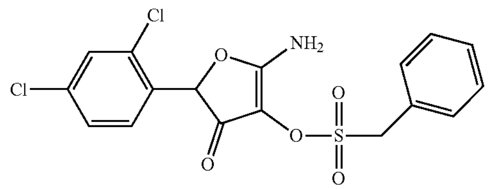 [SMILES: NC1=C(OS(=O)(=O)Cc2ccccc2)C(=O)C(c2ccc(Cl)cc2Cl)O1] | 2-amino-5-(2,4-dichlorophenyl)-4-oxo-4,5-dihydrofuran-3-yl phenylmethanesulfonate | $C_{17}H_{13}Cl_2NO_5S$ | 414.25 |
| 1013 | 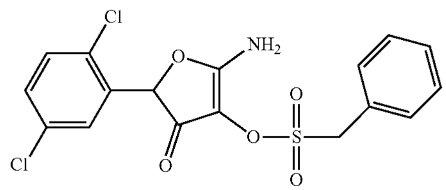 [SMILES: NC1=C(OS(=O)(=O)Cc2ccccc2)C(=O)C(c2cc(Cl)ccc2Cl)O1] | 2-amino-5-(2,5-dichlorophenyl)-4-oxo-4,5-dihydrofuran-3-yl phenylmethanesulfonate | $C_{17}H_{13}Cl_2NO_5S$ | 414.25 |
| 1014 | 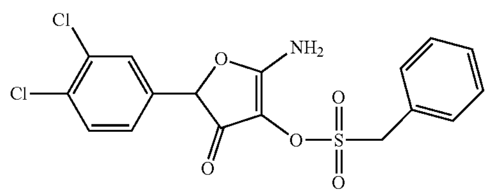 [SMILES: NC1=C(OS(=O)(=O)Cc2ccccc2)C(=O)C(c2ccc(Cl)c(Cl)c2)O1] | 2-amino-5-(3,4-dichlorophenyl)-4-oxo-4,5-dihydrofuran-3-yl phenylmethanesulfonate | $C_{17}H_{13}Cl_2NO_5S$ | 414.25 |
| 1015 | 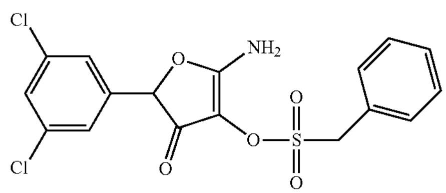 [SMILES: NC1=C(OS(=O)(=O)Cc2ccccc2)C(=O)C(c2cc(Cl)cc(Cl)c2)O1] | 2-amino-5-(3,5-dichlorophenyl)-4-oxo-4,5-dihydrofuran-3-yl phenylmethanesulfonate | $C_{17}H_{13}Cl_2NO_5S$ | 414.25 |
| 1016 | 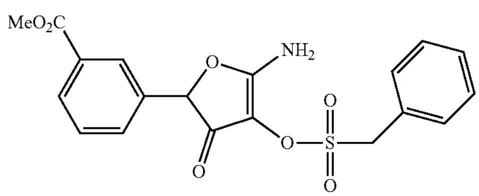 [SMILES: COC(=O)c1cccc(C2OC(N)=C(OS(=O)(=O)Cc3ccccc3)C2=O)c1] | methyl 3-(5-amino-4-((benzylsulfonyl)oxy)-3-oxo-2,3-dihydrofuran-2-yl)benzoate | $C_{19}H_{17}NO_7S$ | 403.40 |
| 1017 | 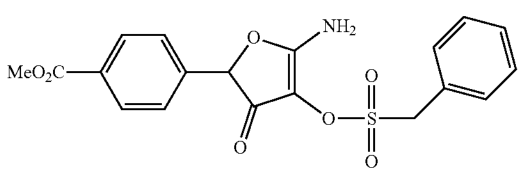 [SMILES: COC(=O)c1ccc(C2OC(N)=C(OS(=O)(=O)Cc3ccccc3)C2=O)cc1] | methyl 4-(5-amino-4-((benzylsulfonyl)oxy)-3-oxo-2,3-dihydrofuran-2-yl)benzoate | $C_{19}H_{17}NO_7S$ | 403.40 |
| 1018 | 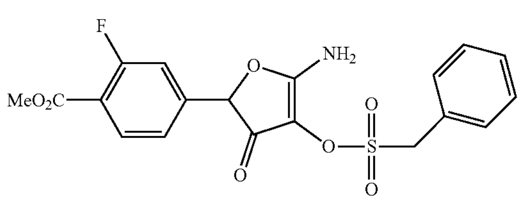 [SMILES: COC(=O)c1ccc(C2OC(N)=C(OS(=O)(=O)Cc3ccccc3)C2=O)cc1F] | methyl 4-(5-amino-4-((benzylsulfonyl)oxy)-3-oxo-2,3-dihydrofuran-2-yl)-2-fluorobenzoate | $C_{19}H_{16}FNO_7S$ | 421.40 |
| 1019 | 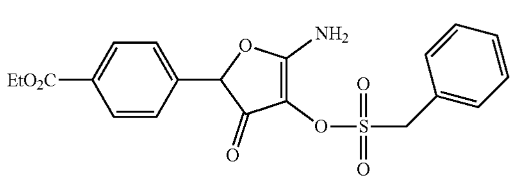 [SMILES: CCOC(=O)c1ccc(C2OC(N)=C(OS(=O)(=O)Cc3ccccc3)C2=O)cc1] | ethyl 4-(5-amino-4-((benzylsulfonyl)oxy)-3-oxo-2,3-dihydrofuran-2-yl)benzoate | $C_{20}H_{19}NO_7S$ | 417.43 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1020 | 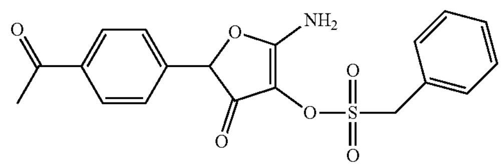 [SMILES: CC(=O)c1ccc(C2OC(N)=C(OS(=O)(=O)Cc3ccccc3)C2=O)cc1] | 5-(4-acetylphenyl)-2-amino-4-oxo-4,5-dihydrofuran-3-yl phenylmethanesulfonate | $C_{19}H_{17}NO_6S$ | 387.41 |
| 1021 | 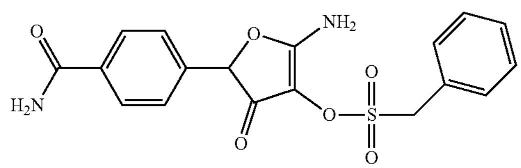 [SMILES: NC(=O)c1ccc(C2OC(N)=C(OS(=O)(=O)Cc3ccccc3)C2=O)cc1] | 2-amino-5-(4-carbamoylphenyl)-4-oxo-4,5-dihydrofuran-3-yl phenylmethanesulfonate | $C_{18}H_{16}N_2O_6S$ | 388.39 |
| 1022 | 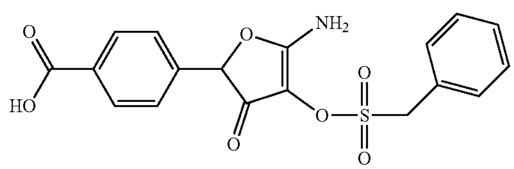 [SMILES: NC1=C(OS(=O)(=O)Cc2ccccc2)C(=O)C(c2ccc(C(=O)O)cc2)O1] | 4-(5-amino-4-((benzylsulfonyl)oxy)-3-oxo-2,3-dihydrofuran-2-yl)benzoic acid | $C_{18}H_{15}NO_7S$ | 389.38 |
| 1027 | 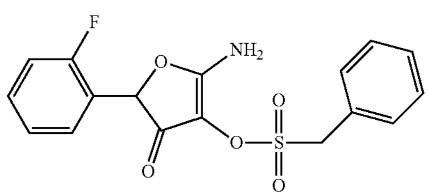 [SMILES: NC1=C(OS(=O)(=O)Cc2ccccc2)C(=O)C(c2ccccc2F)O1] | 2-amino-5-(2-fluorophenyl)-4-oxo-4,5-dihydrofuran-3-yl phenylmethanesulfonate | $C_{17}H_{14}FNO_5S$ | 363.36 |
| 1028 | 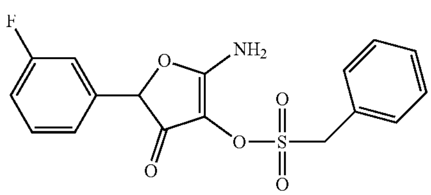 [SMILES: NC1=C(OS(=O)(=O)Cc2ccccc2)C(=O)C(c2cccc(F)c2)O1] | 2-amino-5-(3-fluorophenyl)-4-oxo-4,5-dihydrofuran-3-yl phenylmethanesulfonate | $C_{17}H_{14}FNO_5S$ | 363.36 |
| 1029 | 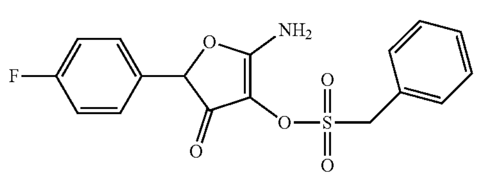 [SMILES: NC1=C(OS(=O)(=O)Cc2ccccc2)C(=O)C(c2ccc(F)cc2)O1] | 2-amino-5-(4-fluorophenyl)-4-oxo-4,5-dihydrofuran-3-yl phenylmethanesulfonate | $C_{17}H_{14}FNO_5S$ | 363.36 |
| 1030 | 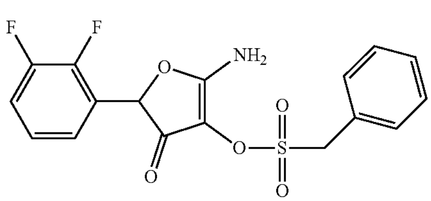 | 2-amino-5-(2,3-difluorophenyl)-4-oxo-4,5-dihydrofuran-3-yl phenylmethanesulfonate | $C_{17}H_{13}F_2NO_5S$ | 381.35 |
| 1031 | 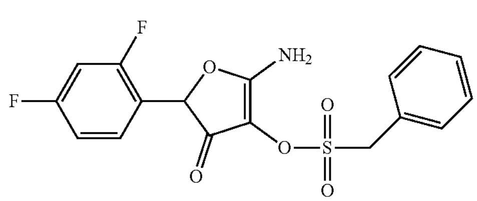 [SMILES: NC1=C(OS(=O)(=O)Cc2ccccc2)C(=O)C(c2ccc(F)cc2F)O1] | 2-amino-5-(2,4-difluorophenyl)-4-oxo-4,5-dihydrofuran-3-yl phenylmethanesulfonate | $C_{17}H_{13}F_2NO_5S$ | 381.35 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1032 | 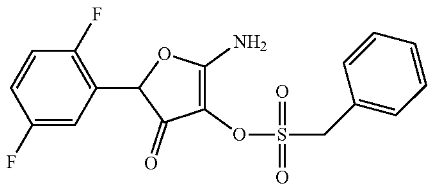 [SMILES: NC1=C(OS(=O)(=O)Cc2ccccc2)C(=O)C(c2cc(F)ccc2F)O1] | 2-amino-5-(2,5-difluorophenyl)-4-oxo-4,5-dihydrofuran-3-yl phenylmethanesulfonate | $C_{17}H_{13}F_2NO_5S$ | 381.35 |
| 1033 | 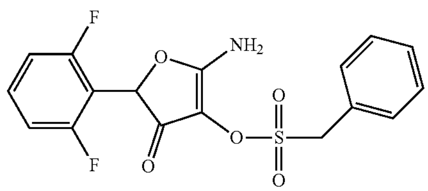 [SMILES: NC1=C(OS(=O)(=O)Cc2ccccc2)C(=O)C(c2c(F)cccc2F)O1] | 2-amino-5-(2,6-difluorophenyl)-4-oxo-4,5-dihydrofuran-3-yl phenylmethanesulfonate | $C_{17}H_{13}F_2NO_5S$ | 381.35 |
| 1034 | 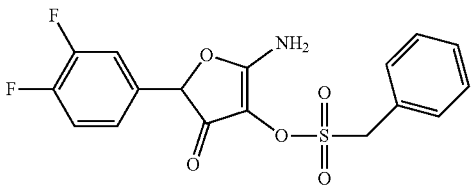 [SMILES: NC1=C(OS(=O)(=O)Cc2ccccc2)C(=O)C(c2ccc(F)c(F)c2)O1] | 2-amino-5-(3,4-difluorophenyl)-4-oxo-4,5-dihydrofuran-3-yl phenylmethanesulfonate | $C_{17}H_{13}F_2NO_5S$ | 381.35 |
| 1035 | 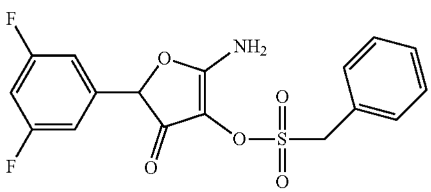 [SMILES: NC1=C(OS(=O)(=O)Cc2ccccc2)C(=O)C(c2cc(F)cc(F)c2)O1] | 2-amino-5-(3,5-difluorophenyl)-4-oxo-4,5-dihydrofuran-3-yl phenylmethanesulfonate | $C_{17}H_{13}F_2NO_5S$ | 381.35 |
| 1036 | 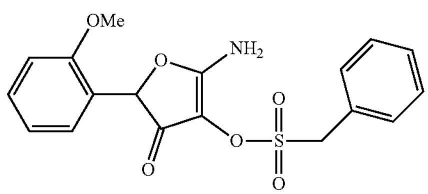 [SMILES: COc1ccccc1C1OC(N)=C(OS(=O)(=O)Cc2ccccc2)C1=O] | 2-amino-5-(2-methoxyphenyl)-4-oxo-4,5-dihydrofuran-3-yl phenylmethanesulfonate | $C_{18}H_{17}NO_6S$ | 375.39 |
| 1037 | 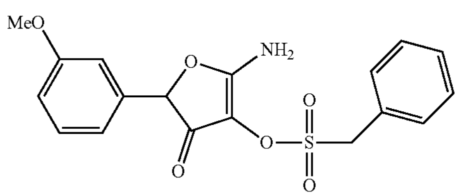 [SMILES: COc1cccc(C2OC(N)=C(OS(=O)(=O)Cc3ccccc3)C2=O)c1] | 2-amino-5-(3-methoxyphenyl)-4-oxo-4,5-dihydrofuran-3-yl phenylmethanesulfonate | $C_{18}H_{17}NO_6S$ | 375.39 |
| 1038 | 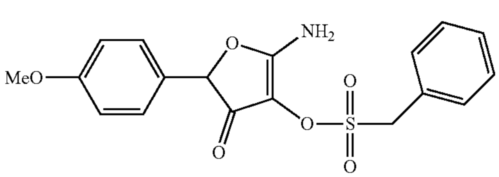 [SMILES: COc1ccc(C2OC(N)=C(OS(=O)(=O)Cc3ccccc3)C2=O)cc1] | 2-amino-5-(4-methoxyphenyl)-4-oxo-4,5-dihydrofuran-3-yl phenylmethanesulfonate | $C_{18}H_{17}NO_6S$ | 375.39 |
| 1039 | 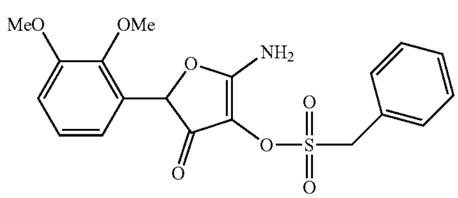 [SMILES: COc1cccc(C2OC(N)=C(OS(=O)(=O)Cc3ccccc3)C2=O)c1OC] | 2-amino-5-(2,3-dimethoxyphenyl)-4-oxo-4,5-dihydrofuran-3-yl phenylmethanesulfonate | $C_{19}H_{19}NO_7S$ | 405.42 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1040 | 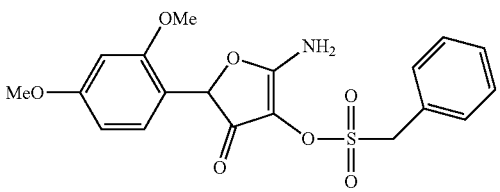 [SMILES: COc1ccc(C2OC(N)=C(OS(=O)(=O)Cc3ccccc3)C2=O)c(OC)c1] | 2-amino-5-(2,4-dimethoxyphenyl)-4-oxo-4,5-dihydrofuran-3-yl phenylmethanesulfonate | $C_{19}H_{19}NO_7S$ | 405.42 |
| 1041 | 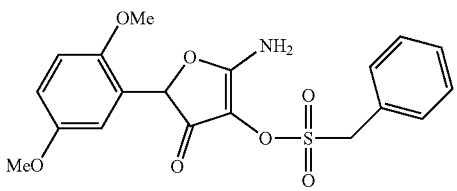 [SMILES: COc1ccc(OC)c(C2OC(N)=C(OS(=O)(=O)Cc3ccccc3)C2=O)c1] | 2-amino-5-(2,5-dimethoxyphenyl)-4-oxo-4,5-dihydrofuran-3-yl phenylmethanesulfonate | $C_{19}H_{19}NO_7S$ | 405.42 |
| 1042 | 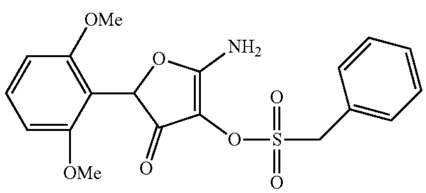 [SMILES: COc1cccc(OC)c1C1OC(N)=C(OS(=O)(=O)Cc2ccccc2)C1=O] | 2-amino-5-(2,6-dimethoxyphenyl)-4-oxo-4,5-dihydrofuran-3-yl phenylmethanesulfonate | $C_{19}H_{19}NO_7S$ | 405.42 |
| 1043 | 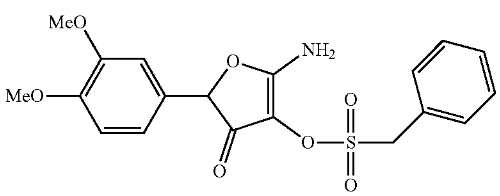 [SMILES: COc1ccc(C2OC(N)=C(OS(=O)(=O)Cc3ccccc3)C2=O)cc1OC] | 2-amino-5-(3,4-dimethoxyphenyl)-4-oxo-4,5-dihydrofuran-3-yl phenylmethanesulfonate | $C_{19}H_{19}NO_7S$ | 405.42 |
| 1044 | 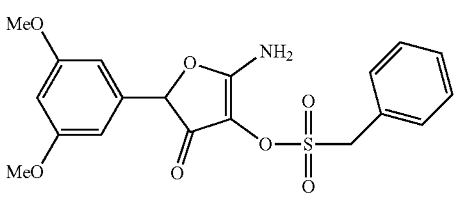 [SMILES: COc1cc(OC)cc(C2OC(N)=C(OS(=O)(=O)Cc3ccccc3)C2=O)c1] | 2-amino-5-(3,5-dimethoxyphenyl)-4-oxo-4,5-dihydrofuran-3-yl phenylmethanesulfonate | $C_{19}H_{19}NO_7S$ | 405.42 |
| 1045 | 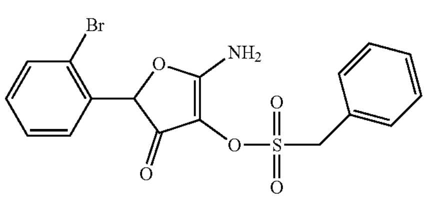 | 2-amino-5-(2-bromophenyl)-4-oxo-4,5-dihydrofuran-3-yl phenylmethanesulfonate | $C_{17}H_{14}BrNO_5S$ | 424.27 |
| 1046 | 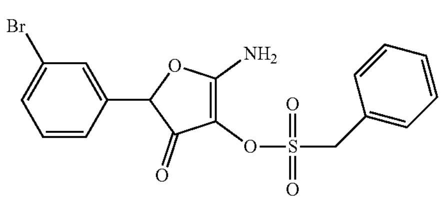 | 2-amino-5-(3-bromophenyl)-4-oxo-4,5-dihydrofuran-3-yl phenylmethanesulfonate | $C_{17}H_{14}BrNO_5S$ | 424.27 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1047 | 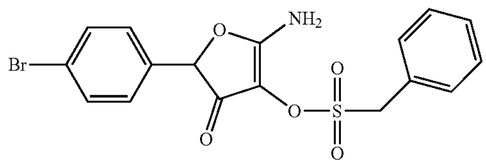 | 2-amino-5-(4-bromophenyl)-4-oxo-4,5-dihydrofuran-3-yl phenylmethanesulfonate | $C_{17}H_{14}BrNO_5S$ | 424.27 |
| 1048 | 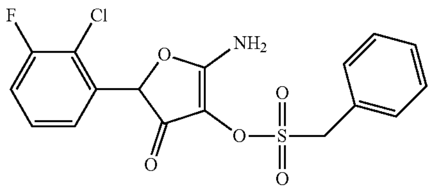 [SMILES: NC1=C(OS(=O)(=O)Cc2ccccc2)C(=O)C(c2cccc(F)c2Cl)O1] | 2-amino-5-(2-chloro-3-fluorophenyl)-4-oxo-4,5-dihydrofuran-3-yl phenylmethanesulfonate | $C_{17}H_{13}ClFNO_5S$ | 397.80 |
| 1049 | 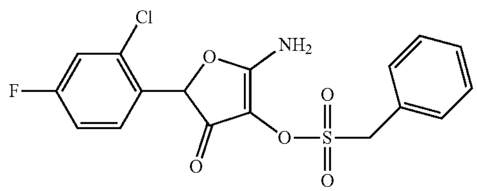 [SMILES: NC1=C(OS(=O)(=O)Cc2ccccc2)C(=O)C(c2ccc(F)cc2Cl)O1] | 2-amino-5-(2-chloro-4-fluorophenyl)-4-oxo-4,5-dihydrofuran-3-yl phenylmethanesulfonate | $C_{17}H_{13}ClFNO_5S$ | 397.80 |
| 1050 | 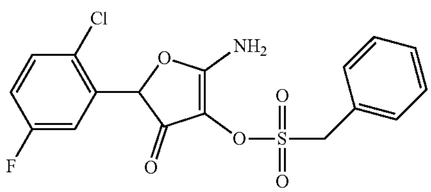 [SMILES: NC1=C(OS(=O)(=O)Cc2ccccc2)C(=O)C(c2cc(F)ccc2Cl)O1] | 2-amino-5-(2-chloro-5-fluorophenyl)-4-oxo-4,5-dihydrofuran-3-yl phenylmethanesulfonate | $C_{17}H_{13}ClFNO_5S$ | 397.80 |
| 1051 | 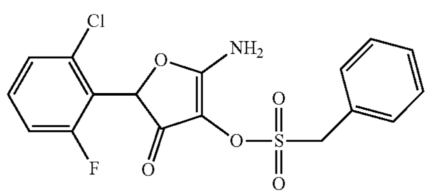 [SMILES: NC1=C(OS(=O)(=O)Cc2ccccc2)C(=O)C(c2c(F)cccc2Cl)O1] | 2-amino-5-(2-chloro-6-fluorophenyl)-4-oxo-4,5-dihydofuran-3-yl phenylmethanesulfonate | $C_{17}H_{13}ClFNO_5S$ | 397.80 |
| 1052 | 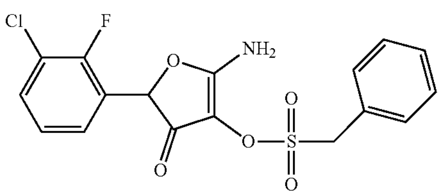 [SMILES: NC1=C(OS(=O)(=O)Cc2ccccc2)C(=O)C(c2cccc(Cl)c2F)O1] | 2-amino-5-(3-chloro-2-fluorophenyl)-4-oxo-4,5-dihydrofuran-3-yl phenylmethanesulfonate | $C_{17}H_{13}ClFNO_5S$ | 397.80 |
| 1053 | 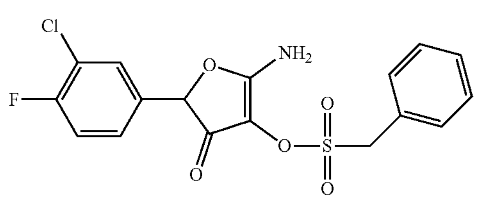 | 2-amino-5-(3-chloro-4-fluorophenyl)-4-oxo-4,5-dihydrofuran-3-yl phenylmethanesulfonate | $C_{17}H_{13}ClFNO_5S$ | 397.80 |
| 1054 | 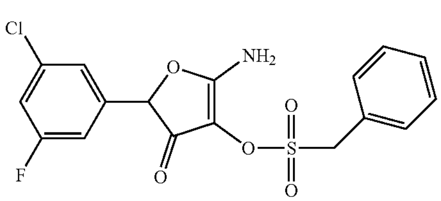 | 2-amino-5-(3-chloro-5-fluorophenyl)-4-oxo-4,5-dihydrofuran-3-yl phenylmethanesulfonate | $C_{17}H_{13}ClFNO_5S$ | 397.80 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1055 | 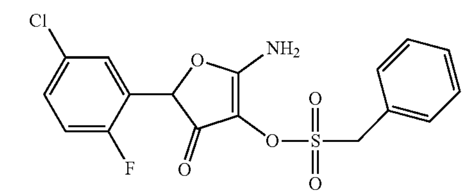 [SMILES: NC1=C(OS(=O)(=O)Cc2ccccc2)C(=O)C(c2cc(Cl)ccc2F)O1] | 2-amino-5-(5-chloro-2-fluorophenyl)-4-oxo-4,5-dihydrofuran-3-yl phenylmethanesulfonate | $C_{17}H_{13}ClFNO_5S$ | 397.80 |
| 1056 | 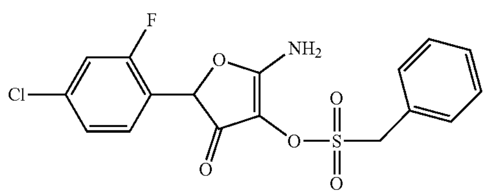 | 2-amino-5-(4-chloro-2-fluorophenyl)-4-oxo-4,5-dihydrofuran-3-yl phenylmethanesulfonate | $C_{17}H_{13}ClFNO_5S$ | 397.80 |
| 1057 | 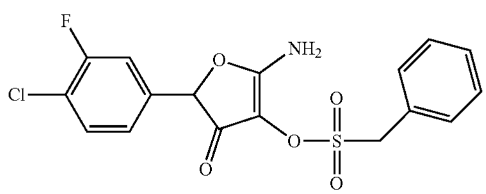 | 2-amino-5-(4-chloro-3-fluorophenyl)-4-oxo-4,5-dihydrofuran-3-yl phenylmethanesulfonate | $C_{17}H_{13}ClFNO_5S$ | 397.80 |
| 1058 | 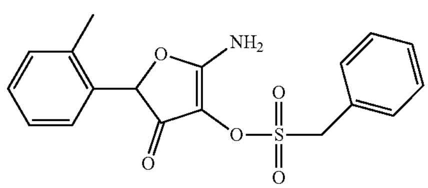 [SMILES: Cc1ccccc1C1OC(N)=C(OS(=O)(=O)Cc2ccccc2)C1=O] | 2-amino-4-oxo-5-(o-tolyl)-4,5-dihydrofuran-3-yl phenylmethanesulfonate | $C_{18}H_{17}NO_5S$ | 359.40 |
| 1059 | 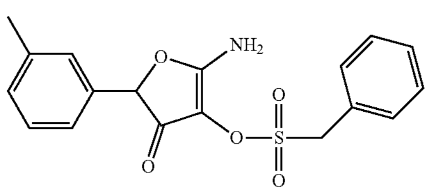 [SMILES: Cc1cccc(C2OC(N)=C(OS(=O)(=O)Cc3ccccc3)C2=O)c1] | 2-amino-4-oxo-5-(m-tolyl)-4,5-dihydrofuran-3-yl phenylmethanesulfonate | $C_{18}H_{17}NO_5S$ | 359.40 |
| 1060 | 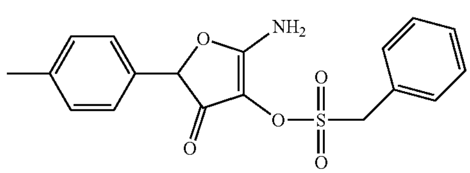 [SMILES: Cc1ccc(C2OC(N)=C(OS(=O)(=O)Cc3ccccc3)C2=O)cc1] | 2-amino-4-oxo-5-(p-tolyl)-4,5-dihydrofuran-3-yl phenylmethanesulfonate | $C_{18}H_{17}NO_5S$ | 359.40 |
| 1061 | 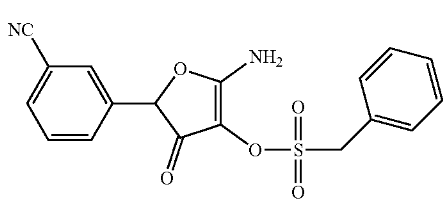 [SMILES: N#Cc1cccc(C2OC(N)=C(OS(=O)(=O)Cc3ccccc3)C2=O)c1] | 2-amino-5-(3-cyanophenyl)-4-oxo-4,5-dihydrofuran-3-yl phenylmethanesulfonate | $C_{18}H_{14}N_2O_5S$ | 370.38 |
| 1062 | 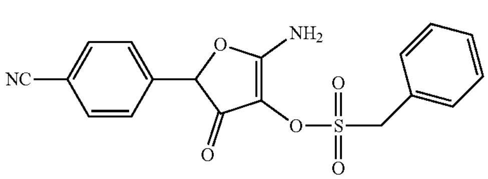 [SMILES: N#Cc1ccc(C2OC(N)=C(OS(=O)(=O)Cc3ccccc3)C2=O)cc1] | 2-amino-5-(4-cyanophenyl)-4-oxo-4,5-dihydrofuran-3-yl phenylmethanesulfonate | $C_{18}H_{14}N_2O_5S$ | 370.38 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1063 | 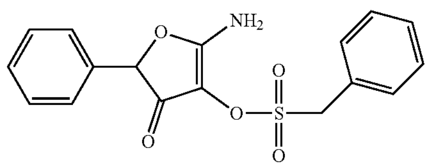 [SMILES: NC1=C(OS(=O)(=O)Cc2ccccc2)C(=O)C(c2ccccc2)O1] | 2-amino-4-oxo-5-phenyl-4,5-dihydrofuran-3-yl phenylmethanesulfonate | $C_{17}H_{15}NO_5S$ | 345.37 |
| 1064 | 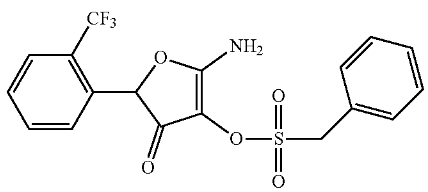 [SMILES: NC1=C(OS(=O)(=O)Cc2ccccc2)C(=O)C(c2ccccc2C(F)(F)F)O1] | 2-amino-4-oxo-5-(2-(trifluoromethyl)phenyl)-4,5-dihydrofuran-3-yl phenylmethanesulfonate | $C_{18}H_{14}F_3NO_5S$ | 413.37 |
| 1065 | 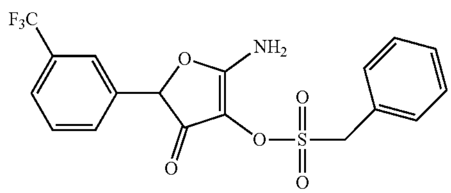 [SMILES: NC1=C(OS(=O)(=O)Cc2ccccc2)C(=O)C(c2cccc(C(F)(F)F)c2)O1] | 2-amino-4-oxo-5-(3-(trifluoromethyl)phenyl)-4,5-dihydrofuran-3-yl phenylmethanesulfonate | $C_{18}H_{14}F_3NO_5S$ | 413.37 |
| 1066 | 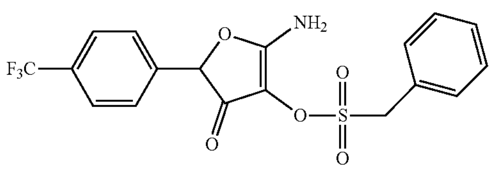 [SMILES: NC1=C(OS(=O)(=O)Cc2ccccc2)C(=O)C(c2ccc(C(F)(F)F)cc2)O1] | 2-amino-4-oxo-5-(4-(trifluoromethyl)phenyl)-4,5-dihydrofuran-3-yl phenylmethanesulfonate | $C_{18}H_{14}F_3NO_5S$ | 413.37 |
| 1067 | 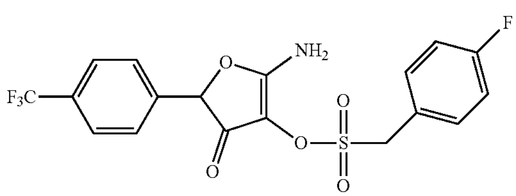 [SMILES: NC1=C(OS(=O)(=O)Cc2ccc(F)cc2)C(=O)C(c2ccc(C(F)(F)F)cc2)O1] | 2-amino-4-oxo-5-(4-(trifluoromethyl)phenyl)-4,5-dihydrofuran-3-yl (4-fluorophenyl)methanesulfonate | $C_{18}H_{13}F_4NO_5S$ | 431.36 |
| 1068 | 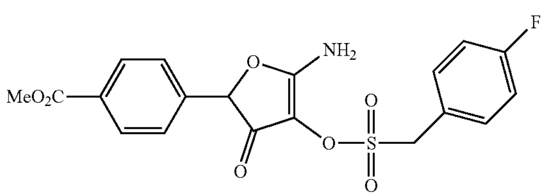 [SMILES: COC(=O)c1ccc(C2OC(N)=C(OS(=O)(=O)Cc3ccc(F)cc3)C2=O)cc1] | methyl 4-(5-amino-4-(((4-fluorobenzyl)sulfonyl)oxy)-3-oxo-2,3-dihydrofuran-2-yl)benzoate | $C_{19}H_{16}FNO_7S$ | 421.40 |
| 1069 | 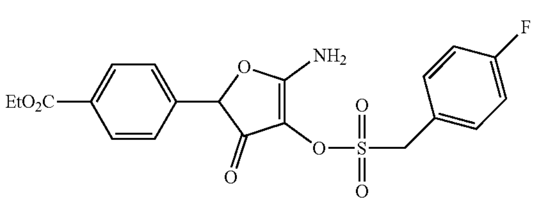 [SMILES: CCOC(=O)c1ccc(C2OC(N)=C(OS(=O)(=O)Cc3ccc(F)cc3)C2=O)cc1] | ethyl 4-(5-amino-4-(((4-fluorobenzyl)sulfonyl)oxy)-3-oxo-2,3-dihydrofuran-2-yl)benzoate | $C_{20}H_{18}FNO_7S$ | 435.42 |
| 1070 | 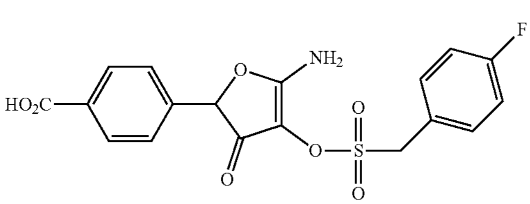 [SMILES: NC1=C(OS(=O)(=O)Cc2ccc(F)cc2)C(=O)C(c2ccc(C(=O)O)cc2)O1] | 4-(5-amino-4-(((4-fluorobenzyl)sulfonyl)oxy)-3-oxo-2,3-dihydrofuran-2-yl)benzoic acid | $C_{18}H_{14}FNO_7S$ | 407.37 |

TABLE 2-continued (#1001-1083)
Structures, Names, and Numbers of Key Unlabeled Compounds Listed in Example 1

| CP # | Structure | Name | Formula | MW |
|---|---|---|---|---|
| 1071 | 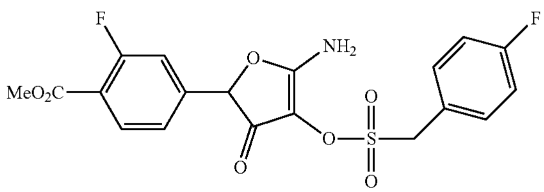 [SMILES: COC(=O)c1ccc(C2OC(N)=C(OS(=O)(=O)Cc3ccc(F)cc3)C2=O)cc1F] | methyl 4-(5-amino-4-(((4-fluorobenzyl)sulfonyl)oxy)-3-oxo-2,3-dihydrofuran-2-yl)-2-fluorobenzoate | $C_{19}H_{15}F_2NO_7S$ | 439.39 |
| 1077 | 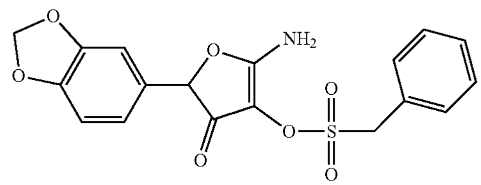 [SMILES: NC1=C(OS(=O)(=O)Cc2ccccc2)C(=O)C(c2ccc3c(c2)OCO3)O1] | 2-amino-5-(benzo[d][1,3]dioxol-5-yl)-4-oxo-4,5-dihydrofuran-3-yl phenylmethanesulfonate | $C_{18}H_{15}NO_7S$ | 389.38 |
| 1078 | 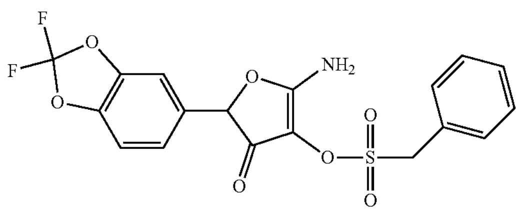 [SMILES: NC1=C(OS(=O)(=O)Cc2ccccc2)C(=O)C(c2ccc3c(c2)OC(F)(F)O3)O1] | 2-amino-5-(2,2-difluorobenzo[d][1,3]dioxol-5-yl)-4-oxo-4,5-dihydrofuran-3-yl phenylmethanesulfonate | $C_{18}H_{13}F_2NO_7S$ | 425.36 |
| 1079 | 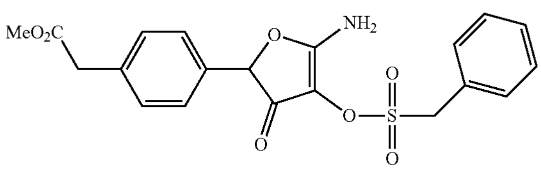 [SMILES: COC(=O)Cc1ccc(C2OC(N)=C(OS(=O)(=O)Cc3ccccc3)C2=O)cc1] | methyl 2-(4-(5-amino-4-((benzylsulfonyl)oxy)-3-oxo-2,3-dihydrofuran-2-yl)phenyl)acetate | $C_{20}H_{19}NO_7S$ | 417.43 |
| 1081 | 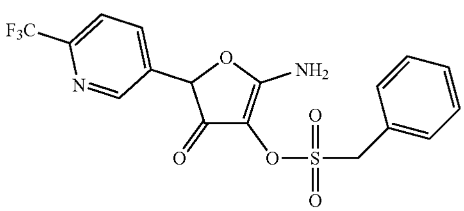 [SMILES: NC1=C(OS(=O)(=O)Cc2ccccc2)C(=O)C(c2ccc(C(F)(F)F)nc2)O1] | 2-amino-4-oxo-5-(6-(trifluoromethyl)pyridin-3-yl)-4,5-dihydrofuran-3-yl phenylmethanesulfonate | $C_{17}H_{13}F_3N_2O_5S$ | 414.36 |
| 1082 | 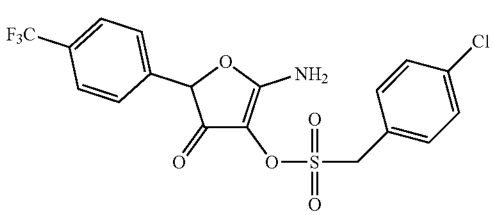 [SMILES: NC1=C(OS(=O)(=O)Cc2ccc(Cl)cc2)C(=O)C(c2ccc(C(F)(F)F)cc2)O1] | 2-amino-4-oxo-5-(4-(trifluoromethyl)phenyl)-4,5-dihydrofuran-3-yl (4-chlorophenyl)methanesulfonate | $C_{18}H_{13}ClF_3NO_5S$ | 447.81 |
| 1083 | 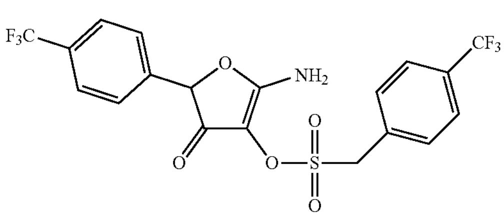 [SMILES: NC1=C(OS(=O)(=O)Cc2ccc(C(F)(F)F)cc2)C(=O)C(c2ccc(C(F)(F)F)cc2)O1] | 2-amino-4-oxo-5-(4-(trifluoromethyl)phenyl)-4,5-dihydrofuran-3-yl (4-(trifluoromethyl)phenyl)methanesulfonate | $C_{19}H_{13}F_6NO_5S$ | 481.37 |

TABLE 3

Compounds by Informal Number and Chemical Name with NMR Spectra

| CP # | Structure and Informal Name | Chemical Name | Formula | Mol Wt |
|---|---|---|---|---|
| 1010 | 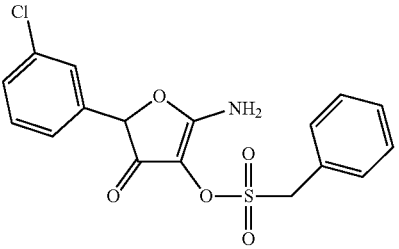<br>MO-I-1101 | 2-amino-5-(3-chlorophenyl)-4-oxo-4,5-dihydrofuran-3-yl phenylmethanesulfonate | $C_{17}H_{14}ClNO_5S$ | 379.81 |
| 1029 | 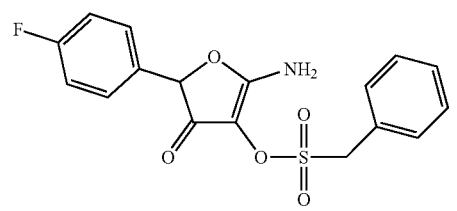<br>MO-I-1103 | 2-amino-5-(4-fluorophenyl)-4-oxo-4,5-dihydrofuran-3-yl phenylmethanesulfonate | $C_{17}H_{14}FNO_5S$ | 363.36 |
| 1028 | 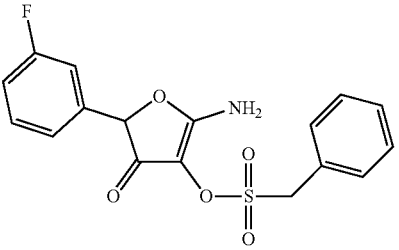<br>MO-I-1104 | 2-amino-5-(3-fluorophenyl)-4-oxo-4,5-dihydrofuran-3-yl phenylmethanesulfonate | $C_{17}H_{14}FNO_5O$ | 363.36 |
| 1027 | 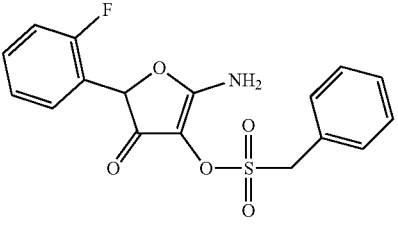<br>MO-I-1105 | 2-amino-5-(2-fluorophenyl)-4-oxo-4,5-dihydrofuran-3-yl phenylmethanesulfonate | $C_{17}H_{14}FNO_5S$ | 363.36 |
| 1030 | 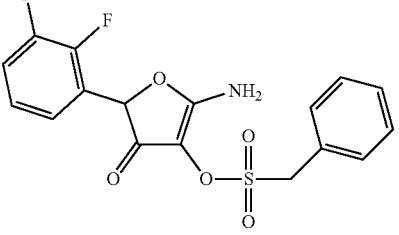<br>MO-I-1130 | 2-amino-5-(2,3-difluorophenyl)-4-oxo-4,5-dihydrofuran-3-yl phenylmethanesulfonate | $C_{17}H_{13}F_2NO_5S$ | 381.35 |

TABLE 3-continued

Compounds by Informal Number and Chemical Name with NMR Spectra

| CP # | Structure and Informal Name | Chemical Name | Formula | Mol Wt |
|---|---|---|---|---|
| 1034 | MO-I-1131 | 2-amino-5-(3,4-difluorophenyl)-4-oxo-4,5-dihydrofuran-3-yl phenylmethanesulfonate | $C_{17}H_{13}F_2NO_5S$ | 381.35 |
| 1031 | MO-I-1132 | 2-amino-5-(2,4-difluorophenyl)-4-oxo-4,5-dihydrofuran-3-yl phenylmethanesulfonate | $C_{17}H_{13}F_2NO_5S$ | 381.35 |
| 1035 | MO-I-1133 | 2-amino-5-(3,5-difluorophenyl)-4-oxo-4,5-dihydrofuran-3-yl phenylmethanesulfonate | $C_{17}H_{13}F_2NO_5S$ | 381.35 |
| 1011 | MO-I-1140 | 2-amino-5-(2,3-dichlorophenyl)-4-oxo-4,5-dihydrofuran-3-yl phenylmethanesulfonate | $C_{17}H_{13}Cl_2NO_5S$ | 414.25 |
| 1014 | MO-I-1144 | 2-amino-5-(3,4-dichlorophenyl)-4-oxo-4,5-dihydrofuran-3-yl phenylmethanesulfonate | $C_{17}H_{13}Cl_2NO_5S$ | 414.25 |

TABLE 3-continued

Compounds by Informal Number and Chemical Name with NMR Spectra

| CP # | Structure and Informal Name | Chemical Name | Formula | Mol Wt |
|---|---|---|---|---|
| 1062 | MO-I-1149 | 2-amino-5-(4-cyanophenyl)-4-oxo-4,5-dihydrofuran-3-yl phenylmethanesulfonate | $C_{18}H_{14}N_2O_5S$ | 370.38 |
| 1066 | MO-I-1151 | 2-amino-4-oxo-5-(4-(trifluoromethyl)phenyl)-4,5-dihydrofuran-3-yl phenylmethanesulfonate | $C_{18}H_{14}F_3NO_5S$ | 413.37 |
| 1047 | MO-I-1152 | 2-amino-5-(4-bromophenyl)-4-oxo-4,5-dihydrofuran-3-yl phenylmethanesulfonate | $C_{17}H_{14}BrNO_5S$ | 424.27 |
| 2081 | MO-I-1181 | 2-amino-4-oxo-5-(6-(trifluoromethyl)pyridin-3-yl)-4,5-dihydrofuran-3-yl phenylmethanesulfonate | C17H13F3N2O5S | 414.36 |
| 1017 | MO-I-1182 | methyl 4-(5-amino-4-((benzylsulfonyl)oxy)-3-oxo-2,3-dihydrofuran-2-yl)benzoate | $C_{19}H_{17}NO_7S$ | 403.40 |
| 1077 | MO-I-1184 | 2-amino-5-(benzo[d][1,3]dioxol-5-yl)-4-oxo-4,5-dihydrofuran-3-yl phenylmethanesulfonate | $C_{18}H_{15}NO_7S$ | 389.38 |

TABLE 3-continued

Compounds by Informal Number and Chemical Name with NMR Spectra

| CP # | Structure and Informal Name | Chemical Name | Formula | Mol Wt |
|---|---|---|---|---|
| 1078 | 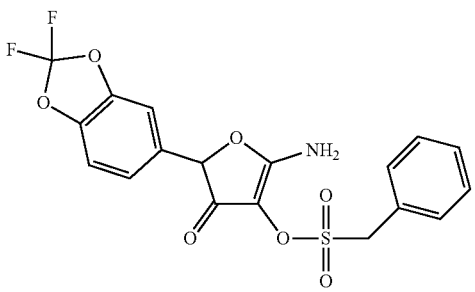<br>MO-I-1185 | 2-amino-5-(2,2-difluorobenzo[d][1,3]dioxol-5-yl)-4-oxo-4,5-dihydrofuran-3-yl phenylmethanesulfonate | $C_{18}H_{13}F_2NO_7S$ | 425.36 |
| 1079 | 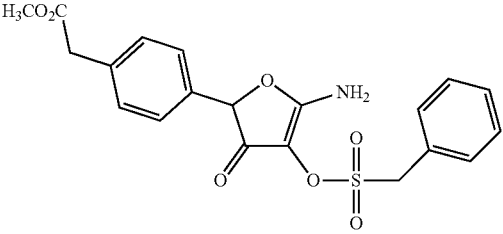<br>MO-I-1188 | methyl 2-(4-(5-amino-4-((benzylsulfonyl)oxy)-3-oxo-2,3-dihydrofuran-2-yl)phenyl)acetate | $C_{20}H_{19}NO_7S$ | 417.43 |
| 2082 | 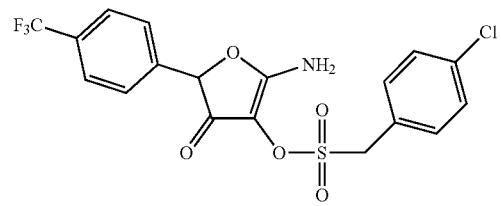<br>MO-I-1151A01100 | 2-amino-4-oxo-5-(4-(trifluoromethyl)phenyl)-4,5-dihydrofuran-3-yl (4-chlorophenyl)methanesulfonate | $C_{18}H_{13}ClF_3NO_5S$ | 447.81 |
| 2067 | 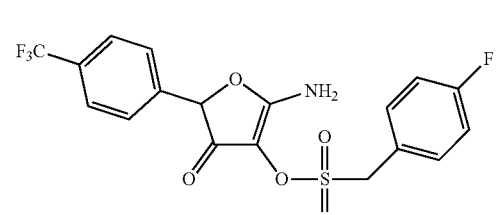<br>MO-I-1151A01103 | 2-amino-4-oxo-5-(4-(trifluoromethyl)phenyl)-4,5-dihydrofuran-3-yl (4-fluorophenyl)methanesulfonate | $C_{18}H_{13}F_4NO_5S$ | 431.36 |
| 2083 | 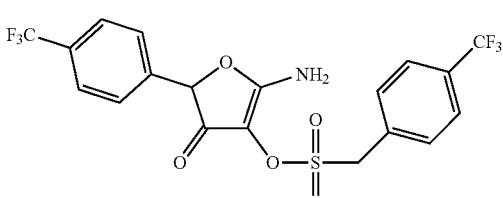<br>MO-I-1151A01151 | 2-amino-4-oxo-5-(4-(trifluoromethyl)phenyl)-4,5-dihydrofuran-3-yl (4-(trifluoromethyl)phenyl)methanesulfonate | $C_{19}H_{13}F_6NO_5S$ | 481.37 |

Example 2—Isotopically-Stabilized (Deuterated) Tetronimide Compounds (#2001-2093)

Synthesis of Exemplary Isotopically-Stabilized Tetronimide Compounds

Synthesis of exemplary isotopically-stabilized (deuterated) compounds are described below.

Compounds of the class designated as 2-(aryl)-4-hydroxy-5-amino-3(2H)furanones are prepared according to the method of Dahn (Experientia (1954), 10, 245-6.).

Sulfonylated compounds are prepared according to U.S. Pat. No. 9,771,356.

TABLE 4

(Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 1007 | 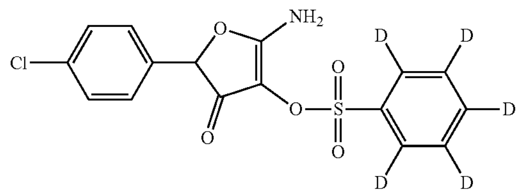 [SMILES: [2H]c1c([2H])c([2H])c(S(=O)(=O)OC2=C(N)OC(c3ccc(Cl)cc3)C2=O)c([2H])c1[2H]] | 2-amino-5-(4-chlorophenyl)-4-oxo-4,5-dihydrofuran-3-yl benzenesulfonate-d5 | $C_{16}H_7D_5ClNO_5S$ | 370.81 |
| 1072 | 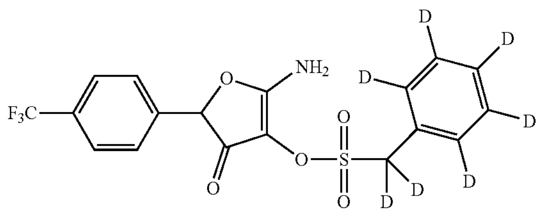 [SMILES: [2H]c1c([2H])c([2H])c(C([2H])([2H])S(=O)(=O)OC2=C(N)OC(c3ccc(C(F)(F)F)cc3)C2=O)c([2H])c1[2H]] | 2-amino-4-oxo-5-(4-(trifluoromethyl)phenyl)-4,5-dihydrofuran-3-yl (phenyl-d5)methanesulfonate-d2 | $C_{18}H_7D_7F_3NO_5S$ | 420.41 |
| 1073 | 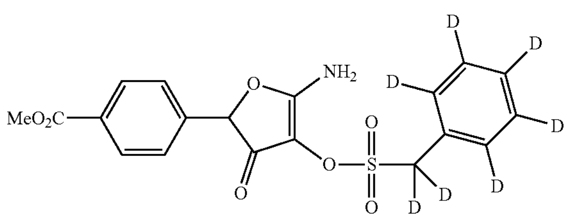 [SMILES: [2H]c1c([2H])c([2H])c(C([2H])([2H])S(=O)(=O)OC2=C(N)OC(c3ccc(C(=O)OC)cc3)C2=O)c([2H])c1[2H]] | methyl 4-(5-amino-3-oxo-4-((((phenyl-d5)methyl-d2)sulfonyl)oxy)-2,3-dihydrofuran-2-yl)benzoate | $C_{19}H_{10}D_7NO_7S$ | 410.45 |
| 1074 | 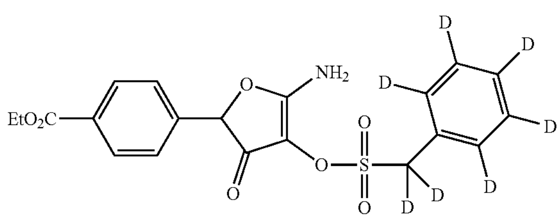 [SMILES: [2H]c1c([2H])c([2H])c(C([2H])([2H])S(=O)(=O)OC2=C(N)OC(c3ccc(C(=O)OCC)cc3)C2=O)c([2H])c1[2H]] | ethyl 4-(5-amino-3-oxo-4-((((phenyl-d5)methyl-d2)sulfonyl)oxy)-2,3-dihydrofuran-2-yl)benzoate | $C_{20}H_{12}D_7NO_7S$ | 424.47 |
| 1075 | 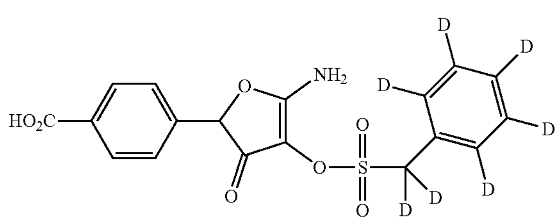 [SMILES: [2H]c1c([2H])c([2H])c(C([2H])([2H])S(=O)(=O)OC2=C(N)OC(c3ccc(C(=O)O)cc3)C2=O)c([2H])c1[2H]] | 4-(5-amino-3-oxo-4-((((phenyl-d5)methyl-d2)sulfonyl)oxy)-2,3-dihydrofuran-2-yl)benzoic acid | $C_{18}H_8D_7NO_7S$ | 396.42 |
| 1076 | 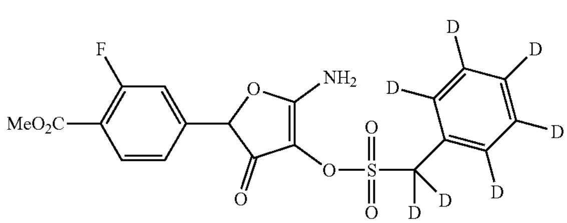 [SMILES: [2H]c1c([2H])c([2H])c(C([2H])([2H])S(=O)(=O)OC2=C(N)OC(c3ccc(C(=O)OC)c(F)c3)C2=O)c([2H])c1[2H]] | methyl 4-(5-amino-3-oxo-4-((((phenyl-d5)methyl-d2)sulfonyl)oxy)-2,3-dihydrofuran-2-yl)-2-fluorobenzoate | $C_{19}H_9D_7FNO_7S$ | 428.44 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 1084 | 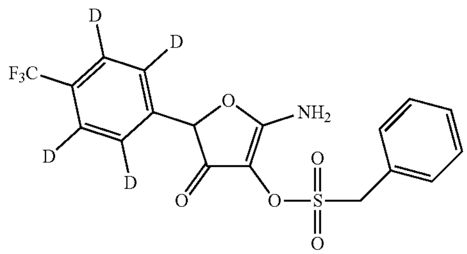 | 2-amino-4-oxo-5-(4-(trifluoromethyl)phenyl-2,3,5,6-d4)-4,5-dihydrofuran-3-yl phenylmethanesulfonate | $C_{18}H_{10}D_4F_3NO_5S$ | 417.39 |
| 1085 | 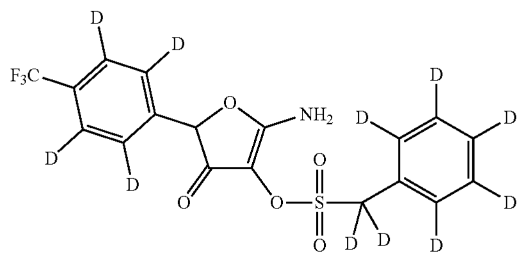 [SMILES: [2H]c1c([2H])c([2H])c(C([2H])([2H])S(=O)(=O)OC2=C(N)OC(c3c([2H])c([2H])c(C(F)(F)F)c([2H])c3[2H])C2=O)c([2H])c1[2H]] | 2-amino-4-oxo-5-(4-(trifluoromethyl)phenyl-2,3,5,6-d4)-4,5-dihydrofuran-3-yl (phenyl-d5)methanesulfonate | $C_{18}H_5D_9F_3NO_5S$ | 422.42 |
| 2001 | 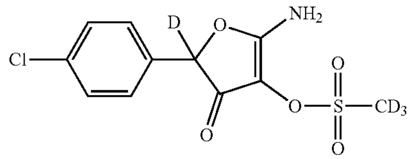 [SMILES: [2H]C1(c2ccc(Cl)cc2)OC(N)=C(OS(=O)(=O)C([2H])([2H])[2H])C1=O] | 2-amino-5-(4-chlorophenyl)-4-oxo-4,5-dihydrofuran-3-yl-5-d methanesulfonate-d3 | $C_{11}H_6D_4ClNO_5S$ | 307.74 |
| 2001(R) | 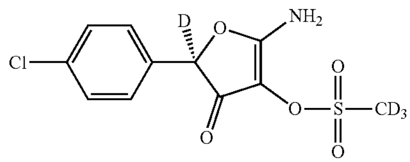 [SMILES: [2H]C([2H])([2H])S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d methanesulfonate-d3 | $C_{11}H_6D_4ClNO_5S$ | 307.74 |
| 2001(S) | 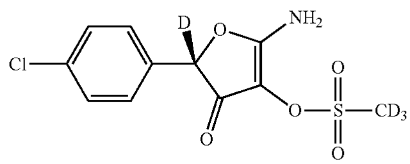 [SMILES: [2H]C([2H])([2H])S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d methanesulfonate-d3 | $C_{11}H_6D_4ClNO_5S$ | 307.74 |
| 2002 | 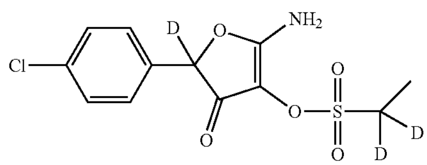 [SMILES: [2H]C1(c2ccc(Cl)cc2)OC(N)=C(OS(=O)(=O)C([2H])([2H])C)C1=O] | 2-amino-5-(4-chlorophenyl)-4-oxo-4,5-dihydrofuran-3-yl-5-d ethane-1-sulfonate-1,1-d2 | $C_{12}H_9D_3ClNO_5S$ | 320.76 |
| 2002(R) | 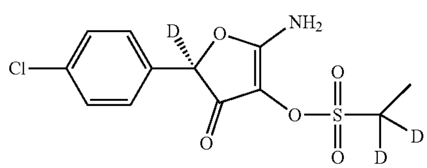 [SMILES: [2H]C([2H])(C)S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d ethane-1-sulfonate-1,1-d2 | $C_{12}H_9D_3ClNO_5S$ | 320.76 |
| 2002(S) | 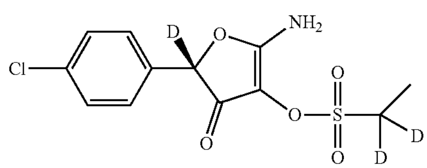 [SMILES: [2H]C([2H])(C)S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d ethane-1-sulfonate-1,1-d2 | $C_{12}H_9D_3ClNO_5S$ | 320.76 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2003 | 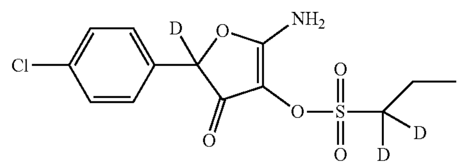 [SMILES: [2H]C1(c2ccc(Cl)cc2)OC(N)=C(OS(=O)(=O)C([2H])([2H])CC)C1=O] | 2-amino-5-(4-chlorophenyl)-4-oxo-4,5-dihydrofuran-3-yl-5-d propane-1-sulfonate-1,1-d2 | $C_{13}H_{11}D_3ClNO_5S$ | 334.79 |
| 2003(R) | 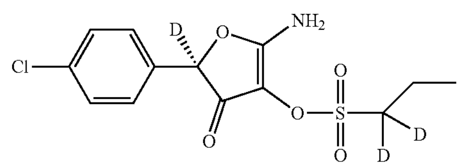 [SMILES: [2H]C([2H])(CC)S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d propane-1-sulfonate-1,1-d2 | $C_{13}H_{11}D_3ClNO_5S$ | 334.79 |
| 2003(S) | 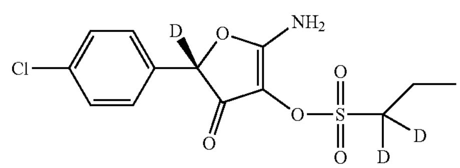 [SMILES: [2H]C([2H])(CC)S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d-propane-1-sulfonate-1,1-d2 | $C_{13}H_{11}D_3ClNO_5S$ | 334.79 |
| 2004 | 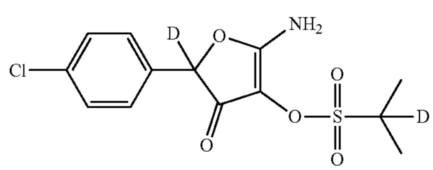 [SMILES: [2H]C1(c2ccc(Cl)cc2)OC(N)=C(OS(=O)(=O)C([2H])(C)C)C1=O] | 2-amino-5-(4-chlorophenyl)-4-oxo-4,5-dihydrofuran-3-yl-5-d propane-2-sulfonate-2-d | $C_{13}H_{12}D_2ClNO_5S$ | 333.78 |
| 2004(R) | 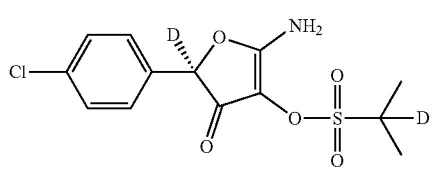 [SMILES: [2H]C(C)(C)S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d propane-2-sulfonate-2-d | $C_{13}H_{12}D_2ClNO_5S$ | 333.78 |
| 2004(S) | 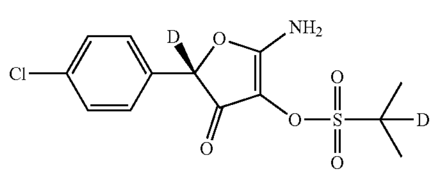 [SMILES: [2H]C(C)(C)S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d propane-2-sulfonate-2-d | $C_{13}H_{12}D_2ClNO_5S$ | 333.78 |
| 2005 | 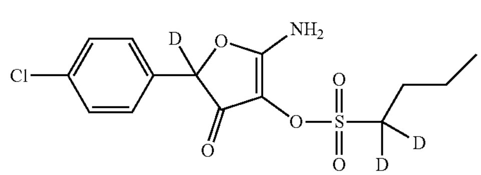 [SMILES: [2H]C1(c2ccc(Cl)cc2)OC(N)=C(OS(=O)(=O)C([2H])([2H])CCC)C1=O] | 2-amino-5-(4-chlorophenyl)-4-oxo-4,5-dihydrofuran-3-yl-5-d butane-1-sulfonate-1,1-d2 | $C_{14}H_{13}D_3ClNO_5S$ | 348.81 |
| 2005(R) | 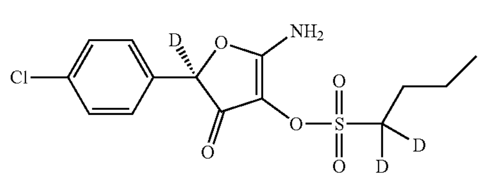 [SMILES: [2H]C([2H])(CCC)S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d butane-1-sulfonate-1,1-d2 | $C_{14}H_{13}D_3ClNO_5S$ | 348.81 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2005(S) | 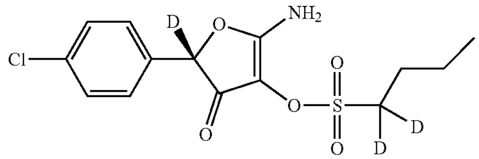 [SMILES: [2H]C([2H])(CCC)S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d butane-1-sulfonate-1,1-d2 | $C_{14}H_{13}D_3ClNO_5S$ | 348.81 |
| 2006 | 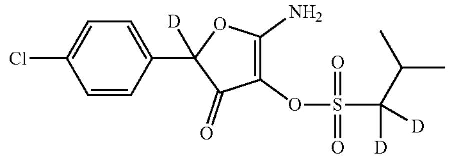 [SMILES: [2H]C1(c2ccc(Cl)cc2)OC(N)=C(OS(=O)(=O)C([2H])([2H])C(C)C)C1=O] | 2-amino-5-(4-chlorophenyl)-4-oxo-4,5-dihydrofuran-3-yl-5-d 2-methylpropane-1-sulfonate-1,1-d2 | $C_{14}H_{13}D_3ClNO_5S$ | 348.81 |
| 2006(R) | 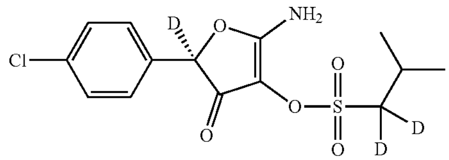 [SMILES: [2H]C([2H])(C(C)C)S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d 2-methylpropane-1-sulfonate-1,1-d2 | $C_{14}H_{13}D_3ClNO_5S$ | 348.81 |
| 2006(S) | 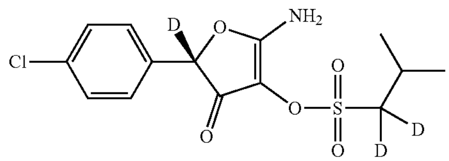 [SMILES: [2H]C([2H])(C(C)C)S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d 2-methylpropane-1-sulfonate-1,1-d2 | $C_{14}H_{13}D_3ClNO_5S$ | 348.81 |
| 2007 | 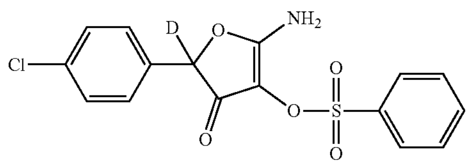 [SMILES: [2H]C1(c2ccc(Cl)cc2)OC(N)=C(OS(=O)(=O)c2ccccc2)C1=O] | 2-amino-5-(4-chlorophenyl)-4-oxo-4,5-dihydrofuran-3-yl-5-d benzenesulfonate | $C_{16}H_{11}DClNO_5S$ | 366.79 |
| 2007(R) | 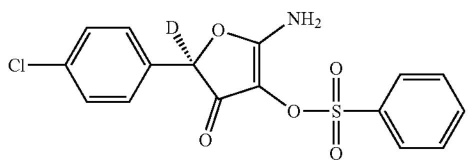 [SMILES: [2H][C@]1(c2ccc(Cl)cc2)OC(N)=C(OS(=O)(=O)c2ccccc2)C1=O] | (R)-2-amino-5-(4-chlorophenyl)-4-oxo-4,5-dihydrofuran-3-yl-5-d benzenesulfonate | $C_{16}H_{11}DClNO_5S$ | 366.79 |
| 2007(S) | 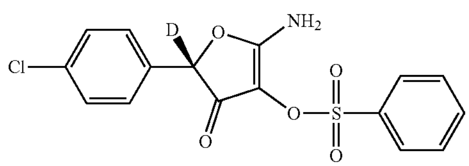 [SMILES: [2H][C@@]1(c2ccc(Cl)cc2)OC(N)=C(OS(=O)(=O)c2ccccc2)C1=O] | (S)-2-amino-5-(4-chlorophenyl)-4-oxo-4,5-dihydrofuran-3-yl-5-d benzenesulfonate | $C_{16}H_{11}DClNO_5S$ | 366.79 |
| 2008 | 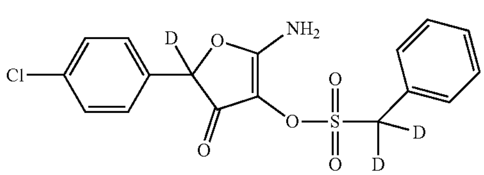 [SMILES: [2H]C1(c2ccc(Cl)cc2)OC(N)=C(OS(=O)(=O)C([2H])([2H])c2ccccc2)C1=O] | 2-amino-5-(4-chlorophenyl)-4-oxo-4,5-dihydrofuran-3-yl-5-d phenylmethanesulfonate-d2 | $C_{17}H_{11}D_3ClNO_5S$ | 382.83 |
| 2008(R) | 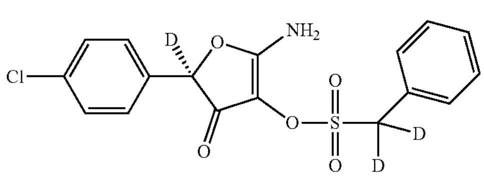 [SMILES: [2H]C([2H])(c1ccccc1)S(=O)(=O)OC1=C(N)O[C@]([2H])(c2ccc(Cl)cc2)C1=O] | (R)-2-amino-5-(4-chlorophenyl)-4-oxo-4,5-dihydrofuran-3-yl-5-d phenylmethanesulfonate-d2 | $C_{17}H_{11}D_3ClNO_5S$ | 382.83 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2008(S) | 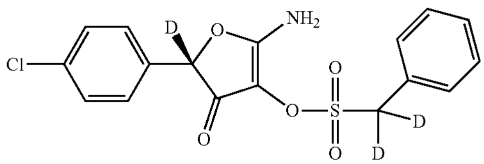 [SMILES: [2H]C([2H])(c1ccccc1)S(=O)(=O)OC1=C(N)O[C@@]([2H])(c2ccc(Cl)cc2)C1=O] | (S)-2-amino-5-(4-chlorophenyl)-4-oxo-4,5-dihydrofuran-3-yl-5-d phenylmethanesulfonate-d2 | $C_{17}H_{11}D_3ClNO_5S$ | 382.83 |
| 2009 | 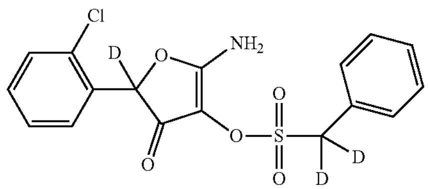 | 2-amino-5-(2-chlorophenyl)-4-oxo-4,5-dihydrofuran-3-yl-5-d phenylmethanesulfonate-d2 | $C_{17}H_{11}D_3ClNO_5S$ | 382.83 |
| 2009(R) | 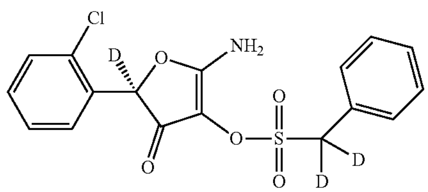 | (R)-2-amino-5-(2-chlorophenyl)-4-oxo-4,5-dihydrofuran-3-yl-5-d phenylmethanesulfonate-d2 | $C_{17}H_{11}D_3ClNO_5S$ | 382.83 |
| 2009(S) | 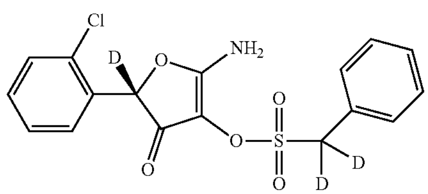 | (S)-2-amino-5-(2-chlorophenyl)-4-oxo-4,5-dihydrofuran-3-yl-5-d phenylmethanesulfonate-d2 | $C_{17}H_{11}D_3ClNO_5S$ | 382.83 |
| 2010 | 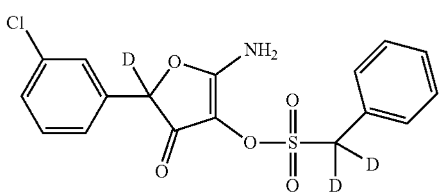 [SMILES: [2H]C1(c2cccc(Cl)c2)OC(N)=C(OS(=O)(=O)C([2H])([2H])c2ccccc2)C1=O] | 2-amino-5-(3-chlorophenyl)-4-oxo-4,5-dihydrofuran-3-yl-5-d phenylmethanesulfonate-d2 | $C_{17}H_{11}D_3ClNO_5S$ | 382.83 |
| 2010(R) | 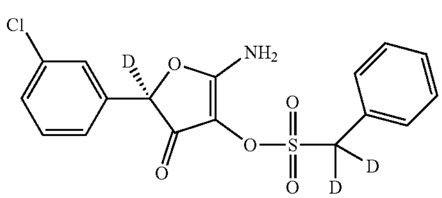 [SMILES: [2H]C([2H])(c1ccccc1)S(=O)(=O)OC1=C(N)O[C@]([2H])(c2cccc(Cl)c2)C1=O] | (R)-2-amino-5-(3-chlorophenyl)-4-oxo-4,5-dihydrofuran-3-yl-5-d phenylmethanesulfonate-d2 | $C_{17}H_{11}D_3ClNO_5S$ | 382.83 |
| 2010(S) | 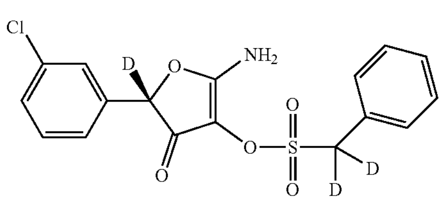 [SMILES: [2H]C([2H])(c1ccccc1)S(=O)(=O)OC1=C(N)O[C@@]([2H])(c2cccc(Cl)c2)C1=O] | (S)-2-amino-5-(3-chlorophenyl)-4-oxo-4,5-dihydrofuran-3-yl-5-d phenylmethanesulfonate-d2 | $C_{17}H_{11}D_3ClNO_5S$ | 382.83 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2011 | 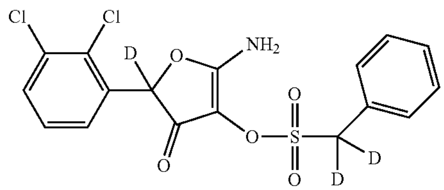 [SMILES: [2H]C1(c2cccc(Cl)c2Cl)OC(N)=C(OS(=O)(=O)C([2H])([2H])c2ccccc2)C1=O] | 2-amino-5-(2,3-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2011(R) | 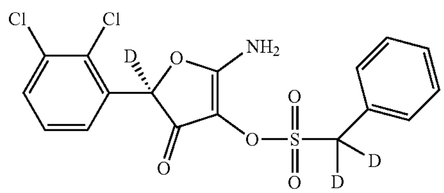 | (R)-2-amino-5-(2,3-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2011(S) | 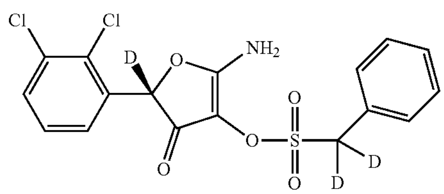 [SMILES: [2H]C([2H])(c1ccccc1)S(=O)(=O)OC1=C(N)O[C@@]([2H])(c2cccc(Cl)c2Cl)C1=O] | (S)-2-amino-5-(2,3-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2012 | 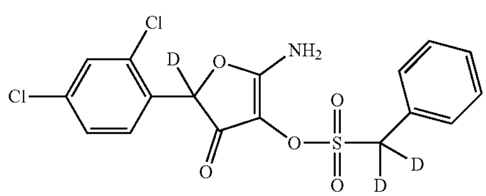 | 2-amino-5-(2,4-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2012(R) | 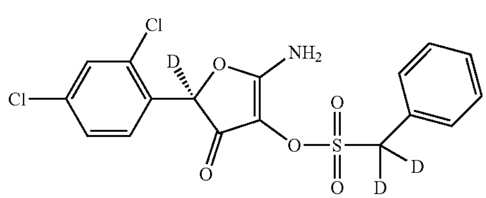 [SMILES: [2H]C([2H])(c1ccccc1)S(=O)(=O)OC1=C(N)O[C@]([2H])(c2ccc(Cl)cc2Cl)C1=O] | (R)-2-amino-5-(2,4-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2012(S) | 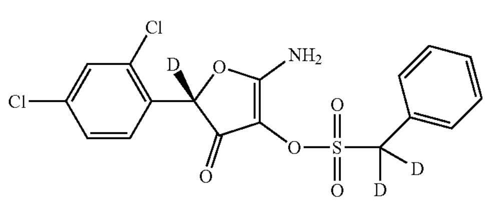 | (S)-2-amino-5-(2,4-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2013 | 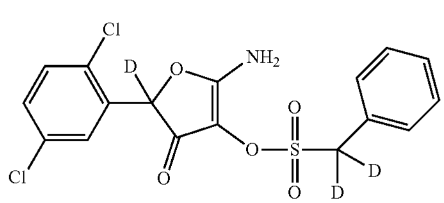 [SMILES: [2H]C1(c2cc(Cl)ccc2Cl)OC(N)=C(OS(=O)(=O)C([2H])([2H])c2ccccc2)C1=O] | 2-amino-5-(2,5-dichlorophenyl)-4-oxo-4,5-dihydrofuran-3-yl-5-d phenylmethanesulfonate-d2 | $C_{17}H_{10}D_3Cl_2NO_5S$ | 417.27 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2013(R) | 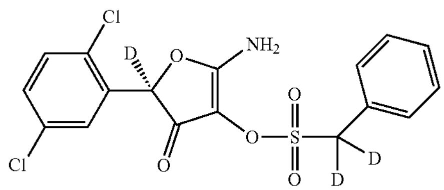 [SMILES: [2H]C([2H])(c1ccccc1)S(=O)(=O)OC1=C(N)O[C@]([2H])(c2cc(Cl)ccc2Cl)C1=O] | (R)-2-amino-5-(2,5-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2014(S) | | (S)-2-amino-5-(2,5-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2014 | 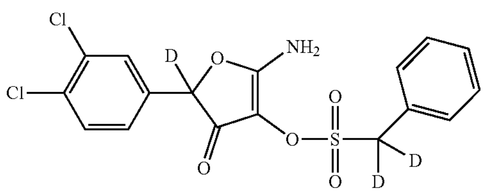 [SMILES: [2H]C1(c2ccc(Cl)c(Cl)c2)OC(N)=C(OS(=O)(=O)C([2H])([2H])c2ccccc2)C1=O] | 2-amino-5-(3,4-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2014(R) | 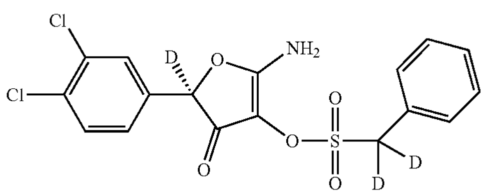 | (R)-2-amino-5-(3,4-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2014(S) | | (S)-2-amino-5-(3,4-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2015 | 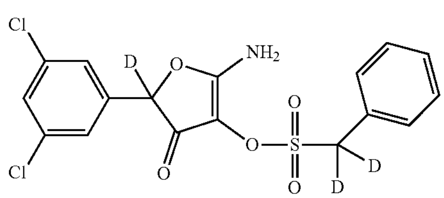 [SMILES: [2H]C1(c2cc(Cl)cc(Cl)c2)OC(N)=C(OS(=O)(=O)C([2H])([2H])c2ccccc2)C1=O] | 2-amino-5-(3,5-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2015(R) | 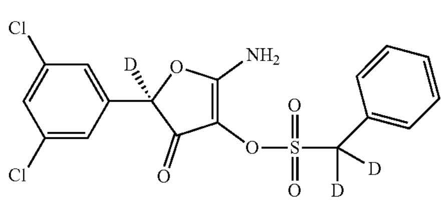 [SMILES: [2H]C([2H])(c1ccccc1)S(=O)(=O)OC1=C(N)O[C@]([2H])(c2cc(Cl)cc(Cl)c2)C1=O] | (R)-2-amino-5-(3,5-dichlorophenyl)-4-oxo-4,5-dihydrofuran-3-yl-5-d phenylmethanesulfonate-d2 | $C_{17}H_{10}D_3Cl_2NO_5S$ | 417.27 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2015(S) | 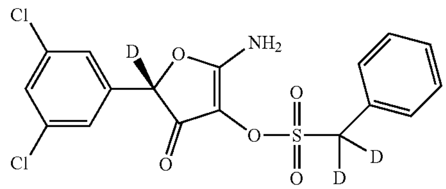 [SMILES: [2H]C([2H])(c1ccccc1)S(=O)(=O)OC1=C(N)O[C@@]([2H])(c2cc(Cl)cc(Cl)c2)C1=O] | (S)-2-amino-5-(3,5-dichlorophenyl)-4-oxo-4,5-dihydrofuran-3-yl-5-d phenylmethanesulfonate-d2 | $C_{17}H_{10}D_3Cl_2NO_5S$ | 417.27 |
| 2016 | 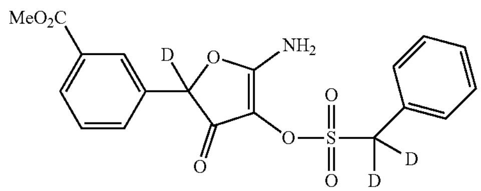 [SMILES: [2H]C1(c2cccc(C(=O)OC)c2)OC(N)=C(OS(=O)(=O)C([2H])([2H])c2ccccc2)C1=O] | methyl 3-(5-amino-3-oxo-4-(((phenylmethyl-d2)sulfonyl)oxy)-2,3-dihydrofuran-2-yl-2-d)benzoate | $C_{19}H_{14}D_3NO_7S$ | 406.42 |
| 2016(R) | 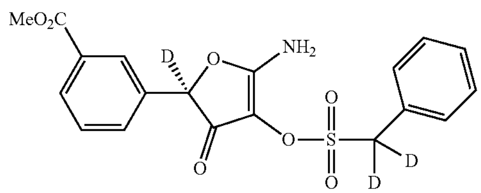 [SMILES: [2H]C([2H])(c1ccccc1)S(=O)(=O)OC1=C(N)O[C@]([2H])(c2cccc(C(=O)OC)c2)C1=O] | methyl (R)-3-(5-amino-3-oxo-4-(((phenylmethyl-d2)sulfonyl)oxy)-2,3-dihydrofuran-2-yl-2-d)benzoate | $C_{19}H_{14}D_3NO_7S$ | 406.42 |
| 2016(S) | 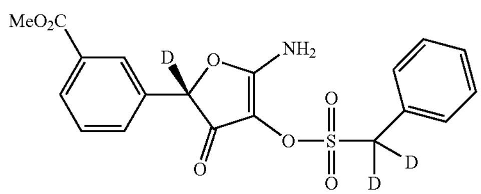 [SMILES: [2H]C([2H])(c1ccccc1)S(=O)(=O)OC1=C(N)O[C@@]([2H])(c2cccc(C(=O)OC)c2)C1=O] | methyl (S)-3-(5-amino-3-oxo-4-(((phenylmethyl-d2)sulfonyl)oxy)-2,3-dihydrofuran-2-yl-2-d)benzoate | $C_{19}H_{14}D_3NO_7S$ | 406.42 |
| 2017 | 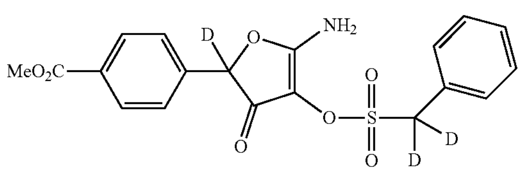 [SMILES: [2H]C1(c2ccc(C(=O)OC)cc2)OC(N)=C(OS(=O)(=O)C([2H])([2H])c2ccccc2)C1=O] | methyl 4-(5-amino-3-oxo-4-(((phenylmethyl-d2)sulfonyl)oxy)-2,3-dihydrofuran-2-yl-2-d)benzoate | $C_{19}H_{14}D_3NO_7S$ | 406.42 |
| 2017(R) | 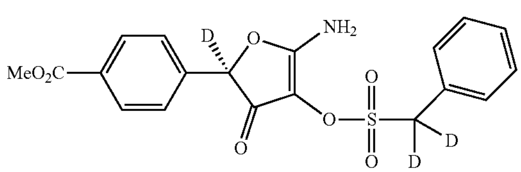 [SMILES: [2H]C([2H])(c1ccccc1)S(=O)(=O)OC1=C(N)O[C@]([2H])(c2ccc(C(=O)OC)cc2)C1=O] | methyl (R)-4-(5-amino-3-oxo-4-(((phenylmethyl-d2)sulfonyl)oxy)-2,3-dihydrofuran-2-yl-2-d)benzoate | $C_{19}H_{14}D_3NO_7S$ | 406.42 |
| 2017(S) | 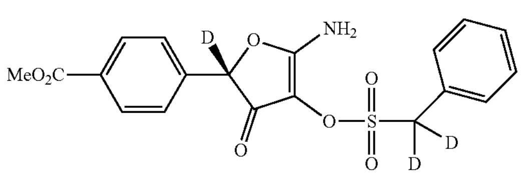 [SMILES: [2H]C([2H])(c1ccccc1)S(=O)(=O)OC1=C(N)O[C@@]([2H])(c2ccc(C(=O)OC)cc2)C1=O] | methyl (S)-4-(5-amino-3-oxo-4-(((phenylmethyl-d2)sulfonyl)oxy)-2,3-dihydrofuran-2-yl-2-d)benzoate | $C_{19}H_{14}D_3NO_7S$ | 406.42 |
| 2018 | 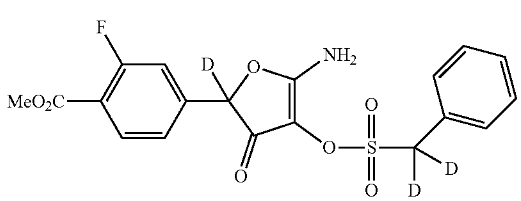 [SMILES: [2H]C1(c2ccc(C(=O)OC)c(F)c2)OC(N)=C(OS(=O)(=O)C([2H])([2H])c2ccccc2)C1=O] | methyl 4-(5-amino-3-oxo-4-(((phenylmethyl-d2)sulfonyl)oxy)-2,3-dihydrofuran-2-yl-2-d)-2-fluorobenzoate | $C_{19}H_{13}D_3FNO_7S$ | 424.41 |

TABLE 4-continued (Selected #1000 series and #2001-2093)
Structures, Names, and Numbers of Key Isotopically-Stabilized Tetronimide Compounds Listed in Example 2

| New # | Name | Formula | MW |
|---|---|---|---|
| 2018(R) | methyl (R)-4-(5-amino-3-oxo-4-(((phenylmethyl-d2)sulfonyl)oxy)-2,3-dihydrofuran-2-yl-2-d)-2-fluorobenzoate | $C_{19}H_{13}D_3FNO_7S$ | 424.41 |
| 2018(S) | methyl (S)-4-(5-amino-3-oxo-4-(((phenylmethyl-d2)sulfonyl)oxy)-2,3-dihydrofuran-2-yl-2-d)-2-fluorobenzoate | $C_{19}H_{13}D_3FNO_7S$ | 424.41 |
| 2019 | ethyl 4-(5-amino-3-oxo-4-(((phenylmethyl-d2)sulfonyl)oxy)-2,3-dihydrofuran-2-yl-2-d)benzoate | $C_{20}H_{16}D_3NO_7S$ | 420.45 |
| 2019(R) | ethyl (R)-4-(5-amino-3-oxo-4-(((phenylmethyl-d2)sulfonyl)oxy)-2,3-dihydrofuran-2-yl-2-d)benzoate | $C_{20}H_{16}D_3NO_7S$ | 420.45 |
| 2019(S) | ethyl (S)-4-(5-amino-3-oxo-4-(((phenylmethyl-d2)sulfonyl)oxy)-2,3-dihydrofuran-2-yl-2-d)benzoate | $C_{20}H_{16}D_3NO_7S$ | 420.45 |
| 2020 | 5-(4-acetylphenyl)-2-amino-4-oxo-4,5-dihydrofuran-3-yl-5-d phenylmethanesulfonate-d2 | $C_{19}H_{14}D_3NO_6S$ | 390.42 |
| 2020(R) | (R)-5-(4-acetylphenyl)-2-amino-4-oxo-4,5-dihydrofuran-3-yl-5-d phenylmethanesulfonate-d2 | $C_{19}H_{14}D_3NO_6S$ | 390.42 |
| 2020(S) | (S)-5-(4-acetylphenyl)-2-amino-4-oxo-4,5-dihydrofuran-3-yl-5-d phenylmethanesulfonate-d2 | $C_{19}H_{14}D_3NO_6S$ | 390.42 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2021 | 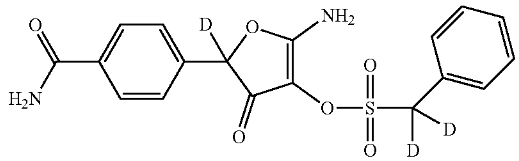 [SMILES: [2H]C1(c2ccc(C(N)=O)cc2)OC(N)=C(OS(=O)(=O)C([2H])([2H])c2ccccc2)C1=O] | 2-amino-5-(4-carbamoylphenyl)-4-oxo-4,5-dihydrofuran-3-yl-5-d phenylmethanesulfonate-d2 | $C_{18}H_{13}D_3N_2O_6S$ | 391.41 |
| 2021(R) | 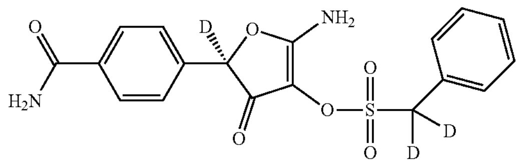 | (R)-2-amino-5-(4-carbamoylphenyl)-4-oxo-4,5-dihydrofuran-3-yl-5-d phenylmethanesulfonate-d2 | $C_{18}H_{13}D_3N_2O_6S$ | 391.41 |
| 2021(S) | 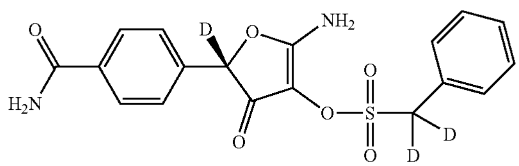 [SMILES: [2H]C([2H])(c1ccccc1)S(=O)(=O)OC1=C(N)O[C@@]([2H])(c2ccc(C(N)=O)cc2)C1=O] | (S)-2-amino-5-(4-carbamoylphenyl)-4-oxo-4,5-dihydrofuran-3-yl-5-d phenylmethanesulfonate-d2 | $C_{18}H_{13}D_3N_2O_6S$ | 391.41 |
| 2022 | 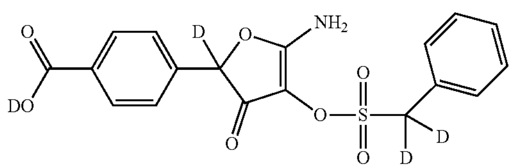 | 4-(5-amino-3-oxo-4-(((phenylmethyl-d2)sulfonyl)oxy)-2,3-dihydrofuran-2-yl-2-d)benzoic acid-d | $C_{18}H_{11}D_4NO_7S$ | 393.40 |
| 2022(R) | 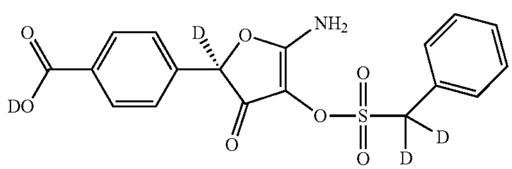 | (R)-4-(5-amino-3-oxo-4-(((phenylmethyl-d2)sulfonyl)oxy)-2,3-dihydrofuran-2-yl-2-d)benzoic acid-d | $C_{18}H_{11}D_4NO_7S$ | 393.40 |
| 2022(S) | 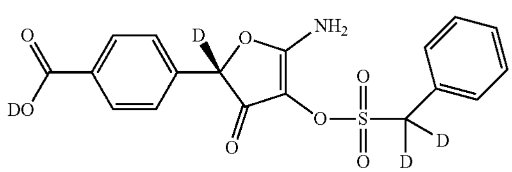 | (S)-4-(5-amino-3-oxo-4-(((phenylmethyl-d2)sulfonyl)oxy)-2,3-dihydrofuran-2-yl-2-d)benzoic acid-d | $C_{18}H_{11}D_4NO_7S$ | 393.40 |
| 2023 | 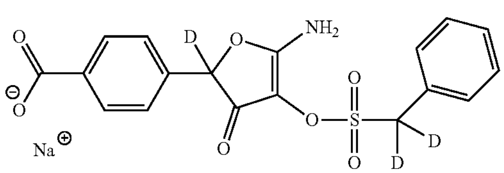 [SMILES: [2H]C1(c2ccc(C(=O)[O-])cc2)OC(N)=C(OS(=O)(=O)C([2H])([2H])c2ccccc2)C1=O ; [Na+]] | sodium 4-(5-amino-3-oxo-4-(((phenylmethyl-d2)sulfonyl)oxy)-2,3-dihydrofuran-2-yl-2-d)benzoate | $C_{18}H_{11}D_3NNaO_7S$ | 414.38 |
| 2023(R) | 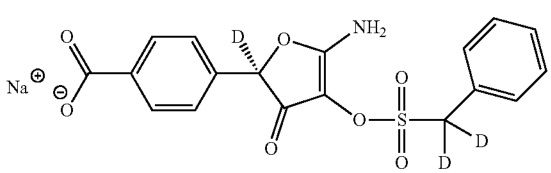 [SMILES: [Na+] ; [2H]C([2H])(c1ccccc1)S(=O)(=O)OC1=C(N)O[C@]([2H])(c2ccc(C(=O)[O-])cc2)C1=O] | sodium (R)-4-(5-amino-3-oxo-4-(((phenylmethyl-d2)sulfonyl)oxy)-2,3-dihydrofuran-2-yl-2-d)benzoate | $C_{18}H_{11}D_3NNaO_7S$ | 414.38 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2023(S) | 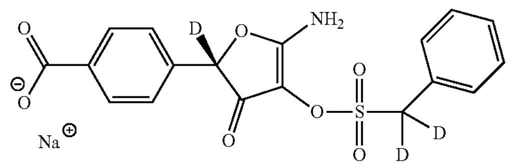 [SMILES: [2H]C([2H])(c1ccccc1)S(=O)(=O)OC1=C(N)O[C@@]([2H])(c2ccc(C(=O)[O-])cc2)C1=O ; [Na+]] | sodium (S)-4-(5-amino-3-oxo-4-(((phenylmethyl-d2)sulfonyl)oxy)-2,3-dihydrofuran-2-yl-2-d)benzoate | $C_{18}H_{11}D_3NNaO_7S$ | 414.38 |
| 2024 | 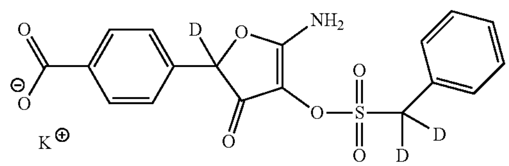 [SMILES: [2H]C1(c2ccc(C(=O)[O-])cc2)OC(N)=C(OS(=O)(=O)C([2H])([2H])c2ccccc2)C1=O ; [K+]] | potassium 4-(5-amino-3-oxo-4-(((phenylmethyl-d2)sulfonyl)oxy)-2,3-dihydrofuran-2-yl-2-d)benzoate | $C_{18}H_{11}D_3KNO_7S$ | 430.49 |
| 2024(R) | 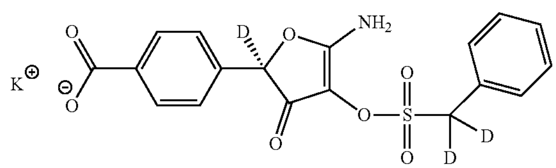 [SMILES: [K+] ; [2H]C([2H])(c1ccccc1)S(=O)(=O)OC1=C(N)O[C@]([2H])(c2ccc(C(=O)[O-])cc2)C1=O] | potassium (R)-4-(5-amino-3-oxo-4-(((phenylmethyl-d2)sulfonyl)oxy)-2,3-dihydrofuran-2-yl-2-d)benzoate | $C_{18}H_{11}D_3KNO_7S$ | 430.49 |
| 2024(S) | 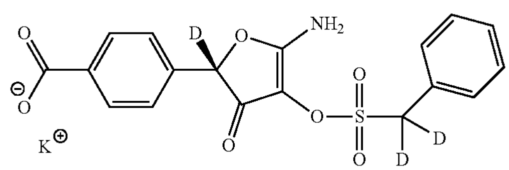 [SMILES: [2H]C([2H])(c1ccccc1)S(=O)(=O)OC1=C(N)O[C@@]([2H])(c2ccc(C(=O)[O-])cc2)C1=O ; [K+]] | potassium (S)-4-(5-amino-3-oxo-4-(((phenylmethyl-d2)sulfonyl)oxy)-2,3-dihydrofuran-2-yl-2-d)benzoate | $C_{18}H_{11}D_3KNO_7S$ | 430.49 |
| 2027 | 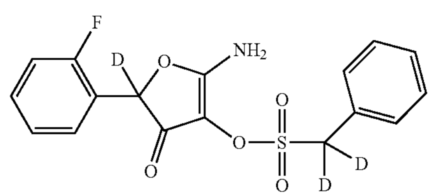 [SMILES: [2H]C1(c2ccccc2F)OC(N)=C(OS(=O)(=O)C([2H])([2H])c2ccccc2)C1=O] | 2-amino-5-(2-fluorophenyl)-4-oxo-4,5-dihydrofuran-3-yl-5-d phenylmethanesulfonate-d2 | $C_{17}H_{11}D_3FNO_5S$ | 366.38 |
| 2027(R) | 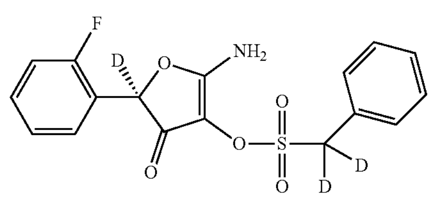 [SMILES: [2H]C([2H])(c1ccccc1)S(=O)(=O)OC1=C(N)O[C@]([2H])(c2ccccc2F)C1=O] | (R)-2-amino-5-(2-fluorophenyl)-4-oxo-4,5-dihydrofuran-3-yl-5-d phenylmethanesulfonate-d2 | $C_{17}H_{11}D_3FNO_5S$ | 366.38 |
| 2027(S) | 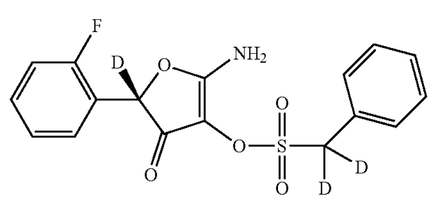 [SMILES: [2H]C([2H])(c1ccccc1)S(=O)(=O)OC1=C(N)O[C@@]([2H])(c2ccccc2F)C1=O] | (S)-2-amino-5-(2-fluorophenyl)-4-oxo-4,5-dihydrofuran-3-yl-5-d phenylmethanesulfonate-d2 | $C_{17}H_{11}D_3FNO_5S$ | 366.38 |
| 2028 | 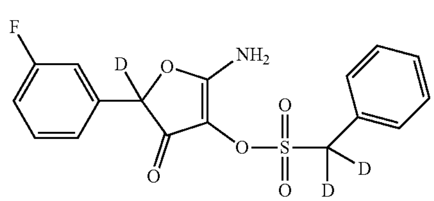 [SMILES: [2H]C1(c2cccc(F)c2)OC(N)=C(OS(=O)(=O)C([2H])([2H])c2ccccc2)C1=O] | 2-amino-5-(3-fluorophenyl)-4-oxo-4,5-dihydrofuran-3-yl-5-d phenylmethanesulfonate-d2 | $C_{17}H_{11}D_3FNO_5S$ | 366.38 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2028(R) | 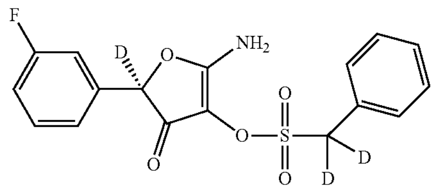 [SMILES: [2H]C([2H])(c1ccccc1)S(=O)(=O)OC1=C(N)O[C@]([2H])(c2cccc(F)c2)C1=O] | (R)-2-amino-5-(3-fluorophenyl)-4-oxo-4,5-dihydrofuran-3-yl-5-d phenylmethanesulfonate-d2 | $C_{17}H_{11}D_3FNO_5S$ | 366.38 |
| 2028(S) | 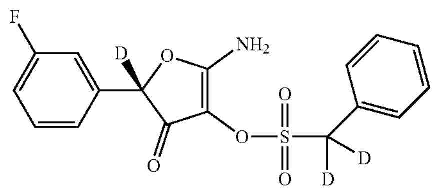 [SMILES: [2H]C([2H])(c1ccccc1)S(=O)(=O)OC1=C(N)O[C@@]([2H])(c2cccc(F)c2)C1=O] | (S)-2-amino-5-(3-fluorophenyl)-4-oxo-4,5-dihydrofuran-3-yl-5-d phenylmethanesulfonate-d2 | $C_{17}H_{11}D_3FNO_5S$ | 366.38 |
| 2029 | 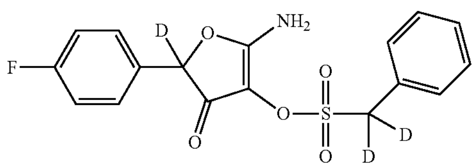 [SMILES: [2H]C1(c2ccc(F)cc2)OC(N)=C(OS(=O)(=O)C([2H])([2H])c2ccccc2)C1=O] | 2-amino-5-(4-fluorophenyl)-4-oxo-4,5-dihydrofuran-3-yl-5-d phenylmethanesulfonate-d2 | $C_{17}H_{11}D_3FNO_5S$ | 366.38 |
| 2029(R) | 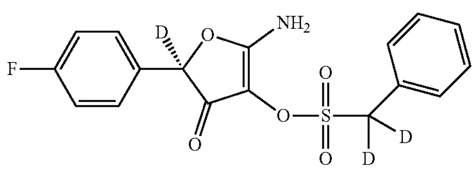 [SMILES: [2H]C([2H])(c1ccccc1)S(=O)(=O)OC1=C(N)O[C@]([2H])(c2ccc(F)cc2)C1=O] | (R)-2-amino-5-(4-fluorophenyl)-4-oxo-4,5-dihydrofuran-3-yl-5-d phenylmethanesulfonate-d2 | $C_{17}H_{11}D_3FNO_5S$ | 366.38 |
| 2029(S) | 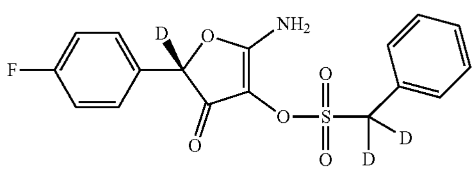 [SMILES: [2H]C([2H])(c1ccccc1)S(=O)(=O)OC1=C(N)O[C@@]([2H])(c2ccc(F)cc2)C1=O] | (S)-2-amino-5-(4-fluorophenyl)-4-oxo-4,5-dihydrofuran-3-yl-5-d phenylmethanesulfonate-d2 | $C_{17}H_{11}D_3FNO_5S$ | 366.38 |
| 2030 | 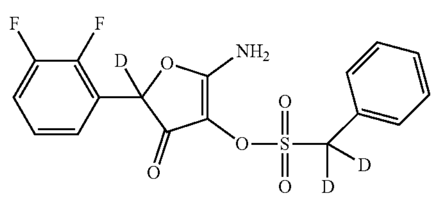 [SMILES: [2H]C1(c2cccc(F)c2F)OC(N)=C(OS(=O)(=O)C([2H])([2H])c2ccccc2)C1=O] | 2-amino-5-(2,3-difluorophenyl)-4-oxo-4,5-dihydrofuran-3-yl-5-d phenylmethanesulfonate-d2 | $C_{17}H_{10}D_3F_2NO_5S$ | 384.37 |
| 2030(R) | 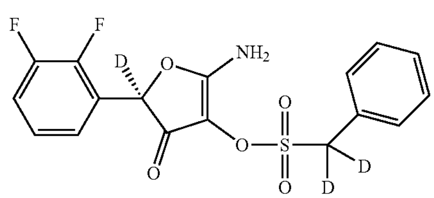 [SMILES: [2H]C([2H])(c1ccccc1)S(=O)(=O)OC1=C(N)O[C@]([2H])(c2cccc(F)c2F)C1=O] | (R)-2-amino-5-(2,3-difluorophenyl)-4-oxo-4,5-dihydrofuran-3-yl-5-d phenylmethanesulfonate-d2 | $C_{17}H_{10}D_3F_2NO_5S$ | 384.37 |
| 2030(S) | 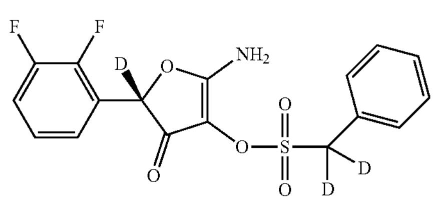 [SMILES: [2H]C([2H])(c1ccccc1)S(=O)(=O)OC1=C(N)O[C@@]([2H])(c2cccc(F)c2F)C1=O] | (S)-2-amino-5-(2,3-difluorophenyl)-4-oxo-4,5-dihydrofuran-3-yl-5-d phenylmethanesulfonate-d2 | $C_{17}H_{10}D_3F_2NO_5S$ | 384.37 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2031 | 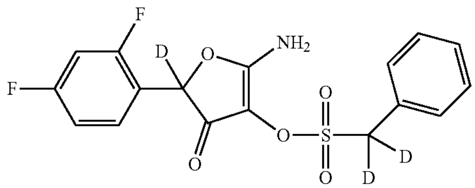 [SMILES: [2H]C1(c2ccc(F)cc2F)OC(N)=C(OS(=O)(=O)C([2H])([2H])c2ccccc2)C1=O] | 2-amino-5-(2,4-difluorophenyl)-4-oxo-4,5-dihydrofuran-3-yl-5-d phenylmethanesulfonate-d2 | $C_{17}H_{10}D_3F_2NO_5S$ | 384.37 |
| 2031(R) | 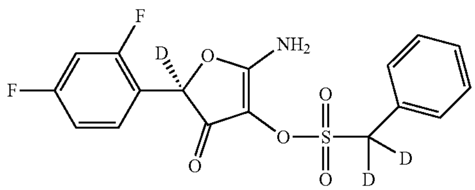 [SMILES: [2H]C([2H])(c1ccccc1)S(=O)(=O)OC1=C(N)O[C@]([2H])(c2ccc(F)cc2F)C1=O] | (R)-2-amino-5-(2,4-difluorophenyl)-4-oxo-4,5-dihydrofuran-3-yl-5-d phenylmethanesulfonate-d2 | $C_{17}H_{10}D_3F_2NO_5S$ | 384.37 |
| 2031(S) | 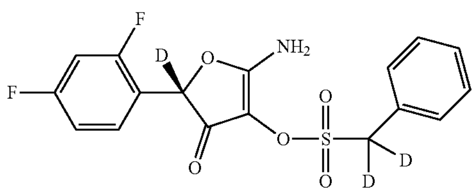 [SMILES: [2H]C([2H])(c1ccccc1)S(=O)(=O)OC1=C(N)O[C@@]([2H])(c2ccc(F)cc2F)C1=O] | (S)-2-amino-5-(2,4-difluorophenyl)-4-oxo-4,5-dihydrofuran-3-yl-5-d phenylmethanesulfonate-d2 | $C_{17}H_{10}D_3F_2NO_5S$ | 384.37 |
| 2032 | 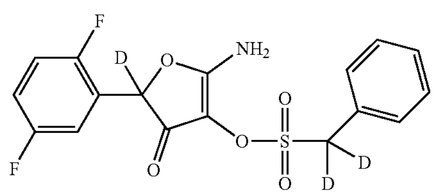 | 2-amino-5-(2,5-difluorophenyl)-4-oxo-4,5-dihydrofuran-3-yl-5-d phenylmethanesulfonate-d2 | $C_{17}H_{10}D_3F_2NO_5S$ | 384.37 |
| 2032(R) | 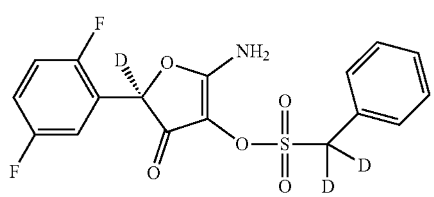 | (R)-2-amino-5-(2,5-difluorophenyl)-4-oxo-4,5-dihydrofuran-3-yl-5-d phenylmethanesulfonate-d2 | $C_{17}H_{10}D_3F_2NO_5S$ | 384.37 |
| 2032(S) | 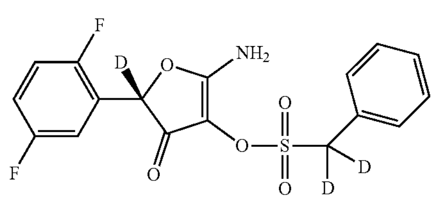 | (S)-2-amino-5-(2,5-difluorophenyl)-4-oxo-4,5-dihydrofuran-3-yl-5-d phenylmethanesulfonate-d2 | $C_{17}H_{10}D_3F_2NO_5S$ | 384.37 |
| 2033 | 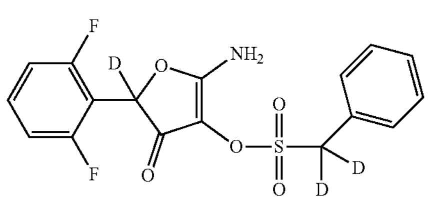 [SMILES: [2H]C1(c2c(F)cccc2F)OC(N)=C(OS(=O)(=O)C([2H])([2H])c2ccccc2)C1=O] | 2-amino-5-(2,6-difluorophenyl)-4-oxo-4,5-dihydrofuran-3-yl-5-d phenylmethanesulfonate-d2 | $C_{17}H_{10}D_3F_2NO_5S$ | 384.37 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2033(R) | 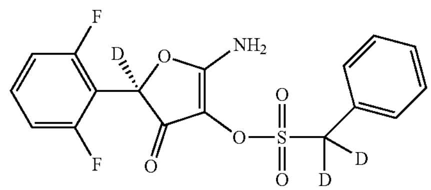 [SMILES: [2H]C([2H])(c1ccccc1)S(=O)(=O)OC1=C(N)O[C@]([2H])(c2c(F)cccc2F)C1=O] | (R)-2-amino-5-(2,6-difluorophenyl)-4-oxo-4,5-dihydrofuran-3-yl-5-d phenylmethanesulfonate-d2 | $C_{17}H_{10}D_3F_2NO_5S$ | 384.37 |
| 2033(S) | 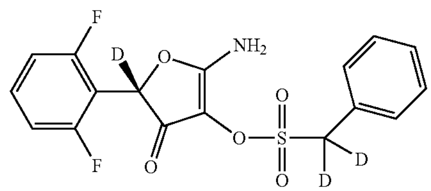 [SMILES: [2H]C([2H])(c1ccccc1)S(=O)(=O)OC1=C(N)O[C@@]([2H])(c2c(F)cccc2F)C1=O] | (S)-2-amino-5-(2,6-difluorophenyl)-4-oxo-4,5-dihydrofuran-3-yl-5-d phenylmethanesulfonate-d2 | $C_{17}H_{10}D_3F_2NO_5S$ | 384.37 |
| 2034 | 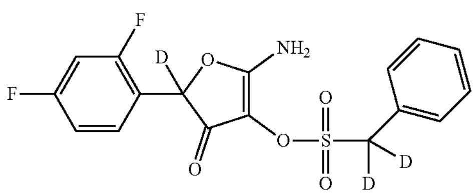 | 2-amino-5-(3,4-difluorophenyl)-4-oxo-4,5-dihydrofuran-3-yl-5-d phenylmethanesulfonate-d2 | $C_{17}H_{10}D_3F_2NO_5S$ | 384.37 |
| 2034(R) | 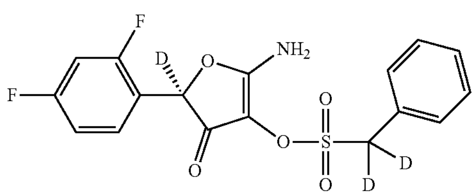 | (R)-2-amino-5-(3,4-difluorophenyl)-4-oxo-4,5-dihydrofuran-3-yl-5-d phenylmethanesulfonate-d2 | $C_{17}H_{10}D_3F_2NO_5S$ | 384.37 |
| 2034(S) | 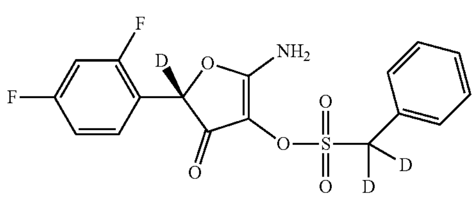 [SMILES: [2H]C([2H])(c1ccccc1)S(=O)(=O)OC1=C(N)O[C@@]([2H])(c2ccc(F)cc2F)C1=O] | (S)-2-amino-5-(3,4-difluorophenyl)-4-oxo-4,5-dihydrofuran-3-yl-5-d phenylmethanesulfonate-d2 | $C_{17}H_{10}D_3F_2NO_5S$ | 384.37 |
| 2035 | 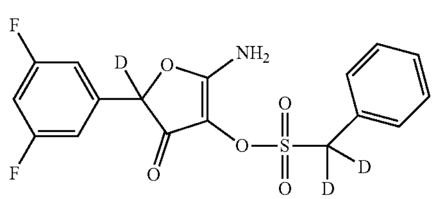 [SMILES: [2H]C1(c2cc(F)cc(F)c2)OC(N)=C(OS(=O)(=O)C([2H])([2H])c2ccccc2)C1=O] | 2-amino-5-(3,5-difluorophenyl)-4-oxo-4,5-dihydrofuran-3-yl-5-d phenylmethanesulfonate-d2 | $C_{17}H_{10}D_3F_2NO_5S$ | 384.37 |
| 2035(R) | 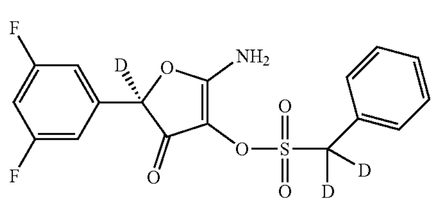 [SMILES: [2H]C([2H])(c1ccccc1)S(=O)(=O)OC1=C(N)O[C@]([2H])(c2cc(F)cc(F)c2)C1=O] | (R)-2-amino-5-(3,5-difluorophenyl)-4-oxo-4,5-dihydrofuran-3-yl-5-d phenylmethanesulfonate-d2 | $C_{17}H_{10}D_3F_2NO_5S$ | 384.37 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2035(S) | 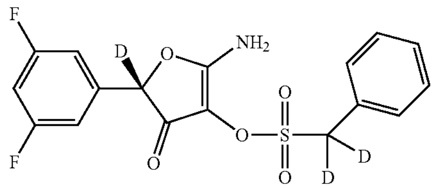 [SMILES: [2H]C([2H])(c1ccccc1)S(=O)(=O)OC1=C(N)O[C@@]([2H])(c2cc(F)cc(F)c2)C1=O] | (S)-2-amino-5-(3,5-difluorophenyl)-4-oxo-4,5-dihydrofuran-3-yl-5-d phenylmethanesulfonate-d2 | $C_{17}H_{10}D_3F_2NO_5S$ | 384.37 |
| 2036 | 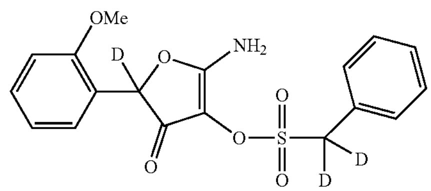 [SMILES: [2H]C1(c2ccccc2OC)OC(N)=C(OS(=O)(=O)C([2H])([2H])c2ccccc2)C1=O] | 2-amino-5-(2-methoxyphenyl)-4-oxo-4,5-dihydrofuran-3-yl-5-d phenylmethanesulfonate-d2 | $C_{18}H_{14}D_3NO_6S$ | 378.41 |
| 2036(R) | 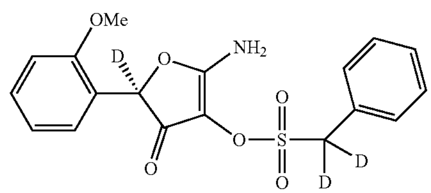 [SMILES: [2H]C([2H])(c1ccccc1)S(=O)(=O)OC1=C(N)O[C@]([2H])(c2ccccc2OC)C1=O] | (R)-2-amino-5-(2-methoxyphenyl)-4-oxo-4,5-dihydrofuran-3-yl-5-d phenylmethanesulfonate-d2 | $C_{18}H_{14}D_3NO_6S$ | 378.41 |
| 2036(S) | 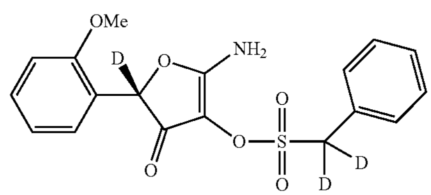 | (S)-2-amino-5-(2-methoxyphenyl)-4-oxo-4,5-dihydrofuran-3-yl-5-d phenylmethanesulfonate-d2 | $C_{18}H_{14}D_3NO_6S$ | 378.41 |
| 2037 | 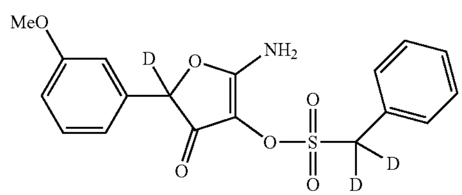 [SMILES: [2H]C1(c2cccc(OC)c2)OC(N)=C(OS(=O)(=O)C([2H])([2H])c2ccccc2)C1=O] | 2-amino-5-(3-methoxyphenyl)-4-oxo-4,5-dihydrofuran-3-yl-5-d phenylmethanesulfonate-d2 | $C_{18}H_{14}D_3NO_6S$ | 378.41 |
| 2037(R) | 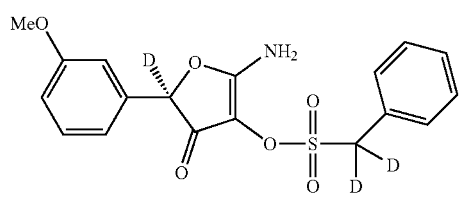 [SMILES: [2H]C([2H])(c1ccccc1)S(=O)(=O)OC1=C(N)O[C@]([2H])(c2cccc(OC)c2)C1=O] | (R)-2-amino-5-(3-methoxyphenyl)-4-oxo-4,5-dihydrofuran-3-yl-5-d phenylmethanesulfonate-d2 | $C_{18}H_{14}D_3NO_6S$ | 378.41 |
| 2037(S) | 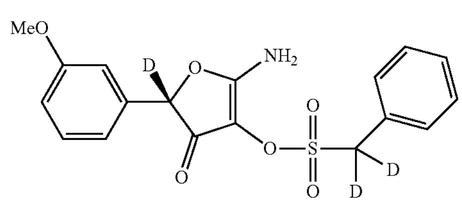 [SMILES: [2H]C([2H])(c1ccccc1)S(=O)(=O)OC1=C(N)O[C@@]([2H])(c2cccc(OC)c2)C1=O] | (S)-2-amino-5-(3-methoxyphenyl)-4-oxo-4,5-dihydrofuran-3-yl-5-d phenylmethanesulfonate-d2 | $C_{18}H_{14}D_3NO_6S$ | 378.41 |
| 2038 | 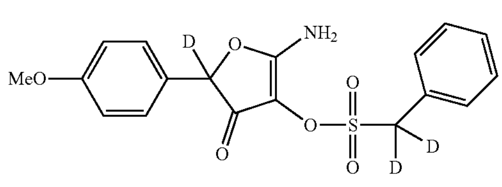 [SMILES: [2H]C1(c2ccc(OC)cc2)OC(N)=C(OS(=O)(=O)C([2H])([2H])c2ccccc2)C1=O] | 2-amino-5-(4-methoxyphenyl)-4-oxo-4,5-dihydrofuran-3-yl-5-d phenylmethanesulfonate-d2 | $C_{18}H_{14}D_3NO_6S$ | 378.41 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2038(R) | 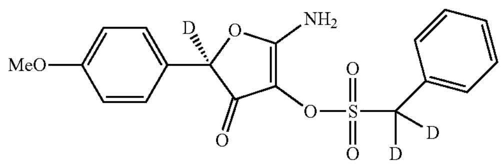 [SMILES: [2H]C([2H])(c1ccccc1)S(=O)(=O)OC1=C(N)O[C@]([2H])(c2ccc(OC)cc2)C1=O] | (R)-2-amino-5-(4-methoxyphenyl)-4-oxo-4,5-dihydrofuran-3-yl-5-d phenylmethanesulfonate-d2 | $C_{18}H_{14}D_3NO_6S$ | 378.41 |
| 2038(S) | 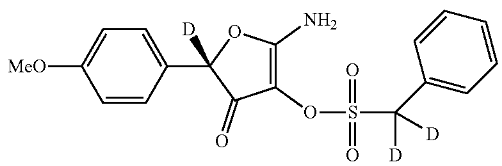 [SMILES: [2H]C([2H])(c1ccccc1)S(=O)(=O)OC1=C(N)O[C@@]([2H])(c2ccc(OC)cc2)C1=O] | (S)-2-amino-5-(4-methoxyphenyl)-4-oxo-4,5-dihydrofuran-3-yl-5-d phenylmethanesulfonate-d2 | $C_{18}H_{14}D_3NO_6S$ | 378.41 |
| 2039 | 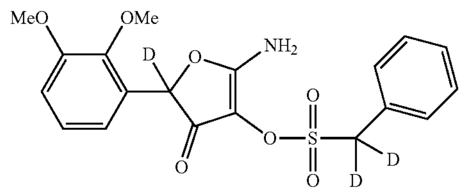 [SMILES: [2H]C1(c2cccc(OC)c2OC)OC(N)=C(OS(=O)(=O)C([2H])([2H])c2ccccc2)C1=O] | 2-amino-5-(2,3-dimethoxyphenyl)-4-oxo-4,5-dihydrofuran-3-yl-5-d phenylmethanesulfonate-d2 | $C_{19}H_{16}D_3NO_7S$ | 408.44 |
| 2039(R) | 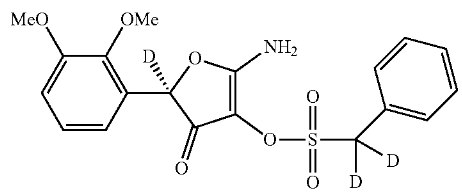 [SMILES: [2H]C([2H])(c1ccccc1)S(=O)(=O)OC1=C(N)O[C@]([2H])(c2cccc(OC)c2OC)C1=O] | (R)-2-amino-5-(2,3-dimethoxyphenyl)-4-oxo-4,5-dihydrofuran-3-yl-5-d phenylmethanesulfonate-d2 | $C_{19}H_{16}D_3NO_7S$ | 408.44 |
| 2039(S) | 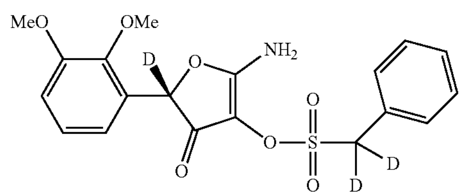 [SMILES: [2H]C([2H])(c1ccccc1)S(=O)(=O)OC1=C(N)O[C@@]([2H])(c2cccc(OC)c2OC)C1=O] | (S)-2-amino-5-(2,3-dimethoxyphenyl)-4-oxo-4,5-dihydrofuran-3-yl-5-d phenylmethanesulfonate-d2 | $C_{19}H_{16}D_3NO_7S$ | 408.44 |
| 2040 | 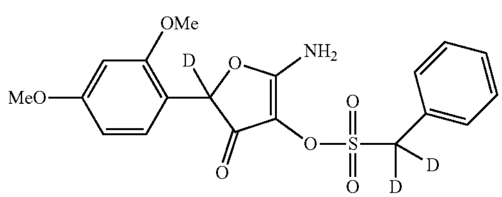 [SMILES: [2H]C1(c2ccc(OC)cc2OC)OC(N)=C(OS(=O)(=O)C([2H])([2H])c2ccccc2)C1=O] | 2-amino-5-(2,4-dimethoxyphenyl)-4-oxo-4,5-dihydrofuran-3-yl-5-d phenylmethanesulfonate-d2 | $C_{19}H_{16}D_3NO_7S$ | 408.44 |
| 2040(R) | 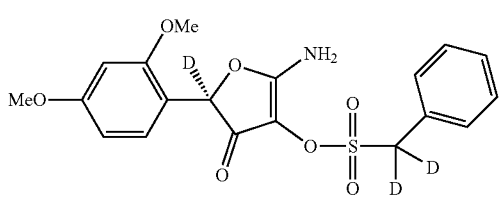 [SMILES: [2H]C([2H])(c1ccccc1)S(=O)(=O)OC1=C(N)O[C@]([2H])(c2ccc(OC)cc2OC)C1=O] | (R)-2-amino-5-(2,4-dimethoxyphenyl)-4-oxo-4,5-dihydrofuran-3-yl-5-d phenylmethanesulfonate-d2 | $C_{19}H_{16}D_3NO_7S$ | 408.44 |
| 2040(S) | 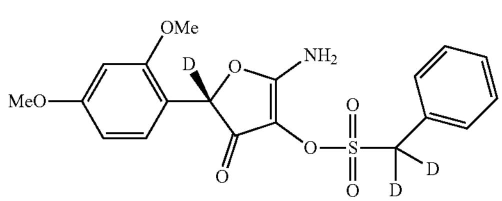 [SMILES: [2H]C([2H])(c1ccccc1)S(=O)(=O)OC1=C(N)O[C@@]([2H])(c2ccc(OC)cc2OC)C1=O] | (S)-2-amino-5-(2,4-dimethoxyphenyl)-4-oxo-4,5-dihydrofuran-3-yl-5-d phenylmethanesulfonate-d2 | $C_{19}H_{16}D_3NO_7S$ | 408.44 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2041 | 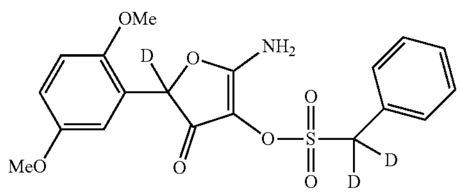 [SMILES: [2H]C1(c2cc(OC)ccc2OC)OC(N)=C(OS(=O)(=O)C([2H])([2H])c2ccccc2)C1=O] | 2-amino-5-(2,5-dimethoxyphenyl)-4-oxo-4,5-dihydrofuran-3-yl-5-d phenylmethanesulfonate-d2 | $C_{19}H_{16}D_3NO_7S$ | 408.44 |
| 2041(R) | 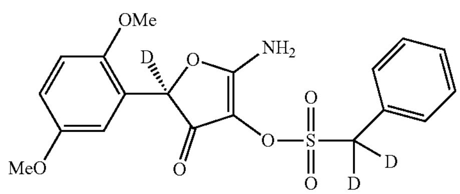 [SMILES: [2H]C([2H])(c1ccccc1)S(=O)(=O)OC1=C(N)O[C@]([2H])(c2cc(OC)ccc2OC)C1=O] | (R)-2-amino-5-(2,5-dimethoxyphenyl)-4-oxo-4,5-dihydrofuran-3-yl-5-d phenylmethanesulfonate-d2 | $C_{19}H_{16}D_3NO_7S$ | 408.44 |
| 2041(S) | 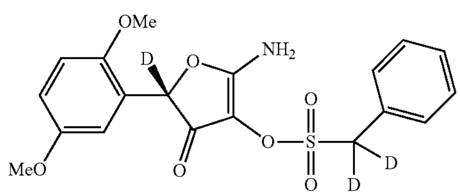 [SMILES: [2H]C([2H])(c1ccccc1)S(=O)(=O)OC1=C(N)O[C@@]([2H])(c2cc(OC)ccc2OC)C1=O] | (S)-2-amino-5-(2,5-dimethoxyphenyl)-4-oxo-4,5-dihydrofuran-3-yl-5-d phenylmethanesulfonate-d2 | $C_{19}H_{16}D_3NO_7S$ | 408.44 |
| 2042 | 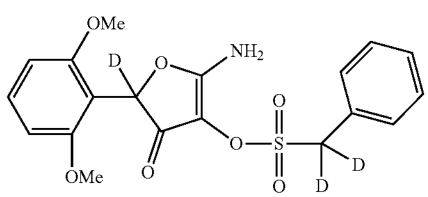 [SMILES: [2H]C1(c2c(OC)cccc2OC)OC(N)=C(OS(=O)(=O)C([2H])([2H])c2ccccc2)C1=O] | 2-amino-5-(2,6-dimethoxyphenyl)-4-oxo-4,5-dihydrofuran-3-yl-5-d phenylmethanesulfonate-d2 | $C_{19}H_{16}D_3NO_7S$ | 408.44 |
| 2042(R) | 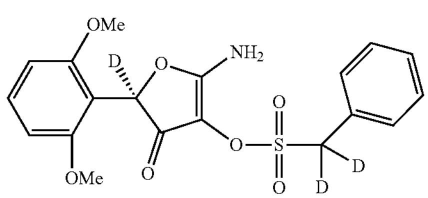 [SMILES: [2H]C([2H])(c1ccccc1)S(=O)(=O)OC1=C(N)O[C@]([2H])(c2c(OC)cccc2OC)C1=O] | (R)-2-amino-5-(2,6-dimethoxyphenyl)-4-oxo-4,5-dihydrofuran-3-yl-5-d phenylmethanesulfonate-d2 | $C_{19}H_{16}D_3NO_7S$ | 408.44 |
| 2042(S) | 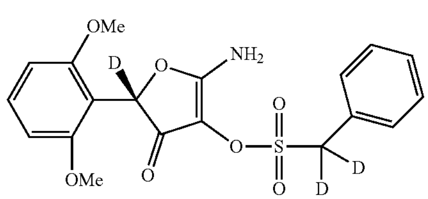 [SMILES: [2H]C([2H])(c1ccccc1)S(=O)(=O)OC1=C(N)O[C@@]([2H])(c2c(OC)cccc2OC)C1=O] | (S)-2-amino-5-(2,6-dimethoxyphenyl)-4-oxo-4,5-dihydrofuran-3-yl-5-d phenylmethanesulfonate-d2 | $C_{19}H_{16}D_3NO_7S$ | 408.44 |
| 2043 | 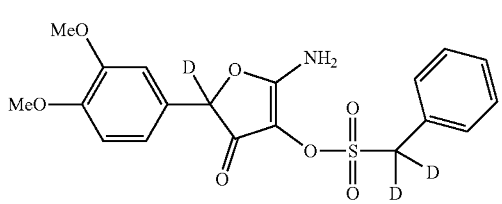 [SMILES: [2H]C1(c2ccc(OC)c(OC)c2)OC(N)=C(OS(=O)(=O)C([2H])([2H])c2ccccc2)C1=O] | 2-amino-5-(3,4-dimethoxyphenyl)-4-oxo-4,5-dihydrofuran-3-yl-5-d phenylmethanesulfonate-d2 | $C_{19}H_{16}D_3NO_7S$ | 408.44 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2043(R) | 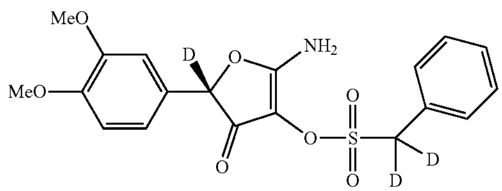 [SMILES: [2H]C([2H])(c1ccccc1)S(=O)(=O)OC1=C(N)O[C@@]([2H])(c2ccc(OC)c(OC)c2)C1=O] | (R)-2-amino-5-(3,4-dimethoxyphenyl)-4-oxo-4,5-dihydrofuran-3-yl-5-d phenylmethanesulfonate-d2 | $C_{19}H_{16}D_3NO_7S$ | 408.44 |
| 2043(S) | 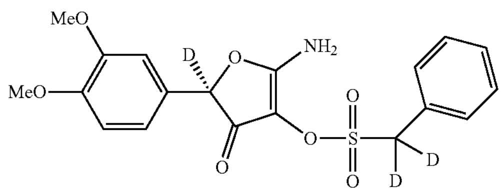 [SMILES: [2H]C([2H])(c1ccccc1)S(=O)(=O)OC1=C(N)O[C@]([2H])(c2ccc(OC)c(OC)c2)C1=O] | (S)-2-amino-5-(3,4-dimethoxyphenyl)-4-oxo-4,5-dihydrofuran-3-yl-5-d phenylmethanesulfonate-d2 | $C_{19}H_{16}D_3NO_7S$ | 408.44 |
| 2044 | 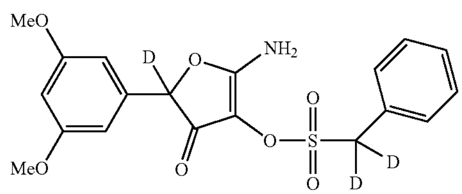 [SMILES: [2H]C1(c2cc(OC)cc(OC)c2)OC(N)=C(OS(=O)(=O)C([2H])([2H])c2ccccc2)C1=O] | 2-amino-5-(3,5-dimethoxyphenyl)-4-oxo-4,5-dihydrofuran-3-yl-5-d phenylmethanesulfonate-d2 | $C_{19}H_{16}D_3NO_7S$ | 408.44 |
| 2044(R) | 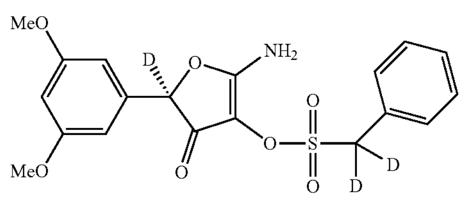 [SMILES: [2H]C([2H])(c1ccccc1)S(=O)(=O)OC1=C(N)O[C@]([2H])(c2cc(OC)cc(OC)c2)C1=O] | (R)-2-amino-5-(3,5-dimethoxyphenyl)-4-oxo-4,5-dihydrofuran-3-yl-5-d phenylmethanesulfonate-d2 | $C_{19}H_{16}D_3NO_7S$ | 408.44 |
| 2044(S) | 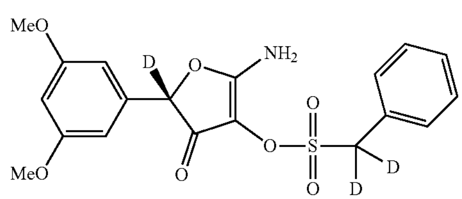 [SMILES: [2H]C([2H])(c1ccccc1)S(=O)(=O)OC1=C(N)O[C@@]([2H])(c2cc(OC)cc(OC)c2)C1=O] | (S)-2-amino-5-(3,5-dimethoxyphenyl)-4-oxo-4,5-dihydrofuran-3-yl-5-d phenylmethanesulfonate-d2 | $C_{19}H_{16}D_3NO_7S$ | 408.44 |
| 2045 | 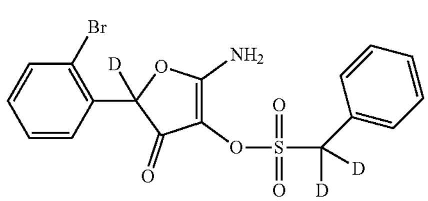 | 2-amino-5-(2-bromophenyl)-4-oxo-4,5-dihydrofuran-3-yl-5-d phenylmethanesulfonate-d2 | $C_{17}H_{11}D_3BrNO_5S$ | 427.28 |
| 2045(R) | 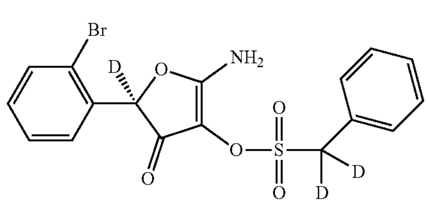 | (R)-2-amino-5-(2-bromophenyl)-4-oxo-4,5-dihydrofuran-3-yl-5-d phenylmethanesulfonate-d2 | $C_{17}H_{11}D_3BrNO_5S$ | 427.28 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2045(S) | 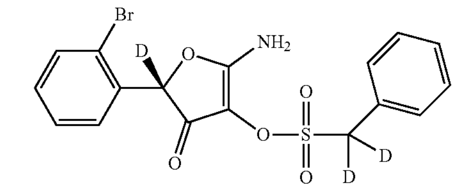 | (S)-2-amino-5-(2-bromophenyl)-4-oxo-4,5-dihydrofuran-3-yl-5-d phenylmethanesulfonate-d2 | $C_{17}H_{11}D_3BrNO_5S$ | 427.28 |
| 2046 | 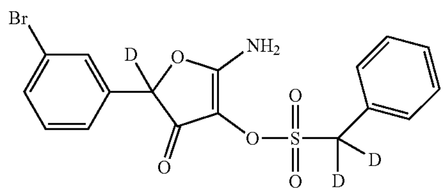 | 2-amino-5-(3-bromophenyl)-4-oxo-4,5-dihydrofuran-3-yl-5-d phenylmethanesulfonate-d2 | $C_{17}H_{11}D_3BrNO_5S$ | 427.28 |
| 2046(R) | 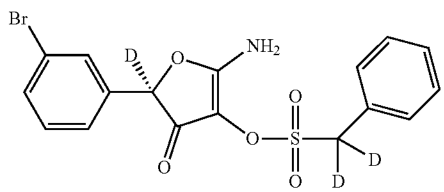 | (R)-2-amino-5-(3-bromophenyl)-4-oxo-4,5-dihydrofuran-3-yl-5-d phenylmethanesulfonate-d2 | $C_{17}H_{11}D_3BrNO_5S$ | 427.28 |
| 2046(S) | 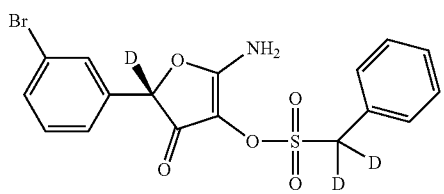 | (S)-2-amino-5-(3-bromophenyl)-4-oxo-4,5-dihydrofuran-3-yl-5-d phenylmethanesulfonate-d2 | $C_{17}H_{11}D_3BrNO_5S$ | 427.28 |
| 2047 | 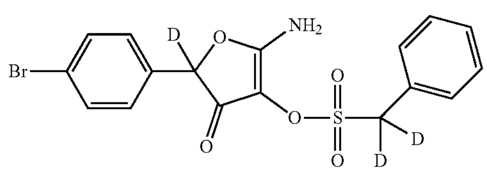 [SMILES: [2H]C1(c2ccc(Br)cc2)OC(N)=C(OS(=O)(=O)C([2H])([2H])c2ccccc2)C1=O] | 2-amino-5-(4-bromophenyl)-4-oxo-4,5-dihydrofuran-3-yl-5-d phenylmethanesulfonate-d2 | $C_{17}H_{11}D_3BrNO_5S$ | 427.28 |
| 2047(R) | 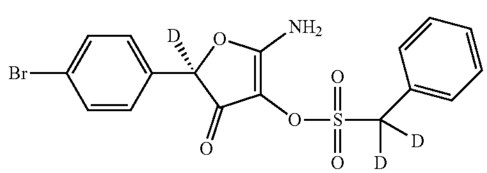 [SMILES: [2H]C([2H])(c1ccccc1)S(=O)(=O)OC1=C(N)O[C@]([2H])(c2ccc(Br)cc2)C1=O] | (R)-2-amino-5-(4-bromophenyl)-4-oxo-4,5-dihydrofuran-3-yl-5-d phenylmethanesulfonate-d2 | $C_{17}H_{11}D_3BrNO_5S$ | 427.28 |
| 2047(S) | 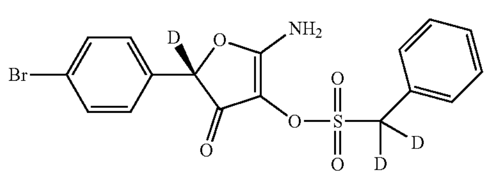 [SMILES: [2H]C([2H])(c1ccccc1)S(=O)(=O)OC1=C(N)O[C@@]([2H])(c2ccc(Br)cc2)C1=O] | (S)-2-amino-5-(4-bromophenyl)-4-oxo-4,5-dihydrofuran-3-yl-5-d phenylmethanesulfonate-d2 | $C_{17}H_{11}D_3BrNO_5S$ | 427.28 |
| 2048 | 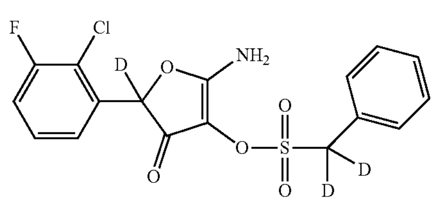 [SMILES: [2H]C1(c2cccc(F)c2Cl)OC(N)=C(OS(=O)(=O)C([2H])([2H])c2ccccc2)C1=O] | 2-amino-5-(2-chloro-3-fluorophenyl)-4-oxo-4,5-dihydrofuran-3-yl-5-d phenylmethanesulfonate-d2 | $C_{17}H_{10}D_3ClFNO_5S$ | 400.82 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2048(R) | 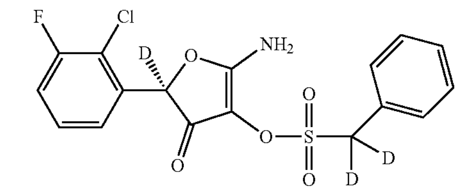 [SMILES: [2H]C([2H])(c1ccccc1)S(=O)(=O)OC1=C(N)O[C@]([2H])(c2cccc(F)c2Cl)C1=O] | (R)-2-amino-5-(2-chloro-3-fluorophenyl)-4-oxo-4,5-dihydrofuran-3-yl-5-d phenylmethanesulfonate-d2 | $C_{17}H_{10}D_3ClFNO_5S$ | 400.82 |
| 2048(S) | 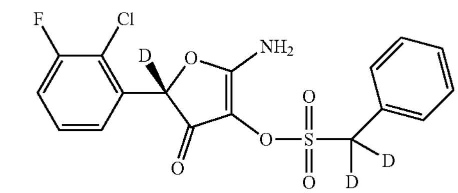 [SMILES: [2H]C([2H])(c1ccccc1)S(=O)(=O)OC1=C(N)O[C@@]([2H])(c2cccc(F)c2Cl)C1=O] | (S)-2-amino-5-(2-chloro-3-fluorophenyl)-4-oxo-4,5-dihydrofuran-3-yl-5-d phenylmethanesulfonate-d2 | $C_{17}H_{10}D_3ClFNO_5S$ | 400.82 |
| 2049 | 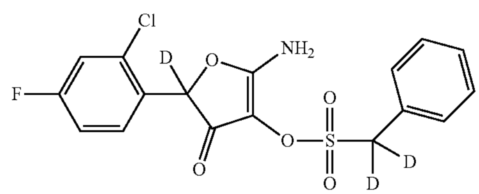 | 2-amino-5-(2-chloro-4-fluorophenyl)-4-oxo-4,5-dihydrofuran-3-yl-5-d phenylmethanesulfonate-d2 | $C_{17}H_{10}D_3ClFNO_5S$ | 400.82 |
| 2049(R) | 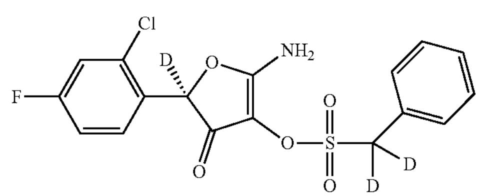 [SMILES: [2H]C([2H])(c1ccccc1)S(=O)(=O)OC1=C(N)O[C@]([2H])(c2ccc(F)cc2Cl)C1=O] | (R)-2-amino-5-(2-chloro-4-fluorophenyl)-4-oxo-4,5-dihydrofuran-3-yl-5-d phenylmethanesulfonate-d2 | $C_{17}H_{10}D_3ClFNO_5S$ | 400.82 |
| 2049(S) | 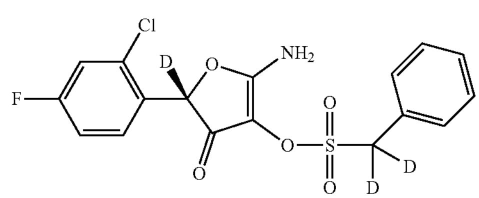 [SMILES: [2H]C([2H])(c1ccccc1)S(=O)(=O)OC1=C(N)O[C@@]([2H])(c2ccc(F)cc2Cl)C1=O] | (S)-2-amino-5-(2-chloro-4-fluorophenyl)-4-oxo-4,5-dihydrofuran-3-yl-5-d phenylmethanesulfonate-d2 | $C_{17}H_{10}D_3ClFNO_5S$ | 400.82 |
| 2050 | 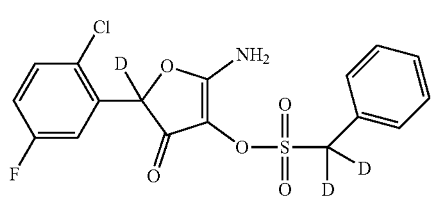 [SMILES: [2H]C1(c2cc(F)ccc2Cl)OC(N)=C(OS(=O)(=O)C([2H])([2H])c2ccccc2)C1=O] | 2-amino-5-(2-chloro-5-fluorophenyl)-4-oxo-4,5-dihydrofuran-3-yl-5-d phenylmethanesulfonate-d2 | $C_{17}H_{10}D_3ClFNO_5S$ | 400.82 |
| 2050(R) | 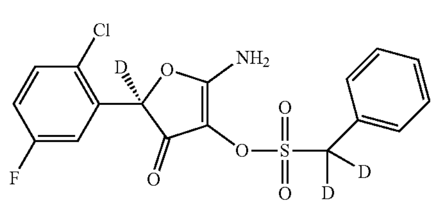 [SMILES: [2H]C([2H])(c1ccccc1)S(=O)(=O)OC1=C(N)O[C@]([2H])(c2cc(F)ccc2Cl)C1=O] | (R)-2-amino-5-(2-chloro-5-fluorophenyl)-4-oxo-4,5-dihydrofuran-3-yl-5-d phenylmethanesulfonate-d2 | $C_{17}H_{10}D_3ClFNO_5S$ | 400.82 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2050(S) | 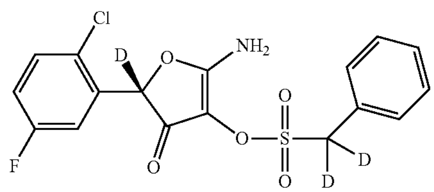 [SMILES: [2H]C([2H])(c1ccccc1)S(=O)(=O)OC1=C(N)O[C@@]([2H])(c2cc(F)ccc2Cl)C1=O] | (S)-2-amino-5-(2-chloro-5-fluorophenyl)-4-oxo-4,5-dihydrofuran-3-yl-5-d phenylmethanesulfonate-d2 | $C_{17}H_{10}D_3ClFNO_5S$ | 400.82 |
| 2051 | 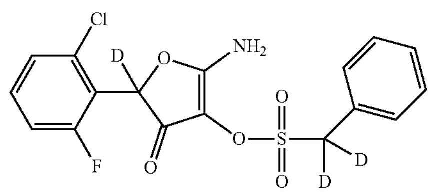 [SMILES: [2H]C1(c2c(F)cccc2Cl)OC(N)=C(OS(=O)(=O)C([2H])([2H])c2ccccc2)C1=O] | 2-amino-5-(2-chloro-6-fluorophenyl)-4-oxo-4,5-dihydrofuran-3-yl-5-d phenylmethanesulfonate-d2 | $C_{17}H_{10}D_3ClFNO_5S$ | 400.82 |
| 2051(R) | 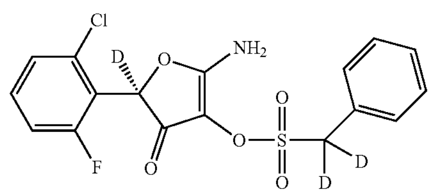 [SMILES: [2H]C([2H])(c1ccccc1)S(=O)(=O)OC1=C(N)O[C@]([2H])(c2c(F)cccc2Cl)C1=O] | (R)-2-amino-5-(2-chloro-6-fluorophenyl)-4-oxo-4,5-dihydrofuran-3-yl-5-d phenylmethanesulfonate-d2 | $C_{17}H_{10}D_3ClFNO_5S$ | 400.82 |
| 2051(S) | 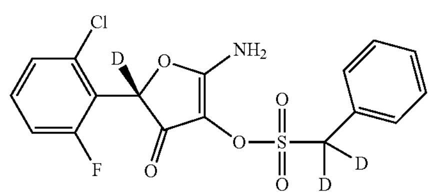 [SMILES: [2H]C([2H])(c1ccccc1)S(=O)(=O)OC1=C(N)O[C@@]([2H])(c2c(F)cccc2Cl)C1=O] | (S)-2-amino-5-(2-chloro-6-fluorophenyl)-4-oxo-4,5-dihydrofuran-3-yl-5-d phenylmethanesulfonate-d2 | $C_{17}H_{10}D_3ClFNO_5S$ | 400.82 |
| 2052 | 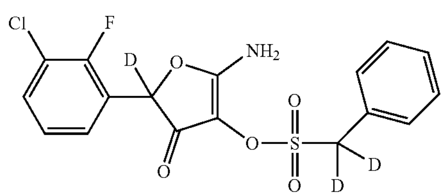 [SMILES: [2H]C1(c2cccc(Cl)c2F)OC(N)=C(OS(=O)(=O)C([2H])([2H])c2ccccc2)C1=O] | 2-amino-5-(3-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2052(R) | 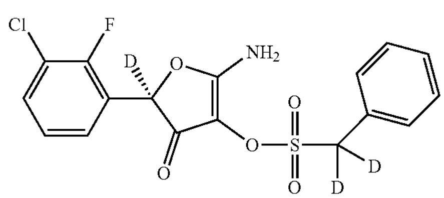 [SMILES: [2H]C([2H])(c1ccccc1)S(=O)(=O)OC1=C(N)O[C@]([2H])(c2cccc(Cl)c2F)C1=O] | (R)-2-amino-5-(3-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2052(S) | 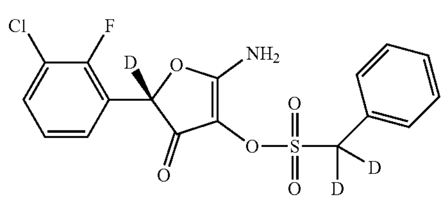 [SMILES: [2H]C([2H])(c1ccccc1)S(=O)(=O)OC1=C(N)O[C@@]([2H])(c2cccc(Cl)c2F)C1=O] | (S)-2-amino-5-(3-chloro-2-fluorophenyl)-4-oxo-4,5-dihydrofuran-3-yl-5-d phenylmethanesulfonate-d2 | $C_{17}H_{10}D_3ClFNO_5S$ | 400.82 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2053 | 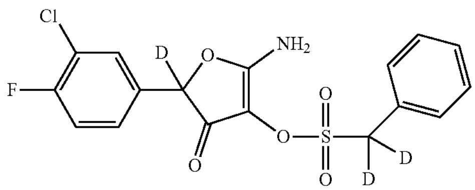 [SMILES: [2H]C1(c2ccc(F)c(Cl)c2)OC(N)=C(OS(=O)(=O)C([2H])([2H])c2ccccc2)C1=O] | 2-amino-5-(3-chloro-4-fluorophenyl)-4-oxo-4,5-dihydrofuran-3-yl-5-d phenylmethanesulfonate-d2 | $C_{17}H_{10}D_3ClFNO_5S$ | 400.82 |
| 2053(R) | 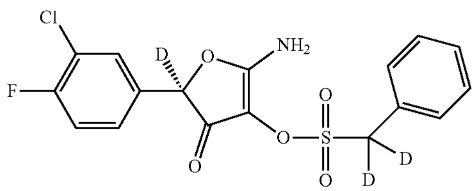 [SMILES: [2H]C([2H])(c1ccccc1)S(=O)(=O)OC1=C(N)O[C@]([2H])(c2ccc(F)c(Cl)c2)C1=O] | (R)-2-amino-5-(3-chloro-4-fluorophenyl)-4-oxo-4,5-dihydrofuran-3-yl-5-d phenylmethanesulfonate-d2 | $C_{17}H_{10}D_3ClFNO_5S$ | 400.82 |
| 2053(S) | 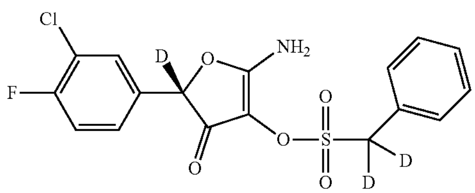 [SMILES: [2H]C([2H])(c1ccccc1)S(=O)(=O)OC1=C(N)O[C@@]([2H])(c2ccc(F)c(Cl)c2)C1=O] | (S)-2-amino-5-(3-chloro-4-fluorophenyl)-4-oxo-4,5-dihydrofuran-3-yl-5-d phenylmethanesulfonate-d2 | $C_{17}H_{10}D_3ClFNO_5S$ | 400.82 |
| 2054 | 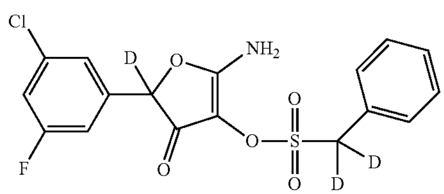 [SMILES: [2H]C1(c2cc(F)cc(Cl)c2)OC(N)=C(OS(=O)(=O)C([2H])([2H])c2ccccc2)C1=O] | 2-amino-5-(3-chloro-5-fluorophenyl)-4-oxo-4,5-dihydrofuran-3-yl-5-d phenylmethanesulfonate-d2 | $C_{17}H_{10}D_3ClFNO_5S$ | 400.82 |
| 2054(R) | 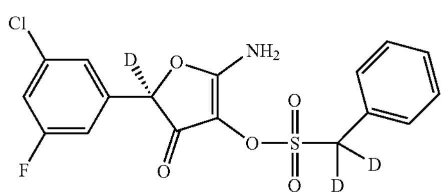 [SMILES: [2H]C([2H])(c1ccccc1)S(=O)(=O)OC1=C(N)O[C@]([2H])(c2cc(F)cc(Cl)c2)C1=O] | (R)-2-amino-5-(3-chloro-5-fluorophenyl)-4-oxo-4,5-dihydrofuran-3-yl-5-d phenylmethanesulfonate-d2 | $C_{17}H_{10}D_3ClFNO_5S$ | 400.82 |
| 2054(S) | 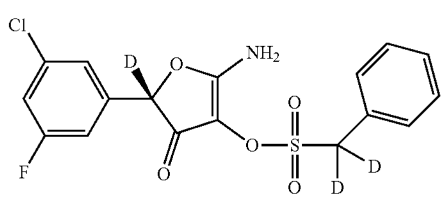 [SMILES: [2H]C([2H])(c1ccccc1)S(=O)(=O)OC1=C(N)O[C@@]([2H])(c2cc(F)cc(Cl)c2)C1=O] | (S)-2-amino-5-(3-chloro-5-fluorophenyl)-4-oxo-4,5-dihydrofuran-3-yl-5-d phenylmethanesulfonate-d2 | $C_{17}H_{10}D_3ClFNO_5S$ | 400.82 |
| 2055 | 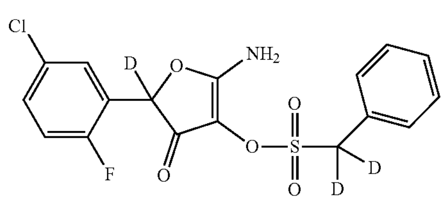 [SMILES: [2H]C1(c2cc(Cl)ccc2F)OC(N)=C(OS(=O)(=O)C([2H])([2H])c2ccccc2)C1=O] | 2-amino-5-(5-chloro-2-fluorophenyl)-4-oxo-4,5-dihydrofuran-3-yl-5-d phenylmethanesulfonate-d2 | $C_{17}H_{10}D_3ClFNO_5S$ | 400.82 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2055(R) | 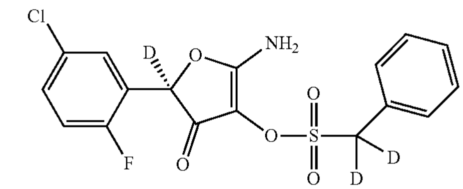 [SMILES: [2H]C([2H])(c1ccccc1)S(=O)(=O)OC1=C(N)O[C@]([2H])(c2cc(Cl)ccc2F)C1=O] | (R)-2-amino-5-(5-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2055(S) | 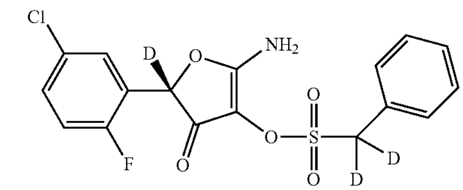 [SMILES: [2H]C([2H])(c1ccccc1)S(=O)(=O)OC1=C(N)O[C@@]([2H])(c2cc(Cl)ccc2F)C1=O] | (S)-2-amino-5-(5-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2056 | 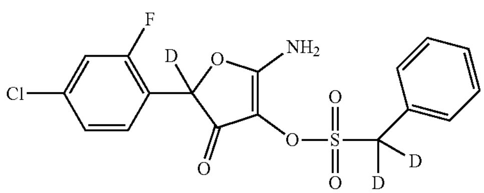 [SMILES: [2H]C1(c2ccc(Cl)cc2F)OC(N)=C(OS(=O)(=O)C([2H])([2H])c2ccccc2)C1=O] | 2-amino-5-(4-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2056(R) | 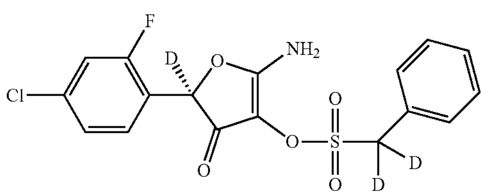 [SMILES: [2H]C([2H])(c1ccccc1)S(=O)(=O)OC1=C(N)O[C@]([2H])(c2ccc(Cl)cc2F)C1=O] | (R)-2-amino-5-(4-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2056(S) | 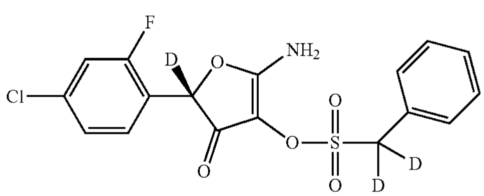 [SMILES: [2H]C([2H])(c1ccccc1)S(=O)(=O)OC1=C(N)O[C@@]([2H])(c2ccc(Cl)cc2F)C1=O] | (S)-2-amino-5-(4-chloro-2-fluorophenyl)-4-oxo-4,5-dihydrofuran-3-yl-5-d phenylmethanesulfonate-d2 | $C_{17}H_{10}D_3ClFNO_5S$ | 400.82 |
| 2057 | 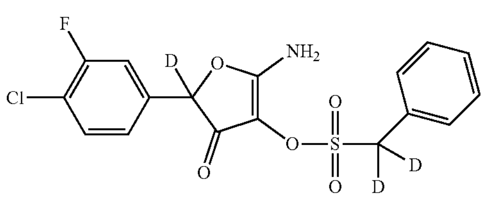 [SMILES: [2H]C1(c2ccc(Cl)c(F)c2)OC(N)=C(OS(=O)(=O)C([2H])([2H])c2ccccc2)C1=O] | 2-amino-5-(4-chloro-3-fluorophenyl)-4-oxo-4,5-dihydrofuran-3-yl-5-d phenylmethanesulfonate-d2 | $C_{17}H_{10}D_3ClFNO_5S$ | 400.82 |
| 2057(R) | 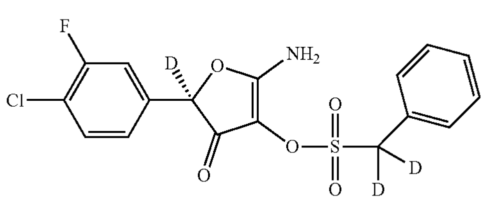 [SMILES: [2H]C([2H])(c1ccccc1)S(=O)(=O)OC1=C(N)O[C@]([2H])(c2ccc(Cl)c(F)c2)C1=O] | (R)-2-amino-5-(4-chloro-3-fluorophenyl)-4-oxo-4,5-dihydrofuran-3-yl-5-d phenylmethanesulfonate-d2 | $C_{17}H_{10}D_3ClFNO_5S$ | 400.82 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2057(S) | 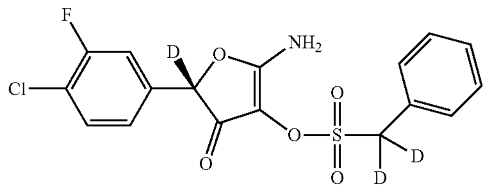 [SMILES: [2H]C([2H])(c1ccccc1)S(=O)(=O)OC1=C(N)O[C@@]([2H])(c2ccc(Cl)c(F)c2)C1=O] | (S)-2-amino-5-(4-chloro-3-fluorophenyl)-4-oxo-4,5-dihydrofuran-3-yl-5-d phenylmethanesulfonate-d2 | $C_{17}H_{10}D_3ClFNO_5S$ | 400.82 |
| 2058 | 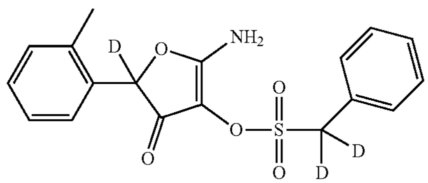 [SMILES: [2H]C1(c2ccccc2C)OC(N)=C(OS(=O)(=O)C([2H])([2H])c2ccccc2)C1=O] | 2-amino-4-oxo-5-(o-tolyl)-4,5-dihydrofuran-3-yl-5-d phenylmethanesulfonate-d2 | $C_{18}H_{14}D_3NO_5S$ | 362.41 |
| 2058(R) | 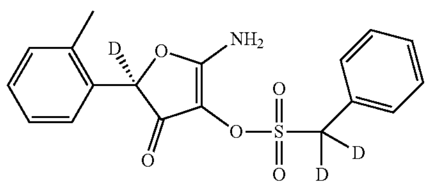 [SMILES: [2H]C([2H])(c1ccccc1)S(=O)(=O)OC1=C(N)O[C@]([2H])(c2ccccc2C)C1=O] | (R)-2-amino-4-oxo-5-(o-tolyl)-4,5-dihydrofuran-3-yl-5-d phenylmethanesulfonate-d2 | $C_{18}H_{14}D_3NO_5S$ | 362.41 |
| 2058(S) | 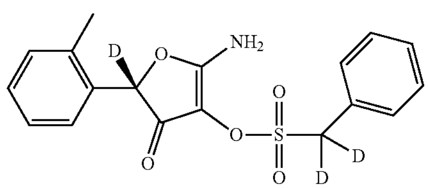 [SMILES: [2H]C([2H])(c1ccccc1)S(=O)(=O)OC1=C(N)O[C@@]([2H])(c2ccccc2C)C1=O] | (S)-2-amino-4-oxo-5-(o-tolyl)-4,5-dihydofuran-3-yl-5-d phenylmethanesulfonate-d2 | $C_{18}H_{14}D_3NO_5S$ | 362.41 |
| 2059 | 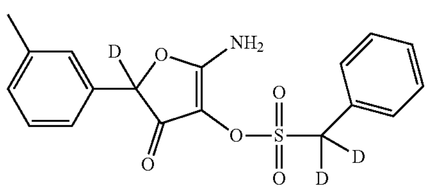 [SMILES: [2H]C1(c2cccc(C)c2)OC(N)=C(OS(=O)(=O)C([2H])([2H])c2ccccc2)C1=O] | 2-amino-4-oxo-5-(m-tolyl)-4,5-dihydrofuran-3-yl-5-d phenylmethanesulfonate-d2 | $C_{18}H_{14}D_3NO_5S$ | 362.41 |
| 2059(R) | 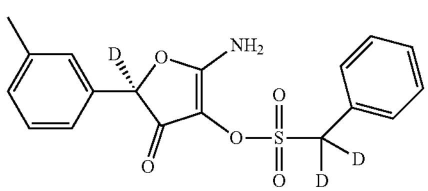 [SMILES: [2H]C([2H])(c1ccccc1)S(=O)(=O)OC1=C(N)O[C@]([2H])(c2cccc(C)c2)C1=O] | (R)-2-amino-4-oxo-5-(m-tolyl)-4,5-dihydrofuran-3-yl-5-d phenylmethanesulfonate-d2 | $C_{18}H_{14}D_3NO_5S$ | 362.41 |
| 2059(S) | 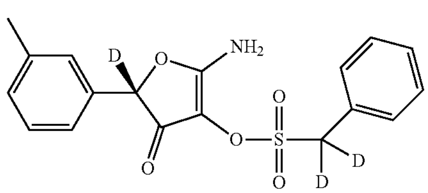 [SMILES: [2H]C([2H])(c1ccccc1)S(=O)(=O)OC1=C(N)O[C@@]([2H])(c2cccc(C)c2)C1=O] | (S)-2-amino-4-oxo-5-(m-tolyl)-4,5-dihydrofuran-3-yl-5-d phenylmethanesulfonate-d2 | $C_{18}H_{14}D_3NO_5S$ | 362.41 |
| 2060 | 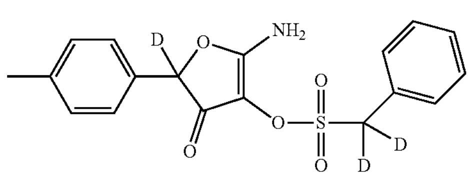 [SMILES: [2H]C1(c2ccc(C)cc2)OC(N)=C(OS(=O)(=O)C([2H])([2H])c2ccccc2)C1=O] | 2-amino-4-oxo-5-(p-tolyl)-4,5-dihydrofuran-3-yl-5-d phenylmethanesulfonate-d2 | $C_{18}H_{14}D_3NO_5S$ | 362.41 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2060(R) | 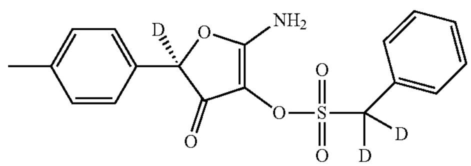 [SMILES: [2H]C([2H])(c1ccccc1)S(=O)(=O)OC1=C(N)O[C@]([2H])(c2ccc(C)cc2)C1=O] | (R)-2-amino-4-oxo-5-(p-tolyl)-4,5-dihydrofuran-3-yl-5-d phenylmethanesulfonate-d2 | $C_{18}H_{14}D_3NO_5S$ | 362.41 |
| 2060(S) | 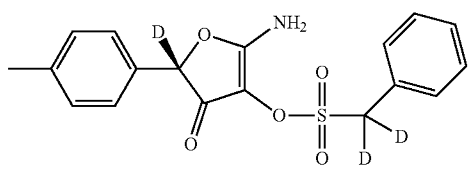 [SMILES: [2H]C([2H])(c1ccccc1)S(=O)(=O)OC1=C(N)O[C@@]([2H])(c2ccc(C)cc2)C1=O] | (S)-2-amino-4-oxo-5-(p-tolyl)-4,5-dihydrofuran-3-yl-5-d phenylmethanesulfonate-d2 | $C_{18}H_{14}D_3NO_5S$ | 362.41 |
| 2061 | 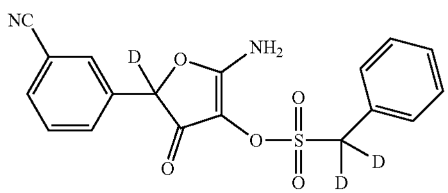 [SMILES: [2H]C1(c2cccc(C#N)c2)OC(N)=C(OS(=O)(=O)C([2H])([2H])c2ccccc2)C1=O] | 2-amino-5-(3-cyanophenyl)-4-oxo-4,5-dihydrofuran-5-d phenylmethanesulfonate-d2 | $C_{18}H_{11}D_3N_2O_5S$ | 373.40 |
| 2061(R) | 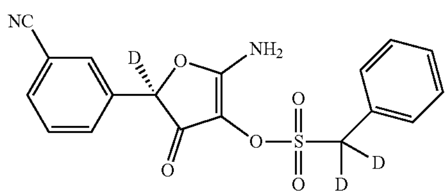 [SMILES: [2H]C([2H])(c1ccccc1)S(=O)(=O)OC1=C(N)O[C@]([2H])(c2cccc(C#N)c2)C1=O] | (R)-2-amino-5-(3-cyanophenyl)-4-oxo-4,5-dihydrofuran-3-yl-5-d phenylmethanesulfonate-d2 | $C_{18}H_{11}D_3N_2O_5S$ | 373.40 |
| 2061(S) | 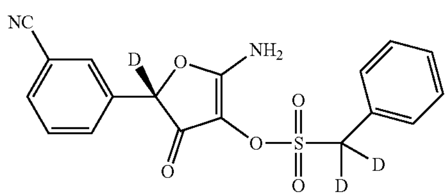 [SMILES: [2H]C([2H])(c1ccccc1)S(=O)(=O)OC1=C(N)O[C@@]([2H])(c2cccc(C#N)c2)C1=O] | (S)-2-amino-5-(3-cyanophenyl)-4-oxo-4,5-dihydrofuran-3-yl-5-d phenylmethanesulfonate-d2 | $C_{18}H_{11}D_3N_2O_5S$ | 373.40 |
| 2062 | 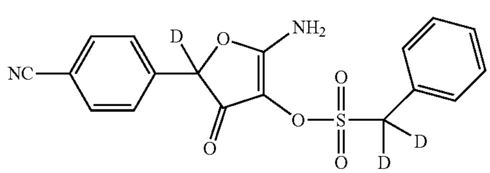 | 2-amino-5-(4-cyanophenyl)-4-oxo-4,5-dihydrofuran-3-yl-5-d phenylmethanesulfonate-d2 | $C_{18}H_{11}D_3N_2O_5S$ | 373.40 |
| 2062(R) | 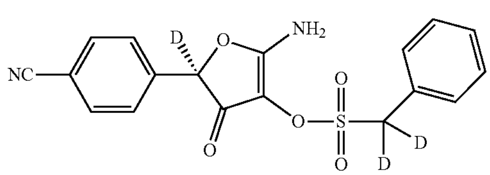 [SMILES: [2H]C([2H])(c1ccccc1)S(=O)(=O)OC1=C(N)O[C@]([2H])(c2ccc(C#N)cc2)C1=O] | (R)-2-amino-5-(4-cyanophenyl)-4-oxo-4,5-dihydrofuran-3-yl-5-d phenylmethanesulfonate-d2 | $C_{18}H_{11}D_3N_2O_5S$ | 373.40 |
| 2062(S) | 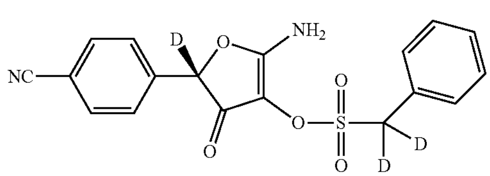 [SMILES: [2H]C([2H])(c1ccccc1)S(=O)(=O)OC1=C(N)O[C@@]([2H])(c2ccc(C#N)cc2)C1=O] | (S)-2-amino-5-(4-cyanophenyl)-4-oxo-4,5-dihydrofuran-3-yl-5-d phenylmethanesulfonate-d2 | $C_{18}H_{11}D_3N_2O_5S$ | 373.40 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2063 | 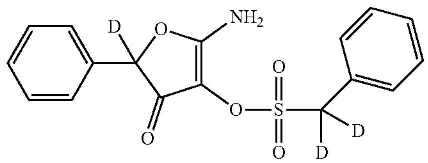 [SMILES: [2H]C1(c2ccccc2)OC(N)=C(OS(=O)(=O)C([2H])([2H])c2ccccc2)C1=O] | 2-amino-4-oxo-5-phenyl-4,5-dihydrofuran-3-yl-5-d phenylmethanesulfonate-d2 | $C_{17}H_{12}D_3NO_5S$ | 348.39 |
| 2063(R) | 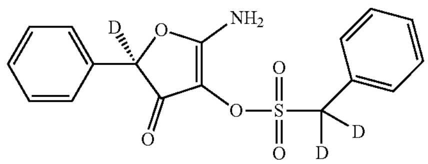 [SMILES: [2H]C([2H])(c1ccccc1)S(=O)(=O)OC1=C(N)O[C@]([2H])(c2ccccc2)C1=O] | (R)-2-amino-4-oxo-5-phenyl-4,5-dihydrofuran-3-yl-5-d phenylmethanesulfonate-d2 | $C_{17}H_{12}D_3NO_5S$ | 348.39 |
| 2063(S) | 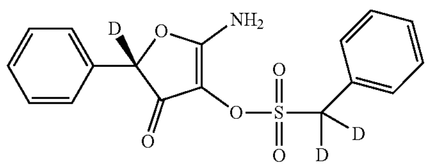 [SMILES: [2H]C([2H])(c1ccccc1)S(=O)(=O)OC1=C(N)O[C@@]([2H])(c2ccccc2)C1=O] | (S)-2-amino-4-oxo-5-phenyl-4,5-dihydrofuran-3-yl-5-d phenylmethanesulfonate-d2 | $C_{17}H_{12}D_3NO_5S$ | 348.39 |
| 2064 | 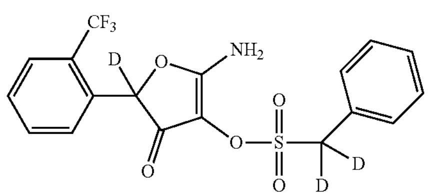 | 2-amino-4-oxo-5-(2-(trifluoromethyl)phenyl)-4,5-dihydrofuran-3-yl-5-d phenylmethanesulfonate-d2 | $C_{18}H_{11}D_3F_3NO_5S$ | 416.39 |
| 2064(R) | 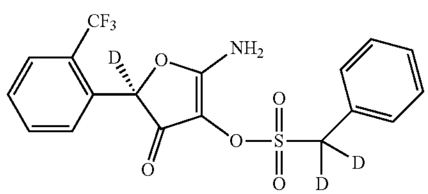 | (R)-2-amino-4-oxo-5-(2-(trifluoromethyl)phenyl)-4,5-dihydrofuran-3-yl-5-d phenylmethanesulfonate-d2 | $C_{18}H_{11}D_3F_3NO_5S$ | 416.39 |
| 2064(S) | 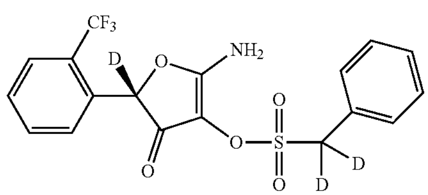 | (S)-2-amino-4-oxo-5-(2-(trifluoromethyl)phenyl)-4,5-dihydrofuran-3-yl-5-d phenylmethanesulfonate-d2 | $C_{18}H_{11}D_3F_3NO_5S$ | 416.39 |
| 2065 | 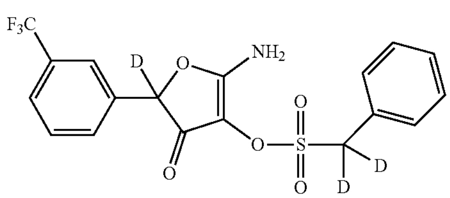 [SMILES: [2H]C1(c2cccc(C(F)(F)F)c2)OC(N)=C(OS(=O)(=O)C([2H])([2H])c2ccccc2)C1=O] | 2-amino-4-oxo-5-(3-(trifluoromethyl)phenyl)-4,5-dihydrofuran-3-yl-5-d phenylmethanesulfonate-d2 | $C_{18}H_{11}D_3F_3NO_5S$ | 416.39 |
| 2065(R) | 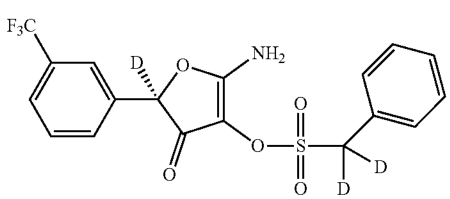 [SMILES: [2H]C([2H])(c1ccccc1)S(=O)(=O)OC1=C(N)O[C@]([2H])(c2cccc(C(F)(F)F)c2)C1=O] | (R)-2-amino-4-oxo-5-(3-(trifluoromethyl)phenyl)-4,5-dihydrofuran-3-yl-5-d phenylmethanesulfonate-d2 | $C_{18}H_{11}D_3F_3NO_5S$ | 416.39 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2065(S) | 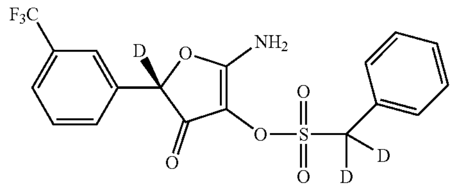 [SMILES: [2H]C([2H])(c1ccccc1)S(=O)(=O)OC1=C(N)O[C@@]([2H])(c2cccc(C(F)(F)F)c2)C1=O] | (S)-2-amino-4-oxo-5-(3-(trifluoromethyl)phenyl)-4,5-dihydrofuran-3-yl-5-d phenylmethanesulfonate-d2 | $C_{18}H_{11}D_3F_3NO_5S$ | 416.39 |
| 2066 | 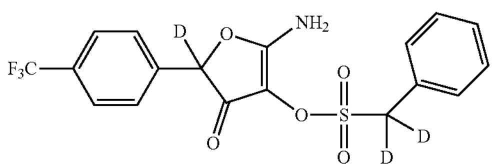 [SMILES: [2H]C1(c2ccc(C(F)(F)F)cc2)OC(N)=C(OS(=O)(=O)C([2H])([2H])c2ccccc2)C1=O] | 2-amino-4-oxo-5-(4-(trifluoromethyl)phenyl)-4,5-dihydrofuran-3-yl-5-d phenylmethanesulfonate-d2 | $C_{18}H_{11}D_3F_3NO_5S$ | 416.39 |
| 2066(R) | 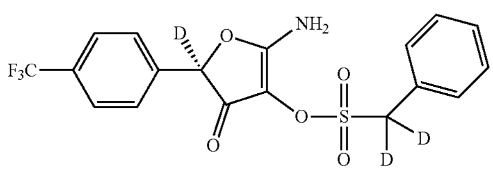 [SMILES: [2H]C([2H])(c1ccccc1)S(=O)(=O)OC1=C(N)O[C@]([2H])(c2ccc(C(F)(F)F)cc2)C1=O] | (R)-2-amino-4-oxo-5-(4-(trifluoromethyl)phenyl)-4,5-dihydrofuran-3-yl-5-d phenylmethanesulfonate-d2 | $C_{18}H_{11}D_3F_3NO_5S$ | 416.39 |
| 2066(S) | 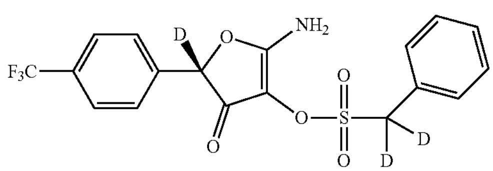 [SMILES: [2H]C([2H])(c1ccccc1)S(=O)(=O)OC1=C(N)O[C@@]([2H])(c2ccc(C(F)(F)F)cc2)C1=O] | (S)-2-amino-4-oxo-5-(4-(trifluoromethyl)phenyl)-4,5-dihydrofuran-3-yl-5-d phenylmethanesulfonate-d2 | $C_{18}H_{11}D_3F_3NO_5S$ | 416.39 |
| 2067 | 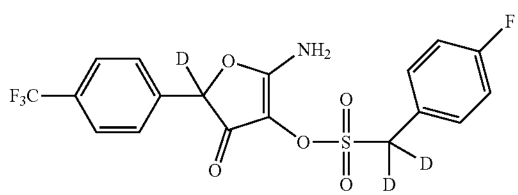 [SMILES: [2H]C1(c2ccc(C(F)(F)F)cc2)OC(N)=C(OS(=O)(=O)C([2H])([2H])c2ccc(F)cc2)C1=O] | 2-amino-4-oxo-5-(4-(trifluoromethyl)phenyl)-4,5-dihydrofuran-3-yl-5-d (4-fluorophenyl)methanesulfonate-d2 | $C_{18}H_{10}D_3F_4NO_5S$ | 434.38 |
| 2067(R) | 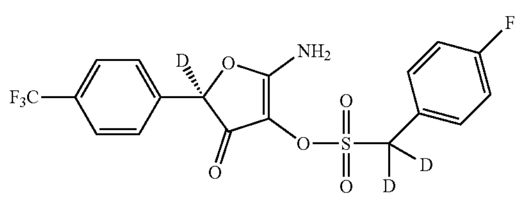 [SMILES: [2H]C([2H])(c1ccc(F)cc1)S(=O)(=O)OC1=C(N)O[C@]([2H])(c2ccc(C(F)(F)F)cc2)C1=O] | (R)-2-amino-4-oxo-5-(4-(trifluoromethyl)phenyl)-4,5-dihydrofuran-3-yl-5-d (4-fluorophenyl)methanesulfonate-d2 | $C_{18}H_{10}D_3F_4NO_5S$ | 434.38 |
| 2067(S) | 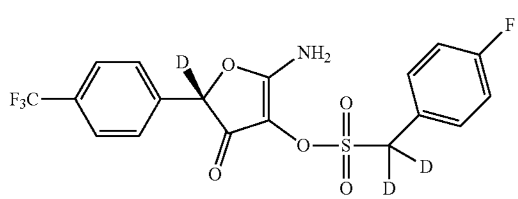 [SMILES: [2H]C([2H])(c1ccc(F)cc1)S(=O)(=O)OC1=C(N)O[C@@]([2H])(c2ccc(C(F)(F)F)cc2)C1=O] | (S)-2-amino-4-oxo-5-(4-(trifluoromethyl)phenyl)-4,5-dihydrofuran-3-yl-5-d (4-fluorophenyl)methanesulfonate-d2 | $C_{18}H_{10}D_3F_4NO_5S$ | 434.38 |
| 2068 | 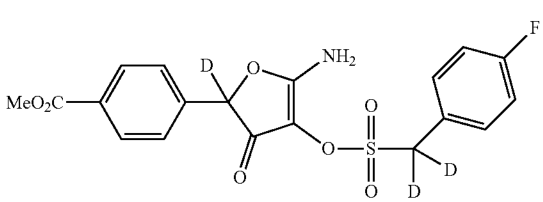 [SMILES: [2H]C1(c2ccc(C(=O)OC)cc2)OC(N)=C(OS(=O)(=O)C([2H])([2H])c2ccc(F)cc2)C1=O] | methyl 4-(5-amino-4-((((4-fluorophenyl)methyl-d2)sulfonyl)oxy)-3-oxo-2,3-dihydrofuran-2-yl-2-d)benzoate | $C_{19}H_{13}D_3FNO_7S$ | 424.41 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2068(R) | 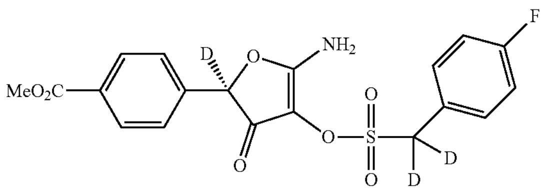 [SMILES: [2H]C([2H])(c1ccc(F)cc1)S(=O)(=O)OC1=C(N)O[C@]([2H])(c2ccc(C(=O)OC)cc2)C1=O] | methyl (R)-4-(5-amino-4-((((4-fluorophenyl)methyl-d2)sulfonyl)oxy)-3-oxo-2,3-dihydrofuran-2-yl-2-d)benzoate | $C_{19}H_{13}D_3FNO_7S$ | 424.41 |
| 2068(S) | 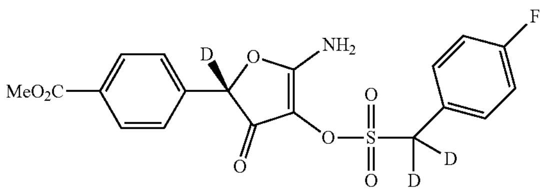 [SMILES: [2H]C([2H])(c1ccc(F)cc1)S(=O)(=O)OC1=C(N)O[C@@]([2H])(c2ccc(C(=O)OC)cc2)C1=O] | methyl (S)-4-(5-amino-4-((((4-fluorophenyl)methyl-d2)sulfonyl)oxy)-3-oxo-2,3-dihydrofuran-2-yl-2-d)benzoate | $C_{19}H_{13}D_3FNO_7S$ | 424.41 |
| 2069 | 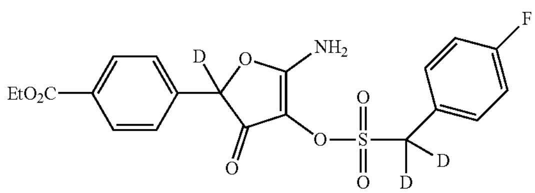 [SMILES: [2H]C1(c2ccc(C(=O)OCC)cc2)OC(N)=C(OS(=O)(=O)C([2H])([2H])c2ccc(F)cc2)C1=O] | ethyl 4-(5-amino-4-((((4-fluorophenyl)methyl-d2)sulfonyl)oxy)-3-oxo-2,3-dihydrofuran-2-yl-2-d)benzoate | $C_{20}H_{15}D_3FNO_7S$ | 438.44 |
| 2069(R) | 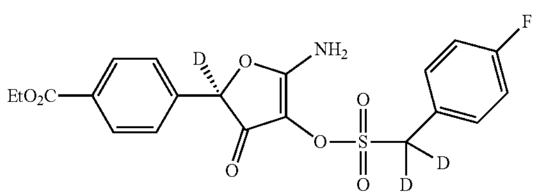 [SMILES: [2H]C([2H])(c1ccc(F)cc1)S(=O)(=O)OC1=C(N)O[C@]([2H])(c2ccc(C(=O)OCC)cc2)C1=O] | ethyl (R)-4-(5-amino-4-((((4-fluorophenyl)methyl-d2)sulfonyl)oxy)-3-oxo-2,3-dihydrofuran-2-yl-2-d)benzoate | $C_{20}H_{15}D_3FNO_7S$ | 438.44 |
| 2069(S) | 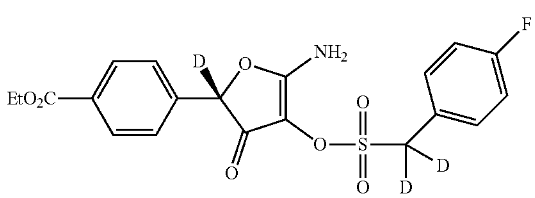 [SMILES: [2H]C([2H])(c1ccc(F)cc1)S(=O)(=O)OC1=C(N)O[C@@]([2H])(c2ccc(C(=O)OCC)cc2)C1=O] | ethyl (S)-4-(5-amino-4-((((4-fluorophenyl)methyl-d2)sulfonyl)oxy)-3-oxo-2,3-dihydrofuran-2-yl-2-d)benzoate | $C_{20}H_{15}D_3FNO_7S$ | 438.44 |
| 2070 | 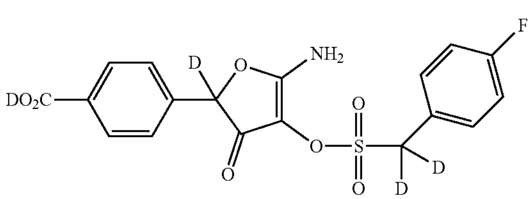 | 4-(5-amino-4-((((4-fluorophenyl)methyl-d2)sulfonyl)oxy)-3-oxo-2,3-dihydrofuran-2-yl-2-d)benzoic acid-d | $C_{18}H_{10}D_4FNO_7S$ | 411.39 |
| 2070(R) | 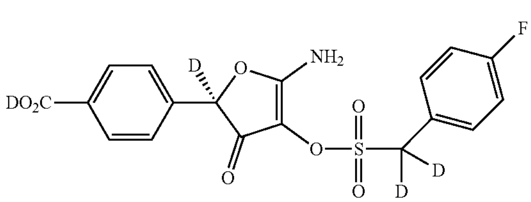 | (R)-4-(5-amino-4-((((4-fluorophenyl)methyl-d2)sulfonyl)oxy)-3-oxo-2,3-dihydrofuran-2-yl-2-d)benzoic acid-d | $C_{18}H_{10}D_4FNO_7S$ | 411.39 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2070(S) | 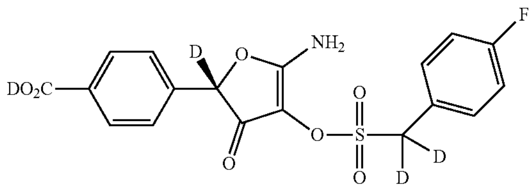 | (S)-4-(5-amino-4-((((4-fluorophenyl)methyl-d2)sulfonyl)oxy)-3-oxo-2,3-dihydrofuran-2-yl-2-d)benzoic acid-d | C$_{18}$H$_{10}$D$_4$FNO$_7$S | 411.39 |
| 2071 | 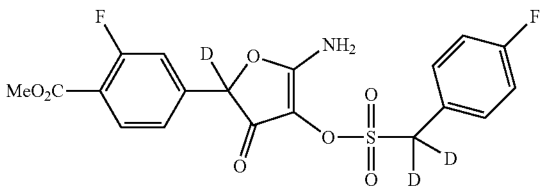 [SMILES: [2H]C1(c2ccc(C(=O)OC)c(F)c2)OC(N)=C(OS(=O)(=O)C([2H])([2H])c2ccc(F)cc2)C1=O] | methyl 4-(5-amino-4-((((4-fluorophenyl)methyl-d2)sulfonyl)oxy)-3-oxo-2,3-dihydofuran-2-yl-2-d)-2-fluorobenzoate | C$_{19}$H$_{12}$D$_3$F$_2$NO$_7$S | 442.40 |
| 2071(R) | 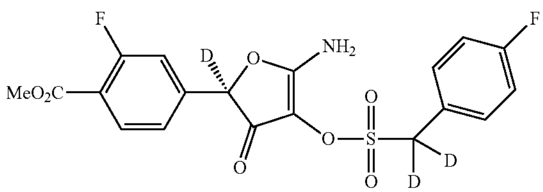 [SMILES: [2H]C([2H])(c1ccc(F)cc1)S(=O)(=O)OC1=C(N)O[C@]([2H])(c2ccc(C(=O)OC)c(F)c2)C1=O] | methyl (R)-4-(5-amino-4-((((4-fluorophenyl)methyl-d2)sulfonyl)oxy)-3-oxo-2,3-dihydrofuran-2-yl-2-d)-2-fluorobenzoate | C$_{19}$H$_{12}$D$_3$F$_2$NO$_7$S | 442.40 |
| 2071(S) | 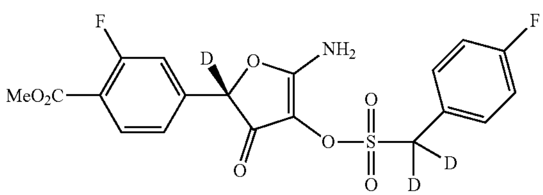 [SMILES: [2H]C([2H])(c1ccc(F)cc1)S(=O)(=O)OC1=C(N)O[C@@]([2H])(c2ccc(C(=O)OC)c(F)c2)C1=O] | methyl (S)-4-(5-amino-4-((((4-fluorophenyl)methyl-d2)sulfonyl)oxy)-3-oxo-2,3-dihydrofuran-2-yl-2-d)-2-fluorobenzoate | C$_{19}$H$_{12}$D$_3$F$_2$NO$_7$S | 442.40 |
| 2072 | 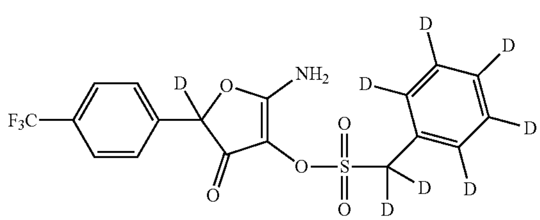 [SMILES: [2H]c1c([2H])c([2H])c(C([2H])([2H])S(=O)(=O)OC2=C(N)OC([2H])(c3ccc(C(F)(F)F)cc3)C2=O)c([2H])c1[2H]] | 2-amino-4-oxo-5-(4-(trifluoromethyl)phenyl)-4,5-dihydrofuran-3-yl-5-d (phenyl-d5) methanesulfonate-d2 | C$_{18}$H$_6$D$_8$F$_3$NO$_5$S | 421.42 |
| 2072(R) | 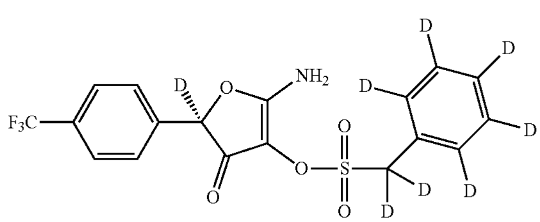 [SMILES: [2H]c1c([2H])c([2H])c(C([2H])([2H])S(=O)(=O)OC2=C(N)O[C@]([2H])(c3ccc(C(F)(F)F)cc3)C2=O)c([2H])c1[2H]] | (R)-2-amino-4-oxo-5-(4-(trifluoromethyl)phenyl)-4,5-dihydrofuran-3-yl-5-d (phenyl-d5) methanesulfonate-d2 | C$_{18}$H$_6$D$_8$F$_3$NO$_5$S | 421.42 |
| 2072(S) | 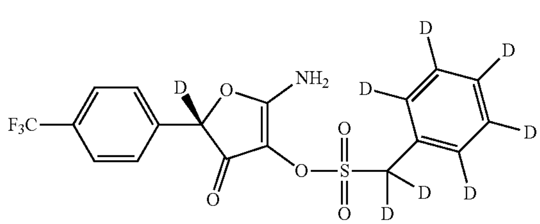 [SMILES: [2H]c1c([2H])c([2H])c(C([2H])([2H])S(=O)(=O)OC2=C(N)O[C@@]([2H])(c3ccc(C(F)(F)F)cc3)C2=O)c([2H])c1[2H]] | (S)-2-amino-4-oxo-5-(4-(trifluoromethyl)phenyl)-4,5-dihydofuran-3-yl-5-d (phenyl-d5) methanesulfonate-d2 | C$_{18}$H$_6$D$_8$F$_3$NO$_5$S | 421.42 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2073 | 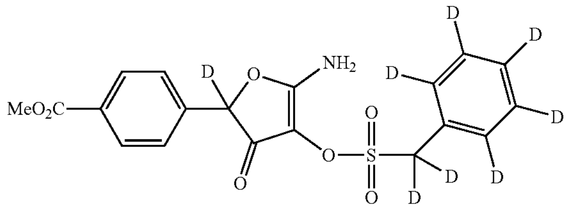 [SMILES: [2H]c1c([2H])c([2H])c(C([2H])([2H])S(=O)(=O)OC2=C(N)OC([2H])(c3ccc(C(=O)OC)cc3)C2=O)c([2H])c1[2H]] | methyl 4-(5-amino-3-oxo-4-((((phenyl-d5)methyl-d2)sulfonyl)oxy)-2,3-dihydrofuran-2-yl-2-d)benzoate | $C_{19}H_9D_8NO_7S$ | 411.45 |
| 2073(R) | 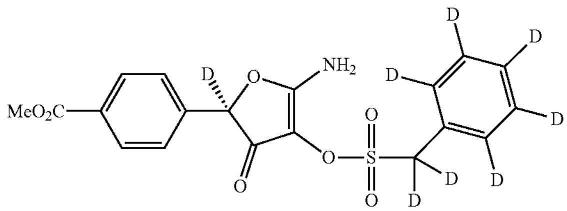 [SMILES: [2H]c1c([2H])c([2H])c(C([2H])([2H])S(=O)(=O)OC2=C(N)O[C@]([2H])(c3ccc(C(=O)OC)cc3)C2=O)c([2H])c1[2H]] | methyl (R)-4-(5-amino-3-oxo-4-((((phenyl-d5)methyl-d2)sulfonyl)oxy)-2,3-dihydrofuran-2-yl-2-d)benzoate | $C_{19}H_9D_8NO_7S$ | 411.45 |
| 2073(S) | 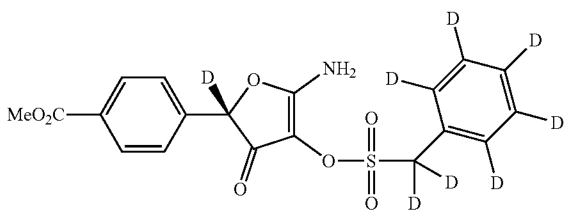 [SMILES: [2H]c1c([2H])c([2H])c(C([2H])([2H])S(=O)(=O)OC2=C(N)O[C@@]([2H])(c3ccc(C(=O)OC)cc3)C2=O)c([2H])c1[2H]] | methyl (S)-4-(5-amino-3-oxo-4-((((phenyl-d5)methyl-d2)sulfonyl)oxy)-2,3-dihydrofuran-2-yl-2-d)benzoate | $C_{19}H_9D_8NO_7S$ | 411.45 |
| 2074 | 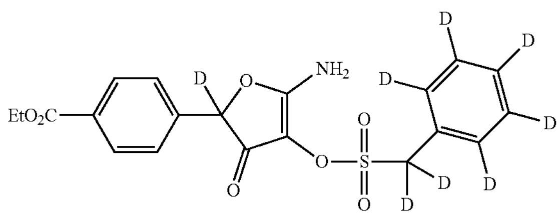 [SMILES: [2H]c1c([2H])c([2H])c(C([2H])([2H])S(=O)(=O)OC2=C(N)OC([2H])(c3ccc(C(=O)OCC)cc3)C2=O)c([2H])c1[2H]] | ethyl 4-(5-amino-3-oxo-4-((((phenyl-d5)methyl-d2)sulfonyl)oxy)-2,3-dihydrofuran-2-yl-2-d)benzoate | $C_{20}H_{11}D_8NO_7S$ | 425.48 |
| 2074(R) | 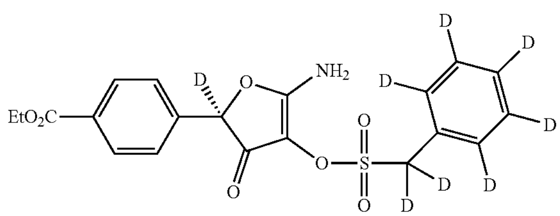 [SMILES: [2H]c1c([2H])c([2H])c(C([2H])([2H])S(=O)(=O)OC2=C(N)O[C@]([2H])(c3ccc(C(=O)OCC)cc3)C2=O)c([2H])c1[2H]] | ethyl (R)-4-(5-amino-3-oxo-4-((((phenyl-d5)methyl-d2)sulfonyl)oxy)-2,3-dihydrofuran-2-yl-2-d)benzoate | $C_{20}H_{11}D_8NO_7S$ | 425.48 |
| 2074(S) | 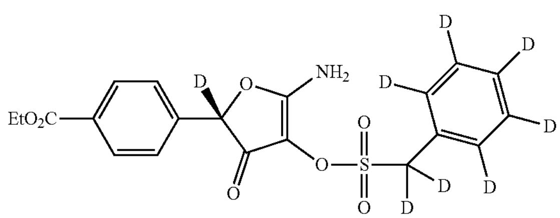 [SMILES: [2H]c1c([2H])c([2H])c(C([2H])([2H])S(=O)(=O)OC2=C(N)O[C@@]([2H])(c3ccc(C(=O)OCC)cc3)C2=O)c([2H])c1[2H]] | ethyl (S)-4-(5-amino-3-oxo-4-((((phenyl-d5)methyl-d2)sulfonyl)oxy)-2,3-dihydofuran-2-yl-2-d)benzoate | $C_{20}H_{11}D_8NO_7S$ | 425.48 |
| 2075 | 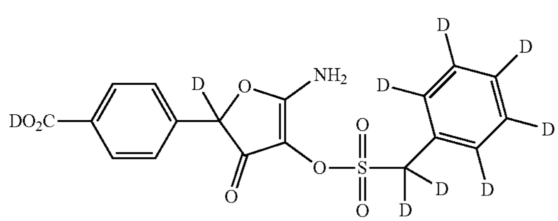 | 4-(5-amino-3-oxo-4-((((phenyl-d5)methyl-d2)sulfonyl)oxy)-2,3-dihydrofuran-2-yl-2-d)benzoic acid-d | $C_{18}H_6D_9NO_7S$ | 398.43 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2075(R) | 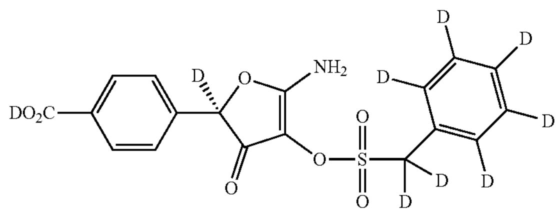 | (R)-4-(5-amino-3-oxo-4-((((phenyl-d5)methyl-d2)sulfonyl)oxy)-2,3-dihydrofuan-2-yl-2-d)benzoic acid-d | $C_{18}H_6D_9NO_7S$ | 398.43 |
| 2075(S) | 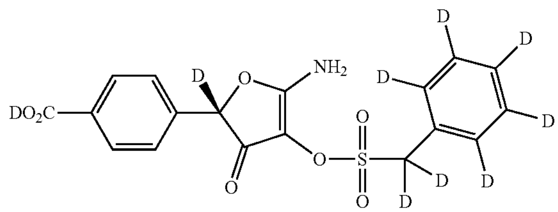 | (S)-4-(5-amino-3-oxo-4-((((phenyl-d5)methyl-d2)sulfonyl)oxy)-2,3-dihydofuran-2-yl-2-d)benzoic acid-d | $C_{18}H_6D_9NO_7S$ | 398.43 |
| 2076 | 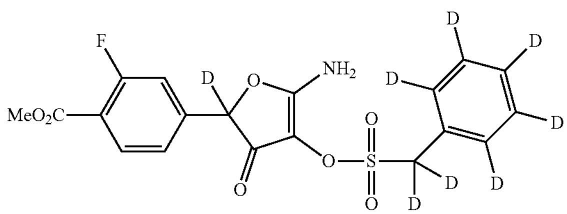 [SMILES: [2H]c1c([2H])c([2H])c(C([2H])([2H])S(=O)(=O)OC2=C(N)OC([2H])(c3ccc(C(=O)OC)c(F)c3)C2=O)c([2H])c1[2H]] | methyl 4-(5-amino-3-oxo-4-((((phenyl-d5)methyl-d2)sulfonyl)oxy)-2,3-dihydrofuran-2-yl-2-d)-2-fluorobenzoate | $C_{19}H_8D_8FNO_7S$ | 429.44 |
| 2076(R) | 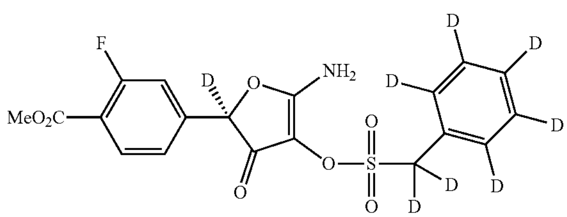 [SMILES: [2H]c1c([2H])c([2H])c(C([2H])([2H])S(=O)(=O)OC2=C(N)O[C@]([2H])(c3ccc(C(=O)OC)c(F)c3)C2=O)c([2H])c1[2H]] | methyl (R)-4-(5-amino-3-oxo-4-((((phenyl-d5)methyl-d2)sulfonyl)oxy)-2,3-dihydrofuran-2-yl-2-d)-2-fluorobenzoate | $C_{19}H_8D_8FNO_7S$ | 429.44 |
| 2076(S) | 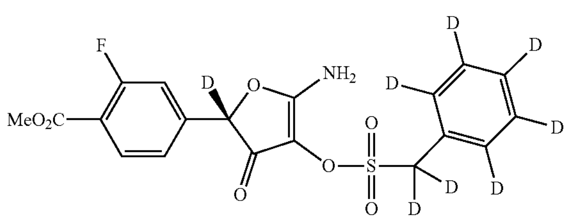 [SMILES: [2H]c1c([2H])c([2H])c(C([2H])([2H])S(=O)(=O)OC2=C(N)O[C@@]([2H])(c3ccc(C(=O)OC)c(F)c3)C2=O)c([2H])c1[2H]] | methyl (S)-4-(5-amino-3-oxo-4-((((phenyl-d5)methyl-d2)sulfonyl)oxy)-2,3-dihydrofuran-2-yl-2-d)-2-fluorobenzoate | $C_{19}H_8D_8FNO_7S$ | 429.44 |
| 2077 | 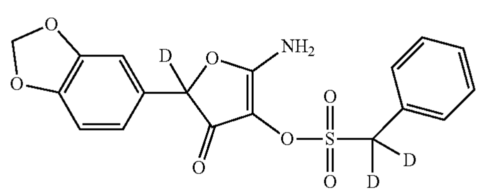 [SMILES: [2H]C1(c2ccc3c(c2)OCO3)OC(N)=C(OS(=O)(=O)C([2H])([2H])c2ccccc2)C1=O] | 2-amino-5-(benzo[d][1,3]dioxol-5-yl)-4-oxo-4,5-dihydofuran-3-yl-5-d phenylmethanesulfonate-d2 | $C_{18}H_{12}D_3NO_7S$ | 392.40 |
| 2077(R) | 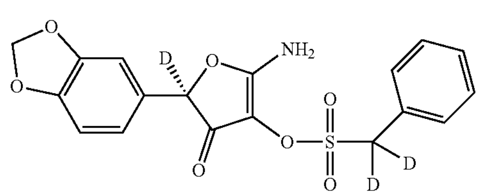 [SMILES: [2H]C([2H])(c1ccccc1)S(=O)(=O)OC1=C(N)O[C@]([2H])(c2ccc3c(c2)OCO3)C1=O] | (R)-2-amino-5-(benzo[d][1,3]dioxol-5-yl)-4-oxo-4,5-dihydrofuran-3-yl-5-d phenylmethanesulfonate-d2 | $C_{18}H_{12}D_3NO_7S$ | 392.40 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2077(S) | 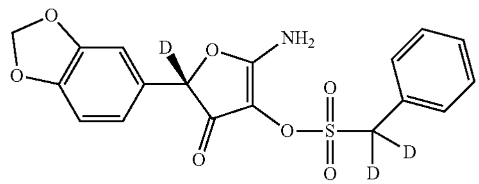 [SMILES: [2H]C([2H])(c1ccccc1)S(=O)(=O)OC1=C(N)O[C@@]([2H])(c2ccc3c(c2)OCO3)C1=O] | (S)-2-amino-5-(benzo[d][1,3]dioxol-5-yl)-4-oxo-4,5-dihydrofuran-3-yl-5-d phenylmethanesulfonate-d2 | $C_{18}H_{12}D_3NO_7S$ | 392.40 |
| 2078 | 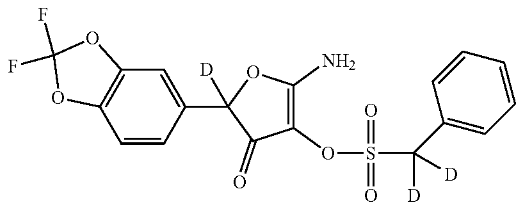 [SMILES: [2H]C1(c2ccc3c(c2)OC(F)(F)O3)OC(N)=C(OS(=O)(=O)C([2H])([2H])c2ccccc2)C1=O] | 2-amino-5-(2,2-difluorobenzo[d][1,3]dioxol-5-yl)-4-oxo-4,5-dihydrofuran-3-yl-5-d phenylmethanesulfonate-d2 | $C_{18}H_{10}D_3F_2NO_7S$ | 428.38 |
| 2078(R) | 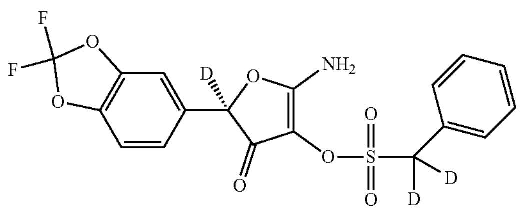 [SMILES: [2H]C([2H])(c1ccccc1)S(=O)(=O)OC1=C(N)O[C@]([2H])(c2ccc3c(c2)OC(F)(F)O3)C1=O] | (R)-2-amino-5-(2,2-difluorobenzo[d][1,3]dioxol-5-yl)-4-oxo-4,5-dihydrofuran-3-yl-5-d phenylmethanesulfonate-d2 | $C_{18}H_{10}D_3F_2NO_7S$ | 428.38 |
| 2078(S) | 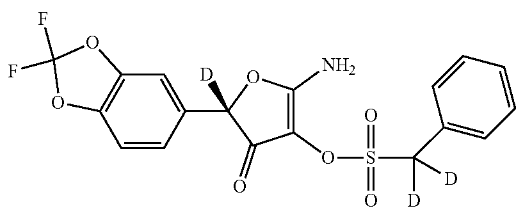 [SMILES: [2H]C([2H])(c1ccccc1)S(=O)(=O)OC1=C(N)O[C@@]([2H])(c2ccc3c(c2)OC(F)(F)O3)C1=O] | (S)-2-amino-5-(2,2-difluorobenzo[d][1,3]dioxol-5-yl)-4-oxo-4,5-dihydrofuran-3-yl-5-d phenylmethanesulfonate-d2 | $C_{18}H_{10}D_3F_2NO_7S$ | 428.38 |
| 2079 | 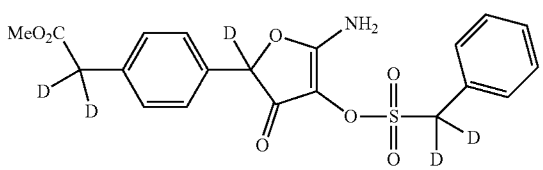 [SMILES: [2H]C([2H])(C(=O)OC)c1ccc(C2([2H])OC(N)=C(OS(=O)(=O)C([2H])([2H])c3ccccc3)C2=O)cc1] | methyl 2-(4-(5-amino-3-oxo-4-(((phenylmethyl-d2)sulfonyl)oxy)-2,3-dihydrofuran-2-yl-2-d)phenyl)acetate-d2 | $C_{20}H_{14}D_5NO_7S$ | 422.46 |
| 2079(R) | 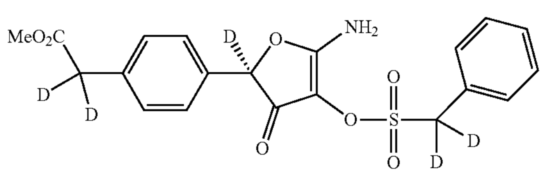 [SMILES: [2H]C([2H])(C(=O)OC)c1ccc([C@@]2([2H])OC(N)=C(OS(=O)(=O)C([2H])([2H])c3ccccc3)C2=O)cc1] | methyl (R)-2-(4-(5-amino-3-oxo-4-(((phenylmethyl-d2)sulfonyl)oxy)-2,3-dihydrofuran-2-yl-2-d)phenyl)acetate-d2 | $C_{20}H_{14}D_5NO_7S$ | 422.46 |
| 2079(S) | 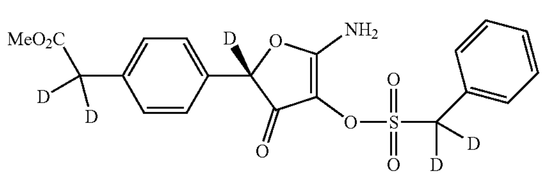 [SMILES: [2H]C([2H])(C(=O)OC)c1ccc([C@]2([2H])OC(N)=C(OS(=O)(=O)C([2H])([2H])c3ccccc3)C2=O)cc1] | methyl (S)-2-(4-(5-amino-3-oxo-4-(((phenylmethyl-d2)sulfonyl)oxy)-2,3-dihydrofuran-2-yl-2-d)phenyl)acetate-d2 | $C_{20}H_{14}D_5NO_7S$ | 422.46 |
| 2080 | 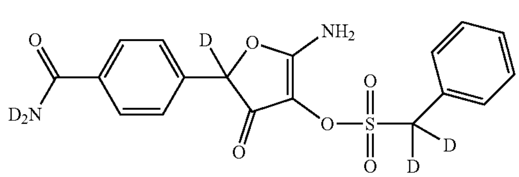 | 2-amino-5-(4-(carbamoyl-d2)phenyl)-4-oxo-4,5-dihydrofuran-3-yl-5-d phenylmethanesulfonate-d2 | $C_{18}H_{11}D_5N_2O_6S$ | 393.42 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2080(R) | 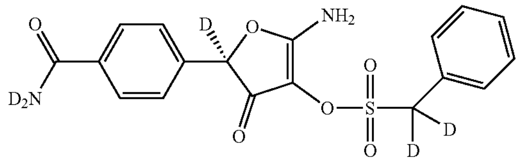 | (R)-2-amino-5-(4-(carbamoyl-d2)phenyl)-4-oxo-4,5-dihydrofuran-3-yl-5-d phenylmethanesulfonate-d2 | $C_{18}H_{11}D_5N_2O_6S$ | 393.42 |
| 2080(S) | 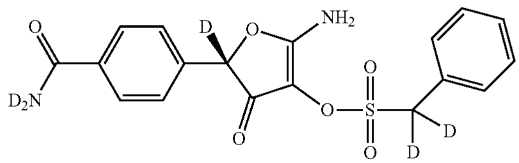 | (S)-2-amino-5-(4-(carbamoyl-d2)phenyl)-4-oxo-4,5-dihydrofuran-3-yl-5-d phenylmethanesulfonate-d2 | $C_{18}H_{11}D_5N_2O_6S$ | 393.42 |
| 2081 | 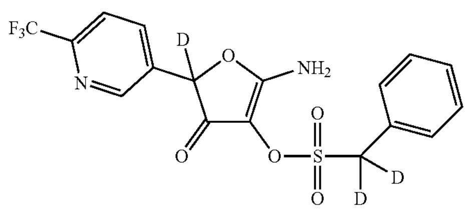 [SMILES: [2H]C1(c2ccc(C(F)(F)F)nc2)OC(N)=C(OS(=O)(=O)C([2H])([2H])c2ccccc2)C1=O] | 2-amino-4-oxo-5-(6-(trifluoromethyl)pyridin-3-yl)-4,5-dihydofuran-3-yl-5-d phenylmethanesulfonate-d2 | $C_{17}H_{10}D_3F_3N_2O_5S$ | 417.37 |
| 2081(R) | 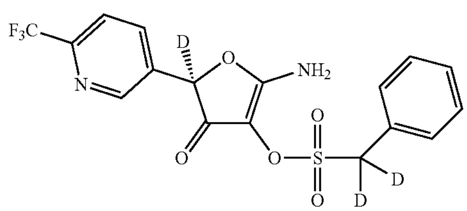 [SMILES: [2H]C([2H])(c1ccccc1)S(=O)(=O)OC1=C(N)O[C@]([2H])(c2ccc(C(F)(F)F)nc2)C1=O] | (R)-2-amino-4-oxo-5-(6-(trifluoromethyl)pyridin-3-yl)-4,5-dihydrofuran-3-yl-5-d phenylmethanesulfonate-d2 | $C_{17}H_{10}D_3F_3N_2O_5S$ | 417.37 |
| 2081(S) | 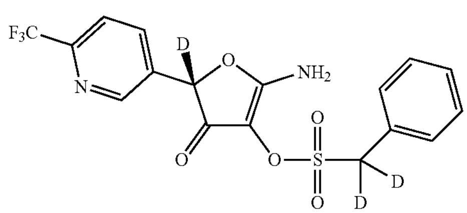 [SMILES: [2H]C([2H])(c1ccccc1)S(=O)(=O)OC1=C(N)O[C@@]([2H])(c2ccc(C(F)(F)F)nc2)C1=O] | (S)-2-amino-4-oxo-5-(6-(trifluoromethyl)pyridin-3-yl)-4,5-dihydrofuran-3-yl-5-d phenylmethanesulfonate-d2 | $C_{17}H_{10}D_3F_3N_2O_5S$ | 417.37 |
| 2082 | 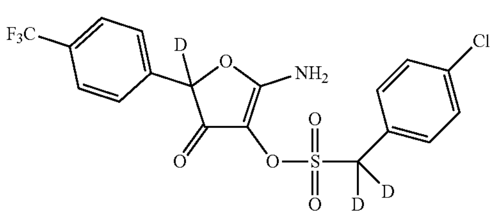 [SMILES: [2H]C1(c2ccc(C(F)(F)F)cc2)OC(N)=C(OS(=O)(=O)C([2H])([2H])c2ccc(Cl)cc2)C1=O] | 2-amino-4-oxo-5-(4-(trifluoromethyl)phenyl)-4,5-dihydofuran-3-yl-5-d (4-chlorophenyl)methanesulfonate-d2 | $C_{18}H_{10}D_3ClF_3NO_5S$ | 450.83 |
| 2082(R) | 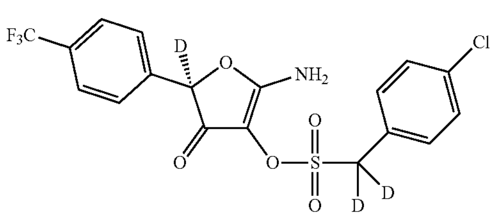 [SMILES: [2H]C([2H])(c1ccc(Cl)cc1)S(=O)(=O)OC1=C(N)O[C@]([2H])(c2ccc(C(F)(F)F)cc2)C1=O] | (R)-2-amino-4-oxo-5-(4-(trifluoromethyl)phenyl)-4,5-dihydrofuran-3-yl-5-d (4-chlorophenyl)methanesulfonate-d2 | $C_{18}H_{10}D_3ClF_3NO_5S$ | 450.83 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2082(S) | 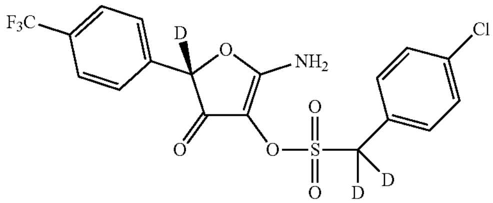 [SMILES: [2H]C([2H])(c1ccc(Cl)cc1)S(=O)(=O)OC1=C(N)O[C@@]([2H])(c2ccc(C(F)(F)F)cc2)C1=O] | (S)-2-amino-4-oxo-5-(4-(trifluoromethyl)phenyl)-4,5-dihydrofuran-3-yl-5-d (4-chlorophenyl) methanesulfonate-d2 | $C_{18}H_{10}D_3ClF_3NO_5S$ | 450.83 |
| 2083 | 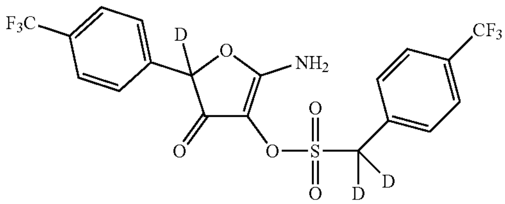 [SMILES: [2H]C1(c2ccc(C(F)(F)F)cc2)OC(N)=C(OS(=O)(=O)C([2H])([2H])c2ccc(C(F)(F)F)cc2)C1=O] | 2-amino-4-oxo-5-(4-(trifluoromethyl)phenyl)-4,5-dihydrofuran-3-yl-5-d (4-(trifluoromethyl)phenyl) methanesulfonate-d2 | $C_{19}H_{10}D_3F_6NO_5S$ | 484.38 |
| 2083(R) | 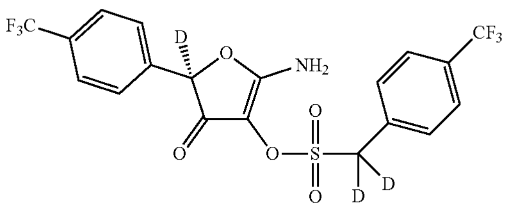 [SMILES: [2H]C([2H])(c1ccc(C(F)(F)F)cc1)S(=O)(=O)OC1=C(N)O[C@]([2H])(c2ccc(C(F)(F)F)cc2)C1=O] | (R)-2-amino-4-oxo-5-(4-(trifluoromethyl)phenyl)-4,5-dihydrofuran-3-yl-5-d (4-(trifluoromethyl)phenyl) methanesulfonate-d2 | $C_{19}H_{10}D_3F_6NO_5S$ | 484.38 |
| 2084 | 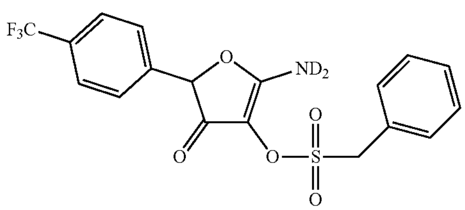 | 2-(amino-d2)-4-oxo-5-(4-(trifluoromethyl)phenyl)-4,5-dihydrofuran-3-yl phenylmethanesulfonate | $C_{18}H_{12}D_2F_3NO_5S$ | 415.38 |
| 2085 | 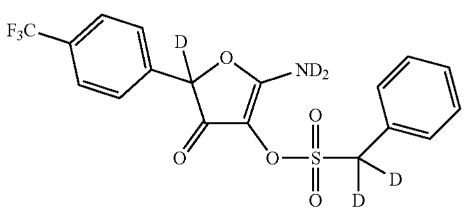 | 2-(amino-d2)-4-oxo-5-(4-(trifluoromethyl)phenyl)-4,5-dihydrofuran-3-yl-5-d phenylmethanesulfonate-d2 | $C_{18}H_9D_5F_3NO_5S$ | 418.40 |
| 2085(R) | 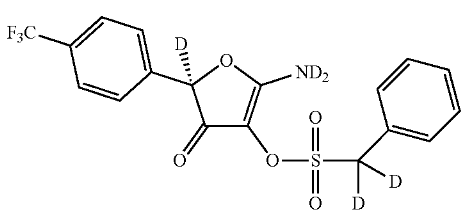 | (R)-2-(amino-d2)-4-oxo-5-(4-(trifluoromethyl)phenyl)-4,5-dihydrofuran-3-yl-5-d phenylmethanesulfonate-d2 | $C_{18}H_9D_5F_3NO_5S$ | 418.40 |
| 2085(S) | 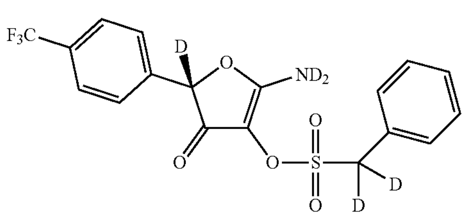 | (S)-2-(amino-d2)-4-oxo-5-(4-(trifluoromethyl)phenyl)-4,5-dihydrofuran-3-yl-5-d phenylmethanesulfonate-d2 | $C_{18}H_9D_5F_3NO_5S$ | 418.40 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2086 | 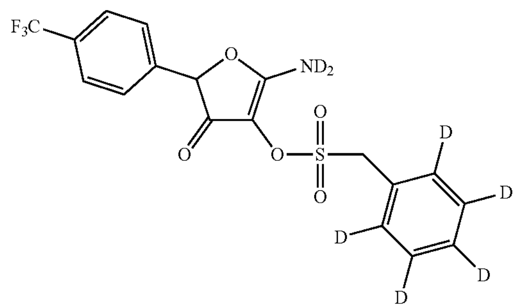 | 2-(amino-d2)-4-oxo-5-(4-(trifluoromethyl)phenyl)-4,5-dihydrofuran-3-yl (phenyl-d5)methanesulfonate | $C_{18}H_7D_7F_3NO_5S$ | 420.41 |
| 2087 | 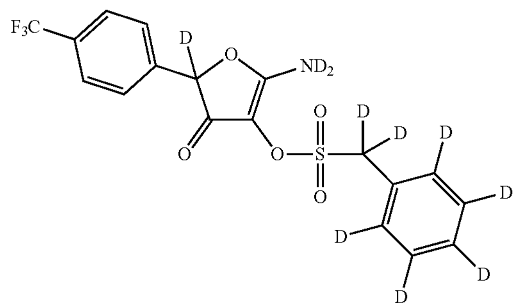 | 2-(amino-d2)-4-oxo-5-(4-(trifluoromethyl)phenyl)-4,5-dihydrofuran-3-yl-5-d (phenyl-d5) methanesulfonate-d2 | $C_{18}H_4D_{10}F_3NO_5S$ | 423.43 |
| 2087(R) | 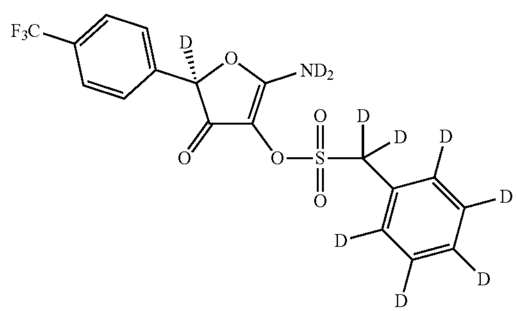 | (R)-2-(amino-d2)-4-oxo-5-(4-(trifluoromethyl)phenyl)-4,5-dihydrofuran-3-yl-5-d (phenyl-d5) methanesulfonate-d2 | $C_{18}H_4D_{10}F_3NO_5S$ | 423.43 |
| 2087(S) | 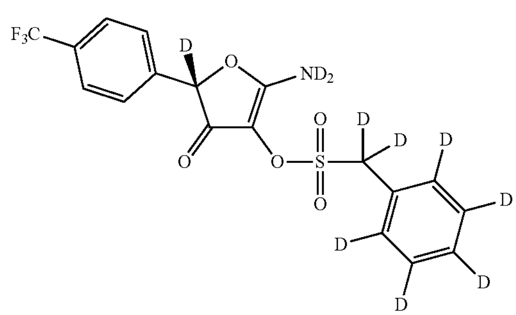 | (S)-2-(amino-d2)-4-oxo-5-(4-(trifluoromethyl)phenyl)-4,5-dihydrofuran-3-yl-5-d (phenyl-d5) methanesulfonate-d2 | $C_{18}H_4D_{10}F_3NO_5S$ | 423.43 |
| 2088 | 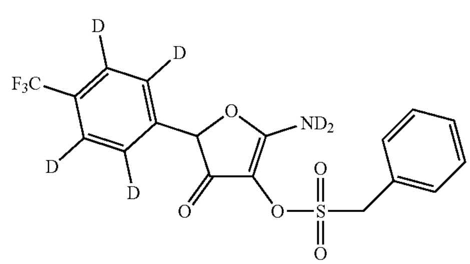 | 2-(amino-d2)-4-oxo-5-(4-(trifluoromethyl)phenyl-2,3,5,6-d4)-4,5-dihydrofuran-3-yl phenylmethanesulfonate | $C_{18}H_8D_6F_3NO_5S$ | 419.40 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2089 | 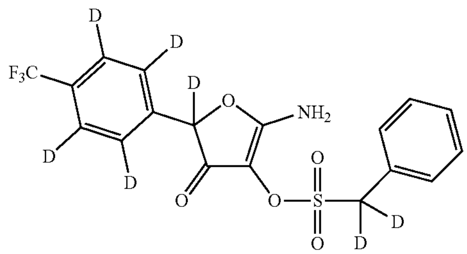 [SMILES: [2H]c1c([2H])c(C2([2H])OC(N)=C(OS(=O)(=O)C([2H])([2H])c3ccccc3)C2=O)c([2H])c([2H])c1C(F)(F)F] | 2-amino-4-oxo-5-(4-(trifluoromethyl)phenyl-2,3,5,6-d4)-4,5-dihydrofuran-3-yl-5-d phenylmethanesulfonate-d2 | $C_{18}H_7D_7F_3NO_5S$ | 420.41 |
| 2089(R) | 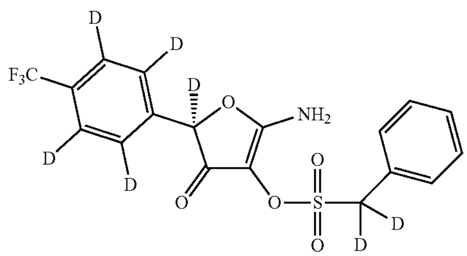 | (R)-2-amino-4-oxo-5-(4-(trifluoromethyl)phenyl-2,3,5,6-d4)-4,5-dihydrofuran-3-yl-5-d phenylmethanesulfonate-d2 | $C_{18}H_7D_7F_3NO_5S$ | 420.41 |
| 2089(S) | 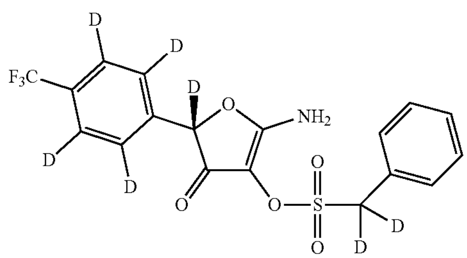 [SMILES: [2H]c1c([2H])c([C@]2([2H])OC(N)=C(OS(=O)(=O)C([2H])([2H])c3ccccc3)C2=O)c([2H])c([2H])c1C(F)(F)F] | (S)-2-amino-4-oxo-5-(4-(trifluoromethyl)phenyl-2,3,5,6-d4)-4,5-dihydrofuran-3-yl-5-d phenylmethanesulfonate-d2 | $C_{18}H_7D_7F_3NO_5S$ | 420.41 |
| 2090 | 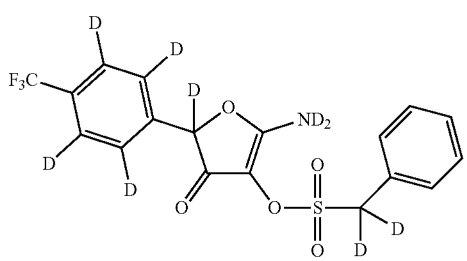 | 2-(amino-d2)-4-oxo-5-(4-(trifluoromethyl)phenyl-2,3,5,6-d4)-4,5-dihydrofuran-3-yl-5-d phenylmethanesulfonate-d2 | $C_{18}H_5D_9F_3NO_5S$ | 422.42 |
| 2091(R) | 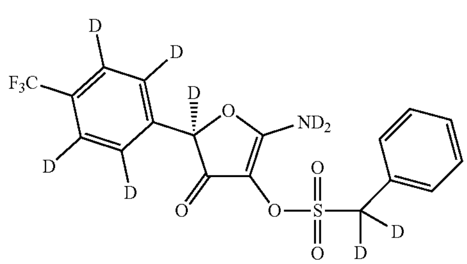 | (R)-2-(amino-d2)-4-oxo-5-(4-(trifluoromethyl)phenyl-2,3,5,6-d4)-4,5-dihydrofuran-3-yl-5-d phenylmethanesulfonate-d2 | $C_{18}H_5D_9F_3NO_5S$ | 422.42 |
| 2090(S) | 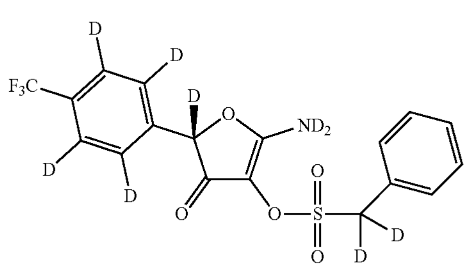 | (S)-2-(amino-d2)-4-oxo-5-(4-(trifluoromethyl)phenyl-2,3,5,6-d4)-4,5-dihydrofuran-3-yl-5-d phenylmethanesulfonate-d2 | $C_{18}H_5D_9F_3NO_5S$ | 422.42 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2091 | 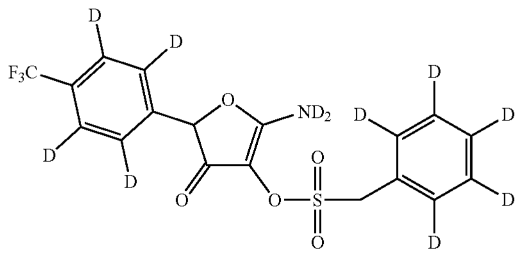 | 2-(amino-d2)-4-oxo-5-(4-(trifluoromethyl)phenyl-2,3,5,6-d4)-4,5-dihydrofuran-3-yl (phenyl-d5)methanesulfonate | $C_{18}H_3D_{11}F_3NO_5S$ | 424.43 |
| 2092 | 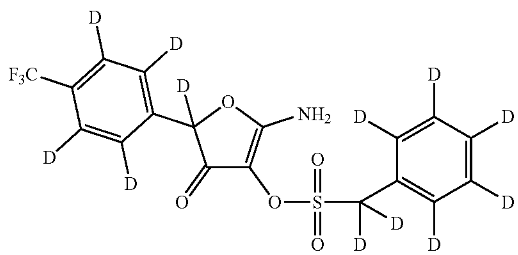 [SMILES: [2H]c1c([2H])c([2H])c(C([2H])([2H])S(=O)(=O)OC2=C(N)OC([2H])(c3c([2H])c([2H])c(C(F)(F)F)c([2H])c3[2H])C2=O)c([2H])c1[2H]] | 2-amino-4-oxo-5-(4-(trifluoromethyl)phenyl-2,3,5,6-d4)-4,5-dihydrofuran-3-yl (phenyl-d5)methanesulfonate-d2 | $C_{18}H_2D_{12}F_3NO_5S$ | 425.44 |
| 2092(R) | 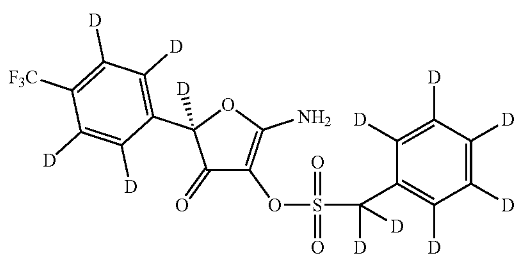 [SMILES: [2H]c1c([2H])c([2H])c(C([2H])([2H])S(=O)(=O)OC2=C(N)O[C@]([2H])(c3c([2H])c([2H])c(C(F)(F)F)c([2H])c3[2H])C2=O)c([2H])c1[2H]] | (R)-2-amino-4-oxo-5-(4-(trifluoromethyl)phenyl-2,3,5,6-d4)-4,5-dihydrofuran-3-yl-5-d (phenyl-d5) methanesulfonate-d2 | $C_{18}H_2D_{12}F_3NO_5S$ | 425.44 |
| 2092(S) | 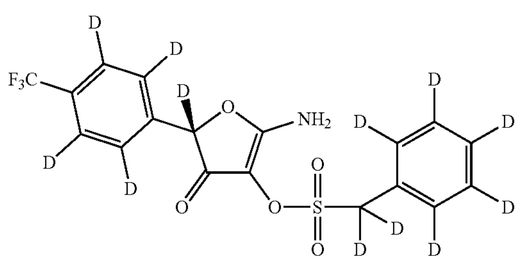 [SMILES: [2H]c1c([2H])c([2H])c(C([2H])([2H])S(=O)(=O)OC2=C(N)O[C@@]([2H])(c3c([2H])c([2H])c(C(F)(F)F)c([2H])c3[2H])C2=O)c([2H])c1[2H]] | (S)-2-amino-4-oxo-5-(4-(trifluoromethyl)phenyl-2,3,5,6-d4)-4,5-dihydrofuran-3-yl-5-d (phenyl-d5) methanesulfonate-d2 | $C_{18}H_2D_{12}F_3NO_5S$ | 425.44 |
| 2093 | 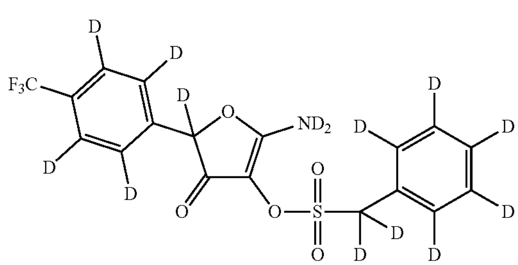 | 2-(amino-d2)-4-oxo-5-(4-(trifluoromethyl)phenyl-2,3,5,6-d4)-4,5-dihydrofuran-3-yl-5-d (phenyl-d5) methanesulfonate-d2 | $C_{18}D_{14}F_3NO_5S$ | 427.45 |

TABLE 4-continued (Selected #1000 series and #2001-2093)
Structures, Names, and Numbers of Key Isotopically-Stabilized Tetronimide Compounds Listed in Example 2

| New # | Structure | Name | Formula | MW |
|---|---|---|---|---|
| 2093(R) | 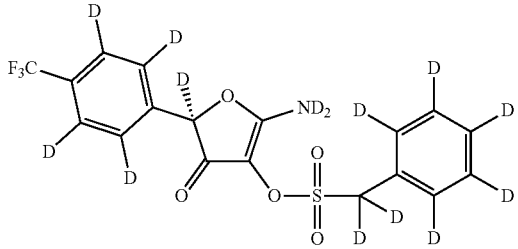 | (R)-2-(amino-d2)-4-oxo-5-(4-(trifluoromethyl)phenyl-2,3,5,6-d4)-4,5-dihydrofuran-3-yl-5-d (phenyl-d5) methanesulfonate-d2 | $C_{18}D_{14}F_3NO_5S$ | 427.45 |
| 2093(S) | 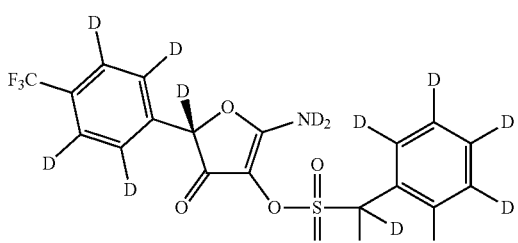 | (S)-2-amino-d2)-4-oxo-5-(4-(trifluoromethyl)phenyl-2,3,5,6-d4)-4,5-dihydrofuran-3-yl-5-d (phenyl-d5) methanesulfonate-d2 | $C_{18}D_{14}F_3NO_5S$ | 427.45 |

Synthesis of Specific #2000 Series of Compounds

Compound {2001}: 2-amino-5-(4-chlorophenyl)-4-oxo-4,5-dihydrofuran-3-yl Methanesulfonate A sample of 1.07 mmoles rac-1001 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2001-$d_4$ is performed to yield 2001(S) and 2001(R). Fractions are collected at −78° C. (dry-ice cooling) to prevent racemization. Evaporation under reduced pressure affords the product as white solids.

Compound {2002}: 2-amino-5-(4-chlorophenyl)-4-oxo-4,5-dihydrofuran-3-yl ethanesulfonate A sample of 1.07 mmoles rac-1002 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2002-$d_3$ is performed to yield 2002(S) and 2002(R). Fractions are collected at −78° C. (dry-ice cooling) to prevent racemization. Evaporation under reduced pressure affords the product as white solids.

Compound {2003}: 2-amino-5-(4-chlorophenyl)-4-oxo-4,5-dihydrofuran-3-yl propane-1-sulfonate A sample of 1.07 mmoles rac-1003 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2003-$d_3$ is performed to yield 2003(S) and 2003(R). Fractions are collected at −78° C. (dry-ice cooling) to prevent racemization. Evaporation under reduced pressure affords the product as white solids.

Compound {2004}: 2-amino-5-(4-chlorophenyl)-4-oxo-4,5-dihydrofuran-3-yl propane-2-sulfonate A sample of 1.07 mmoles rac-1004 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2004-$d_2$ is performed to yield 2004(S) and 2004(R). Fractions are collected at −78° C. (dry-ice cooling) to prevent racemization. Evaporation under reduced pressure affords the product as white solids.

Compound {2005}: 2-amino-5-(4-chlorophenyl)-4-oxo-4,5-dihydrofuran-3-yl butane-1-sulfonate A sample of 1.07 mmoles rac-1005 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2005-$d_3$ is performed to yield 2005(S) and 2005(R). Fractions are collected at −78° C. (dry-ice cooling) to prevent racemization. Evaporation under reduced pressure affords the product as white solids.

Compound {2006}: 2-amino-5-(4-chlorophenyl)-4-oxo-4,5-dihydrofuran-3-yl 2-methylpropane-1-sulfonate A sample of 1.07 mmoles rac-1006 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2006-$d_3$ is performed to yield 2006(S) and 2006(R). Fractions are collected at −78° C. (dry-ice cooling) to prevent racemization. Evaporation under reduced pressure affords the product as white solids.

Compound {2007}: 2-amino-5-(4-chlorophenyl)-4-oxo-4,5-dihydrofuran-3-yl benzenesulfonate-d5

A sample of 1.07 mmoles rac-1007 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2007-d is performed to yield 2007(S) and 2007(R). Fractions are collected at −78° C. (dry-ice cooling) to prevent racemization. Evaporation under reduced pressure affords the product as white solids.

Compound {2008}: 2-amino-5-(4-chlorophenyl)-4-oxo-4,5-dihydrofuran-3-yl phenylmethanesulfonate A sample of 1.07 mmoles rac-1008 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2008-$d_3$ is performed to yield 2008(S) and 2008(R). Fractions are collected at −78° C. (dry-ice cooling) to prevent racemization. Evaporation under reduced pressure affords the product as white solids.

Compound {2009}: 2-amino-5-(2-chlorophenyl)-4-oxo-4,5-dihydrofuran-3-yl phenylmethanesulfonate A sample of 1.07 mmoles rac-1009 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2009-$d_3$ is performed to yield 2009(S) and 2009(R). Fractions are collected at −78° C. (dry-ice cooling) to prevent racemization. Evaporation under reduced pressure affords the product as white solids.

Compound {2010}: 2-amino-5-(3-chlorophenyl)-4-oxo-4,5-dihydrofuran-3-yl phenylmethanesulfonate A sample of 1.07 mmoles rac-1010 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2010-$d_3$ is performed to yield 2010(S) and 2010(R). Fractions are collected at −78° C. (dry-ice cooling) to prevent racemization. Evaporation under reduced pressure affords the product as white solids.

Compound {2011}: 2-amino-5-(2,3-dichlorophenyl)-4-oxo-4,5-dihydrofuran-3-yl phenylmethanesulfonate A sample of 1.07 mmoles rac-1011 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2011-$d_3$ is performed to yield 2011(S) and 2011(R). Fractions are collected at −78° C. (dry-ice cooling) to prevent racemization. Evaporation under reduced pressure affords the product as white solids.

Compound {2012}: 2-amino-5-(2,4-dichlorophenyl)-4-oxo-4,5-dihydrofuran-3-yl phenylmethanesulfonate A sample of 1.07 mmoles rac-1012 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2012-$d_3$ is performed to yield 2012(S) and 2012(R). Fractions are collected at −78° C. (dry-ice cooling) to prevent racemization. Evaporation under reduced pressure affords the product as white solids.

Compound {2013}: 2-amino-5-(2,5-dichlorophenyl)-4-oxo-4,5-dihydrofuran-3-yl phenylmethanesulfonate A sample of 1.07 mmoles rac-1013 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2013-$d_3$ is performed to yield 2013(S) and 2013(R). Fractions are collected at −78° C. (dry-ice cooling) to prevent racemization. Evaporation under reduced pressure affords the product as white solids.

Compound {2014}: 2-amino-5-(3,4-dichlorophenyl)-4-oxo-4,5-dihydrofuran-3-yl phenylmethanesulfonate A sample of 1.07 mmoles rac-1014 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2014-$d_3$ is performed to yield 2014(S) and 2014(R). Fractions are collected at −78° C. (dry-ice cooling) to prevent racemization. Evaporation under reduced pressure affords the product as white solids.

Compound {2015}: 2-amino-5-(3,5-dichlorophenyl)-4-oxo-4,5-dihydrofuran-3-yl phenylmethanesulfonate A sample of 1.07 mmoles rac-1015 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2015-$d_3$ is performed to yield 2015(S) and 2015(R). Fractions are collected at −78° C. (dry-ice cooling) to prevent racemization. Evaporation under reduced pressure affords the product as white solids.

Compound {2016}: methyl 3-(5-amino-4-((benzylsulfonyl)oxy)-3-oxo-2,3-dihydrofuran-2-yl)benzoate A sample of 1.07 mmoles rac-1016 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2016-$d_3$ is performed to yield 2016(S) and 2016(R). Fractions are collected at −78° C. (dry-ice cooling) to prevent racemization. Evaporation under reduced pressure affords the product as white solids.

Compound {2017}: methyl 4-(5-amino-4-((benzylsulfonyl)oxy)-3-oxo-2,3-dihydrofuran-2-yl)benzoate A sample of 1.07 mmoles rac-1017 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2017-$d_3$ is performed to yield 2017(S) and 2017(R). Fractions are collected at −78° C.

Compound {2018}: methyl 4-(5-amino-4-((benzylsulfonyl)oxy)-3-oxo-2,3-dihydrofuran-2-yl)-2-fluorobenzoate A sample of 1.07 mmoles rac-1018 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2018-$d_3$ is performed to yield 2018(S) and 2018(R). Fractions are collected at −78° C. (dry-ice cooling) to prevent racemization. Evaporation under reduced pressure affords the product as white solids.

Compound {2019}: ethyl 4-(5-amino-4-((benzylsulfonyl)oxy)-3-oxo-2,3-dihydrofuran-2-yl)benzoate A sample of 1.07 mmoles rac-1019 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2019-$d_3$ is performed to yield 2019(S) and 2019(R). Fractions are collected at −78° C. (dry-ice cooling) to prevent racemization. Evaporation under reduced pressure affords the product as white solids.

Compound {2020}: 5-(4-acetylphenyl)-2-amino-4-oxo-4,5-dihydrofuran-3-yl phenylmethanesulfonate A sample of 1.07 mmoles rac-1020 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2020-$d_3$ is performed to yield 2020(S) and 2020(R). Fractions are collected at −78° C. (dry-ice cooling) to prevent racemization. Evaporation under reduced pressure affords the product as white solids.

Compound {2021}: 2-amino-5-(4-carbamoylphenyl)-4-oxo-4,5-dihydrofuran-3-yl phenylmethanesulfonate A sample of 1.07 mmoles rac-1021 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2021-$d_3$ is performed to yield 2021(S) and 2021(R). Fractions are collected at −78° C. (dry-ice cooling) to prevent racemization. Evaporation under reduced pressure affords the product as white solids.

Compound {2022}: 4-(5-amino-4-((benzylsulfonyl)oxy)-3-oxo-2,3-dihydrofuran-2-yl)benzoic Acid A sample of 1.07 mmoles rac-1022 is stirring in 10 mL of THF in the presence of 4.69 mmoles $K_2CO_3$ and 2 mL $D_2O$ at room temperature. After 9 days the reaction is neutralized with $CD_3CO_2D$ to a pH=5.0, and concentrated under reduced pressure. Preparative chiral HPLC separation of enantiomers of 2022-$d_3$ is performed to yield 2022(S) and 2022(R). Fractions are collected at −78° C. (dry-ice cooling) to prevent racemization. Evaporation under reduced pressure affords the product as white solids.

Compound {2023}: Sodium 4-(5-amino-4-((benzylsulfonyl)oxy)-3-oxo-2,3-dihydrofuran-2-yl)benzoate A sample of 1.07 mmoles rac-1022 is stirring in 10 mL of THF in the presence of 4.69 mmoles $Na_2CO_3$ and 2 mL $D_2O$ at room temperature. After 9 days the reaction is concentrated under reduced pressure. Preparative chiral HPLC separation of enantiomers of 2023-$d_3$ is performed to yield 2023(S) and 2023(R). Fractions are collected at −78° C. (dry-ice cooling) to prevent racemization. Evaporation under reduced pressure affords the product as white solids.

Compound {2024}: Potassium 4-(5-amino-4-((benzylsulfonyl)oxy)-3-oxo-2,3-dihydrofuran-2-yl)benzoate A sample of 1.07 mmoles rac-1022 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2024-$d_3$ is performed to yield 2024(S) and 2024(R). Fractions are collected at −78° C. (dry-ice cooling) to prevent racemization. Evaporation under reduced pressure affords the product as white solids.

Compound {2025}: potassium 4-(5-amino-4-((benzylsulfonyl)oxy)-3-oxo-2,3-dihydrofuran-2-yl)benzoate A sample of 1.07 mmoles rac-1022 is stirring in 10 mL of THF in the presence of 4.69 mmoles $MgCO_3$ and 2 mL $D_2O$ at room temperature. After 9 days the reaction is concentrated under reduced pressure. Preparative chiral HPLC separation of enantiomers of 2025-$d_3$ is performed to yield 2025(S) and 2025(R). Fractions are collected at −78° C. (dry-ice cooling) to prevent racemization. Evaporation under reduced pressure affords the product as white solids.

Compound {2026}: Calcium 4-(5-amino-4-((benzylsulfonyl)oxy)-3-oxo-2,3-dihydrofuran-2-yl)benzoate A sample of 1.07 mmoles rac-1022 is stirring in 10 mL of THF in the presence of 4.69 mmoles $CaCO_3$ and 2 mL $D_2O$ at room temperature. After 9 days the reaction is concentrated under reduced pressure. Preparative chiral HPLC separation of enantiomers of 2026-$d_3$ is performed to yield 2026(S) and 2026(R). Fractions are collected at −78° C. (dry-ice cooling) to prevent racemization. Evaporation under reduced pressure affords the product as white solids.

Compound {2027}: 2-amino-5-(2-fluorophenyl)-4-oxo-4,5-dihydrofuran-3-yl phenylmethanesulfonate A sample of 1.07 mmoles rac-1027 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2027-$d_3$ is performed to yield 2027(S) and 2027(R). Fractions are collected at −78° C. (dry-ice cooling) to prevent racemization. Evaporation under reduced pressure affords the product as white solids.

Compound {2028}: 2-amino-5-(3-fluorophenyl)-4-oxo-4,5-dihydrofuran-3-yl phenylmethanesulfonate A sample of 1.07 mmoles rac-1028 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2028-$d_3$ is performed to yield 2028(S) and 2028(R). Fractions are collected at −78° C. (dry-ice cooling) to prevent racemization. Evaporation under reduced pressure affords the product as white solids.

Compound {2029}: 2-amino-5-(4-fluorophenyl)-4-oxo-4,5-dihydrofuran-3-yl phenylmethanesulfonate A sample of 1.07 mmoles rac-1029 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2029-$d_3$ is performed to yield 2029(S) and 2029(R). Fractions are collected at −78° C. (dry-ice cooling) to prevent racemization. Evaporation under reduced pressure affords the product as white solids.

Compound {2030}: 2-amino-5-(2,3-difluorophenyl)-4-oxo-4,5-dihydrofuran-3-yl phenylmethanesulfonate A sample of 1.07 mmoles rac-1030 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2030-$d_3$ is performed to yield 2030(S) and 2030(R). Fractions are collected at −78° C. (dry-ice cooling) to prevent racemization. Evaporation under reduced pressure affords the product as white solids.

Compound {2031}: 2-amino-5-(2,4-difluorophenyl)-4-oxo-4,5-dihydrofuran-3-yl phenylmethanesulfonate A sample of 1.07 mmoles rac-1031 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2031-$d_3$ is performed to yield 2031(S) and 2031(R). Fractions are collected at −78° C. (dry-ice cooling) to prevent racemization. Evaporation under reduced pressure affords the product as white solids.

Compound {2032}: 2-amino-5-(2,5-difluorophenyl)-4-oxo-4,5-dihydrofuran-3-yl phenylmethanesulfonate A sample of 1.07 mmoles rac-1032 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2032-$d_3$ is performed to yield 2032(S) and 2032(R). Fractions are collected at −78° C. (dry-ice cooling) to prevent racemization. Evaporation under reduced pressure affords the product as white solids.

Compound {2033}: 2-amino-5-(2,6-difluorophenyl)-4-oxo-4,5-dihydrofuran-3-yl phenylmethanesulfonate A sample of 1.07 mmoles rac-1033 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2033-$d_3$ is performed to yield 2033(S) and 2033(R). Fractions are collected at −78° C. (dry-ice cooling) to prevent racemization. Evaporation under reduced pressure affords the product as white solids.

Compound {2034}: 2-amino-5-(3,4-difluorophenyl)-4-oxo-4,5-dihydrofuran-3-yl phenylmethanesulfonate A sample of 1.07 mmoles rac-1034 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2034-$d_3$ is performed to yield 2034(S) and 2034(R). Fractions are collected at −78° C. (dry-ice cooling) to prevent racemization. Evaporation under reduced pressure affords the product as white solids.

Compound {2035}: 2-amino-5-(3,5-difluorophenyl)-4-oxo-4,5-dihydrofuran-3-yl phenylmethanesulfonate A sample of 1.07 mmoles rac-1035 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2035-$d_3$ is performed to yield 2035(S) and 2035(R). Fractions are collected at −78° C. (dry-ice cooling) to prevent racemization. Evaporation under reduced pressure affords the product as white solids.

Compound {2036}: 2-amino-5-(2-methoxyphenyl)-4-oxo-4,5-dihydrofuran-3-yl phenylmethanesulfonate A sample of 1.07 mmoles rac-1036 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2036-$d_3$ is performed to yield 2036(S) and 2036(R). Fractions are collected at −78° C. (dry-ice cooling) to prevent racemization. Evaporation under reduced pressure affords the product as white solids.

Compound {2037}: 2-amino-5-(3-methoxyphenyl)-4-oxo-4,5-dihydrofuran-3-yl phenylmethanesulfonate A sample of 1.07 mmoles rac-1037 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2037-$d_3$ is performed to yield 2037(S) and 2037(R). Fractions are collected at −78° C. (dry-ice cooling) to prevent racemization. Evaporation under reduced pressure affords the product as white solids.

Compound {2038}: 2-amino-5-(4-methoxyphenyl)-4-oxo-4,5-dihydrofuran-3-yl phenylmethanesulfonate A sample of 1.07 mmoles rac-1038 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2038-$d_3$ is performed to yield 2038(S) and 2038(R). Fractions are collected at −78° C.

Compound {2039}: 2-amino-5-(2,3-dimethoxyphenyl)-4-oxo-4,5-dihydrofuran-3-yl phenylmethanesulfonate A sample of 1.07 mmoles rac-1039 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2039-$d_3$ is performed to yield 2039(S) and 2039(R). Fractions are collected at −78° C. (dry-ice cooling) to prevent racemization. Evaporation under reduced pressure affords the product as white solids.

Compound {2040}: 2-amino-5-(2,4-dimethoxyphenyl)-4-oxo-4,5-dihydrofuran-3-yl phenylmethanesulfonate A sample of 1.07 mmoles rac-1040 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2040-$d_3$ is performed to yield 2040(S) and 2040(R). Fractions are collected at −78° C. (dry-ice cooling) to prevent racemization. Evaporation under reduced pressure affords the product as white solids.

Compound {2041}: 2-amino-5-(2,5-dimethoxyphenyl)-4-oxo-4,5-dihydrofuran-3-yl phenylmethanesulfonate A sample of 1.07 mmoles rac-1041 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2041-$d_3$ is performed to yield 2041(S) and 2041(R). Fractions are collected at −78° C. (dry-ice cooling) to prevent racemization. Evaporation under reduced pressure affords the product as white solids.

Compound {2042}: 2-amino-5-(2,6-dimethoxyphenyl)-4-oxo-4,5-dihydrofuran-3-yl phenylmethanesulfonate A sample of 1.07 mmoles rac-1042 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2042-$d_3$ is performed to yield 2042(S) and 2042(R). Fractions are collected at −78° C. (dry-ice cooling) to prevent racemization. Evaporation under reduced pressure affords the product as white solids.

Compound {2043}: 2-amino-5-(3,4-dimethoxyphenyl)-4-oxo-4,5-dihydrofuran-3-yl phenylmethanesulfonate A sample of 1.07 mmoles rac-1043 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2043-$d_3$ is performed to yield 2043(S) and 2043(R). Fractions are collected at −78° C. (dry-ice cooling) to prevent racemization. Evaporation under reduced pressure affords the product as white solids.

Compound {2044}: 2-amino-5-(3,5-dimethoxyphenyl)-4-oxo-4,5-dihydrofuran-3-yl phenylmethanesulfonate A sample of 1.07 mmoles rac-1044 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2044-$d_3$ is performed to yield 2044(S) and 2044(R). Fractions are collected at −78° C. (dry-ice cooling) to prevent racemization. Evaporation under reduced pressure affords the product as white solids.

Compound {2045}: 2-amino-5-(2-bromophenyl)-4-oxo-4,5-dihydrofuran-3-yl phenylmethanesulfonate A sample of 1.07 mmoles rac-1045 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2045-$d_3$ is performed to yield 2045(S) and 2045(R). Fractions are collected at −78° C. (dry-ice cooling) to prevent racemization. Evaporation under reduced pressure affords the product as white solids.

Compound {2046}: 2-amino-5-(3-bromophenyl)-4-oxo-4,5-dihydrofuran-3-yl phenylmethanesulfonate A sample of 1.07 mmoles rac-1046 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2046-$d_3$ is performed to yield 2046(S) and 2046(R). Fractions are collected at −78° C. (dry-ice cooling) to prevent racemization. Evaporation under reduced pressure affords the product as white solids.

Compound {2047}: 2-amino-5-(4-bromophenyl)-4-oxo-4,5-dihydrofuran-3-yl phenylmethanesulfonate A sample of 1.07 mmoles rac-1047 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2047-$d_3$ is performed to yield 2047(S) and 2047(R). Fractions are collected at −78° C. (dry-ice cooling) to prevent racemization. Evaporation under reduced pressure affords the product as white solids.

Compound {2048}: 2-amino-5-(2-chloro-3-fluorophenyl)-4-oxo-4,5-dihydrofuran-3-yl phenylmethanesulfonate A sample of 1.07 mmoles rac-1048 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2048-$d_3$ is performed to yield 2048(S) and 2048(R). Fractions are collected at −78° C. (dry-ice cooling) to prevent racemization. Evaporation under reduced pressure affords the product as white solids.

Compound {2049}: 2-amino-5-(2-chloro-4-fluorophenyl)-4-oxo-4,5-dihydrofuran-3-yl phenylmethanesulfonate A sample of 1.07 mmoles rac-1049 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2049-$d_3$ is performed to yield 2049(S) and 2049(R). Fractions are collected at −78° C. (dry-ice cooling) to prevent racemization. Evaporation under reduced pressure affords the product as white solids.

Compound {2050}: 2-amino-5-(2-chloro-5-fluorophenyl)-4-oxo-4,5-dihydrofuran-3-yl phenylmethanesulfonate A sample of 1.07 mmoles rac-1050 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2050-$d_3$ is performed to yield 2050(S) and 2050(R). Fractions are collected at −78° C. (dry-ice cooling) to prevent racemization. Evaporation under reduced pressure affords the product as white solids.

Compound {2051}: 2-amino-5-(2-chloro-6-fluorophenyl)-4-oxo-4,5-dihydrofuran-3-yl phenylmethanesulfonate A sample of 1.07 mmoles rac-1051 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2051-$d_3$ is performed to yield 2051(S) and 2051(R). Fractions are collected at −78° C. (dry-ice cooling) to prevent racemization. Evaporation under reduced pressure affords the product as white solids.

Compound {2052}: 2-amino-5-(3-chloro-2-fluorophenyl)-4-oxo-4,5-dihydrofuran-3-yl phenylmethanesulfonate A sample of 1.07 mmoles rac-1052 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2052-$d_3$ is performed to yield 2052(S) and 2052(R). Fractions are collected at −78° C. (dry-ice cooling) to prevent racemization. Evaporation under reduced pressure affords the product as white solids.

Compound {2053}: 2-amino-5-(3-chloro-4-fluorophenyl)-4-oxo-4,5-dihydrofuran-3-yl phenylmethanesulfonate A sample of 1.07 mmoles rac-1053 is stirring in 10 mL of THF in the presence of 4.69 mmoles K2CO3 and 2 mL D2O at room temperature. After 9 days the reaction is concentrated under reduced pressure. Preparative chiral HPLC separation of enantiomers of 2053-$d_3$ is performed to yield 2053(S) and 2053(R). Fractions are collected at −78° C. (dry-ice cooling) to prevent racemization. Evaporation under reduced pressure affords the product as white solids.

Compound {2054}: 2-amino-5-(3-chloro-5-fluorophenyl)-4-oxo-4,5-dihydrofuran-3-yl phenylmethanesulfonate A sample of 1.07 mmoles rac-1054 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2054-$d_3$ is performed to yield 2054(S) and 2054(R). Fractions are collected at −78° C. (dry-ice cooling) to prevent racemization. Evaporation under reduced pressure affords the product as white solids.

Compound {2055}: 2-amino-5-(5-chloro-2-fluorophenyl)-4-oxo-4,5-dihydrofuran-3-yl phenylmethanesulfonate A sample of 1.07 mmoles rac-1055 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2055-$d_3$ is performed to yield 2055(S) and 2055(R). Fractions are collected at −78° C. (dry-ice cooling) to prevent racemization. Evaporation under reduced pressure affords the product as white solids.

Compound {2056}: 2-amino-5-(4-chloro-2-fluorophenyl)-4-oxo-4,5-dihydrofuran-3-yl phenylmethanesulfonate A sample of 1.07 mmoles rac-1056 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2056-$d_3$ is performed to yield 2056(S) and 2056(R). Fractions are collected at −78° C. (dry-ice cooling) to prevent racemization. Evaporation under reduced pressure affords the product as white solids.

Compound {2057}: 2-amino-5-(4-chloro-3-fluorophenyl)-4-oxo-4,5-dihydrofuran-3-yl phenylmethanesulfonate A sample of 1.07 mmoles rac-1057 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2057-$d_3$ is performed to yield 2057(S) and 2057(R). Fractions are collected at −78° C. (dry-ice cooling) to prevent racemization. Evaporation under reduced pressure affords the product as white solids.

Compound {2058}: 2-amino-4-oxo-5-(o-tolyl)-4,5-dihydrofuran-3-yl phenylmethanesulfonate A sample of 1.07 mmoles rac-1058 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2058-$d_3$ is performed to yield 2058(S) and 2058(R). Fractions are collected at −78° C. (dry-ice cooling) to prevent racemization. Evaporation under reduced pressure affords the product as white solids.

Compound {2059}: 2-amino-4-oxo-5-(m-tolyl)-4,5-dihydrofuran-3-yl phenylmethanesulfonate A sample of 1.07 mmoles rac-1059 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2059-$d_3$ is performed to yield 2059(S) and 2059(R). Fractions are collected at −78° C. (dry-ice cooling) to prevent racemization. Evaporation under reduced pressure affords the product as white solids.

Compound {2060}: 2-amino-4-oxo-5-(p-tolyl)-4,5-dihydrofuran-3-yl phenylmethanesulfonate A sample of 1.07 mmoles rac-1060 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2060-$d_3$ is performed to yield 2060(S) and 2060(R). Fractions are collected at −78° C. (dry-ice cooling) to prevent racemization. Evaporation under reduced pressure affords the product as white solids.

Compound {2061}: 2-amino-5-(3-cyanophenyl)-4-oxo-4,5-dihydrofuran-3-yl phenylmethanesulfonate A sample of 1.07 mmoles rac-1061 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2061-$d_3$ is performed to yield 2061(S) and 2061(R). Fractions are collected at −78° C. (dry-ice cooling) to prevent racemization. Evaporation under reduced pressure affords the product as white solids.

Compound {2062}: 2-amino-5-(4-cyanophenyl)-4-oxo-4,5-dihydrofuran-3-yl phenylmethanesulfonate A sample of 1.07 mmoles rac-1062 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2062-$d_3$ is performed to yield 2062(S) and 2062(R). Fractions are collected at −78° C. (dry-ice cooling) to prevent racemization. Evaporation under reduced pressure affords the product as white solids.

Compound {2063}: 2-amino-4-oxo-5-phenyl-4,5-dihydrofuran-3-yl phenylmethanesulfonate A sample of 1.07 mmoles rac-1063 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2063-$d_3$ is performed to yield 2063(S) and 2063(R). Fractions are collected at −78° C. (dry-ice cooling) to prevent racemization. Evaporation under reduced pressure affords the product as white solids.

Compound {2064}: 2-amino-4-oxo-5-(2-(trifluoromethyl)phenyl)-4,5-dihydrofuran-3-yl phenylmethanesulfonate A sample of 1.07 mmoles rac-1064 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2064-$d_3$ is performed to yield 2064(S) and 2064(R). Fractions are collected at −78° C. (dry-ice cooling) to prevent racemization. Evaporation under reduced pressure affords the product as white solids.

Compound {2065}: 2-amino-4-oxo-5-(3-(trifluoromethyl)phenyl)-4,5-dihydrofuran-3-yl phenylmethanesulfonate A sample of 1.07 mmoles rac-1065 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2065-$d_3$ is performed to yield 2065(S) and 2065(R). Fractions are collected at −78° C. (dry-ice cooling) to prevent racemization. Evaporation under reduced pressure affords the product as white solids.

Compound {2066}: 2-amino-4-oxo-5-(4-(trifluoromethyl)phenyl)-4,5-dihydrofuran-3-yl phenylmethanesulfonate A sample of rac-1 (440 mg, 1.07 mmol) was stirred in THF (10 mL) in the presence of $K_2CO_3$ (645 mg, 4.69 mmol; 4.4 eq.) and $D_2O$ (1.77 g, 88.5 mmol; 82.6 eq.) at room temperature. The reaction progress was monitored by LCMS and Mass analysis. After 9 days a sample was taken and concentrated under reduced pressure to give 96-100% pure (LCMS, UV 215 and 254 nm respectively) racemic 1-$d_3$ (38.9 mg) according to $^1$H-NMR analysis. LCMS analysis of the NMR sample (in dmso-d6) showed deuterium/hydrogen exchange after standing at room temperature to give 1-$d_2$ as major component. LCMS analysis using another column and equipment also showed that deuterium loss took place in dmso-d6. A fresh sample was prepared and analyzed directly after dissolving in THF, instead of dmso-d6, to demonstrate the presence of 1-$d_3$ as major component. Calcd. for $C_{18}HD_3F_3NO_5S$ M: 416,39

LCMS purity: 84.6% (at 216 nm) and 89.8% (at 264 nm) MS (ES$^+$): m/z: 417 [M+1] MS (ES$^-$): m/z: 415 [M−1]

$^1$H-NMR (rac-1-$d_3$ in dmso-d6): 7.37 (m, 3H); 7.51 (m, 4H); 7.82 (m, 2H); 8.80 (br s, 2H)

$^{19}$F-NMR (rac-1-$d_3$ in dmso-d6): −61.10 ppm

Preparative chiral HPLC separation of enantiomers of 1-$d_3$ (ca. 380 mg in 8 mL THF) was performed in two batches using a preparative Chiralpak IA column (250×20 mm). Fractions were collected at −78° C. (dry-ice box cooling) to prevent racemization. Evaporation under reduced pressure afforded the first batch of 36.2 mg enantiomer 1 and 32.5 mg enantiomer 2 as white solids. The second batch gave 50.1 mg enantiomer 1 and 51.9 mg enantiomer 2. All enantiomers were >99% chemically pure (LCMS). The ee of the separated enantiomers varied from 96.4 to 99.8% ee. The first eluting enantiomer 1 of 1-$d_3$ had a (−) optical rotation, whereas the second eluting enantiomer 2 of 1-$d_3$ had a (+) optical rotation according to additional chiral laser polarimeter detection in the chiral HPLC.

Calcd. for $C_{18}H_{11}D_3F_3NO_5S$ M: 416, 39 found MS (ES$^+$): m/z: 417 [M+1]

(−)-1-$d_3$ Enantiomer 1

36.2 mg, 99.6% ee; Purity: 99.6% (at 216 nm) and 99.5% (at 264 nm) MS (ES$^+$): m/z: 417 [M+1] MS (ES$^-$): m/z: 415 [M−1]

(+)-1-$d_3$ Enantiomer 2

32.5 mg, 97.5% ee; Purity: 99.5% (at 216 nm) and 99.5% (at 264 nm) MS (ES$^+$): m/z: 417 [M+1] MS (ES$^-$): m/z: 415 [M−1]

Compound {2067}: 2-amino-4-oxo-5-(4-(trifluoromethyl)phenyl)-4,5-dihydrofuran-3-yl (4-fluorophenyl)methanesulfonate A sample of 1.07 mmoles rac-1067 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2067-$d_3$ is performed to yield 2067(S) and 2067(R). Fractions are collected at −78° C. (dry-ice cooling) to prevent racemization. Evaporation under reduced pressure affords the product as white solids.

Compound {2068}: methyl 4-(5-amino-4-(((4-fluorobenzyl)sulfonyl)oxy)-3-oxo-2,3-dihydrofuran-2-yl)benzoate A sample of 1.07 mmoles rac-1068 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2068-$d_3$ is performed to yield 2068(S) and 2068(R). Fractions are collected at −78° C. (dry-ice cooling) to prevent racemization. Evaporation under reduced pressure affords the product as white solids.

Compound {2069}: ethyl 4-(5-amino-4-(((4-fluorobenzyl)sulfonyl)oxy)-3-oxo-2,3-dihydrofuran-2-yl)benzoate A sample of 1.07 mmoles rac-1069 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2069-$d_4$ is performed to yield 2069(S) and 2069(R). Fractions are collected at −78° C. (dry-ice cooling) to prevent racemization. Evaporation under reduced pressure affords the product as white solids.

Compound {2070}: 4-(5-amino-4-(((4-fluorobenzyl)sulfonyl)oxy)-3-oxo-2,3-dihydrofuran-2-yl)benzoic Acid A sample of 1.07 mmoles rac-1070 is stirring in 10 mL of THF in the presence of 4.69 mmoles $K_2CO_3$ and 2 mL $D_2O$ at room temperature. After 9 days the reaction is neutralized with $CD_3CO_2D$ to pH=5.0, and concentrated under reduced pressure. Preparative chiral HPLC separation of enantiomers of 2070-$d_3$ is performed to yield 2070(S) and 2070(R). Fractions are collected at −78° C. (dry-ice cooling) to prevent racemization. Evaporation under reduced pressure affords the product as white solids.

Compound {2071}: methyl 4-(5-amino-4-(((4-fluorobenzyl)sulfonyl)oxy)-3-oxo-2,3-dihydrofuran-2-yl)-2-fluorobenzoate A sample of 1.07 mmoles rac-1071 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2071-$d_8$ is performed to yield 2071(S) and 2071(R). Fractions are collected at −78° C. (dry-ice cooling) to prevent racemization. Evaporation under reduced pressure affords the product as white solids.

Compound {2072}: 2-amino-4-oxo-5-(4-(trifluoromethyl)phenyl)-4,5-dihydrofuran-3-yl (phenyl-d5)methanesulfonate A sample of 1.07 mmoles rac-1072 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2072-$d_8$ is performed to yield 2072(S) and 2072(R). Fractions are collected at −78° C. (dry-ice cooling) to prevent racemization. Evaporation under reduced pressure affords the product as white solids.

Compound {2073}: methyl 4-(5-amino-3-oxo-4-(((((phenyl-d5)methyl)sulfonyl)oxy)-2,3-dihydrofuran-2-yl)benzoate A sample of 1.07 mmoles rac-1073 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2073-$d_8$ is performed to yield 2073(S) and 2073(R). Fractions are collected at −78° C. (dry-ice cooling) to prevent racemization. Evaporation under reduced pressure affords the product as white solids.

Compound {2074}: ethyl 4-(5-amino-3-oxo-4-(((((phenyl-d5)methyl)sulfonyl)oxy)-2,3-dihydrofuran-2-yl)benzoate A sample of 1.07 mmoles rac-1074 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2074-$d_8$ is performed to yield 2074(S) and 2074(R). Fractions are collected at −78° C. (dry-ice cooling) to prevent racemization. Evaporation under reduced pressure affords the product as white solids.

Compound {2075}: 4-(5-amino-3-oxo-4-(((((phenyl-d5)methyl)sulfonyl)oxy)-2,3-dihydrofuran-2-yl)benzoic Acid A sample of 1.07 mmoles rac-1075 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2075-$d_8$ is performed to yield 2075(S) and 2075(R). Fractions are collected at −78° C. (dry-ice cooling) to prevent racemization. Evaporation under reduced pressure affords the product as white solids.

Compound {2076}: methyl 4-(5-amino-3-oxo-4-(((((phenyl-d5)methyl)sulfonyl)oxy)-2,3-dihydrofuran-2-yl)-2-fluorobenzoate A sample of 1.07 mmoles rac-1076 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2076-$d_8$ is performed to yield 2076(S) and 2076(R). Fractions are collected at −78° C. (dry-ice cooling) to prevent racemization. Evaporation under reduced pressure affords the product as white solids.

Compound {2077}: 2-amino-5-(benzo[d][1,3]di-oxol-5-yl)-4-oxo-4,5-dihydrofuran-3-yl phenylmethanesulfonate A sample of 1.07 mmoles rac-1077 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2077-$d_3$ is performed to yield 2077(S) and 2077(R). Fractions are collected at −78° C. (dry-ice cooling) to prevent racemization. Evaporation under reduced pressure affords the product as white solids.

Compound {2078}: 2-amino-5-(2,2-difluorobenzo[d][1,3]dioxol-5-yl)-4-oxo-4,5-dihydrofuran-3-yl phenylmethanesulfonate A sample of 1.07 mmoles rac-1078 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2078-$d_3$ is performed to yield 2078(S) and 2078(R). Fractions are collected at −78° C. (dry-ice cooling) to prevent racemization. Evaporation under reduced pressure affords the product as white solids.

Compound {2079}: methyl 2-(4-(5-amino-4-((benzylsulfonyl)oxy)-3-oxo-2,3-dihydrofuran-2-yl)phenyl)acetate A sample of 1.07 mmoles rac-1079 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2079-$d_8$ is performed to yield 2079(S) and 2079(R). Fractions are collected at −78° C. (dry-ice cooling) to prevent racemization. Evaporation under reduced pressure affords the product as white solids.

Compound {2080}: 2-amino-5-(4-(carbamoyl-d2)phenyl)-4-oxo-4,5-dihydrofuran-3-yl-5-d phenylmethanesulfonate-d2

A sample of 1.07 mmoles rac-1021 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2080-$d_8$ is performed to yield 2080(S) and 2080(R). Fractions are collected at −78° C. (dry-ice cooling) to prevent racemization. Evaporation under reduced pressure affords the product as white solids.

Compound {2081}: 2-amino-4-oxo-5-(6-(trifluoromethyl)pyridin-3-yl)-4,5-dihydrofuran-3-yl-5-d phenylmethanesulfonate-d2

A sample of 1.07 mmoles rac-1081 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2081-$d_3$ is performed to yield 2081(S) and 2081(R). Fractions are collected at −78° C. (dry-ice cooling) to prevent racemization. Evaporation under reduced pressure affords the product as white solids.

Compound {2082}: 2-amino-4-oxo-5-(4-(trifluoromethyl)phenyl)-4,5-dihydrofuran-3-yl-5-d (4-chlorophenyl)methanesulfonate-d2

A sample of 1.07 mmoles rac-1082 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2082-$d_3$ is performed to yield 2082(S) and 2082(R). Fractions are collected at −78° C. (dry-ice cooling) to prevent racemization. Evaporation under reduced pressure affords the product as white solids.

Compound {2083}: 2-amino-4-oxo-5-(4-(trifluoromethyl)phenyl)-4,5-dihydrofuran-3-yl-5-d (4-(trifluoromethyl)phenyl)methanesulfonate-d2

A sample of 1.07 mmoles rac-1083 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2083-$d_3$ is performed to yield 2083(S) and 2083(R). Fractions are collected at −78° C. (dry-ice cooling) to prevent racemization. Evaporation under reduced pressure affords the product as white solids.

Compound {2084}: 2-(amino-d2)-4-oxo-5-(4-(trifluoromethyl)phenyl)-4,5-dihydrofuran-3-yl phenylmethanesulfonate A sample of 1.07 mmoles rac-1066 is stirring in 10 mL of $CF_3CO_2D$ at room temperature. After 1 day the reaction is frozen, and concentrated under reduced pressure.

Compound {2085}: 2-(amino-d2)-4-oxo-5-(4-(trifluoromethyl)phenyl)-4,5-dihydrofuran-3-yl-5-d phenylmethanesulfonate-d2

A sample of 1.07 mmoles rac-2084 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2085-$d_8$ is performed to yield 2085(S) and 2085(R). Fractions are collected at −78° C. (dry-ice cooling) to prevent racemization. Evaporation under reduced pressure affords the product as white solids.

Compound {2086}: 2-(amino-d2)-4-oxo-5-(4-(trifluoromethyl)phenyl)-4,5-dihydrofuran-3-yl (phenyl-d5)methanesulfonate A sample of 1.07 mmoles rac-1072 is stirring in 10 mL of $CF_3CO_2D$ at room temperature. After 1 day the reaction is frozen, and concentrated under reduced pressure.

Compound {2087}: 2-(amino-d2)-4-oxo-5-(4-(trifluoromethyl)phenyl)-4,5-dihydrofuran-3-yl-5-d phenylmethanesulfonate-d2

A sample of 1.07 mmoles rac-2086 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2087-$d_{10}$ is performed to yield 2087(S) and 2087(R). Fractions are collected at −78° C.

(dry-ice cooling) to prevent racemization. Evaporation under reduced pressure affords the product as white solids.

Compound {2088}: 2-(amino-d2)-4-oxo-5-(4-(trifluoromethyl)phenyl-2,3,5,6-d4)-4,5-dihydrofuran-3-yl phenylmethanesulfonate A sample of 1.07 mmoles rac-1084 is stirring in 10 mL of $CF_3CO_2D$ at room temperature. After 1 day the reaction is frozen, and concentrated under reduced pressure.

Compound {2089}: 2-amino-4-oxo-5-(4-(trifluoromethyl)phenyl-2,3,5,6-d4)-4,5-dihydrofuran-3-yl-5-d phenylmethanesulfonate-d2

A sample of 1.07 mmoles rac-1084 is stirring in 10 mL of $CF_3CO_2D$ at room temperature. After 1 day the reaction is frozen, and concentrated under reduced pressure. The sample is resuspending in THF, and is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2089-$d_7$ is performed to yield 2089(S) and 2089(R). Fractions are collected at −78° C. (dry-ice cooling) to prevent racemization. Evaporation under reduced pressure affords the product as white solids.

Compound {2090}: 2-d2-amino-4-oxo-5-(4-(trifluoromethyl)phenyl-2,3,5,6-d4)-4,5-dihydrofuran-3-yl-5-d phenylmethanesulfonate-d2

A sample of 1.07 mmoles rac-1084 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2090-$d_7$ is performed to yield 2090(S) and 2090(R). Fractions are collected at −78° C. (dry-ice cooling) to prevent racemization. Evaporation under reduced pressure affords the product as white solids.

Compound {2090}: 2-amino-4-oxo-5-(4-(trifluoromethyl)phenyl-2,3,5,6-d4)-4,5-dihydrofuran-3-yl-5-d phenylmethanesulfonate-d2

A sample of 1.07 mmoles rac-1084 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2089-$d_7$ is performed to yield 2089(S) and 2089(R). Fractions are collected at −78° C. (dry-ice cooling) to prevent racemization. Evaporation under reduced pressure affords the product as white solids.

Compound {2091}: 2-(amino-d2)-4-oxo-5-(4-(trifluoromethyl)phenyl-2,3,5,6-d4)-4,5-dihydrofuran-3-yl (phenyl-d5)methanesulfonate A sample of 1.07 mmoles rac-1085 is stirring in 10 mL of $CF_3CO_2D$ at room temperature. After 1 day the reaction is frozen, and concentrated under reduced pressure.

Compound {2092}: 2-amino-4-oxo-5-(4-(trifluoromethyl)phenyl-2,3,5,6-d4)-4,5-dihydrofuran-3-yl-5-d (phenyl-d5)methanesulfonate-d2

A sample of 1.07 mmoles rac-1085 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2092-$d_{12}$ is performed to yield 2092(S) and 2092(R). Fractions are collected at −78° C. (dry-ice cooling) to prevent racemization. Evaporation under reduced pressure affords the product as white solids.

Compound {2093}: 2-(amino-d2)-4-oxo-5-(4-(trifluoromethyl)phenyl-2,3,5,6-d4)-4,5-dihydrofuran-3-yl-5-d (phenyl-d5)methanesulfonate-d2

A sample of 1.07 mmoles rac-2091 is stirring in 10 mL of THF in the presence of 4.69 mmoles $K_2CO_3$ and 2 mL $D_2O$ at room temperature. After 9 days the reaction is concentrated under reduced pressure. Preparative chiral HPLC separation of enantiomers of 2093-$d_{14}$ is performed to yield 2093(S) and 2093(R). Fractions are collected at −78° C. (dry-ice cooling) to prevent racemization. Evaporation under reduced pressure affords the product as white solids.

Example 3—Demonstrating Enhanced Metabolic Stability of Exemplary Compounds

Exemplary compounds are typically incubated with human, dog, cat, mouse, rat, or monkey liver or intestinal microsomes under standard reaction conditions. Two samples from each reaction mixture are taken at time intervals, such as 0, 15, 30, 45 and 60 minutes and injected onto an HPLC column to detect and quantify the absolute and/or relative levels of the unmetabolized compound. The Clint and the half-life for each molecule are calculated. Reference compounds for direct comparison include imipramine, propranolol, terfenadine, and verapamil.

Metabolic stability was performed by a commercial laboratory using a standard protocol. Compounds #1066, #2066, #2066(R), and #2066(S) were diluted to 1E-7 M, and incubated with human liver microsomes, or mouse liver microsomes (0.1 mg/mL), and quantified by HPLC. Control compounds were imipramine, propranolol, terfenadine and verapamil, which behaved normally as expected. Metabolic stability, expressed as percent of the parent compound remaining, was calculated by comparing the peak area of the compound at the time point relative to that at time at 0, 15, 30, 45 and 60 minutes. The half-life (T½) was estimated from the slope of the initial linear range of the logarithmic curve of compound remaining (%) vs. time, assuming the first-order kinetics. The apparent intrinsic clearance (CLint, in µL/min/pmol, µL/min/mg or µL/min/Mcell) was calculated.

FIG. 8 illustrates the activities of undeuterated, racemic, and deuterated enantiomers of tetronimide modulator compounds against ASPH in liver microsome assays.

Example 4—Demonstrating In Vitro Biological Activity of Exemplary Compounds

5000 MCF-7 cells were plated in appropriate media, and 0, 1.25, 2.5, 5 or 10 uM of each compound was added. All experiments were performed in triplicate. After 24 hours, cell viability was measured using a standard MTT kit assay.

FIG. 9 illustrates the activities of specific compounds #1066, #2066(R), and #2066(S) against MCF-7 Cells In Vitro.

Example 5—Demonstrating In Vivo Biological Activity of Exemplary Compounds

Mice, such as strains BALB/cJ or C57BL/6NJ or NOD SCID, are divided into 6 groups of 5 mice per compound, one group for untreated, one group for vehicle control, one group for undeuterated compound (for example, #1066), one group for racemic deuterated (for example, #2066), one group for (R) isomer deuterated compound (for example, #2066(R)), and one group for (S) deuterated compound (for example, #2066(S)). The selected mouse strain is injected with a cancer cell line (such as osteosarcoma, mammary carcinoma, ovarian carcinoma, hepatocellular carcinoma, glioblastoma multiform, neuroblastoma, pancreatic adenocarcinoma, and cholangiocarcinoma cells) that is ASPH positive into the right flank subcutaneously. Untreated animals are left untreated. Vehicle control mice are administered Size "M" capsules containing only lactose daily. Mice in the undeuterated compound group are administered undeuterated compound triturated with lactose at 10 mg/kg in a Size "M" capsule daily. Deuterated racemic compound group is administered racemic deuterated compound triturated with lactose a 10 mg/kg in a Size "M" capsule daily. Mice in the (R) deuterated group are administered the (R) deuterated compound 10 mg/kg that has been triturated with lactose and packaged into a Size "M" capsule daily. Mice in the (S) deuterated group are administered the (S) deuterated compound 10 mg/kg that has been triturated with lactose and packaged into a Size "M" capsule daily. The size of the tumor is being measured daily, either until death or until day 30 when all animals are sacrificed. Tumors are being excised upon animal death or sacrifice, all tumors are weighed, and metastasis are being counted. At the time of death or sacrifice, animal blood is collected, and blood or serum cholesterol, complement activity, blood coagulation parameters (INR, aPTT) and liver enzymes (ALT, AST and GGT) are quantified.

Statement Regarding Preferred Aspects Are Meant To Be Illustrative And Not Limiting As To The Scope Of The Invention While the preferred aspects of the invention have been illustrated and described in detail, it will be appreciated by those skilled in the art that that various changes can be made therein without departing from the spirit and scope of the invention. Accordingly, the particular arrangements disclosed are meant to be illustrative only and not limiting as to the scope of the invention, which is to be given the full breadth of the appended claims and any equivalent thereof.

REFERENCES

Statement regarding incorporation by reference of journal articles and patent documents All references, as journal articles or patent documents (published applications or issued patents), cited herein, are incorporated by reference in their entirety, as if written herein.

Journal Articles

1. AIHARA, A., C. K. HUANG, M. J. OLSEN, Q. LIN, W. CHUNG, Q. TANG, X. DONG AND J. R. WANDS (2014). "A cell-surface beta-hydroxylase is a biomarker and therapeutic target for hepatocellular carcinoma." Hepatology 60(4): 1302-1313.
2. BORGAS, D. L., J. S. GAO, M. TONG AND S. M. DE LA MONTE (2015). "Potential Role of Phosphorylation as a Regulator of Aspartyl-(asparaginyl)-beta-hydroxylase: Relevance to Infiltrative Spread of Human Hepatocellular Carcinoma." Liver Cancer 4(3): 139-153.
3. BORGAS, D. L., J. S. GAO, M. TONG, N. ROPER AND S. M. DE LA MONTE (2015). "Regulation of Aspartyl-(Asparaginyl)-beta-Hydroxylase Protein Expression and Function by Phosphorylation in Hepatocellular Carcinoma Cells." J Nat Sci 1(4).
4. CANTARINI, M. C., S. M. DE LA MONTE, M. PANG, M. TONG, A. D'ERRICO, F. TREVISANI AND J. R. WANDS (2006). "Aspartyl-asparagyl beta hydroxylase over-expression in human hepatoma is linked to activation of insulin-like growth factor and notch signaling mechanisms." Hepatology 44(2): 446-457.
5. DINCHUK, J. E., R. J. FOCHT, J. A. KELLEY, N. L. HENDERSON, N. I. ZOLOTARJOVA, R. WYNN, N. T. NEFF, J. LINK, R. M. HUBER, T. C. BURN, M. J. RUPAR, M. R. CUNNINGHAM, B. H. SELLING, J. MA, A. A. STERN, G. F. HOLLIS, R. B. STEIN AND P. A. FRIEDMAN (2002). "Absence of post-translational aspartyl beta-hydroxylation of epidermal growth factor domains in mice leads to developmental defects and an increased incidence of intestinal neoplasia." J Biol Chem 277(15): 12970-12977.
6. DRAKENBERG, T., P. FERNLUND, P. ROEPSTORFF AND J. STENFLO (1983). "beta-Hydroxyaspartic acid in vitamin K-dependent protein C." Proc Natl Acad Sci USA 80(7): 1802-1806.
7. EL ASMAR, Z., J. TERRAND, M. JENTY, L. HOST, M. MLIH, A. ZERR, H. JUSTINIANO, R. L. MATZ, C. BOUDIER, E. SCHOLLER, J. M. GARNIER, D. BERTACCINI, D. THIERSE, C. SCHAEFFER, A. VAN DORSSELAER, J. HERZ, V. BRUBAN AND P. BOUCHER (2016). "Convergent Signaling Pathways Controlled by LRP1 (Receptor-related Protein 1) Cytoplasmic and Extracellular Domains Limit Cellular Cholesterol Accumulation." J Biol Chem 291(10): 5116-5127.
8. FURLER, R. L., D. F. NIXON, C. A. BRANTNER, A. POPRATILOFF AND C. H. UITTENBOGAART (2018). "TGF-beta Sustains Tumor Progression through Biochemical and Mechanical Signal Transduction." Cancers (Basel) 10(6).
9. GUNDOGAN, F., G. ELWOOD, D. GRECO, L. P. RUBIN, H. PINAR, R. I. CARLSON, J. R. WANDS AND S. M. DE LA MONTE (2007). "Role of aspartyl-(asparaginyl) beta-hydroxylase in placental implantation: Relevance to early pregnancy loss." Hum Pathol 38(1): 50-59.
10. IWAGAMI, Y., S. CASULLI, K. NAGAOKA, M. KIM, R. I. CARLSON, K. OGAWA, M. S. LEBOWITZ, S. FULLER, B. BISWAS, S. STEWART, X. DONG, H. GHANBARI AND J. R. WANDS (2017). "Lambda phage-based vaccine induces antitumor immunity in hepatocellular carcinoma." Heliyon 3(9): e00407.
11. LAVAISSIERE, L., S. JIA, M. NISHIYAMA, S. DE LA MONTE, A. M. STERN, J. R. WANDS AND P. A. FRIEDMAN (1996). "Overexpression of human aspartyl (asparaginyl)beta-hydroxylase in hepatocellular carcinoma and cholangiocarcinoma." J Clin Invest 98(6): 1313-1323.
12. NODA, T., M. SHIMODA, V. ORTIZ, A. E. SIRICA AND J. R. WANDS (2012). "Immunization with aspartate-beta-hydroxylase-loaded dendritic cells produces antitumor effects in a rat model of intrahepatic cholangiocarcinoma." Hepatology 55(1): 86-97.
13. REVSKAYA, E., Z. JIANG, A. MORGENSTERN, F. BRUCHERTSEIFER, M. SESAY, S. WALKER, S. FULLER, M. S. LEBOWITZ, C. GRAVEKAMP, H. A. GHANBARI AND E. DADACHOVA (2017). "A Radio-labeled Fully Human Antibody to Human Aspartyl (Asparaginyl) beta-Hydroxylase Is a Promising Agent for Imaging and Therapy of Metastatic Breast Cancer." Cancer Biother Radiopharm 32(2): 57-65.

14. TONG, M., J. S. GAO, D. BORGAS AND S. M. DE LA MONTE (2013). "Phosphorylation Modulates Aspartyl-(Asparaginyl)-beta Hydroxylase Protein Expression, Catalytic Activity and Migration in Human Immature Neuronal Cerebellar Cells." Cell Biol (Henderson, Nev.) 6(2).
15. WU, G., Z. MA, Y. CHENG, W. HU, C. DENG, S. JIANG, T. LI, F. CHEN AND Y. YANG (2018). "Targeting Gas6/TAM in cancer cells and tumor microenvironment." Mol Cancer 17(1): 20.
16. YANG, H., K. SONG, T. XUE, X. P. XUE, T. HUYAN, W. WANG AND H. WANG (2010). "The distribution and expression profiles of human Aspartyl/Asparaginyl beta-hydroxylase in tumor cell lines and human tissues." Oncol Rep 24(5): 1257-1264.
17. YEUNG, Y. A., A. H. FINNEY, I. A. KOYRAKH, M. S. LEBOWITZ, H. A. GHANBARI, J. R. WANDS AND K. D. WITTRUP (2007). "Isolation and characterization of human antibodies targeting human aspartyl (asparaginyl) beta-hydroxylase." Hum Antibodies 16(3-4): 163-176.
18. DAHN, H., LAWENDEL, J. S., HOEGGER, E. F. ET AL. (1954) "Ober eine neue Herstellung aromatisch substituierter Reduktone." Experientia 10: 245.
19. PDB ID 5JZZ: McDonough, M. A., Pfeffer, I., Munzel, M. (2016) Aspartyl/Asparaginyl beta-hydroxylase (AspH)oxygenase and TPR domains in complex with manganese, N-oxalylglycine and cyclic peptide substrate mimic of factor X. DOI: 10.2210/pdb5JZZ/pdb. Deposited as PDB ID 5JZZ on 2016 May 16, Released on 2017 Jun. 6.
20. TIMMINS, G. S. (2014) "Deuterated drugs: where are we now?" Expert Opin. Ther. Patents 24(10):1067-1075.

Patent Documents

U.S. Pat. No. 9,771,356.

The invention claimed is:

1. A method of treating one or more conditions associated with a disease selected from the group consisting of hypercholesterolemia, a viral disease, and blood coagulation disorders, by administering one or more doses of a pharmaceutical composition comprising one or more deuterated compounds of Formulas {I-A}, {I-B}, {I-C}, {I-D}, {I-E}, {I-F}, I-G}, or {I-H}:or one or more pharmaceutically-acceptable esters, metabolites, prodrugs, or solvates thereof and a pharmaceutically-acceptable carrier in one or more amounts effective to treat one or more conditions associated said disease;

wherein at least one deuterated compound is represented by any one of the following Formulas:

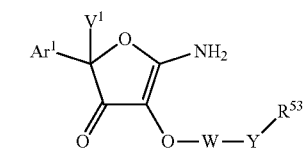
{I-A}

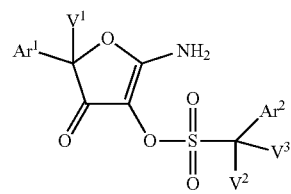
{I-B}

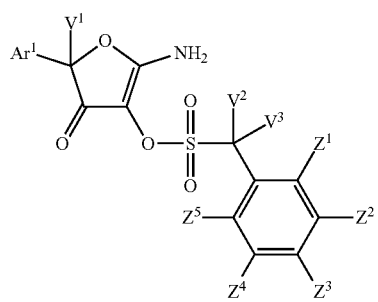
{I-C}

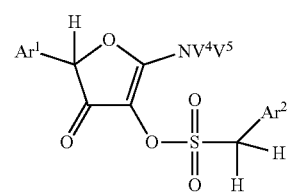
{I-D}

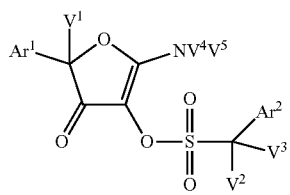
{I-E}

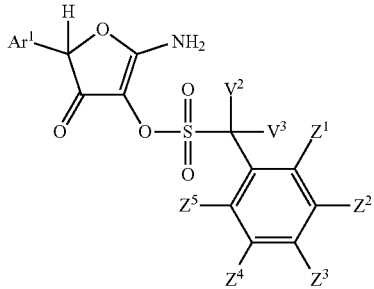
{I-F}

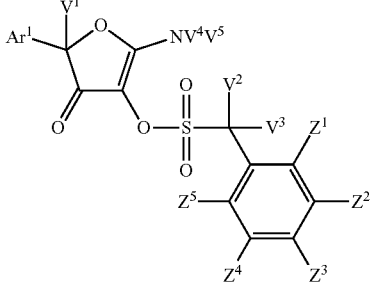
{I-G}

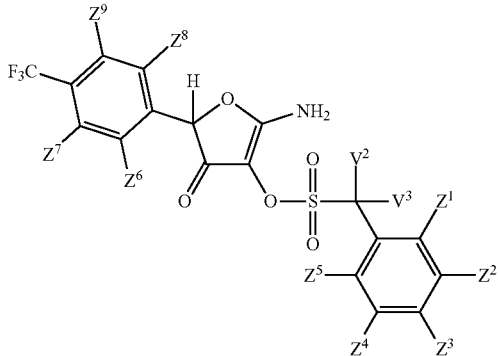
{I-H} or a salt, ester, metabolite, prodrug, or solvate thereof, wherein $Ar^1$ is a substituted or unsubstituted $C_6$-$C_{20}$ aryl or 5- to 20-membered heteroaryl;

wherein at least one of $V^1$, $V^2$, $V^3$, $V^4$, $V^5$, or $Z^1$, $Z^2$, $Z^3$, $Z^4$, $Z^5$, $Z^6$, $Z^7$, $Z^8$, or $Z^9$ is a deuterium atom (D) and any atom not designated as deuterium is present as hydrogen (H, or not shown) at its natural isotopic abundance;

wherein W is C(O), C(S), or S(O)$_2$;

wherein Y is a single bond, O, CR$^{50}$R$^{51}$, or NR$^{52}$ when W is CO and Y is a single bond, CR$^{50}$R$^{51}$ or NR$^{52}$ when W is SO$_2$;

wherein R$^{53}$ is selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_6$-C$_{20}$ aryl, substituted or unsubstituted C$_7$-C$_{26}$ arylalkyl, substituted or unsubstituted 5 to 20-membered heteroaryl, and substituted or unsubstituted 6-26 membered heteroarylalkyl; and wherein Ar$^2$, designated as an unsubstituted or substituted C$_6$-C$_{20}$ heteroaryl is selected from the group consisting of: phenyl; naphthyl; pyridyl; pyridine; pyridone; pyrimidine; pyradazine; pyrazine; purine; furan; thiophene; oxazole; thiazole; isoxazole; isothiazole; oxadiazole; thiadiazole; pyrrole; imidazole; triazole; tetrazole; and diazepine.

2. The method of claim 1 wherein said deuterated compound is selected from the group consisting of 2001 2-amino-5-(4-chlorophenyl)-4-oxo-4,5-dihydrofuran-3-yl-5-d methanesulfonate-d3;
2001(R) (R)-2-amino-5-(4-chlorophenyl)-4-oxo-4,5-dihydrofuran-3-yl-5-d methanesulfonate-d3;
2001(S) (S)-2-amino-5-(4-chlorophenyl)-4-oxo-4,5-dihydrofuran-3-yl-5-d methanesulfonate-d3;
2002 2-amino-5-(4-chlorophenyl)-4-oxo-4,5-dihydrofuran-3-yl-5-d ethane-1-sulfonate-1,1-d2;
2002(R) (R)-2-amino-5-(4-chlorophenyl)-4-oxo-4,5-dihydrofuran-3-yl-5-d ethane-1-sulfonate-1,1-d2;
2002(S) (S)-2-amino-5-(4-chlorophenyl)-4-oxo-4,5-dihydrofuran-3-yl-5-d ethane-1-sulfonate-1,1-d2;
2003 2-amino-5-(4-chlorophenyl)-4-oxo-4,5-dihydrofuran-3-yl-5-d propane-1-sulfonate-1,1-d2;
2003(R) (R)-2-amino-5-(4-chlorophenyl)-4-oxo-4,5-dihydrofuran-3-yl-5-d propane-1-sulfonate-1,1-d2;
2003(S) (S)-2-amino-5-(4-chlorophenyl)-4-oxo-4,5-dihydrofuran-3-yl-5-d propane-1-sulfonate-1,1-d2;
2004 2-amino-5-(4-chlorophenyl)-4-oxo-4,5-dihydrofuran-3-yl-5-d propane-2-sulfonate-2-d;
2004(R) (R)-2-amino-5-(4-chlorophenyl)-4-oxo-4,5-dihydrofuran-3-yl-5-d propane-2-sulfonate-2-d;
2004(S) (S)-2-amino-5-(4-chlorophenyl)-4-oxo-4,5-dihydrofuran-3-yl-5-d propane-2-sulfonate-2-d;
2005 2-amino-5-(4-chlorophenyl)-4-oxo-4,5-dihydrofuran-3-yl-5-d butane-1-sulfonate-1,1-d2;
2005(R) (R)-2-amino-5-(4-chlorophenyl)-4-oxo-4,5-dihydrofuran-3-yl-5-d butane-1-sulfonate-1,1-d2;
2005(S) (S)-2-amino-5-(4-chlorophenyl)-4-oxo-4,5-dihydrofuran-3-yl-5-d butane-1-sulfonate-1,1-d2;
2006 2-amino-5-(4-chlorophenyl)-4-oxo-4,5-dihydrofuran-3-yl-5-d 2-methylpropane-1-sulfonate-1,1-d2;
2006(R) (R)-2-amino-5-(4-chlorophenyl)-4-oxo-4,5-dihydrofuran-3-yl-5-d 2-methylpropane-1-sulfonate-1,1-d2;
2006(S) (S)-2-amino-5-(4-chlorophenyl)-4-oxo-4,5-dihydrofuran-3-yl-5-d 2-methylpropane-1-sulfonate-1,1-d2;
2007 2-amino-5-(4-chlorophenyl)-4-oxo-4,5-dihydrofuran-3-yl-5-d benzenesulfonate;
2007(R) (R)-2-amino-5-(4-chlorophenyl)-4-oxo-4,5-dihydrofuran-3-yl-5-d benzenesulfonate;
2007(S) (S)-2-amino-5-(4-chlorophenyl)-4-oxo-4,5-dihydrofuran-3-yl-5-d benzenesulfonate;
2008 2-amino-5-(4-chlorophenyl)-4-oxo-4,5-dihydrofuran-3-yl-5-d phenylmethanesulfonate-d2;
2008(R) (R)-2-amino-5-(4-chlorophenyl)-4-oxo-4,5-dihydrofuran-3-yl-5-d phenylmethanesulfonate-d2;
2008(S) (S)-2-amino-5-(4-chlorophenyl)-4-oxo-4,5-dihydrofuran-3-yl-5-d phenylmethanesulfonate-d2;
2009 2-amino-5-(2-chlorophenyl)-4-oxo-4,5-dihydrofuran-3-yl-5-d phenylmethanesulfonate-d2;
2009(R) (R)-2-amino-5-(2-chlorophenyl)-4-oxo-4,5-dihydrofuran-3-yl-5-d phenylmethanesulfonate-d2;
2009(S) (S)-2-amino-5-(2-chlorophenyl)-4-oxo-4,5-dihydrofuran-3-yl-5-d phenylmethanesulfonate-d2;
2010 2-amino-5-(3-chlorophenyl)-4-oxo-4,5-dihydrofuran-3-yl-5-d phenylmethanesulfonate-d2;
2010(R) (R)-2-amino-5-(3-chlorophenyl)-4-oxo-4,5-dihydrofuran-3-yl-5-d phenylmethanesulfonate-d2;
2010(S) (S)-2-amino-5-(3-chlorophenyl)-4-oxo-4,5-dihydrofuran-3-yl-5-d phenylmethanesulfonate-d2;
2011 2-amino-5-(2,3-dichlorophenyl)-4-oxo-4,5-dihydrofuran-3-yl-5-d phenylmethanesulfonate-d2;
2011(R) (R)-2-amino-5-(2,3-dichlorophenyl)-4-oxo-4,5-dihydrofuran-3-yl-5-d phenylmethanesulfonate-d2;
2011(S) (S)-2-amino-5-(2,3-dichlorophenyl)-4-oxo-4,5-dihydrofuran-3-yl-5-d phenylmethanesulfonate-d2;
2012 2-amino-5-(2,4-dichlorophenyl)-4-oxo-4,5-dihydrofuran-3-yl-5-d phenylmethanesulfonate-d2;
2012(R) (R)-2-amino-5-(2,4-dichlorophenyl)-4-oxo-4,5-dihydrofuran-3-yl-5-d phenylmethanesulfonate-d2;
2012(S) (S)-2-amino-5-(2,4-dichlorophenyl)-4-oxo-4,5-dihydrofuran-3-yl-5-d phenylmethanesulfonate-d2;
2013 2-amino-5-(2,5-dichlorophenyl)-4-oxo-4,5-dihydrofuran-3-yl-5-d phenylmethanesulfonate-d2;
2013(R) (R)-2-amino-5-(2,5-dichlorophenyl)-4-oxo-4,5-dihydrofuran-3-yl-5-d phenylmethanesulfonate-d2;
2013(S) (S)-2-amino-5-(2,5-dichlorophenyl)-4-oxo-4,5-dihydrofuran-3-yl-5-d phenylmethanesulfonate-d2;
2014 2-amino-5-(3,4-dichlorophenyl)-4-oxo-4,5-dihydrofuran-3-yl-5-d phenylmethanesulfonate-d2;
2014(R) (R)-2-amino-5-(3,4-dichlorophenyl)-4-oxo-4,5-dihydrofuran-3-yl-5-d phenylmethanesulfonate-d2;
2014(S) (S)-2-amino-5-(3,4-dichlorophenyl)-4-oxo-4,5-dihydrofuran-3-yl-5-d phenylmethanesulfonate-d2;
2015 2-amino-5-(3,5-dichlorophenyl)-4-oxo-4,5-dihydrofuran-3-yl-5-d phenylmethanesulfonate-d2;
2015(R) (R)-2-amino-5-(3,5-dichlorophenyl)-4-oxo-4,5-dihydrofuran-3-yl-5-d phenylmethanesulfonate-d2;
2015(S) (S)-2-amino-5-(3,5-dichlorophenyl)-4-oxo-4,5-dihydrofuran-3-yl-5-d phenylmethanesulfonate-d2;
2016 methyl 3-(5-amino-3-oxo-4-(((phenylmethyl-d2)sulfonyl)oxy)-2,3-dihydrofuran-2-yl-2-d)benzoate;
2016(R) methyl (R)-3-(5-amino-3-oxo-4-(((phenylmethyl-d2)sulfonyl)oxy)-2,3-dihydrofuran-2-yl-2-d)benzoate;
2016(S) methyl (S)-3-(5-amino-3-oxo-4-(((phenylmethyl-d2)sulfonyl)oxy)-2,3-dihydrofuran-2-yl-2-d)benzoate;
2017 methyl 4-(5-amino-3-oxo-4-(((phenylmethyl-d2)sulfonyl)oxy)-2,3-dihydrofuran-2-yl-2-d)benzoate;
2017(R) methyl (R)-4-(5-amino-3-oxo-4-(((phenylmethyl-d2)sulfonyl)oxy)-2,3-dihydrofuran-2-yl-2-d)benzoate;
2017(S) methyl (S)-4-(5-amino-3-oxo-4-(((phenylmethyl-d2)sulfonyl)oxy)-2,3-dihydrofuran-2-yl-2-d)benzoate;
2018 methyl 4-(5-amino-3-oxo-4-(((phenylmethyl-d2)sulfonyl)oxy)-2,3-dihydrofuran-2-yl-2-d)-2-fluorobenzoate;

2018(R) methyl (R)-4-(5-amino-3-oxo-4-(((phenylmethyl-d2)sulfonyl)oxy)-2,3-dihydrofuran-2-yl-2-d)-2-fluorobenzoate;
2018(S) methyl (S)-4-(5-amino-3-oxo-4-(((phenylmethyl-d2)sulfonyl)oxy)-2,3-dihydrofuran-2-yl-2-d)-2-fluorobenzoate;
2019 ethyl 4-(5-amino-3-oxo-4-(((phenylmethyl-d2)sulfonyl)oxy)-2,3-dihydrofuran-2-yl-2-d)benzoate;
2019(R) ethyl (R)-4-(5-amino-3-oxo-4-(((phenylmethyl-d2)sulfonyl)oxy)-2,3-dihydrofuran-2-yl-2-d)benzoate;
2019(S) ethyl (S)-4-(5-amino-3-oxo-4-(((phenylmethyl-d2)sulfonyl)oxy)-2,3-dihydrofuran-2-yl-2-d)benzoate;
2020 5-(4-acetylphenyl)-2-amino-4-oxo-4,5-dihydrofuran-3-yl-5-d phenylmethanesulfonate-d2;
2020(R) (R)-5-(4-acetylphenyl)-2-amino-4-oxo-4,5-dihydrofuran-3-yl-5-d phenylmethanesulfonate-d2;
2020(S) (S)-5-(4-acetylphenyl)-2-amino-4-oxo-4,5-dihydrofuran-3-yl-5-d phenylmethanesulfonate-d2;
2021 2-amino-5-(4-carbamoylphenyl)-4-oxo-4,5-dihydrofuran-3-yl-5-d phenylmethanesulfonate-d2;
2021(R) (R)-2-amino-5-(4-carbamoylphenyl)-4-oxo-4,5-dihydrofuran-3-yl-5-d phenylmethanesulfonate-d2;
2021(S) (S)-2-amino-5-(4-carbamoylphenyl)-4-oxo-4,5-dihydrofuran-3-yl-5-d phenylmethanesulfonate-d2;
2022 4-(5-amino-3-oxo-4-(((phenylmethyl-d2)sulfonyl)oxy)-2,3-dihydrofuran-2-yl-2-d)benzoic acid-d;
2022(R) (R)-4-(5-amino-3-oxo-4-(((phenylmethyl-d2)sulfonyl)oxy)-2,3-dihydrofuran-2-yl-2-d)benzoic acid-d;
2022(S) (S)-4-(5-amino-3-oxo-4-(((phenylmethyl-d2)sulfonyl)oxy)-2,3-dihydrofuran-2-yl-2-d)benzoic acid-d;
2023 sodium 4-(5-amino-3-oxo-4-(((phenylmethyl-d2)sulfonyl)oxy)-2,3-dihydrofuran-2-yl-2-d)benzoate;
2023(R) sodium (R)-4-(5-amino-3-oxo-4-(((phenylmethyl-d2)sulfonyl)oxy)-2,3-dihydrofuran-2-yl-2-d)benzoate;
2023(S) sodium (S)-4-(5-amino-3-oxo-4-(((phenylmethyl-d2)sulfonyl)oxy)-2,3-dihydrofuran-2-yl-2-d)benzoate;
2024 potassium 4-(5-amino-3-oxo-4-(((phenylmethyl-d2)sulfonyl)oxy)-2,3-dihydrofuran-2-yl-2-d)benzoate;
2024(R) potassium (R)-4-(5-amino-3-oxo-4-(((phenylmethyl-d2)sulfonyl)oxy)-2,3-dihydrofuran-2-yl-2-d)benzoate;
2024(S) potassium (S)-4-(5-amino-3-oxo-4-(((phenylmethyl-d2)sulfonyl)oxy)-2,3-dihydrofuran-2-yl-2-d)benzoate;
2027 2-amino-5-(2-fluorophenyl)-4-oxo-4,5-dihydrofuran-3-yl-5-d phenylmethanesulfonate-d2;
2027(R) (R)-2-amino-5-(2-fluorophenyl)-4-oxo-4,5-dihydrofuran-3-yl-5-d phenylmethanesulfonate-d2;
2027(S) (S)-2-amino-5-(2-fluorophenyl)-4-oxo-4,5-dihydrofuran-3-yl-5-d phenylmethanesulfonate-d2;
2028 2-amino-5-(3-fluorophenyl)-4-oxo-4,5-dihydrofuran-3-yl-5-d phenylmethanesulfonate-d2;
2028(R) (R)-2-amino-5-(3-fluorophenyl)-4-oxo-4,5-dihydrofuran-3-yl-5-d phenylmethanesulfonate-d2;
2028(S) (S)-2-amino-5-(3-fluorophenyl)-4-oxo-4,5-dihydrofuran-3-yl-5-d phenylmethanesulfonate-d2;
2029 2-amino-5-(4-fluorophenyl)-4-oxo-4,5-dihydrofuran-3-yl-5-d phenylmethanesulfonate-d2;
2029(R) (R)-2-amino-5-(4-fluorophenyl)-4-oxo-4,5-dihydrofuran-3-yl-5-d phenylmethanesulfonate-d2;
2029(S) (S)-2-amino-5-(4-fluorophenyl)-4-oxo-4,5-dihydrofuran-3-yl-5-d phenylmethanesulfonate-d2;
2030 2-amino-5-(2,3-difluorophenyl)-4-oxo-4,5-dihydrofuran-3-yl-5-d phenylmethanesulfonate-d2;
2030(R) (R)-2-amino-5-(2,3-difluorophenyl)-4-oxo-4,5-dihydrofuran-3-yl-5-d phenylmethanesulfonate-d2;
2030(S) (S)-2-amino-5-(2,3-difluorophenyl)-4-oxo-4,5-dihydrofuran-3-yl-5-d phenylmethanesulfonate-d2;
2031 2-amino-5-(2,4-difluorophenyl)-4-oxo-4,5-dihydrofuran-3-yl-5-d phenylmethanesulfonate-d2;
2031(R) (R)-2-amino-5-(2,4-difluorophenyl)-4-oxo-4,5-dihydrofuran-3-yl-5-d phenylmethanesulfonate-d2;
2031(S) (S)-2-amino-5-(2,4-difluorophenyl)-4-oxo-4,5-dihydrofuran-3-yl-5-d phenylmethanesulfonate-d2;
2032 2-amino-5-(2,5-difluorophenyl)-4-oxo-4,5-dihydrofuran-3-yl-5-d phenylmethanesulfonate-d2;
2032(R) (R)-2-amino-5-(2,5-difluorophenyl)-4-oxo-4,5-dihydrofuran-3-yl-5-d phenylmethanesulfonate-d2;
2032(S) (S)-2-amino-5-(2,5-difluorophenyl)-4-oxo-4,5-dihydrofuran-3-yl-5-d phenylmethanesulfonate-d2;
2033 2-amino-5-(2,6-difluorophenyl)-4-oxo-4,5-dihydrofuran-3-yl-5-d phenylmethanesulfonate-d2;
2033(R) (R)-2-amino-5-(2,6-difluorophenyl)-4-oxo-4,5-dihydrofuran-3-yl-5-d phenylmethanesulfonate-d2;
2033(S) (S)-2-amino-5-(2,6-difluorophenyl)-4-oxo-4,5-dihydrofuran-3-yl-5-d phenylmethanesulfonate-d2;
2034 2-amino-5-(3,4-difluorophenyl)-4-oxo-4,5-dihydrofuran-3-yl-5-d phenylmethanesulfonate-d2;
2034(R) (R)-2-amino-5-(3,4-difluorophenyl)-4-oxo-4,5-dihydrofuran-3-yl-5-d phenylmethanesulfonate-d2;
2034(S) (S)-2-amino-5-(3,4-difluorophenyl)-4-oxo-4,5-dihydrofuran-3-yl-5-d phenylmethanesulfonate-d2;
2035 2-amino-5-(3,5-difluorophenyl)-4-oxo-4,5-dihydrofuran-3-yl-5-d phenylmethanesulfonate-d2;
2035(R) (R)-2-amino-5-(3,5-difluorophenyl)-4-oxo-4,5-dihydrofuran-3-yl-5-d phenylmethanesulfonate-d2;
2035(S) (S)-2-amino-5-(3,5-difluorophenyl)-4-oxo-4,5-dihydrofuran-3-yl-5-d phenylmethanesulfonate-d2;
2036 2-amino-5-(2-methoxyphenyl)-4-oxo-4,5-dihydrofuran-3-yl-5-d phenylmethanesulfonate-d2;
2036(R) (R)-2-amino-5-(2-methoxyphenyl)-4-oxo-4,5-dihydrofuran-3-yl-5-d phenylmethanesulfonate-d2;
2036(S) (S)-2-amino-5-(2-methoxyphenyl)-4-oxo-4,5-dihydrofuran-3-yl-5-d phenylmethanesulfonate-d2;
2037 2-amino-5-(3-methoxyphenyl)-4-oxo-4,5-dihydrofuran-3-yl-5-d phenylmethanesulfonate-d2;
2037(R) (R)-2-amino-5-(3-methoxyphenyl)-4-oxo-4,5-dihydrofuran-3-yl-5-d phenylmethanesulfonate-d2;
2037(S) (S)-2-amino-5-(3-methoxyphenyl)-4-oxo-4,5-dihydrofuran-3-yl-5-d phenylmethanesulfonate-d2;
2038 2-amino-5-(4-methoxyphenyl)-4-oxo-4,5-dihydrofuran-3-yl-5-d phenylmethanesulfonate-d2;
2038(R) (R)-2-amino-5-(4-methoxyphenyl)-4-oxo-4,5-dihydrofuran-3-yl-5-d phenylmethanesulfonate-d2;
2038(S) (S)-2-amino-5-(4-methoxyphenyl)-4-oxo-4,5-dihydrofuran-3-yl-5-d phenylmethanesulfonate-d2;
2039 2-amino-5-(2,3-dimethoxyphenyl)-4-oxo-4,5-dihydrofuran-3-yl-5-d phenylmethanesulfonate-d2;
2039(R) (R)-2-amino-5-(2,3-dimethoxyphenyl)-4-oxo-4,5-dihydrofuran-3-yl-5-d phenylmethanesulfonate-d2;
2039(S) (S)-2-amino-5-(2,3-dimethoxyphenyl)-4-oxo-4,5-dihydrofuran-3-yl-5-d phenylmethanesulfonate-d2;
2040 2-amino-5-(2,4-dimethoxyphenyl)-4-oxo-4,5-dihydrofuran-3-yl-5-d phenylmethanesulfonate-d2;
2040(R) (R)-2-amino-5-(2,4-dimethoxyphenyl)-4-oxo-4,5-dihydrofuran-3-yl-5-d phenylmethanesulfonate-d2;
2040(S) (S)-2-amino-5-(2,4-dimethoxyphenyl)-4-oxo-4,5-dihydrofuran-3-yl-5-d phenylmethanesulfonate-d2;

2041 2-amino-5-(2,5-dimethoxyphenyl)-4-oxo-4,5-dihydrofuran-3-yl-5-d phenylmethanesulfonate-d2;
2041(R) (R)-2-amino-5-(2,5-dimethoxyphenyl)-4-oxo-4,5-dihydrofuran-3-yl-5-d phenylmethanesulfonate-d2;
2041(S) (S)-2-amino-5-(2,5-dimethoxyphenyl)-4-oxo-4,5-dihydrofuran-3-yl-5-d phenylmethanesulfonate-d2;
2042 2-amino-5-(2,6-dimethoxyphenyl)-4-oxo-4,5-dihydrofuran-3-yl-5-d phenylmethanesulfonate-d2;
2042(R) (R)-2-amino-5-(2,6-dimethoxyphenyl)-4-oxo-4,5-dihydrofuran-3-yl-5-d phenylmethanesulfonate-d2;
2042(S) (S)-2-amino-5-(2,6-dimethoxyphenyl)-4-oxo-4,5-dihydrofuran-3-yl-5-d phenylmethanesulfonate-d2;
2043 2-amino-5-(3,4-dimethoxyphenyl)-4-oxo-4,5-dihydrofuran-3-yl-5-d phenylmethanesulfonate-d2;
2043(R) (R)-2-amino-5-(3,4-dimethoxyphenyl)-4-oxo-4,5-dihydrofuran-3-yl-5-d phenylmethanesulfonate-d2;
2043(S) (S)-2-amino-5-(3,4-dimethoxyphenyl)-4-oxo-4,5-dihydrofuran-3-yl-5-d phenylmethanesulfonate-d2;
2044 2-amino-5-(3,5-dimethoxyphenyl)-4-oxo-4,5-dihydrofuran-3-yl-5-d phenylmethanesulfonate-d2;
2044(R) (R)-2-amino-5-(3,5-dimethoxyphenyl)-4-oxo-4,5-dihydrofuran-3-yl-5-d phenylmethanesulfonate-d2;
2044(S) (S)-2-amino-5-(3,5-dimethoxyphenyl)-4-oxo-4,5-dihydrofuran-3-yl-5-d phenylmethanesulfonate-d2;
2045 2-amino-5-(2-bromophenyl)-4-oxo-4,5-dihydrofuran-3-yl-5-d phenylmethanesulfonate-d2;
2045(R) (R)-2-amino-5-(2-bromophenyl)-4-oxo-4,5-dihydrofuran-3-yl-5-d phenylmethanesulfonate-d2;
2045(S) (S)-2-amino-5-(2-bromophenyl)-4-oxo-4,5-dihydrofuran-3-yl-5-d phenylmethanesulfonate-d2;
2046 2-amino-5-(3-bromophenyl)-4-oxo-4,5-dihydrofuran-3-yl-5-d phenylmethanesulfonate-d2;
2046(R) (R)-2-amino-5-(3-bromophenyl)-4-oxo-4,5-dihydrofuran-3-yl-5-d phenylmethanesulfonate-d2;
2046(S) (S)-2-amino-5-(3-bromophenyl)-4-oxo-4,5-dihydrofuran-3-yl-5-d phenylmethanesulfonate-d2;
2047 2-amino-5-(4-bromophenyl)-4-oxo-4,5-dihydrofuran-3-yl-5-d phenylmethanesulfonate-d2;
2047(R) (R)-2-amino-5-(4-bromophenyl)-4-oxo-4,5-dihydrofuran-3-yl-5-d phenylmethanesulfonate-d2;
2047(S) (S)-2-amino-5-(4-bromophenyl)-4-oxo-4,5-dihydrofuran-3-yl-5-d phenylmethanesulfonate-d2;
2048 2-amino-5-(2-chloro-3-fluorophenyl)-4-oxo-4,5-dihydrofuran-3-yl-5-d phenylmethanesulfonate-d2;
2048(R) (R)-2-amino-5-(2-chloro-3-fluorophenyl)-4-oxo-4,5-dihydrofuran-3-yl-5-d phenylmethanesulfonate-d2;
2048(S) (S)-2-amino-5-(2-chloro-3-fluorophenyl)-4-oxo-4,5-dihydrofuran-3-yl-5-d phenylmethanesulfonate-d2;
2049 2-amino-5-(2-chloro-4-fluorophenyl)-4-oxo-4,5-dihydrofuran-3-yl-5-d phenylmethanesulfonate-d2;
2049(R) (R)-2-amino-5-(2-chloro-4-fluorophenyl)-4-oxo-4,5-dihydrofuran-3-yl-5-d phenylmethanesulfonate-d2;
2049(S) (S)-2-amino-5-(2-chloro-4-fluorophenyl)-4-oxo-4,5-dihydrofuran-3-yl-5-d phenylmethanesulfonate-d2;
2050 2-amino-5-(2-chloro-5-fluorophenyl)-4-oxo-4,5-dihydrofuran-3-yl-5-d phenylmethanesulfonate-d2;
2050(R) (R)-2-amino-5-(2-chloro-5-fluorophenyl)-4-oxo-4,5-dihydrofuran-3-yl-5-d phenylmethanesulfonate-d2;
2050(S) (S)-2-amino-5-(2-chloro-5-fluorophenyl)-4-oxo-4,5-dihydrofuran-3-yl-5-d phenylmethanesulfonate-d2;
2051 2-amino-5-(2-chloro-6-fluorophenyl)-4-oxo-4,5-dihydrofuran-3-yl-5-d phenylmethanesulfonate-d2;
2051(R) (R)-2-amino-5-(2-chloro-6-fluorophenyl)-4-oxo-4,5-dihydrofuran-3-yl-5-d phenylmethanesulfonate-d2;
2051(S) (S)-2-amino-5-(2-chloro-6-fluorophenyl)-4-oxo-4,5-dihydrofuran-3-yl-5-d phenylmethanesulfonate-d2;
2052 2-amino-5-(3-chloro-2-fluorophenyl)-4-oxo-4,5-dihydrofuran-3-yl-5-d phenylmethanesulfonate-d2;
2052(R) (R)-2-amino-5-(3-chloro-2-fluorophenyl)-4-oxo-4,5-dihydrofuran-3-yl-5-d phenylmethanesulfonate-d2;
2052(S) (S)-2-amino-5-(3-chloro-2-fluorophenyl)-4-oxo-4,5-dihydrofuran-3-yl-5-d phenylmethanesulfonate-d2;
2053 2-amino-5-(3-chloro-4-fluorophenyl)-4-oxo-4,5-dihydrofuran-3-yl-5-d phenylmethanesulfonate-d2;
2053(R) (R)-2-amino-5-(3-chloro-4-fluorophenyl)-4-oxo-4,5-dihydrofuran-3-yl-5-d phenylmethanesulfonate-d2;
2053(S) (S)-2-amino-5-(3-chloro-4-fluorophenyl)-4-oxo-4,5-dihydrofuran-3-yl-5-d phenylmethanesulfonate-d2;
2054 2-amino-5-(3-chloro-5-fluorophenyl)-4-oxo-4,5-dihydrofuran-3-yl-5-d phenylmethanesulfonate-d2;
2054(R) (R)-2-amino-5-(3-chloro-5-fluorophenyl)-4-oxo-4,5-dihydrofuran-3-yl-5-d phenylmethanesulfonate-d2;
2054(S) (S)-2-amino-5-(3-chloro-5-fluorophenyl)-4-oxo-4,5-dihydrofuran-3-yl-5-d phenylmethanesulfonate-d2;
2055 2-amino-5-(5-chloro-2-fluorophenyl)-4-oxo-4,5-dihydrofuran-3-yl-5-d phenylmethanesulfonate-d2;
2055(R) (R)-2-amino-5-(5-chloro-2-fluorophenyl)-4-oxo-4,5-dihydrofuran-3-yl-5-d phenylmethanesulfonate-d2;
2055(S) (S)-2-amino-5-(5-chloro-2-fluorophenyl)-4-oxo-4,5-dihydrofuran-3-yl-5-d phenylmethanesulfonate-d2;
2056 2-amino-5-(4-chloro-2-fluorophenyl)-4-oxo-4,5-dihydrofuran-3-yl-5-d phenylmethanesulfonate-d2;
2056(R) (R)-2-amino-5-(4-chloro-2-fluorophenyl)-4-oxo-4,5-dihydrofuran-3-yl-5-d phenylmethanesulfonate-d2;
2056(S) (S)-2-amino-5-(4-chloro-2-fluorophenyl)-4-oxo-4,5-dihydrofuran-3-yl-5-d phenylmethanesulfonate-d2;
2057 2-amino-5-(4-chloro-3-fluorophenyl)-4-oxo-4,5-dihydrofuran-3-yl-5-d phenylmethanesulfonate-d2;
2057(R) (R)-2-amino-5-(4-chloro-3-fluorophenyl)-4-oxo-4,5-dihydrofuran-3-yl-5-d phenylmethanesulfonate-d2;
2057(S) (S)-2-amino-5-(4-chloro-3-fluorophenyl)-4-oxo-4,5-dihydrofuran-3-yl-5-d phenylmethanesulfonate-d2;
2058 2-amino-4-oxo-5-(o-tolyl)-4,5-dihydrofuran-3-yl-5-d phenylmethanesulfonate-d2;
2058(R) (R)-2-amino-4-oxo-5-(o-tolyl)-4,5-dihydrofuran-3-yl-5-d phenylmethanesulfonate-d2;
2058(S) (S)-2-amino-4-oxo-5-(o-tolyl)-4,5-dihydrofuran-3-yl-5-d phenylmethanesulfonate-d2;
2059 2-amino-4-oxo-5-(m-tolyl)-4,5-dihydrofuran-3-yl-5-d phenylmethanesulfonate-d2;
2059(R) (R)-2-amino-4-oxo-5-(m-tolyl)-4,5-dihydrofuran-3-yl-5-d phenylmethanesulfonate-d2;
2059(S) (S)-2-amino-4-oxo-5-(m-tolyl)-4,5-dihydrofuran-3-yl-5-d phenylmethanesulfonate-d2;
2060 2-amino-4-oxo-5-(p-tolyl)-4,5-dihydrofuran-3-yl-5-d phenylmethanesulfonate-d2;
2060(R) (R)-2-amino-4-oxo-5-(p-tolyl)-4,5-dihydrofuran-3-yl-5-d phenylmethanesulfonate-d2;
2060(S) (S)-2-amino-4-oxo-5-(p-tolyl)-4,5-dihydrofuran-3-yl-5-d phenylmethanesulfonate-d2;
2061 2-amino-5-(3-cyanophenyl)-4-oxo-4,5-dihydrofuran-3-yl-5-d phenylmethanesulfonate-d2;

2061(R) (R)-2-amino-5-(3-cyanophenyl)-4-oxo-4,5-dihydrofuran-3-yl-5-d phenylmethanesulfonate-d2;
2061(S) (S)-2-amino-5-(3-cyanophenyl)-4-oxo-4,5-dihydrofuran-3-yl-5-d phenylmethanesulfonate-d2;
2062 2-amino-5-(4-cyanophenyl)-4-oxo-4,5-dihydrofuran-3-yl-5-d phenylmethanesulfonate-d2;
2062(R) (R)-2-amino-5-(4-cyanophenyl)-4-oxo-4,5-dihydrofuran-3-yl-5-d phenylmethanesulfonate-d2;
2062(S) (S)-2-amino-5-(4-cyanophenyl)-4-oxo-4,5-dihydrofuran-3-yl-5-d phenylmethanesulfonate-d2;
2063 2-amino-4-oxo-5-phenyl-4,5-dihydrofuran-3-yl-5-d phenylmethanesulfonate-d2;
2063(R) (R)-2-amino-4-oxo-5-phenyl-4,5-dihydrofuran-3-yl-5-d phenylmethanesulfonate-d2;
2063(S) (S)-2-amino-4-oxo-5-phenyl-4,5-dihydrofuran-3-yl-5-d phenylmethanesulfonate-d2;
2064 2-amino-4-oxo-5-(2-(trifluoromethyl)phenyl)-4,5-dihydrofuran-3-yl-5-d phenylmethanesulfonate-d2;
2064(R) (R)-2-amino-4-oxo-5-(2-(trifluoromethyl)phenyl)-4,5-dihydrofuran-3-yl-5-d phenylmethanesulfonate-d2;
2064(S) (S)-2-amino-4-oxo-5-(2-(trifluoromethyl)phenyl)-4,5-dihydrofuran-3-yl-5-d phenylmethanesulfonate-d2;
2065 2-amino-4-oxo-5-(3-(trifluoromethyl)phenyl)-4,5-dihydrofuran-3-yl-5-d phenylmethanesulfonate-d2;
2065(R) (R)-2-amino-4-oxo-5-(3-(trifluoromethyl)phenyl)-4,5-dihydrofuran-3-yl-5-d phenylmethanesulfonate-d2;
2065(S) (S)-2-amino-4-oxo-5-(3-(trifluoromethyl)phenyl)-4,5-dihydrofuran-3-yl-5-d phenylmethanesulfonate-d2;
2066 2-amino-4-oxo-5-(4-(trifluoromethyl)phenyl)-4,5-dihydrofuran-3-yl-5-d phenylmethanesulfonate-d2;
2066(R) (R)-2-amino-4-oxo-5-(4-(trifluoromethyl)phenyl)-4,5-dihydrofuran-3-yl-5-d phenylmethanesulfonate-d2;
2066(S) (S)-2-amino-4-oxo-5-(4-(trifluoromethyl)phenyl)-4,5-dihydrofuran-3-yl-5-d phenylmethanesulfonate-d2;
2067 2-amino-4-oxo-5-(4-(trifluoromethyl)phenyl)-4,5-dihydrofuran-3-yl-5-d (4-fluorophenyl)methanesulfonate-d2;
2067(R) (R)-2-amino-4-oxo-5-(4-(trifluoromethyl)phenyl)-4,5-dihydrofuran-3-yl-5-d (4-fluorophenyl)methanesulfonate-d2;
2067(S) (S)-2-amino-4-oxo-5-(4-(trifluoromethyl)phenyl)-4,5-dihydrofuran-3-yl-5-d (4-fluorophenyl)methanesulfonate-d2;
2068 methyl 4-(5-amino-4-((((4-fluorophenyl)methyl-d2)sulfonyl)oxy)-3-oxo-2,3-dihydrofuran-2-yl-2-d)benzoate;
2068(R) methyl (R)-4-(5-amino-4-((((4-fluorophenyl)methyl-d2)sulfonyl)oxy)-3-oxo-2,3-dihydrofuran-2-yl-2-d)benzoate;
2068(S) methyl (S)-4-(5-amino-4-((((4-fluorophenyl)methyl-d2)sulfonyl)oxy)-3-oxo-2,3-dihydrofuran-2-yl-2-d)benzoate;
2069 ethyl 4-(5-amino-4-((((4-fluorophenyl)methyl-d2)sulfonyl)oxy)-3-oxo-2,3-dihydrofuran-2-yl-2-d)benzoate;
2069(R) ethyl (R)-4-(5-amino-4-((((4-fluorophenyl)methyl-d2)sulfonyl)oxy)-3-oxo-2,3-dihydrofuran-2-yl-2-d)benzoate;
2069(S) ethyl (S)-4-(5-amino-4-((((4-fluorophenyl)methyl-d2)sulfonyl)oxy)-3-oxo-2,3-dihydrofuran-2-yl-2-d)benzoate;
2070 4-(5-amino-4-((((4-fluorophenyl)methyl-d2)sulfonyl)oxy)-3-oxo-2,3-dihydrofuran-2-yl-2-d)benzoic acid-d;
2070(R) (R)-4-(5-amino-4-((((4-fluorophenyl)methyl-d2)sulfonyl)oxy)-3-oxo-2,3-dihydrofuran-2-yl-2-d)benzoic acid-d;
2070(S) (S)-4-(5-amino-4-((((4-fluorophenyl)methyl-d2)sulfonyl)oxy)-3-oxo-2,3-dihydrofuran-2-yl-2-d)benzoic acid-d;
2071 methyl 4-(5-amino-4-((((4-fluorophenyl)methyl-d2)sulfonyl)oxy)-3-oxo-2,3-dihydrofuran-2-yl-2-d)-2-fluorobenzoate;
2071(R) methyl (R)-4-(5-amino-4-((((4-fluorophenyl)methyl-d2)sulfonyl)oxy)-3-oxo-2,3-dihydrofuran-2-yl-2-d)-2-fluorobenzoate;
2071(S) methyl (S)-4-(5-amino-4-((((4-fluorophenyl)methyl-d2)sulfonyl)oxy)-3-oxo-2,3-dihydrofuran-2-yl-2-d)-2-fluorobenzoate;
2072 2-amino-4-oxo-5-(4-(trifluoromethyl)phenyl)-4,5-dihydrofuran-3-yl-5-d (phenyl-d5)methanesulfonate-d2;
2072(R) (R)-2-amino-4-oxo-5-(4-(trifluoromethyl)phenyl)-4,5-dihydrofuran-3-yl-5-d (phenyl-d5)methanesulfonate-d2;
2072(S) (S)-2-amino-4-oxo-5-(4-(trifluoromethyl)phenyl)-4,5-dihydrofuran-3-yl-5-d (phenyl-d5)methanesulfonate-d2;
2073 methyl 4-(5-amino-3-oxo-4-((((phenyl-d5)methyl-d2)sulfonyl)oxy)-2,3-dihydrofuran-2-yl-2-d)benzoate;
2073(R) methyl (R)-4-(5-amino-3-oxo-4-((((phenyl-d5)methyl-d2)sulfonyl)oxy)-2,3-dihydrofuran-2-yl-2-d)benzoate;
2073(S) methyl (S)-4-(5-amino-3-oxo-4-((((phenyl-d5)methyl-d2)sulfonyl)oxy)-2,3-dihydrofuran-2-yl-2-d)benzoate;
2074 ethyl 4-(5-amino-3-oxo-4-((((phenyl-d5)methyl-d2)sulfonyl)oxy)-2,3-dihydrofuran-2-yl-2-d)benzoate;
2074(R) ethyl (R)-4-(5-amino-3-oxo-4-((((phenyl-d5)methyl-d2)sulfonyl)oxy)-2,3-dihydrofuran-2-yl-2-d)benzoate;
2074(S) ethyl (S)-4-(5-amino-3-oxo-4-((((phenyl-d5)methyl-d2)sulfonyl)oxy)-2,3-dihydrofuran-2-yl-2-d)benzoate;
2075 4-(5-amino-3-oxo-4-((((phenyl-d5)methyl-d2)sulfonyl)oxy)-2,3-dihydrofuran-2-yl-2-d)benzoic acid-d;
2075(R) (R)-4-(5-amino-3-oxo-4-((((phenyl-d5)methyl-d2)sulfonyl)oxy)-2,3-dihydrofuran-2-yl-2-d)benzoic acid-d;
2075(S) (S)-4-(5-amino-3-oxo-4-((((phenyl-d5)methyl-d2)sulfonyl)oxy)-2,3-dihydrofuran-2-yl-2-d)benzoic acid-d;
2076 methyl 4-(5-amino-3-oxo-4-((((phenyl-d5)methyl-d2)sulfonyl)oxy)-2,3-dihydrofuran-2-yl-2-d)-2-fluorobenzoate;
2076(R) methyl (R)-4-(5-amino-3-oxo-4-((((phenyl-d5)methyl-d2)sulfonyl)oxy)-2,3-dihydrofuran-2-yl-2-d)-2-fluorobenzoate;
2076(S) methyl (S)-4-(5-amino-3-oxo-4-((((phenyl-d5)methyl-d2)sulfonyl)oxy)-2,3-dihydrofuran-2-yl-2-d)-2-fluorobenzoate;
2077 2-amino-5-(benzo[d][1,3]dioxol-5-yl)-4-oxo-4,5-dihydrofuran-3-yl-5-d phenylmethanesulfonate-d2;
2077(R) (R)-2-amino-5-(benzo[d][1,3]dioxol-5-yl)-4-oxo-4,5-dihydrofuran-3-yl-5-d phenylmethanesulfonate-d2;

2077(S) (S)-2-amino-5-(benzo[d][1,3]dioxol-5-yl)-4-oxo-4,5-dihydrofuran-3-yl-5-d phenylmethanesulfonate-d2;
2078 2-amino-5-(2,2-difluorobenzo[d][1,3]dioxol-5-yl)-4-oxo-4,5-dihydrofuran-3-yl-5-d phenylmethanesulfonate-d2;
2078(R) (R)-2-amino-5-(2,2-difluorobenzo[d][1,3]dioxol-5-yl)-4-oxo-4,5-dihydrofuran-3-yl-5-d phenylmethanesulfonate-d2;
2078(S) (S)-2-amino-5-(2,2-difluorobenzo[d][1,3]dioxol-5-yl)-4-oxo-4,5-dihydrofuran-3-yl-5-d phenylmethanesulfonate-d2;
2079 methyl 2-(4-(5-amino-3-oxo-4-(((phenylmethyl-d2)sulfonyl)oxy)-2,3-dihydrofuran-2-yl-2-d)phenyl)acetate-d2;
2079(R) methyl (R)-2-(4-(5-amino-3-oxo-4-(((phenylmethyl-d2)sulfonyl)oxy)-2,3-dihydrofuran-2-yl-2-d)phenyl)acetate-d2;
2079(S) methyl (S)-2-(4-(5-amino-3-oxo-4-(((phenylmethyl-d2)sulfonyl)oxy)-2,3-dihydrofuran-2-yl-2-d)phenyl)acetate-d2;
2080 2-amino-5-(4-(carbamoyl-d2)phenyl)-4-oxo-4,5-dihydrofuran-3-yl-5-d phenylmethanesulfonate-d2;
2080(R) (R)-2-amino-5-(4-(carbamoyl-d2)phenyl)-4-oxo-4,5-dihydrofuran-3-yl-5-d phenylmethanesulfonate-d2;
2080(S) (S)-2-amino-5-(4-(carbamoyl-d2)phenyl)-4-oxo-4,5-dihydrofuran-3-yl-5-d phenylmethanesulfonate-d2;
2081 2-amino-4-oxo-5-(6-(trifluoromethyl)pyridin-3-yl)-4,5-dihydrofuran-3-yl-5-d phenylmethanesulfonate-d2;
2081(R) (R)-2-amino-4-oxo-5-(6-(trifluoromethyl)pyridin-3-yl)-4,5-dihydrofuran-3-yl-5-d phenylmethanesulfonate-d2;
2081(S) (S)-2-amino-4-oxo-5-(6-(trifluoromethyl)pyridin-3-yl)-4,5-dihydrofuran-3-yl-5-d phenylmethanesulfonate-d2;
2082 2-amino-4-oxo-5-(4-(trifluoromethyl)phenyl)-4,5-dihydrofuran-3-yl-5-d (4-chlorophenyl)methanesulfonate-d2;
2082(R) (R)-2-amino-4-oxo-5-(4-(trifluoromethyl)phenyl)-4,5-dihydrofuran-3-yl-5-d (4-chlorophenyl)methanesulfonate-d2;
2082(S) (S)-2-amino-4-oxo-5-(4-(trifluoromethyl)phenyl)-4,5-dihydrofuran-3-yl-5-d (4-chlorophenyl)methanesulfonate-d2;
2083 2-amino-4-oxo-5-(4-(trifluoromethyl)phenyl)-4,5-dihydrofuran-3-yl-5-d (4-(trifluoromethyl)phenyl)methanesulfonate-d2;
2083(R) (R)-2-amino-4-oxo-5-(4-(trifluoromethyl)phenyl)-4,5-dihydrofuran-3-yl-5-d (4-(trifluoromethyl)phenyl)methanesulfonate-d2;
2084 2-(amino-d2)-4-oxo-5-(4-(trifluoromethyl)phenyl)-4,5-dihydrofuran-3-yl phenylmethanesulfonate;
2085 2-(amino-d2)-4-oxo-5-(4-(trifluoromethyl)phenyl)-4,5-dihydrofuran-3-yl-5-d phenylmethanesulfonate-d2;
2085(R) (R)-2-(amino-d2)-4-oxo-5-(4-(trifluoromethyl)phenyl)-4,5-dihydrofuran-3-yl-5-d phenylmethanesulfonate-d2;
2085(S) (S)-2-(amino-d2)-4-oxo-5-(4-(trifluoromethyl)phenyl)-4,5-dihydrofuran-3-yl-5-d phenylmethanesulfonate-d2;
2086 2-(amino-d2)-4-oxo-5-(4-(trifluoromethyl)phenyl)-4,5-dihydrofuran-3-yl (phenyl-d5)methanesulfonate;
2087 2-(amino-d2)-4-oxo-5-(4-(trifluoromethyl)phenyl)-4,5-dihydrofuran-3-yl-5-d (phenyl-d5)methanesulfonate-d2;
2087(R) (R)-2-(amino-d2)-4-oxo-5-(4-(trifluoromethyl)phenyl)-4,5-dihydrofuran-3-yl-5-d (phenyl-d5)methanesulfonate-d2;
2087(S) (S)-2-(amino-d2)-4-oxo-5-(4-(trifluoromethyl)phenyl)-4,5-dihydrofuran-3-yl-5-d (phenyl-d5)methanesulfonate-d2;
2088 2-(amino-d2)-4-oxo-5-(4-(trifluoromethyl)phenyl-2,3,5,6-d4)-4,5-dihydrofuran-3-yl phenylmethanesulfonate;
2089 2-amino-4-oxo-5-(4-(trifluoromethyl)phenyl-2,3,5,6-d4)-4,5-dihydrofuran-3-yl-5-d phenylmethanesulfonate-d2;
2089(R) (R)-2-amino-4-oxo-5-(4-(trifluoromethyl)phenyl-2,3,5,6-d4)-4,5-dihydrofuran-3-yl-5-d phenylmethanesulfonate-d2;
2089(S) (S)-2-amino-4-oxo-5-(4-(trifluoromethyl)phenyl-2,3,5,6-d4)-4,5-dihydrofuran-3-yl-5-d phenylmethanesulfonate-d2;
2090 2-(amino-d2)-4-oxo-5-(4-(trifluoromethyl)phenyl-2,3,5,6-d4)-4,5-dihydrofuran-3-yl-5-d phenylmethanesulfonate-d2;
2090(R) (R)-2-(amino-d2)-4-oxo-5-(4-(trifluoromethyl)phenyl-2,3,5,6-d4)-4,5-dihydrofuran-3-yl-5-d phenylmethanesulfonate-d2;
2090(S) (S)-2-(amino-d2)-4-oxo-5-(4-(trifluoromethyl)phenyl-2,3,5,6-d4)-4,5-dihydrofuran-3-yl-5-d phenylmethanesulfonate-d2;
2091 2-(amino-d2)-4-oxo-5-(4-(trifluoromethyl)phenyl-2,3,5,6-d4)-4,5-dihydrofuran-3-yl (phenyl-d5)methanesulfonate;
2092 2-amino-4-oxo-5-(4-(trifluoromethyl)phenyl-2,3,5,6-d4)-4,5-dihydrofuran-3-yl-5-d (phenyl-d5)methanesulfonate-d2;
2092(R) (R)-2-amino-4-oxo-5-(4-(trifluoromethyl)phenyl-2,3,5,6-d4)-4,5-dihydrofuran-3-yl-5-d (phenyl-d5)methanesulfonate-d2;
2092(S) (S)-2-amino-4-oxo-5-(4-(trifluoromethyl)phenyl-2,3,5,6-d4)-4,5-dihydrofuran-3-yl-5-d (phenyl-d5)methanesulfonate-d2;
2093 2-(amino-d2)-4-oxo-5-(4-(trifluoromethyl)phenyl-2,3,5,6-d4)-4,5-dihydrofuran-3-yl-5-d (phenyl-d5)methanesulfonate-d2;
2093(R) (R)-2-(amino-d2)-4-oxo-5-(4-(trifluoromethyl)phenyl-2,3,5,6-d4)-4,5-dihydrofuran-3-yl-5-d (phenyl-d5)methanesulfonate-d2; and
2093(S) (S)-2-(amino-d2)-4-oxo-5-(4-(trifluoromethyl)phenyl-2,3,5,6-d4)-4,5-dihydrofuran-3-yl-5-d (phenyl-d5)methanesulfonate-d2.

3. The method of claim 2, wherein said deuterated compound is selected from the group consisting of:
2008 2-amino-5-(4-chlorophenyl)-4-oxo-4,5-dihydrofuran-3-yl-5-d phenylmethanesulfonate-d2;
2008(R) (R)-2-amino-5-(4-chlorophenyl)-4-oxo-4,5-dihydrofuran-3-yl-5-d phenylmethanesulfonate-d2;
2008(S) (S)-2-amino-5-(4-chlorophenyl)-4-oxo-4,5-dihydrofuran-3-yl-5-d phenylmethanesulfonate-d2;
2014 2-amino-5-(3,4-dichlorophenyl)-4-oxo-4,5-dihydrofuran-3-yl-5-d phenylmethanesulfonate-d2;
2014(R) (R)-2-amino-5-(3,4-dichlorophenyl)-4-oxo-4,5-dihydrofuran-3-yl-5-d phenylmethanesulfonate-d2;
2014(S) (S)-2-amino-5-(3,4-dichlorophenyl)-4-oxo-4,5-dihydrofuran-3-yl-5-d phenylmethanesulfonate-d2;
2017 methyl 4-(5-amino-3-oxo-4-(((phenylmethyl-d2)sulfonyl)oxy)-2,3-dihydrofuran-2-yl-2-d)benzoate;
2017(R) methyl (R)-4-(5-amino-3-oxo-4-(((phenylmethyl-d2)sulfonyl)oxy)-2,3-dihydrofuran-2-yl-2-d)benzoate;

2017(S) methyl (S)-4-(5-amino-3-oxo-4-(((phenylmethyl-d2)sulfonyl)oxy)-2,3-dihydrofuran-2-yl-2-d)benzoate;
2018 methyl 4-(5-amino-3-oxo-4-(((phenylmethyl-d2)sulfonyl)oxy)-2,3-dihydrofuran-2-yl-2-d)-2-fluorobenzoate;
2018(R) methyl (R)-4-(5-amino-3-oxo-4-(((phenylmethyl-d2)sulfonyl)oxy)-2,3-dihydrofuran-2-yl-2-d)-2-fluorobenzoate;
2018(S) methyl (S)-4-(5-amino-3-oxo-4-(((phenylmethyl-d2)sulfonyl)oxy)-2,3-dihydrofuran-2-yl-2-d)-2-fluorobenzoate;
2052 2-amino-5-(3-chloro-2-fluorophenyl)-4-oxo-4,5-dihydrofuran-3-yl-5-d phenylmethanesulfonate-d2;
2052(R) (R)-2-amino-5-(3-chloro-2-fluorophenyl)-4-oxo-4,5-dihydrofuran-3-yl-5-d phenylmethanesulfonate-d2;
2052(S) (S)-2-amino-5-(3-chloro-2-fluorophenyl)-4-oxo-4,5-dihydrofuran-3-yl-5-d phenylmethanesulfonate-d2;
2066 2-amino-4-oxo-5-(4-(trifluoromethyl)phenyl)-4,5-dihydrofuran-3-yl-5-d phenylmethanesulfonate-d2;
2066(R) (R)-2-amino-4-oxo-5-(4-(trifluoromethyl)phenyl)-4,5-dihydrofuran-3-yl-5-d phenylmethanesulfonate-d2;
2066(S) (S)-2-amino-4-oxo-5-(4-(trifluoromethyl)phenyl)-4,5-dihydrofuran-3-yl-5-d phenylmethanesulfonate-d2.

4. The method treating hypercholesterolemia of claim 1, comprising administering to a subject in need thereof, a therapeutically effective amount of said pharmaceutical composition in one or more amounts effective to treat one or more conditions associated with hyperlipidemia.

5. The method of treating a viral disease of claim 1, comprising administering to a subject in need thereof, a therapeutically effective amount of said pharmaceutical composition in one or more amounts effective to treat one or more conditions associated with viral disease.

6. The method of claim 5, wherein said viral disease is selected from the group consisting of hepatitis B, hepatitis C, hepatitis D, and human papillomavirus.

7. The method of treating blood coagulation disorders of claim 1, comprising administering to a subject in need thereof, a therapeutically effective amount of a said pharmaceutical composition in one or more amounts effective to treat one or more conditions associated with blood coagulation.

8. The method of claim 7, wherein said blood coagulation disorder is selected from the group consisting of thrombosis, venous thrombosis, coronary thrombosis, cerebral venous sinus thrombosis, pulmonary embolism, and hepatic vein thrombosis.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Consensus target sequence for human ASPH (a
      peptide-aspartate beta-dioxygenase) is CX[D/N]XXXX[Y/F]XC, where
      the residue at position 3 is hydroxylated.
<220> FEATURE:
<221> NAME/KEY: MISC_FEATURE
<222> LOCATION: (2)..(2)
<223> OTHER INFORMATION: X at position 2 is any amino acid in a
      consensus target sequence for human ASPH (a peptide-aspartate
      beta-dioxygenase) is CX[D/N]XXXX[Y/F]XC, where the residue at
      position 3 is hydroxylated.
<220> FEATURE:
<221> NAME/KEY: MISC_FEATURE
<222> LOCATION: (3)..(3)
<223> OTHER INFORMATION: X at position 3 is Aspartic Acid (D) or
      Asparagine (N) in a consensus target sequence for human ASPH (a
      peptide-aspartate beta-dioxygenase) is CX[D/N]XXXX[Y/F]XC, where
      the residue at position 3 is hydroxylated.
<220> FEATURE:
<221> NAME/KEY: MOD_RES
<222> LOCATION: (3)..(3)
<223> OTHER INFORMATION: GAMMA-CARBOXYGLUTAMIC ACID/HYDROXYLATION of
      asparagine, aspartic acid, proline or lysine, in a consensus
      target sequence for human ASPH (a peptide-aspartate
      beta-dioxygenase) is CX[D/N]XXXX[Y/F]XC, where aa residue 3 is
      hydroxylated.
<220> FEATURE:
<221> NAME/KEY: MISC_FEATURE
<222> LOCATION: (4)..(7)
<223> OTHER INFORMATION: XXXX from positions 4 to 7 represent any amino
      acid in a consensus target sequence for human ASPH (a
      peptide-aspartate beta-dioxygenase) is CX[D/N]XXXX[Y/F]XC, where
      the residue at position 3 is hydroxylated.
<220> FEATURE:
<221> NAME/KEY: MISC_FEATURE
<222> LOCATION: (8)..(8)
<223> OTHER INFORMATION: X at position 8 is Tyrosine (Y) or
      Phenylalanine (F) in a consensus target sequence for human ASPH (a
      peptide-aspartate beta-dioxygenase) is CX[D/N]XXXX[Y/F]XC, where
      the residue at position 3 is hydroxylated.
<220> FEATURE:
<221> NAME/KEY: MISC_FEATURE
<222> LOCATION: (9)..(9)
<223> OTHER INFORMATION: X at position 9 is any amino acid in a
      consensus target sequence for human ASPH (a peptide-aspartate
      beta-dioxygenase) is CX[D/N]XXXX[Y/F]XC, where the residue at
      position 3 is hydroxylated.
```

```
<400> SEQUENCE: 1

Cys Xaa Xaa Xaa Xaa Xaa Xaa Xaa Xaa Cys
1               5                   10
```